(12) United States Patent
Grant et al.

(10) Patent No.: US 11,890,403 B2
(45) Date of Patent: Feb. 6, 2024

(54) HEMODIALYSIS SYSTEM

(71) Applicant: DEKA Products Limited Partnership, Manchester, NH (US)

(72) Inventors: Kevin L. Grant, Litchfield, NH (US); Michael J. Wilt, Windham, NH (US); Brian D. Tracey, Litchfield, NH (US); Brett A. Rudolf, Hooksett, NH (US); David E. Collins, Merrimac, MA (US); Lisa A. Gustin, Manchester, NH (US); James D. Dale, Milton, FL (US); Jesse T. Bodwell, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 808 days.

(21) Appl. No.: 17/026,804

(22) Filed: Sep. 21, 2020

(65) Prior Publication Data

US 2021/0060231 A1 Mar. 4, 2021

Related U.S. Application Data

(63) Continuation of application No. 15/670,626, filed on Aug. 7, 2017, now Pat. No. 10,780,213, which is a
(Continued)

(51) Int. Cl.
| | |
|---|---|
| *A61M 1/36* | (2006.01) |
| *A61M 1/16* | (2006.01) |
| *A61M 1/14* | (2006.01) |

(52) U.S. Cl.
CPC ............ *A61M 1/3653* (2013.01); *A61M 1/14* (2013.01); *A61M 1/1658* (2013.01);
(Continued)

(58) Field of Classification Search
CPC ........ A61M 1/14; A61M 1/16; A61M 1/1658; A61M 1/168; A61M 1/1682;
(Continued)

(56) References Cited

U.S. PATENT DOCUMENTS

| 356,997 A | 2/1887 | Gil |
|---|---|---|
| 2,203,859 A | 6/1940 | Brendlin |

(Continued)

FOREIGN PATENT DOCUMENTS

| CA | 1119971 A | 3/1982 |
|---|---|---|
| CA | 1323312 C | 10/1993 |

(Continued)

OTHER PUBLICATIONS

[No Author Listed], 2008K Hemodialysis Machine Operator's Manual. Fresenius Medical Care. 2018. https://laz2qm2bxvodlae4oellp3es-wpengine.netdna-ssl.com/wp-content/uploads/2018/09/490136_Rev_K.pdf. 240 pages.
(Continued)

*Primary Examiner* — Benjamin J Klein
(74) *Attorney, Agent, or Firm* — Wolf, Greenfield & Sacks, P.C.

(57) ABSTRACT

A drain cassette for a dialysis unit has a fluid channel between venous and arterial connection ports, and a valve may controllably open and close fluid communication between a drain outlet port and the venous connection port or the arterial connection port. A blood circuit assembly and drain cassette may be removable from the dialysis unit, e.g., by hand and without the use of tools. A blood circuit assembly may include a single, unitary member that defines portions of a pair of blood pumps, control valves, channels to accurately position flexible tubing for an occluder, an air trap support, and/or other portions of the assembly. A blood circuit assembly engagement device may assist with retain-
(Continued)

ing a blood circuit assembly on the dialysis unit, and/or with removal of the assembly. An actuator may operate a retainer element and an ejector element that interact with the assembly.

25 Claims, 77 Drawing Sheets

Related U.S. Application Data continuation of application No. 14/122,166, filed as application No. PCT/US2012/039369 on May 24, 2012, now Pat. No. 9,724,458.

(60) Provisional application No. 61/489,464, filed on May 24, 2011.

(52) U.S. Cl.
CPC ........ *A61M 1/1682* (2014.02); *A61M 1/1686* (2013.01); *A61M 1/365* (2014.02); *A61M 1/367* (2013.01); *A61M 1/3643* (2013.01); *A61M 1/3644* (2014.02); *A61M 1/3647* (2014.02); *A61M 1/3649* (2014.02); *A61M 1/3652* (2014.02); *A61M 1/3656* (2014.02); *A61M 1/3672* (2013.01); *A61M 1/36225* (2022.05); *A61M 1/362227* (2022.05); *A61M 1/362261* (2022.05); *A61M 1/362265* (2022.05); *A61M 1/168* (2013.01); *A61M 1/36224* (2022.05); *A61M 1/362266* (2022.05); *A61M 2205/12* (2013.01); *A61M 2205/121* (2013.01); *A61M 2205/128* (2013.01)

(58) Field of Classification Search
CPC .............. A61M 1/1686; A61M 1/3621; A61M 1/3622; A61M 1/362227; A61M 1/36224; A61M 1/36225; A61M 1/362261; A61M 1/362265; A61M 1/326626; A61M 1/3627; A61M 1/3643; A61M 1/3644; A61M 1/3647; A61M 1/3649; A61M 1/365; A61M 1/3652; A61M 1/3653; A61M 1/3656; A61M 1/367; A61M 1/3672; A61M 2205/121; A61M 2205/128
See application file for complete search history.

(56) References Cited

U.S. PATENT DOCUMENTS

| | | |
|---|---|---|
| 2,339,876 A | 1/1944 | Phillips |
| 2,529,028 A | 11/1950 | Landon |
| 3,083,943 A | 4/1963 | Stewart, Jr. et al. |
| 3,200,648 A | 8/1965 | Waggaman |
| 3,508,656 A | 4/1970 | Serfass et al. |
| 3,656,873 A | 4/1972 | Schiff |
| RE27,849 E | 12/1973 | Wortman |
| 3,827,561 A | 8/1974 | Serfass et al. |
| 3,936,729 A | 2/1976 | Winslow, Jr. |
| 3,958,547 A | 5/1976 | Ogawa |
| 3,989,044 A | 11/1976 | Meierhoefer |
| 3,996,027 A | 12/1976 | Schnell et al. |
| 4,107,039 A | 8/1978 | Lindsay, Jr. et al. |
| 4,114,144 A | 9/1978 | Hyman |
| 4,133,312 A | 1/1979 | Burd |
| 4,137,168 A | 1/1979 | Perrot |
| 4,161,264 A | 7/1979 | Malmgren et al. |
| 4,222,127 A | 9/1980 | Donachy et al. |
| 4,282,099 A | 8/1981 | Jones |
| 4,309,592 A | 1/1982 | Le Boeuf |
| 4,344,429 A | 8/1982 | Gupton et al. |
| 4,346,703 A | 8/1982 | Dennehey et al. |
| 4,362,156 A | 12/1982 | Feller, Jr. et al. |
| 4,367,736 A | 1/1983 | Gupton |
| 4,369,781 A | 1/1983 | Gilson et al. |
| 4,386,634 A | 6/1983 | Stasz et al. |
| 4,411,783 A | 10/1983 | Dickens et al. |
| 4,439,188 A | 3/1984 | Dennehey et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,490,254 A | 12/1984 | Gordon et al. |
| 4,583,920 A | 4/1986 | Lindner |
| 4,623,450 A | 11/1986 | Vantard et al. |
| 4,624,664 A | 11/1986 | Peluso et al. |
| 4,658,244 A | 4/1987 | Meijer |
| 4,664,891 A | 5/1987 | Cosentino et al. |
| 4,680,445 A | 7/1987 | Ogawa |
| 4,695,385 A | 9/1987 | Boag |
| 4,752,292 A | 6/1988 | Lopez et al. |
| 4,770,769 A | 9/1988 | Schael |
| 4,778,447 A | 10/1988 | Velde et al. |
| 4,779,625 A | 10/1988 | Cole |
| 4,781,535 A | 11/1988 | Frawley et al. |
| 4,808,161 A | 2/1989 | Kamen |
| 4,822,343 A | 4/1989 | Beiser |
| 4,828,693 A | 5/1989 | Lindsay et al. |
| 4,857,050 A | 8/1989 | Lentz et al. |
| 4,903,655 A | 2/1990 | Vonderau et al. |
| 4,927,411 A | 5/1990 | Pastrone et al. |
| 4,950,235 A | 8/1990 | Slate et al. |
| 4,969,363 A | 11/1990 | Mochizuki |
| 5,046,496 A | 9/1991 | Betts et al. |
| 5,088,901 A | 2/1992 | Brauer |
| 5,098,262 A | 3/1992 | Wecker et al. |
| 5,110,477 A | 5/1992 | Howard et al. |
| 5,116,316 A | 5/1992 | Sertic et al. |
| 5,125,069 A | 6/1992 | O'Boyle |
| 5,135,489 A | 8/1992 | Jepson et al. |
| 5,178,182 A | 1/1993 | Kamen |
| 5,242,384 A | 9/1993 | Robinson et al. |
| 5,245,693 A | 9/1993 | Ford et al. |
| 5,247,434 A | 9/1993 | Peterson et al. |
| 5,275,724 A | 1/1994 | Bucchianeri et al. |
| 5,277,820 A | 1/1994 | Ash |
| 5,278,072 A | 1/1994 | Wall et al. |
| 5,281,206 A | 1/1994 | Lopez |
| 5,326,476 A | 7/1994 | Grogan et al. |
| 5,349,896 A | 9/1994 | Delaney, III et al. |
| 5,350,357 A | 9/1994 | Kamen et al. |
| 5,362,383 A | 11/1994 | Zimmerman et al. |
| 5,381,510 A | 1/1995 | Ford et al. |
| 5,385,540 A | 1/1995 | Abbott et al. |
| 5,410,255 A | 4/1995 | Bailey |
| 5,411,472 A | 5/1995 | Steg, Jr. et al. |
| 5,420,962 A | 5/1995 | Bakke |
| 5,427,509 A | 6/1995 | Chapman et al. |
| 5,431,627 A | 7/1995 | Pastrone et al. |
| 5,441,343 A | 8/1995 | Pylkki et al. |
| 5,441,636 A | 8/1995 | Chevallet et al. |
| 5,462,416 A | 10/1995 | Dennehey et al. |
| 5,469,070 A | 11/1995 | Koluvek |
| 5,476,368 A | 12/1995 | Rabenau et al. |
| 5,480,294 A | 1/1996 | Di Perna et al. |
| 5,487,827 A | 1/1996 | Peterson et al. |
| 5,496,273 A | 3/1996 | Pastrone et al. |
| 5,499,909 A | 3/1996 | Yamada et al. |
| 5,516,429 A | 5/1996 | Snodgrass et al. |
| 5,536,258 A | 7/1996 | Folden |
| 5,558,255 A | 9/1996 | Sancoff et al. |
| 5,568,362 A | 10/1996 | Hansson |
| 5,580,460 A | 12/1996 | Polaschegg |
| 5,591,344 A | 1/1997 | Kenley et al. |
| 5,609,572 A | 3/1997 | Lang |
| 5,609,770 A | 3/1997 | Zimmerman et al. |
| 5,616,248 A | 4/1997 | Schal |
| 5,628,908 A | 5/1997 | Kamen et al. |
| 5,632,894 A | 5/1997 | White et al. |
| 5,634,896 A | 6/1997 | Bryant et al. |
| 5,640,995 A | 6/1997 | Packard et al. |
| 5,645,531 A | 7/1997 | Thompson et al. |
| 5,651,765 A | 7/1997 | Haworth et al. |

(56) References Cited

U.S. PATENT DOCUMENTS

| | | |
|---|---|---|
| 5,651,893 A | 7/1997 | Kenley et al. |
| 5,676,644 A | 10/1997 | Toavs et al. |
| 5,704,520 A | 1/1998 | Gross |
| 5,714,060 A | 2/1998 | Kenley et al. |
| 5,729,653 A | 3/1998 | Magliochetti et al. |
| 5,730,720 A | 3/1998 | Sites et al. |
| 5,755,683 A | 5/1998 | Houle et al. |
| 5,776,091 A | 7/1998 | Brugger et al. |
| 5,795,317 A | 8/1998 | Brierton et al. |
| 5,830,185 A | 11/1998 | Block, Jr. |
| 5,836,908 A | 11/1998 | Beden et al. |
| 5,839,715 A | 11/1998 | Leinsing |
| 5,849,065 A | 12/1998 | Wojke |
| 5,863,421 A | 1/1999 | Peter, Jr. et al. |
| 5,875,282 A | 2/1999 | Jordan et al. |
| 5,899,873 A | 5/1999 | Jones et al. |
| 5,932,103 A | 8/1999 | Kenley et al. |
| 5,932,110 A | 8/1999 | Shah et al. |
| 5,947,931 A | 9/1999 | Bierman |
| 5,961,305 A | 10/1999 | Eek et al. |
| 6,039,078 A | 3/2000 | Tamari |
| 6,044,691 A | 4/2000 | Kenley et al. |
| 6,044,868 A | 4/2000 | Gretz et al. |
| 6,059,111 A | 5/2000 | Davila et al. |
| 6,062,068 A | 5/2000 | Bowling et al. |
| 6,101,406 A | 8/2000 | Hacker et al. |
| 6,136,201 A | 10/2000 | Shah et al. |
| 6,142,446 A | 11/2000 | Leinsing |
| 6,146,354 A | 11/2000 | Beil |
| 6,153,102 A | 11/2000 | Kenley et al. |
| 6,165,149 A | 12/2000 | Utterberg et al. |
| 6,165,154 A | 12/2000 | Gray et al. |
| 6,171,261 B1 | 1/2001 | Niermann et al. |
| 6,176,904 B1 | 1/2001 | Gupta |
| 6,261,065 B1 | 7/2001 | Nayak et al. |
| 6,261,262 B1 | 7/2001 | Briggs et al. |
| 6,264,680 B1 | 7/2001 | Ash |
| 6,284,131 B1 | 9/2001 | Hogard et al. |
| 6,293,108 B1 | 9/2001 | Cho et al. |
| 6,295,918 B1 | 10/2001 | Simmons et al. |
| 6,331,252 B1 | 12/2001 | El Sayyid et al. |
| 6,331,778 B1 | 12/2001 | Daily et al. |
| 6,336,911 B1 | 1/2002 | Westerbeck |
| 6,347,633 B1 | 2/2002 | Groth et al. |
| 6,394,983 B1 | 5/2002 | Mayoral et al. |
| 6,406,452 B1 | 6/2002 | Westerbeck |
| 6,413,233 B1 | 7/2002 | Sites et al. |
| 6,415,797 B1 | 7/2002 | Groth et al. |
| 6,416,293 B1 | 7/2002 | Bouchard et al. |
| 6,419,462 B1 | 7/2002 | Horie et al. |
| 6,423,053 B1 | 7/2002 | Lee |
| 6,435,844 B1 | 8/2002 | Fukami |
| 6,481,980 B1 | 11/2002 | Vandlik et al. |
| 6,505,691 B2 | 1/2003 | Judge et al. |
| 6,517,510 B1 | 2/2003 | Stewart et al. |
| 6,520,747 B2 | 2/2003 | Gray et al. |
| 6,537,445 B2 | 3/2003 | Muller |
| 6,558,340 B1 | 5/2003 | Traeger |
| 6,579,074 B2 | 6/2003 | Chiba |
| 6,579,253 B1 | 6/2003 | Burbank et al. |
| 6,595,944 B2 | 7/2003 | Balschat et al. |
| 6,595,957 B1 | 7/2003 | Griffiths et al. |
| 6,620,119 B1 | 9/2003 | Utterberg et al. |
| 6,649,063 B2 | 11/2003 | Brugger et al. |
| 6,655,257 B1 | 12/2003 | Meyer |
| 6,660,974 B2 | 12/2003 | Faries, Jr. et al. |
| 6,692,457 B2 | 2/2004 | Flaherty |
| 6,750,468 B2 | 6/2004 | Malmstrom et al. |
| 6,752,599 B2 | 6/2004 | Park |
| 6,758,975 B2 | 7/2004 | Peabody et al. |
| 6,768,085 B2 | 7/2004 | Faries, Jr. et al. |
| 6,775,473 B2 | 8/2004 | Augustine et al. |
| 6,788,885 B2 | 9/2004 | Mitsunaga et al. |
| 6,814,547 B2 | 11/2004 | Childers et al. |
| 6,814,718 B2 | 11/2004 | McGuckin, Jr. et al. |
| 6,818,179 B1 | 11/2004 | Edgson et al. |
| 6,826,948 B1 | 12/2004 | Bhatti et al. |
| 6,860,866 B1 | 3/2005 | Graf et al. |
| 6,877,419 B2 | 4/2005 | Ohrle et al. |
| 6,905,479 B1 | 6/2005 | Bouchard et al. |
| 7,029,245 B2 | 4/2006 | Maianti et al. |
| 7,041,076 B1 | 5/2006 | Westberg et al. |
| 7,044,432 B2 | 5/2006 | Beden et al. |
| 7,083,719 B2 | 8/2006 | Bowman, Jr. et al. |
| 7,147,613 B2 | 12/2006 | Burbank et al. |
| 7,153,286 B2 | 12/2006 | Busby et al. |
| 7,168,334 B1 | 1/2007 | Drott |
| 7,175,606 B2 | 2/2007 | Bowman, Jr. et al. |
| 7,232,418 B2 | 6/2007 | Neri et al. |
| 7,238,164 B2 | 7/2007 | Childers et al. |
| 7,273,465 B2 | 9/2007 | Ash |
| 7,284,374 B2 | 10/2007 | Buerger et al. |
| 7,303,540 B2 * | 12/2007 | O'Mahony ............ G16H 40/63 604/4.01 |
| 7,318,892 B2 | 1/2008 | Connell et al. |
| 7,327,273 B2 | 2/2008 | Hung et al. |
| 7,410,294 B2 | 8/2008 | Shiraki et al. |
| 7,465,285 B2 | 12/2008 | Hutchinson et al. |
| 7,476,209 B2 | 1/2009 | Gara et al. |
| 7,488,448 B2 | 2/2009 | Wieting et al. |
| 7,500,962 B2 | 3/2009 | Childers et al. |
| 7,559,524 B2 | 7/2009 | Gray et al. |
| 7,563,240 B2 | 7/2009 | Gross et al. |
| 7,563,243 B2 | 7/2009 | Mendels |
| 7,563,248 B2 | 7/2009 | Smisson, III et al. |
| 7,575,564 B2 | 8/2009 | Childers |
| 7,615,028 B2 | 11/2009 | O'Mahony |
| 7,648,627 B2 | 1/2010 | Beden et al. |
| 7,699,806 B2 | 4/2010 | Ware et al. |
| 7,708,714 B2 | 5/2010 | Connell et al. |
| 7,717,682 B2 | 5/2010 | Orr |
| 7,727,176 B2 | 6/2010 | Tonelli et al. |
| 7,736,328 B2 | 6/2010 | Childers et al. |
| 7,758,532 B2 | 7/2010 | Mori et al. |
| 7,776,006 B2 | 8/2010 | Childers et al. |
| 7,780,619 B2 | 8/2010 | Brugger et al. |
| 7,789,849 B2 | 9/2010 | Busby et al. |
| 7,794,141 B2 | 9/2010 | Perry et al. |
| 7,798,997 B2 | 9/2010 | Kamen et al. |
| 7,815,595 B2 | 10/2010 | Busby et al. |
| 7,867,214 B2 | 1/2011 | Childers et al. |
| 7,878,553 B2 | 2/2011 | Wicks et al. |
| 7,892,197 B2 | 2/2011 | Folden et al. |
| 7,892,331 B2 | 2/2011 | Childers et al. |
| 7,900,659 B2 | 3/2011 | Whitley et al. |
| 7,935,074 B2 | 5/2011 | Plahey et al. |
| 7,967,022 B2 | 6/2011 | Grant et al. |
| 8,002,726 B2 | 8/2011 | Karoor et al. |
| 8,029,454 B2 | 10/2011 | Kelly et al. |
| 8,038,639 B2 | 10/2011 | Lo et al. |
| 8,042,563 B2 | 10/2011 | Wilt et al. |
| 8,066,671 B2 | 11/2011 | Busby et al. |
| 8,075,526 B2 | 12/2011 | Busby et al. |
| 8,105,265 B2 | 1/2012 | Demers et al. |
| 8,113,244 B2 | 2/2012 | Kamen et al. |
| 8,122,923 B2 | 2/2012 | Kraus et al. |
| 8,137,553 B2 | 3/2012 | Fulkerson et al. |
| 8,246,826 B2 | 8/2012 | Wilt et al. |
| 8,266,967 B2 | 9/2012 | Kitani et al. |
| 8,273,049 B2 | 9/2012 | Demers et al. |
| 8,287,480 B2 | 10/2012 | Sasaki et al. |
| 8,292,594 B2 | 10/2012 | Tracey et al. |
| 8,317,492 B2 | 11/2012 | Demers et al. |
| 8,357,298 B2 | 1/2013 | Demers et al. |
| 8,366,316 B2 | 2/2013 | Kamen et al. |
| 8,366,655 B2 | 2/2013 | Kamen et al. |
| 8,388,908 B2 | 3/2013 | Blaga et al. |
| 8,393,690 B2 | 3/2013 | Grant et al. |
| 8,409,441 B2 | 4/2013 | Wilt |
| 8,425,471 B2 | 4/2013 | Grant et al. |
| 8,444,587 B2 | 5/2013 | Kelly et al. |
| 8,459,292 B2 | 6/2013 | Wilt et al. |
| 8,491,184 B2 | 7/2013 | Kamen et al. |
| 8,499,780 B2 | 8/2013 | Wilt et al. |

(56) References Cited

U.S. PATENT DOCUMENTS

| | | |
|---|---|---|
| 8,512,553 B2 | 8/2013 | Cicchello et al. |
| 8,535,525 B2 | 9/2013 | Heyes et al. |
| 8,545,698 B2 | 10/2013 | Wilt et al. |
| 8,562,834 B2 | 10/2013 | Kamen et al. |
| 8,597,505 B2 | 12/2013 | Fulkerson et al. |
| 8,673,139 B2 | 3/2014 | Hedmann et al. |
| 8,721,879 B2 | 5/2014 | van der Merwe et al. |
| 8,721,884 B2 | 5/2014 | Wilt et al. |
| 8,771,508 B2 | 7/2014 | Grant et al. |
| 8,858,787 B2 | 10/2014 | Muller et al. |
| 8,863,772 B2 | 10/2014 | Dale et al. |
| 8,870,549 B2 | 10/2014 | Tracey et al. |
| 8,870,811 B2 | 10/2014 | Gavin et al. |
| 8,888,470 B2 | 11/2014 | Demers et al. |
| 8,906,240 B2 | 12/2014 | Crnkovich et al. |
| 8,926,294 B2 | 1/2015 | Demers et al. |
| 8,968,232 B2 | 3/2015 | Kamen et al. |
| 8,985,133 B2 | 3/2015 | Grant et al. |
| 8,992,075 B2 | 3/2015 | Kamen et al. |
| 8,992,189 B2 | 3/2015 | Wilt et al. |
| 9,028,691 B2 | 5/2015 | Grant et al. |
| 9,072,831 B2 | 7/2015 | Kelly et al. |
| 9,089,653 B2 | 7/2015 | O'Mahony |
| 9,115,708 B2 | 8/2015 | van der Merwe et al. |
| 9,248,225 B2 | 2/2016 | Demers et al. |
| 9,272,082 B2 | 3/2016 | Demers et al. |
| 9,302,037 B2 | 4/2016 | Wilt et al. |
| 9,302,039 B2 | 4/2016 | Kelly et al. |
| 9,364,655 B2 | 6/2016 | Grant et al. |
| 9,517,295 B2 | 12/2016 | Wilt et al. |
| 9,535,021 B2 | 1/2017 | Kamen et al. |
| 9,539,379 B2 | 1/2017 | Grant et al. |
| 9,550,018 B2 | 1/2017 | Demers et al. |
| 9,555,179 B2 | 1/2017 | Wilt et al. |
| 9,597,442 B2 | 3/2017 | Wilt |
| 9,603,985 B2 | 3/2017 | Wilt et al. |
| 9,649,418 B2 | 5/2017 | Demers et al. |
| 9,677,554 B2 | 6/2017 | Wilt et al. |
| 9,700,660 B2 | 7/2017 | Demers et al. |
| 9,700,711 B2 | 7/2017 | Grant et al. |
| 9,717,834 B2 | 8/2017 | Wilt et al. |
| 9,719,964 B2 | 8/2017 | Blumberg, Jr. |
| 9,724,012 B2 | 8/2017 | Chetham |
| 9,724,458 B2 | 8/2017 | Grant et al. |
| 9,795,728 B2 | 10/2017 | Grant et al. |
| 9,907,897 B2 | 3/2018 | Burbank et al. |
| 9,951,768 B2 | 4/2018 | Grant et al. |
| 9,987,407 B2 | 6/2018 | Grant et al. |
| 9,999,717 B2 | 6/2018 | van der Merwe et al. |
| 10,060,867 B2 | 8/2018 | Kamen et al. |
| 10,077,766 B2 | 9/2018 | Demers et al. |
| 10,098,998 B2 | 10/2018 | Wilt |
| 10,201,650 B2 | 2/2019 | Wilt et al. |
| 10,302,075 B2 | 5/2019 | Tracey et al. |
| 10,415,559 B2 | 9/2019 | Demers et al. |
| 10,441,697 B2 | 10/2019 | Kamen et al. |
| 10,443,591 B2 | 10/2019 | Wilt et al. |
| 10,449,280 B2 | 10/2019 | Wilt et al. |
| 10,463,774 B2 | 11/2019 | Ballantyne et al. |
| 10,500,327 B2 | 12/2019 | Grant et al. |
| 10,537,671 B2 | 1/2020 | Wilt et al. |
| 10,576,194 B2 | 3/2020 | Distler et al. |
| 10,682,450 B2 | 6/2020 | Wilt et al. |
| 10,697,913 B2 | 6/2020 | Kamen et al. |
| 10,780,210 B2 | 9/2020 | Grant et al. |
| 10,780,213 B2 | 9/2020 | Grant et al. |
| 10,799,628 B2 | 10/2020 | Wilt et al. |
| 10,850,089 B2 | 12/2020 | Grant et al. |
| 10,851,769 B2 | 12/2020 | Demers et al. |
| 10,871,157 B2 | 12/2020 | Tracey et al. |
| 11,033,671 B2 | 6/2021 | van der Merwe et al. |
| 11,052,181 B2 | 7/2021 | Wilt et al. |
| 11,103,625 B2 | 8/2021 | Wilt |
| 11,110,212 B2 | 9/2021 | Grant et al. |
| 11,154,646 B2 | 10/2021 | Wilt et al. |
| 11,197,951 B2 | 12/2021 | Wilt et al. |
| 11,311,656 B2 | 4/2022 | Kamen et al. |
| 11,371,498 B2 | 6/2022 | Grant et al. |
| 11,419,965 B2 | 8/2022 | Demers et al. |
| 2002/0022809 A1 | 2/2002 | Sudo et al. |
| 2002/0092103 A1 | 7/2002 | Bruno et al. |
| 2002/0150476 A1 | 10/2002 | Lucke et al. |
| 2003/0114795 A1 | 6/2003 | Faries et al. |
| 2003/0194332 A1 | 10/2003 | Jahn et al. |
| 2003/0220599 A1 | 11/2003 | Lundtveit et al. |
| 2003/0220607 A1 | 11/2003 | Busby et al. |
| 2004/0101026 A1 | 5/2004 | Nitta et al. |
| 2004/0109769 A1 | 6/2004 | Jahn et al. |
| 2004/0136843 A1 | 7/2004 | Jahn et al. |
| 2004/0138607 A1 | 7/2004 | Burbank et al. |
| 2004/0243049 A1 | 12/2004 | Brugger et al. |
| 2005/0020958 A1 | 1/2005 | Paolini et al. |
| 2005/0045540 A1 | 3/2005 | Connell et al. |
| 2005/0095141 A1 | 5/2005 | Lanigan et al. |
| 2005/0095154 A1* | 5/2005 | Tracey .............. F04B 49/22 417/477.9 |
| 2005/0209563 A1 | 9/2005 | Hopping et al. |
| 2005/0234385 A1 | 10/2005 | Vandlik et al. |
| 2005/0274658 A1 | 12/2005 | Rosenbaum et al. |
| 2006/0025823 A1 | 2/2006 | Jonsen |
| 2006/0084906 A1 | 4/2006 | Burbank et al. |
| 2006/0093531 A1 | 5/2006 | Tremoulet et al. |
| 2006/0195064 A1 | 8/2006 | Plahey et al. |
| 2007/0060786 A1 | 3/2007 | Gura et al. |
| 2007/0077156 A1 | 4/2007 | Orr |
| 2007/0106228 A1 | 5/2007 | Bell et al. |
| 2007/0166181 A1 | 7/2007 | Nilson |
| 2007/0253463 A1 | 11/2007 | Perry et al. |
| 2007/0255527 A1 | 11/2007 | Schick et al. |
| 2008/0015515 A1 | 1/2008 | Hopkins et al. |
| 2008/0058697 A1 | 3/2008 | Kamen et al. |
| 2008/0077068 A1 | 3/2008 | Orr |
| 2008/0105600 A1 | 5/2008 | Connell et al. |
| 2008/0132828 A1 | 6/2008 | Howard |
| 2008/0205481 A1 | 8/2008 | Faries et al. |
| 2008/0208111 A1 | 8/2008 | Kamen et al. |
| 2008/0216898 A1 | 9/2008 | Grant et al. |
| 2008/0240929 A1 | 10/2008 | Kamen et al. |
| 2008/0253427 A1 | 10/2008 | Kamen et al. |
| 2008/0253911 A1 | 10/2008 | Demers et al. |
| 2009/0007642 A1 | 1/2009 | Busby et al. |
| 2009/0008331 A1* | 1/2009 | Wilt ................ A61M 1/1621 210/321.71 |
| 2009/0012447 A1 | 1/2009 | Huitt et al. |
| 2009/0012452 A1 | 1/2009 | Slepicka et al. |
| 2009/0012454 A1 | 1/2009 | Childers |
| 2009/0012455 A1 | 1/2009 | Childers et al. |
| 2009/0012456 A1 | 1/2009 | Childers et al. |
| 2009/0012457 A1 | 1/2009 | Childers et al. |
| 2009/0012458 A1 | 1/2009 | Childers et al. |
| 2009/0076433 A1 | 3/2009 | Folden et al. |
| 2009/0084719 A1* | 4/2009 | Childers .......... A61M 1/1524 210/151 |
| 2009/0088675 A1 | 4/2009 | Kelly et al. |
| 2009/0095679 A1 | 4/2009 | Demers et al. |
| 2009/0101549 A1* | 4/2009 | Kamen .................. A61M 1/16 210/85 |
| 2009/0101566 A1 | 4/2009 | Crnkovich et al. |
| 2009/0105629 A1 | 4/2009 | Grant et al. |
| 2009/0107335 A1 | 4/2009 | Wilt et al. |
| 2009/0114582 A1 | 5/2009 | Grant et al. |
| 2009/0124963 A1 | 5/2009 | Hogard et al. |
| 2009/0137940 A1 | 5/2009 | Orr |
| 2009/0154524 A1 | 6/2009 | Girelli |
| 2009/0173682 A1 | 7/2009 | Robinson et al. |
| 2009/0192367 A1 | 7/2009 | Braig et al. |
| 2010/0051529 A1 | 3/2010 | Grant et al. |
| 2010/0056975 A1 | 3/2010 | Dale et al. |
| 2010/0087777 A1 | 4/2010 | Hopping et al. |
| 2010/0168643 A1* | 7/2010 | Frugier ................ A61M 1/34 604/6.16 |
| 2010/0170848 A1 | 7/2010 | Brunsman |
| 2010/0192686 A1 | 8/2010 | Kamen et al. |
| 2010/0327849 A1 | 12/2010 | Kamen et al. |

(56) References Cited

U.S. PATENT DOCUMENTS

| | | | |
|---|---|---|---|
| 2011/0005992 | A1 | 1/2011 | Kelly et al. |
| 2011/0092875 | A1 | 4/2011 | Beck |
| 2011/0105877 | A1 | 5/2011 | Wilt et al. |
| 2011/0144569 | A1 | 6/2011 | Britton et al. |
| 2011/0218600 | A1 | 9/2011 | Kamen et al. |
| 2012/0035533 | A1 | 2/2012 | Britton et al. |
| 2012/0071816 | A1 | 3/2012 | Busby et al. |
| 2012/0106289 | A1 | 5/2012 | Wilt et al. |
| 2012/0207627 | A1 | 8/2012 | Demers et al. |
| 2013/0010825 | A1 | 1/2013 | Kamen et al. |
| 2013/0074959 | A1 | 3/2013 | Demers et al. |
| 2013/0126413 | A1 | 5/2013 | van der Merwe et al. |
| 2013/0284648 | A1 | 10/2013 | Grant et al. |
| 2013/0304020 | A1 | 11/2013 | Wilt et al. |
| 2014/0102299 | A1 | 4/2014 | Wilt et al. |
| 2014/0112828 | A1 | 4/2014 | Grant et al. |
| 2014/0199193 | A1 | 7/2014 | Wilt et al. |
| 2014/0309611 | A1 | 10/2014 | Wilt et al. |
| 2014/0322053 | A1 | 10/2014 | van der Merwe et al. |
| 2015/0050166 | A1 | 2/2015 | Tracey et al. |
| 2015/0196698 | A1 | 7/2015 | Grant et al. |
| 2015/0196699 | A9 | 7/2015 | Wilt et al. |
| 2015/0204807 | A1 | 7/2015 | Kamen et al. |
| 2015/0224242 | A1 | 8/2015 | Grant et al. |
| 2015/0265760 | A1 | 9/2015 | Wilt et al. |
| 2016/0030657 | A1 | 2/2016 | Kelly et al. |
| 2016/0082173 | A1 | 3/2016 | Coll et al. |
| 2016/0175505 | A1 | 6/2016 | Demers et al. |
| 2016/0175506 | A1 | 6/2016 | Wilt et al. |
| 2018/0372084 | A1 | 12/2018 | Grant et al. |
| 2019/0160220 | A1 | 5/2019 | Wilt et al. |
| 2019/0298231 | A1 | 10/2019 | Grant et al. |
| 2019/0321535 | A1 | 10/2019 | Beavers et al. |
| 2019/0344002 | A1 | 11/2019 | McGill et al. |
| 2020/0054809 | A1 | 2/2020 | Kamen et al. |
| 2020/0139031 | A1 | 5/2020 | Wilt et al. |
| 2020/0191132 | A1 | 6/2020 | Demers et al. |
| 2020/0215252 | A1 | 7/2020 | Distler et al. |
| 2020/0222609 | A1 | 7/2020 | Ballantyne et al. |
| 2020/0376185 | A1 | 12/2020 | Wilt et al. |
| 2020/0376186 | A1 | 12/2020 | Wilt et al. |
| 2020/0400595 | A1 | 12/2020 | Kamen et al. |
| 2021/0060231 | A1 | 3/2021 | Grant et al. |
| 2021/0285435 | A1 | 9/2021 | Tracey et al. |
| 2021/0290928 | A1 | 9/2021 | Grant et al. |
| 2021/0316058 | A1 | 10/2021 | van der Merwe et al. |
| 2021/0332813 | A1 | 10/2021 | Wilt et al. |
| 2021/0361841 | A1 | 11/2021 | van der Merwe et al. |
| 2022/0096718 | A1 | 3/2022 | Grant et al. |
| 2022/0133968 | A1 | 5/2022 | Wilt et al. |
| 2022/0152286 | A1 | 5/2022 | Wilt et al. |
| 2022/0241479 | A1 | 8/2022 | Kamen et al. |
| 2022/0282721 | A1 | 9/2022 | Grant et al. |

FOREIGN PATENT DOCUMENTS

| | | |
|---|---|---|
| CA | 2341993 A1 | 3/2000 |
| CA | 2704411 A1 | 5/2009 |
| CN | 1057786 A | 1/1992 |
| EP | 0 406 562 A2 | 1/1991 |
| EP | 1195171 A2 | 4/2002 |
| EP | 1 362 604 A1 | 11/2003 |
| EP | 1666078 A2 | 6/2006 |
| EP | 1837046 A1 | 9/2007 |
| FR | 2660755 A1 | 10/1991 |
| GB | 1508116 A | 4/1978 |
| GB | 2110564 A | 6/1983 |
| JP | S60-30489 A | 2/1985 |
| JP | S64-29267 A | 1/1989 |
| JP | H01-39748 U | 3/1989 |
| JP | H06-154314 A | 6/1994 |
| JP | H06-237988 A | 8/1994 |
| JP | H06-312014 A | 11/1994 |
| JP | H09-287441 A | 11/1997 |
| JP | H09-321641 A | 12/1997 |
| JP | H10-196814 A | 7/1998 |
| JP | 3007078 B1 | 2/2000 |
| JP | 2001-009025 A | 1/2001 |
| JP | 3124924 B2 | 1/2001 |
| JP | 2002-113096 A | 4/2002 |
| JP | 2002-539896 A | 11/2002 |
| JP | 2003-000706 A | 1/2003 |
| JP | 2003-196607 A | 7/2003 |
| JP | 2004-016413 A | 1/2004 |
| JP | 2004-030988 A | 1/2004 |
| JP | 2004-329793 A | 11/2004 |
| JP | 2005-013502 A | 1/2005 |
| JP | 2006-198141 A | 8/2006 |
| JP | 2006-218130 A | 8/2006 |
| JP | 2006-261558 A | 9/2006 |
| JP | 2007-035582 A | 2/2007 |
| JP | 2007-222667 A | 9/2007 |
| JP | 2008-136673 A | 6/2008 |
| JP | 5031184 B2 | 9/2012 |
| JP | S64-76865 B2 | 3/2019 |
| KR | 10-2002-0010601 A | 2/2002 |
| WO | WO 84/02473 A1 | 7/1984 |
| WO | WO 96/25214 A1 | 8/1996 |
| WO | WO 96/40320 A1 | 12/1996 |
| WO | WO 97/05913 A1 | 2/1997 |
| WO | WO 98/37801 A1 | 9/1998 |
| WO | WO 99/10028 A1 | 3/1999 |
| WO | WO 00/57935 A1 | 10/2000 |
| WO | WO 01/19430 A1 | 3/2001 |
| WO | WO 2001/037895 A2 | 5/2001 |
| WO | WO 2003/008076 A1 | 1/2003 |
| WO | WO 03/099353 A2 | 12/2003 |
| WO | WO 03/101510 A1 | 12/2003 |
| WO | WO 2004/060449 A2 | 7/2004 |
| WO | WO 2004/069309 A1 | 8/2004 |
| WO | WO 05/044339 A2 | 5/2005 |
| WO | WO 2005/089832 A2 | 9/2005 |
| WO | WO 2006/120415 A1 | 11/2006 |
| WO | WO 2007/019519 A2 | 2/2007 |
| WO | WO 2007/062197 A1 | 5/2007 |
| WO | WO 2007/120812 A2 | 10/2007 |
| WO | WO 2009/051669 A1 | 4/2009 |
| WO | WO 2015/183981 A2 | 12/2015 |

OTHER PUBLICATIONS

Misra, The basics of hemodialysis equipment. Hemodial Int. Jan. 2005;9(1):30-6.

Smith, Temperature Correction in Conductivity Measurements. Limnology and Oceanography. 1962;7(3):330-334.

Office Action for AU Application No. 2012258687 filed May 24, 2012, which Office Action is dated Nov. 2, 2015, and claims as pending for AU Application No. 2012258687 as of Nov. 2, 2015.

Office Action for CA Application No. 2,837,200 filed May 24, 2012, which Office Action is dated Feb. 1, 2019, and claims as pending for CA Application No. 2,837,200 as of Oct. 22, 2018.

Office Action for EP Application No. 12726672.4 filed Dec. 19, 2013, published as EP 2 714 134 on Apr. 9, 2014, which Office Action is dated Dec. 4, 2014, and claims as pending for EP Application No. 12726672.4 as of Dec. 4, 2014.

Office Action for EP Application No. 17164160.8 filed Mar. 31, 2017, which Office Action is dated Jul. 5, 2017, and claims as pending for EP Application No. 17164160.8 as of Jul. 5, 2017.

Office Action for JP Application No. 2014-512107 filed Nov. 22, 2013, which Office Action is dated Mar. 15, 2016, and claims as pending for JP Application No. 2014-512107 as of Mar. 15, 2016.

Office Action for JP Application No. 2019-082604 filed May 24, 2012, which Office Action was dated Apr. 21, 2020, and claims as pending for JP Application No. 2019-082604 as of Aug. 28, 2019.

Office Action for MX Application No. MX/a/2013/013875 filed Mar. 21, 2013, which Office Action is dated Dec. 14, 2017, and claims as pending for MX Application No. MX/a/2013/013875 as of Dec. 14, 2017.

Office Action for U.S. Appl. No. 14/122,166, filed Nov. 25, 2013, published as US 2014-0112828 on Apr. 24, 2014, which Office

(56) References Cited

OTHER PUBLICATIONS

Action is dated Jan. 4, 2016, and claims as pending for U.S. Appl. No. 14/122,166 as of Jan. 4, 2016.
Office Action for U.S. Appl. No. 14/122,166, filed Nov. 25, 2013, published as US 2014-0112828 on Apr. 24, 2014, which Office Action is dated Sep. 29, 2016, and claims as pending for U.S. Appl. No. 14/122,166 as of Sep. 29, 2016.
International Search Report and Written Opinion for PCT Application No. PCT/US2012/039369 dated Jan. 16, 2013.
Invitation to Pay Additional Fees for PCT Application No. PCT/US2012/039369 dated Sep. 27, 2012.
International Preliminary Report on Patentability for PCT Application No. PCT/US2012/039369 dated Dec. 5, 2013.
Search Report and Written Opinion for SG Application No. 10201604142S filed May 24, 2017, which Report is dated Nov. 7, 2017, and claims as pending for SG Application No. 10201604142S as of Nov. 7, 2017.
Examination Report for AU Application No. 2018214033 dated Mar. 12, 2020 and claims pending as of Mar. 12, 2020.
Examination Report for AU Application No. 2021202618 dated Jan. 10, 2023.
Office Action for JP Application No. 2021-007915 dated Apr. 5, 2022 and claims pending as of Apr. 5, 2022.
Office Action for AU Application No. 2021202618 dated Aug. 1, 2022 and claims pending as of Aug. 1, 2022.
Extended European Search Report for EP Application No. 22177790.7 dated Sep. 19, 2022 and claims pending as of Sep. 19, 2022.
Office Action for AU Application No. 2021202618 dated Jan. 10, 2023 and claims pending as of Jan. 10, 2023.
JP 2021-007915, Apr. 5, 2022, Office Action.
AU 2021202618, Aug. 1, 2022, Office Action.
EP 22177790.7, Sep. 19, 2022, Extended European Search Report.
AU 2012258687, Nov. 2, 2015, Office Action.
CA 2,837,200, Feb. 1, 2019, Office Action.
EP 12726672.4, Dec. 4, 2014, Office Action.
EP 17164160.8, Jul. 5, 2017, Office Action.
JP 2014-512107, Mar. 15, 2016, Office Action.
JP 2019-082604, Apr. 21, 2020, Office Action.
MX/a/2013/013875, Dec. 14, 2017, Office Action.
PCT/US2012/039369, Jan. 16, 2013, International Search Report and Written Opinion.
PCT/US2012/039369, Sep. 27, 2012, Invitation to Pay Additional Fees.
PCT/US2012/039369, Dec. 5, 2013, International Preliminary Report on Patentability.
SG 10201604142S, Nov. 7, 2017, Search Report and Written Opinion.
AU 2018214033, Mar. 12, 2020, Examination Report.

\* cited by examiner

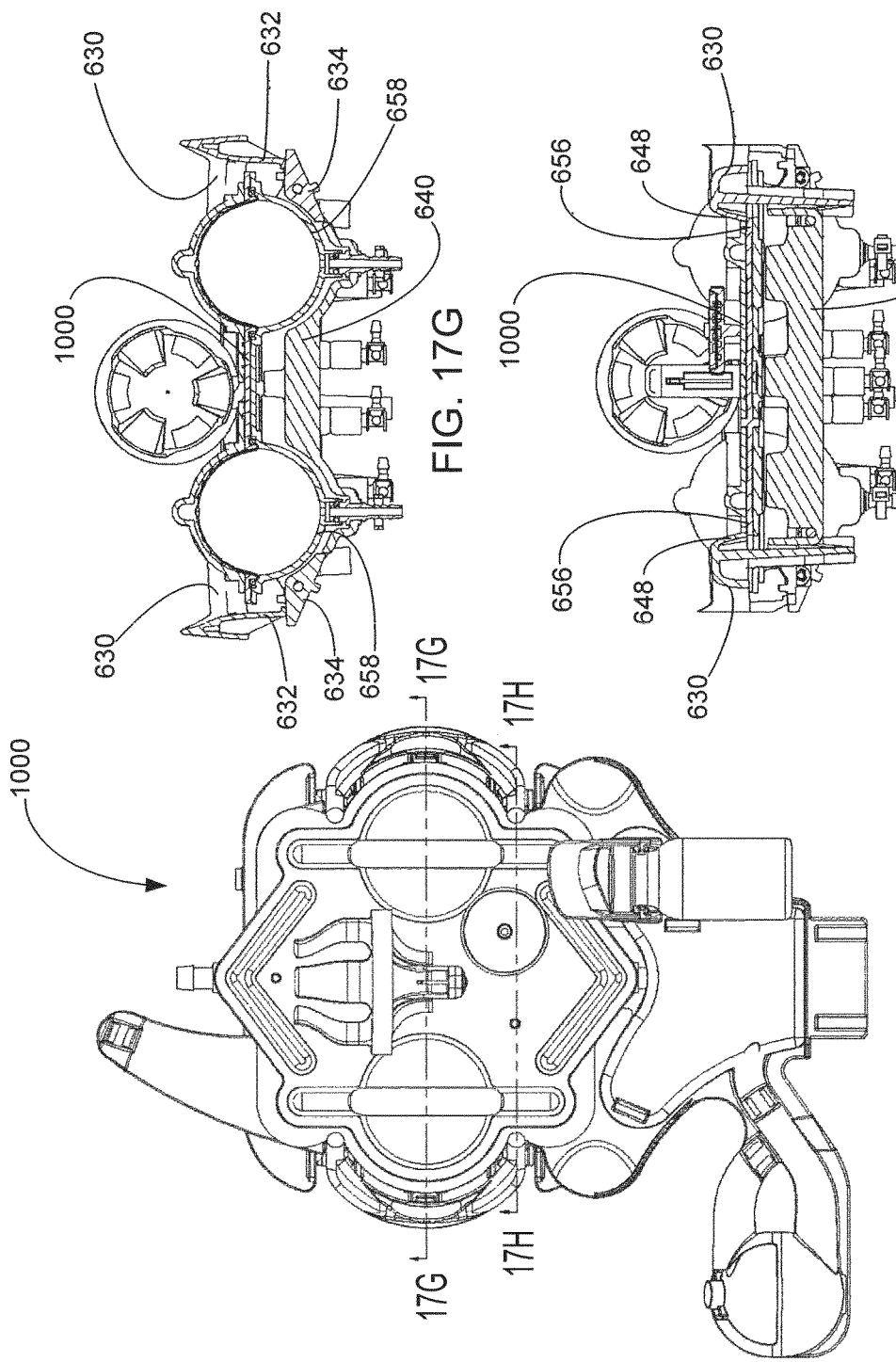

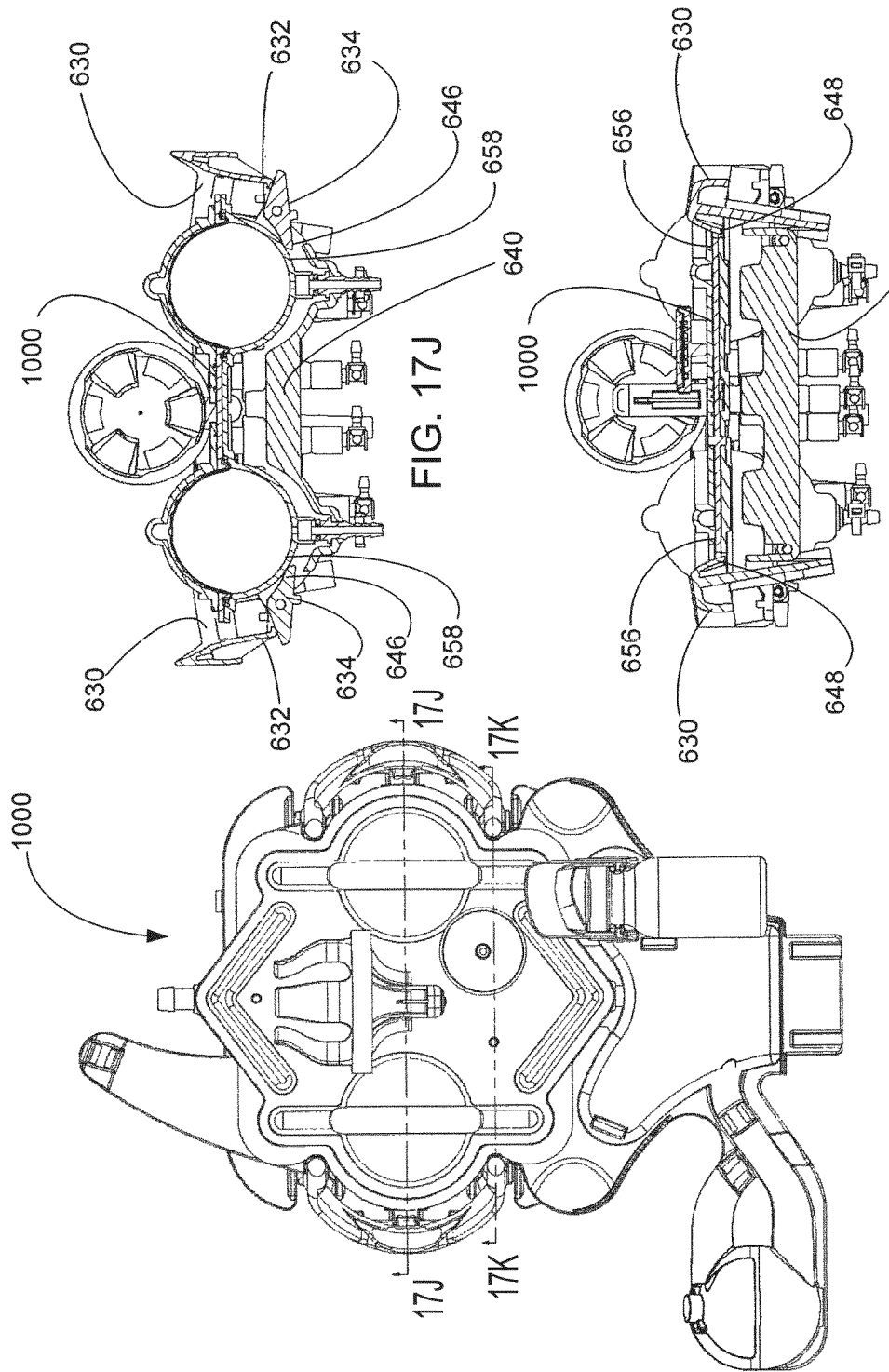

Section A-A

Section A-A

HEMODIALYSIS SYSTEM

RELATED APPLICATIONS

This application is a continuation of U.S. patent application Ser. No. 15/670,626, filed Aug. 7, 2017 and entitled "Hemodialysis System," now. U.S. Pat. No. 10,780,213 issued Sep. 22, 2020, which is a continuation of U.S. patent application Ser. No. 14/122,166, filed Nov. 25, 2013 and entitled "Hemodialysis System," now U.S. Pat. No. 9,724,458 issued Aug. 8, 2017, which is a National Stage of International Patent Application No. PCT/US2012/039369, filed May 24, 2012 and entitled "HEMODIALYSIS SYSTEM" which claims priority under 35 U.S.C. § 119(e) to U.S. Provisional Patent Application No. 61/489,464, filed May 24, 2011 and entitled "HEMODIALYSIS SYSTEM." Each of these applications is incorporated herein by reference in its entirety for all purposes.

FIELD OF INVENTION

The present invention generally relates to hemodialysis and similar dialysis systems, e.g., systems able to treat blood or other bodily fluids extracorporeally.

BACKGROUND

Many factors make hemodialysis inefficient, difficult, and expensive. These factors include the complexity of hemodialysis, the safety concerns related to hemodialysis, and the very large amount of dialysate needed for hemodialysis. Moreover, hemodialysis is typically performed in a dialysis center requiring skilled technicians. Therefore any increase in the ease and efficiency of the dialysis process could have an impact on treatment cost or patient outcome.

SUMMARY OF INVENTION

Aspects of the invention generally relate to hemodialysis and similar dialysis systems. Illustrative embodiments described herein involve, in some cases, interrelated products, alternative solutions to a particular problem, and/or a plurality of different uses of one or more systems and/or articles. Although the various systems and methods described herein are described in relation to hemodialysis, it should be understood that the various systems and method described herein are applicable to other dialysis systems and/or in any extracorporeal system able to treat blood or other bodily fluids, such as hemofiltration, hemodiafiltration, etc.

In one aspect of the invention, a drain cassette for a dialysis unit includes a venous connection port for connection to, and fluid communication with, a venous blood line connector, an arterial connection port for connection to, and fluid communication with, an arterial blood line connector, a fluid channel fluidly connecting the venous connection port and the arterial connection port, a drain outlet port in fluid communication with the fluid channel and arranged to removably couple with a drain connector on an exposed panel of the dialysis unit, and a valve arranged to control flow in the fluid channel. The valve may be arranged to control in the fluid channel to either controllably open and close fluid communication in the fluid channel between the drain outlet port and the venous connection port, or to controllably open and close fluid communication in the fluid channel between the drain outlet port and the arterial connection port. Such an arrangement may allow for purging and/or rinsing of venous and arterial lines to drain, e.g., in preparation for a treatment. In addition, the drain cassette may be removable from the dialysis unit, allowing an operator to remove and replace blood-contacting portions of the drain cassette when preparing the dialysis unit for treating another patient.

In one embodiment, the drain cassette may include a body that defines the arterial and venous connection ports and the fluid channel. A check valve may be arranged to allow flow from the fluid channel and out of the drain outlet port and to resist flow from the drain outlet port to the fluid channel. Thus, fluid or other material in a drain line downstream of the check valve may be prevented from entering the fluid channel. The valve that controls flow in the fluid channel may be a pneumatically-controlled valve, and a pneumatic control port on the drain cassette may be arranged to removably mate with a port on the exposed panel of the dialysis unit and fluidly couple the valve with the port on the exposed panel to allow control of the valve.

In one embodiment, the drain cassette may include a latch arranged to releasably lock the drain cassette to the exposed panel. For example, the latch may include a handle and a male bayonet-type connector arranged to engage with a female bayonet-type receiver on the panel of the dialysis unit. Thus, the latch may be operated, e.g., by inserting the bayonet connector into the receiver and turning the handle, to both connect and disconnect the drain cassette with respect to the panel. Such mounting and dismounting of the cassette may also cause coupling/uncoupling of one or more ports, electrical connectors or other components of the drain cassette with a corresponding port, connector, etc. on the panel. For example, a drain port, pneumatic valve control port and electrical connector coupled with one or more sensors in the drain cassette may simultaneously couple with corresponding ports/connectors on the panel in a single connection operation, which may include pushing the drain cassette onto the panel and turning the latch handle.

The drain outlet port may fluidly communicate with the fluid channel at a point above where the arterial and venous connection ports communicate with the fluid channel, e.g., so that air in the fluid channel may be evacuated by introducing fluid at the connection ports. In one embodiment, the fluid channel has a U shape with the arterial and venous connection ports fluidly connected to the fluid channel at ends of the U shape, and the drain outlet port fluidly connected to the fluid channel at a central bend of the U shape.

One or more sensors may be included to detect characteristics of fluid in the fluid channel or elsewhere in the drain cassette. For example, a conductivity sensor may be arranged to detect a conductivity of fluid in the fluid channel, and a temperature sensor may be arranged to detect a temperature of fluid in the fluid channel. The one or more sensors may be coupled to an electrical connector arranged to electrically connect the one or more sensors to a corresponding electrical connector on the exposed panel. In one embodiment, the electrical connector and the drain outlet port are arranged to simultaneously couple with a corresponding electrical connector and drain connector on the exposed panel of the dialysis unit in a single connection operation. In some arrangements, a pneumatic control port coupled to the valve may be arranged to removably mate with a control port on the exposed panel, and to simultaneously couple with the corresponding control port in the same single connection operation used to connect the drain port and electrical connector.

The valve may be arranged so that the drain outlet port is in permanently open fluid communication with the arterial connection port, and the valve may controllably open and close fluid communication in the fluid channel between the drain outlet port and the venous connection port. Alternately, the drain outlet port may be in permanently open fluid communication with the venous connection port, and the valve may be arranged to controllably open and close fluid communication in the fluid channel between the drain outlet port and the arterial connection port.

In another aspect of the invention, a blood circuit assembly and a drain cassette may be engageable with an exposed panel of a dialysis unit for operation in a dialysis treatment, and may be removable from the exposed panel for replacement without the use of tools. Such an arrangement may allow for easy replacement of all blood-contacting components of a dialysis unit so that the dialysis unit can be used for multiple, different patients (e.g., in a clinical setting) while minimizing risk of a prior patient's blood borne materials from coming into contact with a subsequent patient's treatment components. For example, the blood circuit assembly may include a pair of pneumatic pumps for circulating blood received from a patient through a circuit including a dialyzer unit and returned to the patient, an air trap arranged to remove air from blood circulating in the circuit, a pair of dialyzer connections arranged to connect to the inlet and outlet of a dialyzer unit, and a pair of blood line connectors, including an arterial blood line connector for receiving blood from the patient and providing blood to the pneumatic pumps and a venous blood line connector for returning blood to the patient. The pneumatic pumps may have pneumatic control ports arranged for alignment and mating with corresponding ports located on an exposed panel of the dialysis unit by pushing the control ports into engagement with the corresponding ports with mounting of the blood circuit assembly to the exposed panel. Thus, the blood circuit assembly may be relatively easily mounted to, and dismounted from, the panel of the dialysis unit. The drain cassette may include a venous connection port for connection to, and fluid communication with, the venous blood line connector, an arterial connection port for connection to, and fluid communication with, the arterial blood line connector, a fluid channel fluidly connecting the venous connection port and the arterial connection port, a drain outlet port in fluid communication with the fluid channel and arranged to removably couple with a drain connector on an exposed panel of the dialysis unit, and a valve arranged to control flow in the fluid channel Like the blood circuit assembly, and discussed above, the drain cassette may be arranged to be easily mounted to the panel of the dialysis unit for control by the dialysis unit in the treatment process, and dismounted from the panel for replacement.

In one embodiment, flexible tubing may fluidly connect the pumps, the air trap, the dialyzer connections and the blood line connectors of the blood circuit assembly. For example, the flexible tubing may fluidly connect the arterial blood line connector to an inlet for the pump cassette, an outlet for the pump cassette to a dialyzer inlet connector, a dialyzer outlet connector to an inlet of the air trap, and an outlet of the air trap to the venous blood line connector. The blood line connectors may be arranged for a threaded luer-type connection to a patient access, and arranged for a press-in type connection to the drain cassette connection ports. Such arrangement may allow for easy connection to the drain cassette, as well as allow for disinfection of the connectors, e.g., the press-in connection to the drain cassette may allow disinfecting fluid to flow around the patient access connection part of the connector. The drain cassette may include other features mentioned above.

In another aspect of the invention, a blood circuit assembly for a dialysis unit includes a pair of pneumatic pumps for circulating blood received from a patient through a circuit including a dialyzer unit and returning the blood to the patient, an air trap arranged to remove air from blood circulating in the circuit, a pair of dialyzer connections arranged to connect to the inlet and outlet of a dialyzer unit, a pair of blood line connectors, including an arterial blood line connector for receiving blood from the patient and providing blood to the pneumatic pumps and a venous blood line connector for returning blood to the patient, and flexible tubing fluidly connecting the pumps, the air trap, the dialyzer connections and the blood line connectors. The pneumatic pumps may have pneumatic control ports arranged for alignment and mating with corresponding ports located on an exposed panel of the dialysis unit by pushing the control ports into engagement with the corresponding ports with mounting of the blood circuit assembly to the exposed panel.

Also, the pumps may be defined, at least in part, by a single unitary member that additionally defines a plurality of routing channels for at least a portion of the flexible tubing. In one embodiment, the single unitary member or other organizing tray configuration defines an air trap cavity that receives the air trap. In some arrangements, the inlet of the air trap is supported by the air trap cavity or other support at a position above an outlet of the air trap when the blood circuit assembly is mounted to a dialysis unit. This configuration may make removal of air from the blood lines more effective.

In another embodiment, the single unitary member may define the pneumatic control ports for the pumps, a concave chamber portion for the pumps, a chamber portion of a plurality of valves used to control flow through the pumps, routing channels for flexible tubing to position the tubing for engagement with an occluder when the assembly is mounted to the dialysis unit, and/or other features. For example, the organizing tray may include circuit tube engagement members having a hole through which a respective circuit tube passes that engage with the tube to allow the circuit tube to be pulled and stretched for engagement with an occluder of the dialysis unit. Having a single part define multiple portions of the blood circuit assembly and/or to accurately route flexible tubing may make assembly of the blood circuit assembly easier and more effective, e.g., by ensuring that various components are properly positioned on the panel of the dialysis unit.

In another embodiment, the flexible tubing may connect components as follows: the arterial blood line connector may be connected to an inlet for the pump cassette, an outlet for the pump cassette may be connected to a dialyzer inlet connector, a dialyzer outlet connector may be connected to an inlet of the air trap, and an outlet of the air trap may be connected to the venous blood line connector.

In some embodiments, the blood circuit assembly may include an anticoagulant connection for engaging with an anticoagulant source and providing anticoagulant into the circuit. For example, a pump for pumping anticoagulant from the anticoagulant source to the circuit may be included, e.g., as part of a pump cassette. The anticoagulant connection may include a vial holder and a spike, and the anticoagulant source may be a vial of heparin.

In another aspect of the invention, a blood circuit assembly engagement device for a dialysis unit includes an actuator, movable between a retention position and an ejection position, mounted to a panel of the dialysis unit adjacent a plurality of control ports, a retainer element coupled to the actuator and arranged, with the actuator in the retention position, to retain a blood circuit assembly mounted to the panel of the dialysis unit on the panel, and arranged, with the actuator in the ejection position, to release the blood circuit assembly for removal from the panel of the dialysis unit, and an ejector element coupled to the actuator and arranged, with the actuator moved from the retention position to the ejection position, to urge the blood circuit assembly away from the panel. Such an arrangement may make mounting, retention and removal of a blood circuit assembly with respect to a dialysis unit more accurate and effective. For example, if the retainer element is not positioned in the retention position with a blood circuit assembly mounted to the panel, a user can easily verify that the assembly is not properly engaged with the panel. The actuator can then be used to eject the assembly, allowing replacement of the assembly on the panel.

In one embodiment, the actuator is pivotally mounted to the panel, and the retainer element is fixed to the actuator. The ejector element may be pivotable between an inactive position and an ejection position, and pivoted based on movement of the actuator. For example, the actuator may be arranged to be moved from the retention position and the ejection position by a user's thumb. In one arrangement, first and second blood circuit assembly engagement devices are provided on the panel, with the first engagement device arranged on a first side of a blood circuit assembly mounted to the panel, and the second engagement device arranged on a second side of the blood circuit assembly. The first and second sides may be opposed to each other such that the actuators of the engagement devices are movable by respective first and second thumbs of a user. For example, using both thumbs, a user may press on the actuators to move the actuators away from each other to move the actuators from respective retention positions to ejection positions. The ejection members may be arranged to contact a portion of a pump chamber in the ejection position, e.g., a rear chamber wall portion of the pump, and the retention elements may be arranged, with the actuator in the retention position and a blood circuit assembly mounted to the panel, to contact an outer surface of the blood circuit assembly to lock the blood circuit assembly in place.

Also described herein are occlusion assemblies configured to facilitate the opening and closing by occlusion of flexible tubing. In particular embodiments, the occlusion assemblies are associated with or form part of a medical infusion device, such as a hemodialysis device, peritoneal dialysis device, plasmapheresis device, etc., and may be controllably and automatically operated to facilitate fluid handling by such devices. The occlusion assemblies may be designed to position and immobilized the tubing and may include a frame or other support feature providing tubing guides and/or configured for attachment to or integration with a fluid handling assembly of a device of which they are part or with which they are used. The occlusion assemblies comprise a tubing occluder, which may be a mechanism constructed and positioned to apply a force to the tube(s) associated with the occlusion assembly to occlude the tubes and to release the force to allow the tubes to open for fluid flow. The occlusion assemblies and tubing occluders may be configured to include a single tube in certain cases, and in other cases to occlude multiple tubes, whether an odd number of tubes or an even number of tubes. Certain occlusion assemblies are specifically configured for occluding one or more pairs of tubes and may include tubing occluders having a separate occluding member for occluding each of the pair of collapsible tubes. The occlusion assemblies may include automatic actuators for operating the tubing occluders, and in certain cases also include a manual actuator to provide an override function. The occlusion assemblies may include a door designed and positioned to cover at least a portion of the tubes be included and tubing occluder mechanism. Such occlusion assemblies may include safety features, for example, to prevent a release of occlusion force on the tubing when the door is not in a closed position and/or convenience features, for example a retainer mechanism to hold the tube occluder in a non-occluding position when the door is open with the tube occluder in the non-occluding position.

In one aspect, a variety of occlusion assemblies for occluding at least one collapsible tube of a medical infusion device are described. In certain embodiments, the occlusion assembly is configured for occluding at least one pair of collapsible tubes and comprises, for each pair of collapsible tubes, a first occluding member and a second occluding member, the first occluding member positioned adjacent to a first collapsible tube of the pair and the second occluding member positioned adjacent to a second collapsible to the pair, when the tubes are installed in the occlusion assembly for operation. The first occluding member and the second occluding member are further positioned adjacent from each other such that a space is defined between them. These space is on an opposite side of each occluding member then is the collapsible tubes to which it is adjacent. The occlusion assembly further comprises a spreader positioned within the space between the occluding members and movable from a first position to a second position, wherein movement from the first position to the second position causes the spreader to force at least a portion of the first and second occluding members to move apart from each other to increase the size of the space between them and forced a tube-contacting portion of each occluding member against the collapsible tube to which it is adjacent to occlude the collapsible tube. The occlusion assembly further comprises at least one actuator constructed and positioned to move the spreader between the first and second positions.

In certain embodiments the occlusion assembly is configured for occluding at least one collapsible tube and comprises a frame comprising a tubing guide configured for positioning the collapsible tube, a tubing occluder mounted to the frame and comprising an occluding member constructed and positioned to controllably occlude or release occlusion of the collapsible tube, a door hingeably mounted to the frame and positioned to cover at least a portion of the collapsible tube and tubing occluder when in a closed position and to provide user access to the collapsible tube when in an open position, and a switch configured and positioned to detect when the door is in a closed position and to permit operation of the tubing occluder to release occlusion of the collapsible tube only when the door is in the closed position.

In certain embodiments and occlusion assembly for collapsing at least one collapsible tube comprises a tubing occluder comprising an occluding member constructed and positioned to controllably occlude or release occlusion of the collapsible tube, and automatic actuator operatively coupled to the tubing occluder to cause essentially linear motion of at least a portion of the tubing occluder to cause the occluding member to move from an occluding position to a non-occluding position, and an override mechanism operatively coupled to the tubing occluder to cause essentially linear motion of at least a portion of the tubing occluder to cause the occluding member to move from an occluding position to a non-occluding position upon manual operation of the override mechanism by a user.

In certain embodiments, and occlusion assembly for occluding at least one collapsible tube comprises a frame comprising a tubing guide configured for positioning the collapsible tube, a tubing occluder mounted to the frame and comprising an occluding member constructed and positioned to controllably occlude or release occlusion of the collapsible tube, a door hindgeably mounted to the frame and positioned to cover at least a portion of the collapsible tube and tubing occluder when in a closed position and to provide user access to the collapsible tube when in an open position, and a retainer mechanism engaged by the door when the door is in the closed position and configured to permit operation of the tubing occluder to occlude or release occlusion of the collapsible tube when the door is in the closed position and configured to engage and retain the tubing occluder in a non-occluding configuration when the door is opened while the tubing occluder is positioned in the non-occluding configuration.

In another aspect a method of operating an occlusion assembly for occluding at least one pair of collapsible tubes of a medical infusion devices disclosed. In one embodiment, the method involves moving a spreader of the occlusion assembly from a first position to a second position, wherein the spreader is positioned within a space defined between a first occluding member and a second occluding member to cause the spreader to force at least a portion of the first and second occluding members to move apart from each other to increase the size of the space between them and force a tube-contacting portion of each occluding member against a collapsible tube to which it is adjacent to occlude the collapsible tube.

In another aspect of the invention, an enclosure for containing a portable hemodialysis unit is provided, where the hemodialysis unit includes suitable components for performing hemodialysis including a dialyzer, one or more pumps to circulate blood through the dialyzer, a source of dialysate, and one or more pumps to circulate the dialysate through the dialyzer. The enclosure may include a housing that supports the components of the hemodialysis unit and has a front panel at which blood circuit connections and dialysate fluidic connections are located. For example, the front panel may support blood line connections for patient blood access, connections for a reagent supply, dialyzer connections for both blood flow and dialysate, etc. Thus, in one embodiment, an operator may complete all necessary fluid circuit connections for the blood circuit and reagent supply at the housing front panel. The enclosure may also include a pair of vertical, side-by-side doors hingedly mounted to the housing at opposite sides of the front panel so that the doors are movable between open and closed positions. With the doors in an open position, an operator may have access to the blood circuit connections and dialysate fluidic connections. Also, with the doors in the closed position, access to the patient access and dialysate fluidic connections may be blocked, and the doors may allow for the retention of heat in the housing suitable for disinfection during a disinfection cycle. For example, at least one of the doors may include a seal to resist air exchange between an interior and an exterior of housing when the doors are in the closed position to help retain heat and/or help resist entry of dust, dirt or other contaminants.

In one embodiment, each of the vertical, side-by-side doors is mounted to the housing via a hinge plate that is pivotally mounted to the door at a first end, and is pivotally mounted to the housing at a second end opposite the first end. Thus, the doors may be positionable at two open positions, e.g., a first open position in which blood circuit connections and dialysate fluidic connections are exposed and the hinge plate is adjacent the housing, and a second open position in which the hinge plate is positioned away from the housing. One or more retainer members may be included to maintain the doors in an open position relative to a corresponding hinge plate. For example, the retainer member may include at least one magnet attached to the door or the hinge plate that tends to keep the door in an open position relative to the hinge plate and the housing. Also, one or more retainer members may maintain the hinge plates in a closed position relative to the housing, e.g., in a position close to the housing, and/or maintain the hinge plates in an open position away from the housing.

In one embodiment, at least one of the doors may include a container holder that is movable between a folded position and an extended position in which the container holder is arranged to support a container, such as reagent supply container. In addition, or alternately, one or both of the doors may include a hook to support a control interface for the hemodialysis unit, such as a remote interface unit that is connected to the housing by a communication cable. These features may make use of the dialysis unit easier by supporting components in a convenient location.

In another embodiment, the front panel may include at least one flanged portion to support blood lines of a blood circuit assembly. For example, the front panel may include several flanged sections arranged at a periphery of the front panel, such as at lower corners and at a top edge of the front panel. Blood circuit lines that connect to a patient may be relatively long (e.g., up to 3-4 feet or more), and may be wrapped around the periphery of the front panel and retained in place by the flanged portions. The flanged portions may be arranged to support the blood lines and allow the doors to be moved to the closed position without contacting the blood lines, e.g., to avoid pinching of the blood lines at door hinge points.

In one embodiment, the blood circuit connections at the front panel include arterial and venous blood line connectors for the blood circuit, and the dialysate fluidic connections at the front panel include a connection point for a reagent supply, dialyzer dialysate connections, and a blood line connection point for connecting the arterial and venous blood lines to a directing circuit of the dialysis unit.

The hemodialysis unit may include a control interface that is connected to the housing by a flexible cable and that is arranged to allow a user to receive information from and provide information to the hemodialysis unit. In one embodiment, the enclosure may include a control interface mounting area at a top of the enclosure where the control interface is mountable. For example, the control interface may include a foldable leg or other support that permits the control interface to be stood in a near vertical orientation on the top of the housing.

In another embodiment, the enclosure may include an electronics section that is separated and insulated from a disinfection section that is heated to disinfect components of the hemodialysis unit. For example, the disinfection section may include all of the liquid circuit components, such as valves, pumps, conduits, etc., of the various portions of the dialysis unit. The electronics section may include motors, computers or other data processing devices, computer memory, and/or other temperature sensitive electronics or other components. By isolating the electronics section from the disinfection section (at least to some degree), components in the electronics section may be spared exposure to the heat or other environmental conditions in the disinfection section whether during a disinfection operation or otherwise.

In another aspect of the invention, a portable hemodialysis system may be arranged so that power for the fluid circuit pumps of a dialysis unit may be provided by a modular power unit, e.g., a unit that can be selectively connected to or disconnected from the dialysis unit. As a result, failure of a power unit need not necessarily disable the entire dialysis system. Instead, the power unit may be replaced with another power unit, allowing for treatment to continue. For example, a modular assembly for a portable hemodialysis system may include a dialysis unit, e.g., including a housing that contains suitable components for performing hemodialysis, such as a dialyzer, one or more pumps to circulate blood through the dialyzer, a source of dialysate, and one or more pumps to circulate the dialysate through the dialyzer. The housing may have a front panel at which blood circuit connections and dialysate fluidic connections are located, e.g., where an operator may make patient blood access connections, connect a reagent supply, and/or connect a dialyzer. The modular assembly may also include a power unit having a housing that contains suitable components for providing operating power to the pumps of the dialysis unit. The power unit may be selectively connected to the dialysis unit and provide power to the dialysis unit for the pumps when connected to the dialysis unit, but may be incapable of providing power to the dialysis unit when disconnected from the dialysis unit. The power unit may be selectively connected to and disconnected from the dialysis unit by operation of a single handle, e.g., an operator may turn or otherwise operate a single handle to disconnect the power unit from the dialysis unit. In one embodiment, the dialysis unit and the power unit are sized and weighted to each be carried by hand by a human.

In one embodiment, the pumps of the dialysis unit are pneumatic pumps and the power unit provides pneumatic power to the dialysis unit. For example, the power unit may provide air pressure and/or vacuum to the dialysis unit to power the pumps. The power unit may include one or more air pressure pumps and/or air vacuum pumps, and the dialysis unit may include a plurality of valves to control application of pneumatic power to the pumps. To aid with use of the hemodialysis system in the home, the power unit and dialysis unit electrical power requirements may be provided by standard residential electrical power, e.g., approximately 110V, 15 amp electrical power. The dialysis unit may provide electrical power to the power unit, and the power unit may use the electrical power to generate operating power for the pumps.

In another aspect of the invention, a blood circuit assembly for a dialysis unit may be arranged to allow the replacement of most or all blood circuit components in a single operation. For example, the blood circuit assembly may include an organizing tray, a pair of pneumatic pumps mounted to the organizing tray for circulating blood received from a patient through a circuit including a dialyzer unit and returned to the patient, an air trap mounted to the organizing tray arranged to remove air from blood circulating in the circuit, a pair of dialyzer connections arranged to connect to the inlet and outlet of a dialyzer unit, and a pair of blood line connectors, one inlet blood line connector for receiving blood from the patient and providing blood to the pneumatic pumps and the other outlet blood line connector for returning blood to the patient.

In one embodiment, an anticoagulant connection is provided for engaging with an anticoagulant source and providing anticoagulant into the blood circuit. For example, the anticoagulant connection may include a pump for pumping anticoagulant from the anticoagulant source, such as heparin from a vial of heparin, to the circuit. The anticoagulant connection may include a vial holder arranged to hold two or more differently sized vials, and a spike to pierce the vial. In one embodiment, the pair of pneumatic pumps, the anticoagulant connection, and the anticoagulant pump are part of a pump cassette.

In another embodiment, the blood circuit assembly may be selectively mounted to and removed from a dialysis unit. To aid in handling of the blood circuit assembly, the organizing tray may include a pair of handles arranged for gripping by a user. The organizing tray may also include openings adjacent each of the handles for receiving retaining tabs on a dialysis unit that engage with the blood circuit assembly and retain the blood circuit assembly on the dialysis unit.

In one embodiment, the inlet blood line connector is connected to an inlet for the pump cassette, an outlet for the pump cassette is connected to a dialyzer inlet connector, a dialyzer outlet connector is connected to an inlet of the air trap, and an outlet of the air trap is connected to the outlet blood line connector. The inlet of the air trap may be located above the outlet of the air trap when the blood circuit assembly is mounted to a dialysis unit, e.g., to aid in trapping of air circulating in the circuit during treatment. The blood line connectors may be arranged for a threaded luer-type connection to a patient access, as well as be arranged for a press-in type connection to the dialysis unit. Such an arrangement may make it easier for an operator to connect the blood line connectors to the dialysis unit after treatment (e.g., for later disinfection and/or priming of the blood circuit) while allowing the connectors to engage with standard luer-type connectors at a patient blood access.

In one embodiment, the organizing tray may include circuit tube engagement members having a hole or slot through which a respective circuit tube passes. The engagement members may engage with the respective circuit tube to allow the circuit tube to be pulled and stretched for engagement with an occluder of the dialysis unit. For example, the circuit tubes of the blood circuit assembly may include silicone tubing that has to be stretched (and thereby reduced in diameter) to engage with an occluder. The circuit tube engagement members may resist the pull of an operator on the tubes, allowing the tubes to be stretched and placed in engagement with the occluder.

In another aspect of the invention, a method for replacing a blood circuit assembly of a dialysis unit includes grasping a pair of handles on an organizing tray of a blood circuit assembly that is mounted to a dialysis unit, disengaging locking tabs of the dialysis unit from the blood circuit assembly to free the blood circuit assembly from the dialysis unit, and pulling on the handles on the organizing tray of the blood circuit assembly to remove the blood circuit assembly from the dialysis unit. Disengagement of the locking tabs may be performed by flexing the locking tabs away from each other such that each locking tab is moved toward a nearest one of the handles. After removal of the blood circuit assembly, a replacement blood circuit assembly may be provided, openings in the organizing tray of the replacement blood circuit assembly may be aligned with the locking tabs so that each locking tab is received into a respective opening, and the organizing tray may be pushed relative to the dialysis unit such that the locking tabs engage with the replacement blood circuit assembly to mount the replacement blood circuit assembly to the dialysis unit. Mounting the replacement blood circuit assembly may also involve connecting control ports on the dialysis unit to mating ports on the assembly so that fluid control signals may be provided for pumps and valves of the blood circuit assembly. Other blood circuit connections may be made, such as inlet and outlet connections for the dialyzer, and the blood line connectors may be connected to receive dialysate into the blood circuit.

In another aspect of the invention, an air trap for a blood circuit in a dialysis unit includes a blood inlet supply line, a blood outlet supply line, and a container having an approximately spherical internal wall, an inlet at a top end of the container connected to the blood inlet supply line, and an outlet at a bottom end of the container connected to the blood outlet supply line. The inlet may be offset from a vertical axis of the approximately spherical internal wall such that blood entering the container through the inlet is directed to flow in around the approximately spherical wall in a spiral-like path. Such flow in the container may help to remove air bubbles from the blood as it flows from the inlet to the outlet, with any removed air remaining near the top of the container. The inlet port may be arranged to introduce blood into the container in a direction that is approximately tangential to the approximately spherical inner wall of the container and/or in a direction that is approximately perpendicular to the vertical axis of the container.

In one embodiment, a self-sealing port may be located at a top of the container, e.g., in the form of a split septum that is arranged to permit introduction of fluid into, and withdrawal of liquid from, the container by inserting a needleless device through the split septum. The self-sealing port may be arranged to be self-cleaning when disinfection liquid is circulated through the container, e.g., the port may be suitably exposed to flowing disinfection liquid to remove debris and/or heat material on the port to achieve desired disinfection.

In another aspect of the invention, a tube securing arrangement of a blood circuit assembly includes a organizing tray that supports components of a blood circuit assembly and includes a pair of tube engagement members each having a hole, a pair of patient inlet and outlet lines arranged to connect with patient access points for receiving liquid from and/or providing liquid to the patient, and a pair of stops on the patient inlet and outlet lines, respectively. The patient inlet and outlet lines may each pass through a hole of a respective tube engagement member so that the stop engages with the tube engagement member. With this arrangement, the tube engagement members may resist pulling and stretching of the inlet and outlet lines when engaging the lines with an occluder. The tube engagement members may be flexible to allow a user to press inwardly on the engagement member and seat the respective inlet or outlet line in the occluder, yet resist downward pulling of the line.

In another aspect of the invention, a hemodialysis system includes a dialyzer mount arranged to support a plurality of differently sized and/or shaped dialyzer units and to accommodate different distances between dialysate connections on the dialyzer units. The dialyzer mount, which may be located on a front panel of the dialysis unit, may include a pair of flange portions that are each arranged to engage with a respective dialysate quick-connect fitting connected to a dialysate port of the dialyzer. Each flange portion may be arranged to engage with a groove on the quick connect fitting that is located between a portion of the base of the quick connect fitting and a slide element of the quick connect fitting. For example, the dialyzer mount may include a pair of keyhole features with each keyhole feature having an upper insertion area sized to receive a portion of the base of the quick-connect fitting inserted into the upper insertion area, and a lower flanged portion having a width that is smaller than an overall a width of the base of the quick-connect fitting and that engages with a groove on the quick connect fitting. The lower flanged portion may include a pair of opposite flanges that engage with the groove and allow the quick-connect fitting to slide along the flanges.

In one embodiment, the bottom keyhole feature may include an adjustable support that is moveable in a vertical direction. For example, the adjustable support may be movable along the opposed flanges. Thus, the adjustable support may be fixable in a plurality of different positions on the flanges to support the weight of the dialyzer. In one arrangement, the adjustable support includes a "U" shaped member and at least one thumb screw that may be tightened to fix the "U" shaped member in place.

In another aspect of the invention, a blood line connector for a blood circuit of a hemodialysis unit may have the ability to make two different types of fluid tight connections, e.g., a screw-type connection with a luer connector at a patient access and a press-in type connection with a dialysate circuit of the hemodialysis unit. For example, the blood line connector may include a tube connection end arranged to sealingly engage with a blood circuit tube, and a patient access connection end with a frustoconical member having an internally threaded portion arranged to engage with an externally threaded patient access, and a pair of locking arms extending rearwardly from the frustoconical member. The locking arms may each have a finger depression portion and a barbed portion, and may be arranged to engage with a mating connector on the dialysis unit at the barbed portions to lock the frustoconical member in sealing engagement with the mating connector when making a press-in type connection. The barbed portions may disengage from the mating connector when the finger depression portions are urged toward each other. In one embodiment, the patient access connection end may include a central tube extending from the center of the frustoconical member. The internally threaded portion of the frustoconical member and the central tube may be arranged to mate with a female luer-type patient access connector or any other suitable screw-type connection.

In another aspect of the invention, a method for operating a dialysis unit includes connecting blood line connectors of arterial and venous blood lines for a dialysis unit to patient access connectors in communication with a patient blood system. In one embodiment, the patient access connectors may require a corresponding blood line connector to establish a threaded engagement with the patient access connector, thereby forming a luer or screw-type connection between the blood line connectors and the patient access connectors. The dialysis unit may be operated to withdraw blood from a patient access connector and into an arterial blood line, subject the withdrawn blood to a dialysis process to produce treated blood, and return the treated blood to the patient via the venous blood line and the other patient access connector. Thereafter, the blood line connectors may be disconnected from the patient access connectors by unscrewing the blood line connectors from a corresponding patient access connector, and the blood line connectors may be connected to a directing circuit of the dialysis unit. The blood line connectors may be connected to the directing circuit by a press-in connection with a corresponding connection point on the dialysis unit, e.g., by pushing the blood line connectors into the connection points to establish the press-in connection.

In another aspect of the invention, a reagent supply arrangement for a hemodialysis system may be arranged to provide two or more reagent materials for use in preparing a dialysate and may include a connector arranged to help prevent the connection of a reagent material to the wrong port. For example, the reagent supply may include an E-prong connector having three parallel prongs with two outer prongs arranged in a common plane and a center prong arranged above the common plane, a first supply line for a first reagent connected in fluid communication with one of the outer prongs, a second supply line for a second reagent connected in fluid communication with the other of the outer prongs, a liquid line connected in fluid communication with the center prong, and a container for housing the first reagent having an inlet connected to the liquid line and an outlet connected to the first supply line for the first reagent. The E-prong connector may help prevent the improper connection of the first and second supply lines to the dialysis unit, e.g., because the central prong being located out of the plane of the two outer prongs ensure connection of the E-prong connector in only one way to the dialysis unit.

In one embodiment, the container includes a bicarbonate material suitable for use in generating a dialysate for the hemodialysis system. The liquid line may be a water supply line that provides water to the container, allowing the water to mix with the bicarbonate (which may be in powder or other solid form) and flow to the first supply line. The second supply line may be an acid supply line that includes a connector and provides acid material to the E-prong connector. The reagent supply may also include an acid bag spike that is removably engaged with the connector of the acid supply line. The acid bag spike may include a spike member and a pair of spring clips at an end of the acid bag spike opposite the connector of the acid supply line, allowing the acid bag spike to be fluidly connected with an acid bag or other acid source.

In another aspect of the invention, a method for operating a hemodialysis system includes providing a dialysis unit having an enclosure containing suitable components for performing hemodialysis including a dialyzer, one or more pumps to circulate blood through the dialyzer, a source of dialysate, and one or more pumps to circulate the dialysate through the dialyzer. The enclosure may include a housing that supports the components and has a front panel at which blood circuit connections and dialysate fluidic connections are made. A reagent supply may be provided including an E-prong connector, a first supply line for a first reagent connected in fluid communication with one of the outer prongs, a second supply line for a second reagent connected in fluid communication with the other of the outer prongs, a liquid line connected in fluid communication with the center prong, and a container for housing the first reagent having an inlet connected to the liquid line and an outlet connected to the first supply line for the first reagent. The E-prong connector may be engaged with a connection point at the front panel of the dialysis unit, thereby allowing the dialysis unit to provide water to the liquid line of the reagent supply, and allowing the dialysis unit to receive the first and second reagents from the first and second supply lines.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Aspects of the invention are described with reference to illustrative embodiments, which are described with reference to the drawings in which like numerals reference like elements, and wherein:

FIG. 17F shows a front view of a blood pump cassette in a retained condition on a panel of a dialysis unit in an illustrative embodiment;

FIG. 17G shows a cross-sectional view along the line 17G-17G in FIG. 17F; FIG. 17H shows a cross-sectional view along the line 17H-17H in FIG. 17F;

FIG. 17I shows a front view of a blood pump cassette in an ejecting condition in an illustrative embodiment;

FIG. 17J shows a cross-sectional view along the line 17J-17J in FIG. 17I;

FIG. 17K shows a cross-sectional view along the line 17K-17K in FIG. 17I;

FIG. 20 B is a rear exploded view of the blood pump cassette of FIG. 20A;

DETAILED DESCRIPTION

Figure 1:
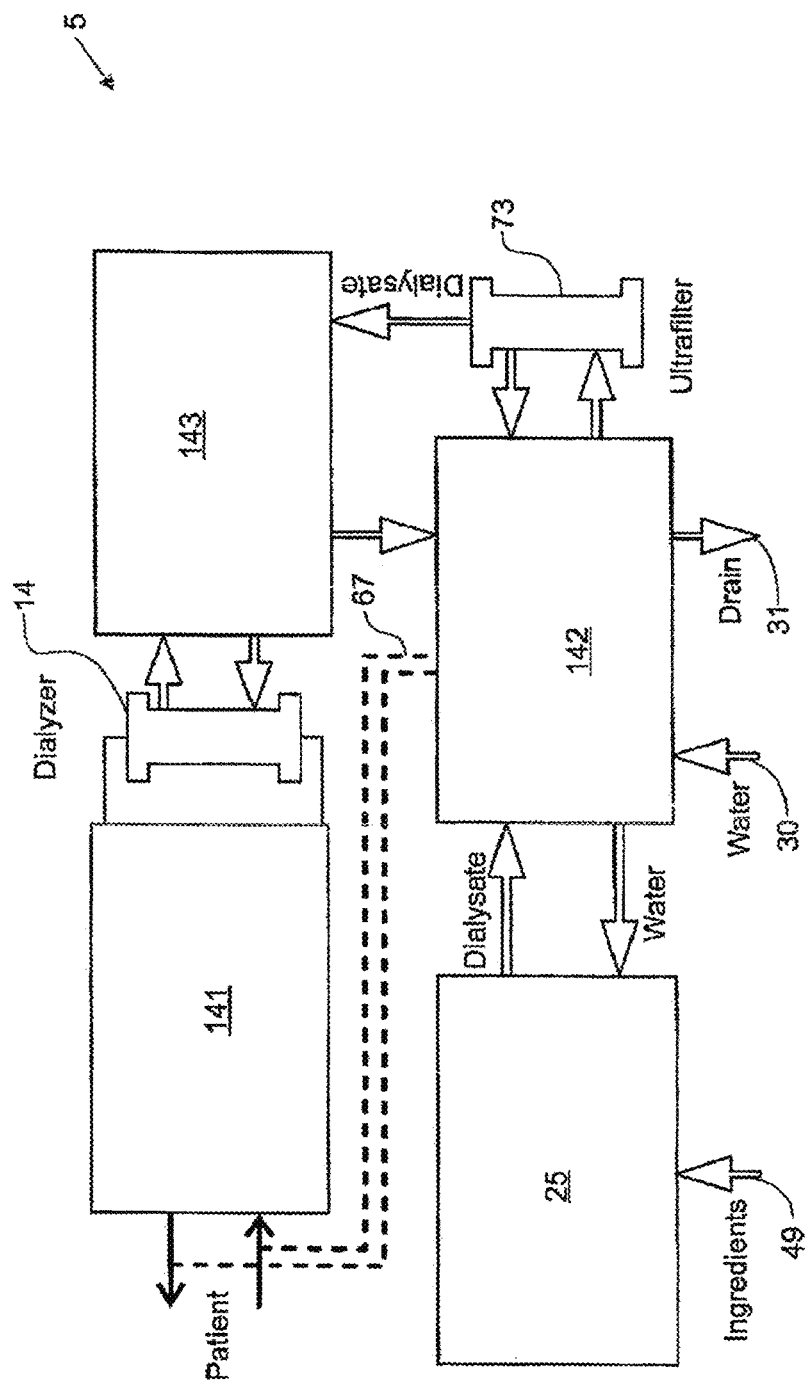
FIG. 1 is a schematic representation of fluid handling components of a hemodialysis system in an illustrative embodiment.

Various aspects of the invention are generally directed to new systems for hemodialysis and the like, such as hemofiltration systems, hemodiafiltration systems, plasmapheresis systems, etc. Accordingly, although the various systems and methods described herein are described in relation to hemodialysis, it should be understood that the various systems and method described herein are applicable to other dialysis systems and/or in any extracorporeal system able to treat blood or other bodily fluids, such as plasma.

As discussed below, a hemodialysis system typically includes a blood flow path and a dialysate flow path. It should be noted that within such flow paths, the flow of fluid is not necessarily linear, and there may be any number of "branches" within the flow path that a fluid can flow from an inlet of the flow path to an outlet of the flow path. Examples of such branching are discussed in detail below. In the blood flow path, blood is drawn from a patient, and is passed through a dialyzer, before being returned to the patient. The blood is treated by the dialyzer, and waste molecules (e.g., urea, creatinine, etc.) and water are passed from the blood, through a semi-permeable membrane in the dialyzer, into a dialysate solution that passes through the dialyzer by the dialysate flow path. In various embodiments, blood may be drawn from the patient from two lines (e.g., an arterial line and a venous line, i.e., "dual needle" flow), or in some cases, blood may be drawn from the patient and returned through the same or catheter needle (e.g., the two lines or lumens may both be present within the same needle, i.e., a form of "dual lumen" flow). In still other embodiments, a "Y" site or "T" site is used, where blood is drawn from the patient and returned to the patient through one patient connection having two branches (one being the fluid path for the drawn blood, the second fluid path for the return blood, i.e., a form of "single needle" flow). The patient may be any subject in need of hemodialysis or similar treatments, including non-human subjects, such as dogs, cats, monkeys, and the like, as well as humans.

In the dialysate flow path, fresh dialysate is prepared and is passed through the dialyzer to treat the blood from the blood flow path. The dialysate may also be equalized for blood treatment within the dialyzer (i.e., the pressure between the dialysate and the blood are equalized), often exactly, or in some embodiments, at least within about 1% or about 2% of the pressure of the blood. In some cases, it may be desirable to maintain a greater pressure difference (either positive or negative) between the blood flow path and dialysate flow path. After passing through the dialyzer, the used dialysate, containing waste molecules (as discussed below), is discarded in some fashion. The dialysate in some cases may be re-circulated in a "multi-pass" arrangement, which may be beneficial in capturing larger molecules having low mobility across the dialyzer. In some cases, the dialysate is heated prior to treatment of the blood within the dialyzer using an appropriate heater, such as an electrical resistive heater. The dialysate may also be filtered to remove contaminants, infectious organisms, debris, and the like, for instance, using an ultrafilter. The ultrafilter may have a pore size chosen to prevent species such as these from passing therethrough. For instance, the pore size may be less than about 0.3 micrometers, less than about 0.2 micrometers, less than about 0.1 micrometers, or less than about 0.05 micrometers, etc. The dialysate is used to draw waste molecules (e.g., urea, creatinine, ions such as potassium, phosphate, etc.) and water from the blood into the dialysate through osmosis or convective transport, and dialysate solutions are well-known to those of ordinary skill in the art.

The dialysate typically contains various ions such as sodium, chloride, bicarbonate, potassium and calcium that are similar in concentration to that of normal blood. In some cases, the bicarbonate, may be at a concentration somewhat higher than found in normal blood. Typically, the dialysate is prepared by mixing water from a water supply with one or more ingredients: an "acid" (which may contain various species such as acetic acid, dextrose, NaCl, CaCl, KCl, MgCl, etc.), sodium bicarbonate ($NaHCO_3$), and/or sodium chloride (NaCl). The preparation of dialysate, including using the appropriate concentrations of salts, osmolarity, pH, and the like, is well-known to those of ordinary skill in the art. As discussed in detail below, the dialysate need not be prepared at the same rate that the dialysate is used to treat the blood. For instance, the dialysate can be made concurrently or prior to dialysis, and stored within a dialysate storage vessel or the like.

Within the dialyzer, the dialysate and the blood typically are separated by a semi-permeable membrane. Typically, the semipermeable membrane is formed from a polymer such as cellulose, polyarylethersulfone, polyamide, polyvinylpyrrolidone, polycarbonate, polyacrylonitrile, or the like, which allows the transport of ions or small molecules (e.g., urea, water, etc.), but does not allow bulk transport or convection during treatment of the blood. In some cases (such as high-flux dialyzers), even larger molecules, such as beta-2-microglobulin, may pass through the membrane. In some cases, for example, ions and molecules may pass through the dialyzer by convective flow if a hydrostatic pressure difference exists across the semi-permeable membrane.

It should be noted that, as used herein, "fluid" means anything having fluidic properties, including but not limited to, gases such as air, and liquids such as water, aqueous solution, blood, dialysate, etc.

FIG. 1 shows a schematic block diagram of fluid circuitry for a hemodialysis system that incorporates various aspects of the invention. In this illustrative embodiment, the dialysis system 5 includes a blood flow circuit 141 that draws blood from a patient, passes the blood through a dialyzer 14, and returns the treated blood to the patient. A balancing circuit or an internal dialysate circuit 143 receives dialysate from an ultrafilter 73, passes the dialysate through the dialyzer 14, and receives used dialysate from the dialyzer 14. A directing circuit or an external dialysate circuit 142 provides fresh dialysate to the ultrafilter 73, and receives used dialysate from the internal dialysate circuit 143 (which may be directed to a drain 31). The directing circuit 142 can also receive water from a water supply 30 and pass it to a mixing circuit 25. The mixing circuit 25 forms dialysate using water from the directing circuit 142 and reagent ingredients 49, such as citric acid, salt and a bicarbonate, that may be received from a renewable source. The mixing circuit 25 may prepare dialysate, for example, on an as-needed basis, during and/or in advance of dialysis. New dialysate prepared by the mixing circuit 25 may be provided to the directing circuit 142, which may provide the dialysate to the ultrafilter 73, as described above. The directing circuit 142 may include a heater to heat the dialysate to a suitable temperature and/or to heat fluid in the system for disinfection. Conduits 67 (shown in dotted line) may be connected between the blood flow circuit 141 and the directing circuit 142, e.g., for disinfection of the hemodialysis system.

Figure 2:
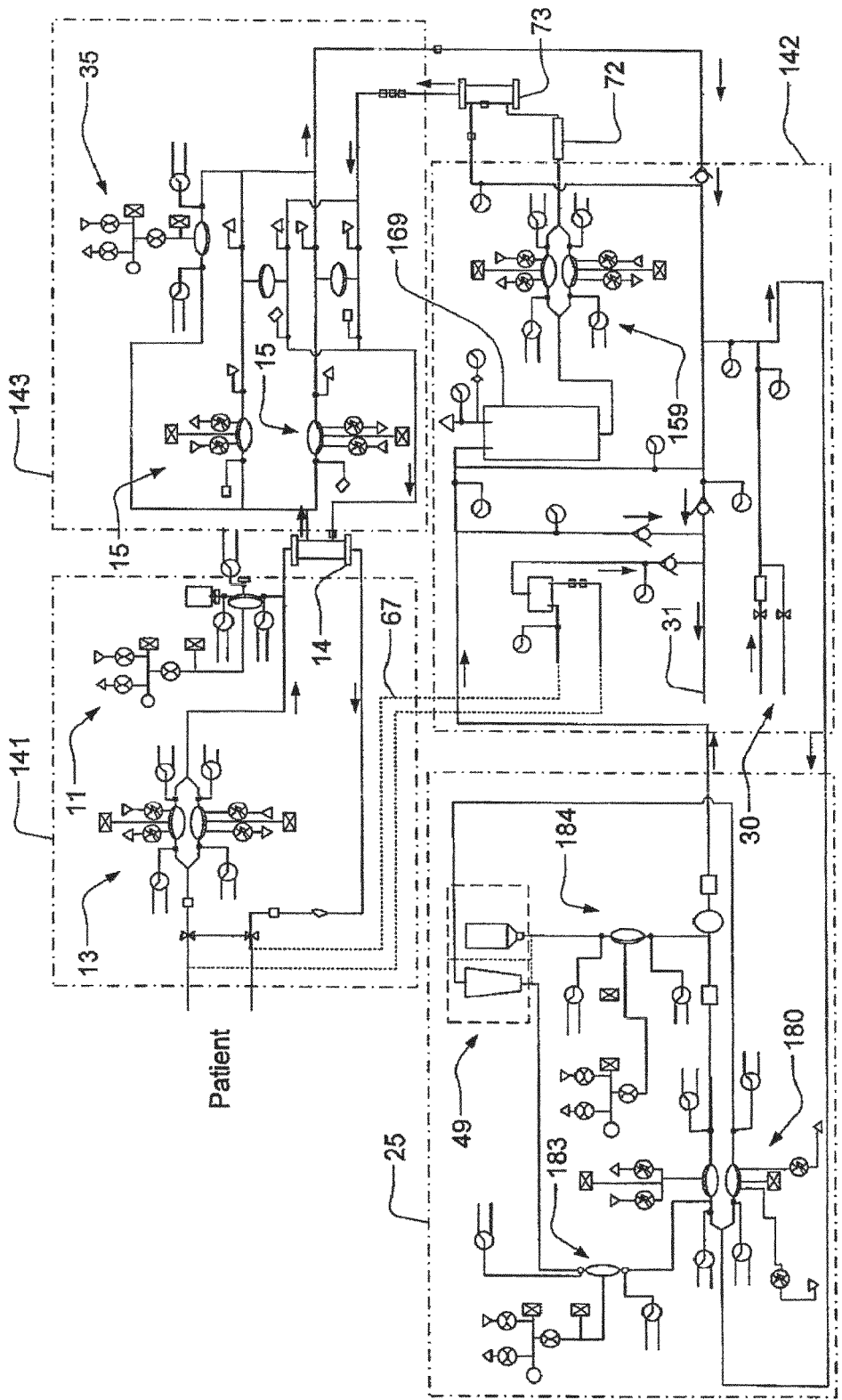
FIG. 2 shows a schematic fluid flow diagram for the dialysis system of FIG. 1.

FIG. 2 is a schematic diagram showing a more detailed circuit arrangement for the dialysis system 5 shown in FIG. 1. It should be understood, of course, that FIG. 2 is only one possible embodiment of the general hemodialysis system of FIG. 1, and in other embodiments, other fluid circuits, modules, flow paths, layouts, etc. are possible. Examples of such systems are discussed in more detail below, and also can be found in the following, each of which is incorporated herein by reference: U.S. application Ser. No. 12/072,908, filed Feb. 27, 2008, U.S. Provisional Application 60/903, 582, filed Feb. 27, 2007, U.S. Provisional Application 60/904,024, filed Feb. 27, 2007, U.S. patent application Ser. No. 11/871,680, filed Oct. 12, 2007, U.S. patent application Ser. No. 11/871,712, filed Oct. 12, 2007, U.S. patent application Ser. No. 11/871,787, filed Oct. 12, 2007, U.S. patent application Ser. No. 11/871,793, filed Oct. 12, 2007, or U.S. patent application Ser. No. 11/871,803, filed Oct. 12, 2007.

The blood flow circuit 141 includes an anticoagulant supply 11 and a blood flow pump 13 which pumps blood from a patient through a dialyzer 14 and returns the blood to the patient. The anticoagulant supply 11, although shown in the path of blood flowing towards the dialyzer, may be instead located in another suitable location. e.g., any location upstream or downstream from blood flow pump 13. The balancing circuit 143 includes two dialysate pumps 15, which pump dialysate into the dialyzer 14, and a bypass pump 35. The flow of blood through the blood flow circuit 141 in some cases, is synchronized with the flow of dialysate in the dialysate flow path. In an embodiment, the flow of dialysate into and out of the dialyzer 14 and the balancing circuit 143 is balanced volumewise using balancing chambers in the balancing circuit 143. The directing circuit 142 includes a dialysate pump 159, which pumps dialysate from a dialysate tank 169 through a heater 72 and/or the ultrafilter 73 to the balancing circuit 143. The directing circuit 142 also receives waste fluid from balancing circuit 143 and directs it to a drain 31. In some cases, the blood flow circuit 141 can be connected via conduits 67 to the directing circuit 142, e.g., for disinfection, as discussed below. Dialysate in the dialysate tank 169 is provided by the mixing circuit 25, which produces the dialysate using water from a water supply 30 provided via the directing circuit 142 and dialysate ingredients 49 (e.g., bicarbonate and acid). A series of mixing pumps 180, 183, 184 are used to mix the various components and produce the dialysate.

Figure 3:
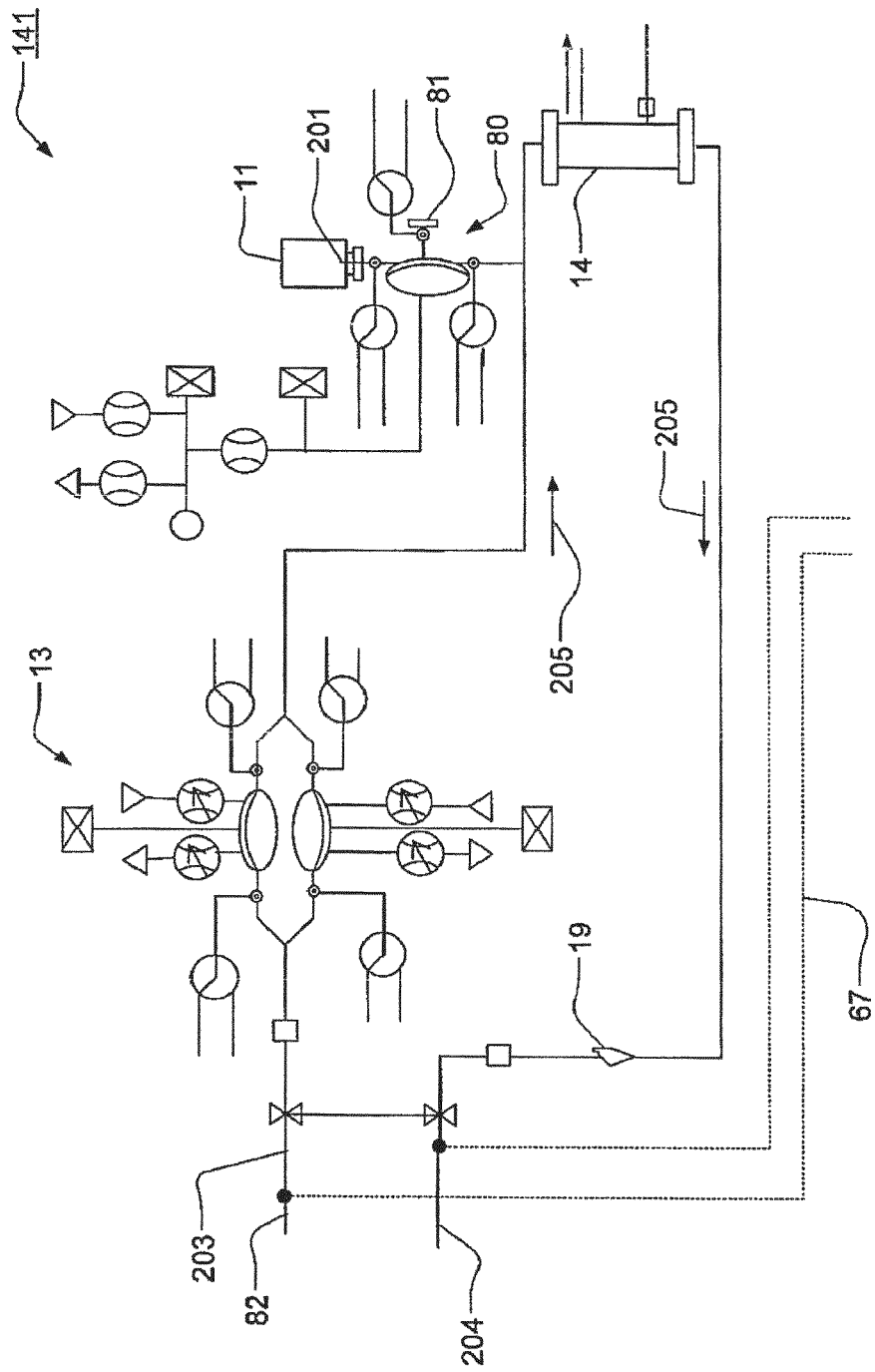
FIG. 3 is a schematic fluid flow diagram for the blood flow circuit of the FIG. 2 embodiment.

FIG. 3 shows a close-up view of the blood flow circuit 141 in this illustrative embodiment. Under normal operation, blood flows from a patient through arterial line 203 via blood flow pump 13 to the dialyzer 14 (the direction of flow during normal dialysis is indicated by arrows 205; in some modes of operation, however, the flow may be in different directions, as discussed below). Optionally, an anticoagulant may be introduced into the blood via anticoagulant pump 80 from an anticoagulant supply. After passing through dialyzer 14 and undergoing dialysis, the blood returns to the patient through venous line 204, optionally passing through an air trap and/or a blood sample port 19. The pump 13 may include, for instance, pumps 23 that are actuated by a control fluid.

For example, in one embodiment, the blood flow pump 13 may comprise two (or more) pod pumps 23. Each pod pump, in this particular example, may include a rigid chamber with a flexible diaphragm or membrane dividing each chamber into a pumping compartment and control compartment. There may be four entry/exit valves for these compartments, two for the pumping compartment and two for the control compartment. The valves for the control compartment of the chambers may be two-way proportional valves, one connected to a first control fluid source (e.g., a high pressure air source), and the other connected to a second control fluid source (e.g., a low pressure air source) or a vacuum source. The fluid valves can be opened and closed to direct fluid flow when the pod pumps 23 are operating. Non-limiting examples of pod pumps are described in U.S. Provisional Application 60/792,073, filed Apr. 14, 2006, or in U.S. patent application Ser. No. 11/787,212, filed Apr. 13, 2007, each incorporated herein by reference. If more than one pod pump is present, the pod pumps may be operated in any suitable fashion, e.g., synchronously, asynchronously, in-phase, out-of-phase, etc. For instance, in some embodiments, the two-pump pumps can be cycled out of phase to affect the pumping cycle, e.g., one pump chamber fills while the second pump chamber empties. A phase relationship anywhere between 0° (the pod pumps fill and empty in unison) and 180° (one pod pump fills as the other empties) can be selected in order to impart any desired pumping cycle. A phase relationship of 180° may yield continuous flow into and out of the set of pod pumps. This is useful, for instance, when continuous flow is desired, e.g., for use with dual needle or dual lumen catheter flow. Setting a phase relationship of 0°, however, may be useful in some cases for single needle/single lumen flow or in other cases. In a 0° relationship, the pod pumps will first fill from the needle, then deliver blood through the blood flow path and back to the patient using the same needle. In addition, running at phases between 0° and 180° can be used in some cases, to achieve a push/pull relationship (hemodiafiltration or continuous back flush) across the dialyzer.

An anticoagulant (e.g., heparin, or any other suitable anticoagulant) may be contained within a vial 11 (or other anticoagulant supply, such as a tube or a bag), and blood flow circuit 141 may include a spike 201 (which, in one embodiment, is a needle) that can pierce the seal of the vial. The spike 201 may be formed from plastic, stainless steel, or another suitable material, and may be a sterilizable material in some cases, e.g., the material may be able to withstand sufficiently high temperatures and/or radiation so as to sterilize the material.

An anticoagulant pump 80, which can act as a metering chamber in some cases, can be used to control the flow of anticoagulant into the blood circuit. The anticoagulant pump 80 may be a pod pump or a membrane-based metering pump, and/or may be actuated by a control fluid, such as air. For example, the anticoagulant pump 80 may include a rigid chamber with a flexible diaphragm dividing the chamber into a pumping compartment and a control compartment. One valve for the control compartment of the chamber may be connected to a first control fluid source (e.g., a high pressure air source), and the other valve connected to a second control fluid source (e.g., a low pressure air source) or a vacuum source. Valves for the pumping compartment of the chamber can be opened and closed in coordination with the control compartment, thus controlling the flow of anticoagulant into the blood. In one set of embodiments, air provided through a filter 81 may also be introduced into the blood flow path by the anticoagulant pump 80, e.g., to provide air into the vial 11 after or before anticoagulant is withdrawn from the vial.

Fluid Management System ("FMS") measurements may be used to measure the volume of fluid pumped through a pump chamber during a stroke of the membrane, or to detect air in the pumping chamber. FMS methods are described in U.S. Pat. Nos. 4,808,161; 4,826,482; 4,976,162; 5,088,515; and 5,350,357, which are hereby incorporated herein by reference in their entireties. In one illustrative embodiment, the volume of liquid delivered by an anticoagulant pump, a dialysate pump, or other membrane-based fluid pump is determined using an FMS algorithm in which changes in chamber pressure are used to calculate a volume measurement at the end of a fill stroke and at the end of a delivery stroke. The difference between the computed volumes at the end of fill and delivery strokes may be used to determine the actual stroke volume. This actual stroke volume can be compared to an expected stroke volume for the particular sized chamber. If the actual and expected volumes are significantly different, the stroke has not properly completed and an error message can be generated.

The blood flow circuit 141 may also include an air trap 19 to remove air bubbles that may be present within the blood flow path. In some cases, the air trap 19 is able to separate any air that may be present from the blood due to gravity, and/or may include a port for sampling blood.

Figure 4:
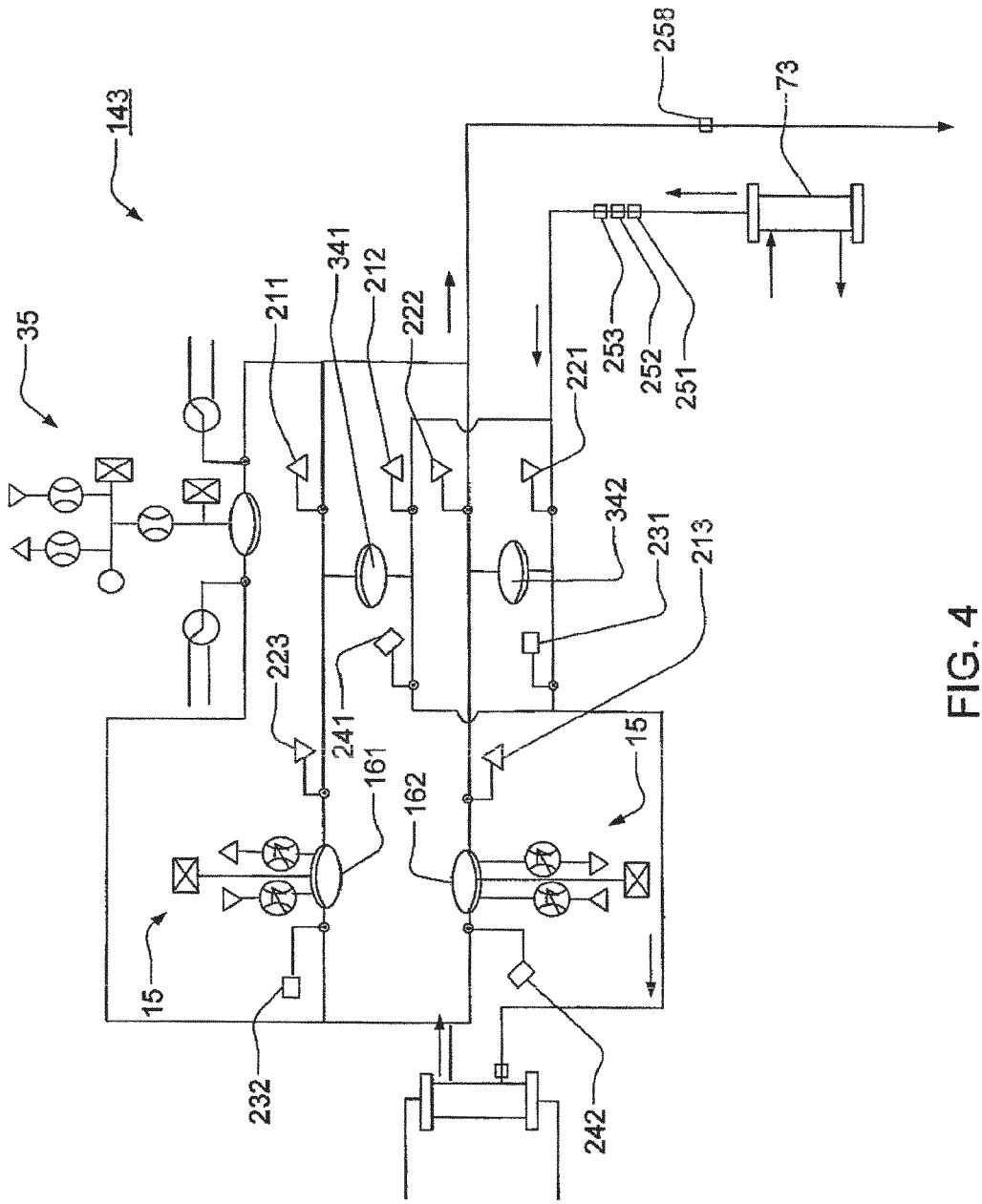
FIG. 4 is a schematic fluid flow diagram for the balancing circuit of the FIG. 2 embodiment.

FIG. 4 shows a close-up view of the balancing circuit 143 in the FIG. 2 embodiment. In the balancing circuit 143, dialysate flows from the optional ultrafilter 73 into a dialysate pump 15. In this embodiment, the dialysate pump 15 includes two pod pumps 161, 162, two balancing chambers 341, 342, and a pump 35 for bypassing the balancing chambers 341, 342. The balancing chambers 341, 342 may be constructed such that they are formed from a rigid chamber with a flexible diaphragm dividing the chamber into two separate fluid compartments, so that entry of fluid into one compartment can be used to force fluid out of the other compartment and vice versa. Non-limiting examples of pumps that can be used as pod pumps and/or balancing chambers are described in U.S. Provisional Application 60/792,073, filed Apr. 14, 2006, or in U.S. patent application Ser. No. 11/787,212, filed Apr. 13, 2007.

In one embodiment, balancing of flow in the internal dialysate circuit works as follows. A set of pneumatically operated valves 211, 212, 213, 241, 242 has its operation synchronized and controlled together, where valves 211, 212, 213 are ganged and valves 241 and 242 are ganged, and a second set of pneumatically operated valves 221, 222, 223, 231, 232 similarly have its operation synchronized and controlled together, where valves 221, 222, 223 are ganged, and valves 231 and 232 are ganged. At a first point of time, the first set of valves 211, 212, 213, 241, 242 is opened while the second set of valves 221, 222, 223, 231, 232 is closed. Fresh dialysate flows into balancing chamber 341 while used dialysate flows from dialyzer 14 into pod pump 161. Fresh dialysate does not flow into balancing chamber 342 since valve 221 is closed. As fresh dialysate flows into balancing chamber 341, used dialysate within balancing chamber 341 is forced out and exits balancing circuit 143 (the used dialysate cannot enter pod pump 161 since valve 223 is closed). Simultaneously, pod pump 162 forces used dialysate present within the pod pump into balancing chamber 342 (through valve 213, which is open; valves 242 and 222 are closed, ensuring that the used dialysate flows into balancing chamber 342). This causes fresh dialysate contained within balancing chamber 342 to exit the balancing circuit 143 into dialyzer 14. Also, pod pump 161 draws in used dialysate from dialyzer 14 into pod pump 161.

Once pod pump 161 and balancing chamber 341 have filled with dialysate, the first set of valves 211, 212, 213, 241, 242 is closed and the second set of valves 221, 222, 223, 231, 232 is opened. Fresh dialysate flows into balancing chamber 342 instead of balancing chamber 341, as valve 212 is closed while valve 221 is now open. As fresh dialysate flows into balancing chamber 342, used dialysate within the chamber is forced out and exits balancing circuit, since valve 213 is now closed. Also, pod pump 162 now draws used dialysate from the dialyzer into the pod pump, while used dialysate is prevented from flowing into pod pump 161 as valve 232 is now closed and valve 222 is now open. Pod pump 161 forces used dialysate contained within the pod pump (from the previous step) into balancing chamber 341, since valves 232 and 211 are closed and valve 223 is open. This causes fresh dialysate contained within balancing chamber 341 to be directed into the dialyzer 14 (since valve 241 is now open while valve 212 is now closed). At the end of this step, pod pump 162 and balancing chamber 342 have filled with dialysate. This puts the state of the system back into the configuration at the beginning of this description, and the cycle is thus able to repeat, ensuring a constant flow of dialysate to and from the dialyzer 14. In an embodiment, the fluid (e.g. pneumatic) pressures on the control side of the balancing chamber valves are monitored to ensure they are functioning (e.g., opening and closing) properly.

As a specific example, a vacuum (e.g., 4 p.s.i. of vacuum) can be applied to the port for the first set of valves, causing those valves to open, while positive pressure (e.g., 20 p.s.i. of air pressure) is applied to the second set of valves, causing those valves to close (or vice versa). The pod pumps each urge dialysate into one of the volumes in one of the balancing chambers 341, 342. By forcing dialysate into a volume of a balancing chamber, an equal amount of dialysate is squeezed by the diaphragm out of the other volume in the balancing chamber. In each balancing chamber, one volume is occupied by fresh dialysate heading towards the dialyzer and the other volume is occupied by used dialysate heading from the dialyzer. Thus, the volumes of dialysate entering and leaving the dialyzer are kept substantially equal.

The bypass pump 35 can direct the flow of dialysate from the dialyzer 14 through balancing circuit 143 without passing through either of pod pumps 161 or 162. In this embodiment, the bypass pump 35 is a pod pump, similar to those described above, with a rigid chamber and a flexible diaphragm dividing each chamber into a fluid compartment and a control compartment. This pump may be the same or different from the other pod pumps and/or metering pumps described above. When control fluid is used to actuate the bypass pump 35, the additional drop in pressure on the exiting (spent) dialysate side of the dialyzer causes additional ultrafiltration of fluid from the blood in the dialyzer. This may cause a net efflux of fluid from the patient's blood, through the dialyzer, and ultimately to drain. Such a bypass may be useful, for example, in reducing the amount of fluid a patient has, which is often increased due to the patient's inability to excrete excess fluid (primarily water) through the kidneys. As shown in FIG. 4, the bypass pump 35 may be controlled by a control fluid (e.g., air), irrespective of the operation of pod pumps 161 and 162. This configuration may allow for easier control of net fluid removal from a patient, without having to operate the inside dialysate pumps either out of balance or out of phase with the blood pumps in order to achieve such fluid withdrawal from the patient.

To achieve balanced flow across the dialyzer, the blood flow pump, the pumps of the balancing circuit, and the pumps of the directing circuit (discussed below) may be operated to work together to ensure that flow into the dialyzer is generally equal to flow out of the dialyzer. If ultrafiltration is required, the ultrafiltration pump (if one is present) may be run independently of some or all of the other blood and/or dialysate pumps to achieve the desired ultrafiltration rate.

To prevent outgassing of the dialysate, the pumps of the balancing circuit may be kept at pressures above atmospheric pressure. In contrast, however, the blood flow pump and the directing circuit pumps use pressures below atmosphere to pull the diaphragm towards the chamber wall to complete a fill stroke. Because of the potential of fluid transfer across the semi-permeable membrane of the dialyzer and because the pumps of the balancing circuit run at positive pressures, the balancing circuit pumps may be able to use information from the blood flow pump(s) in order to synchronize the delivery strokes of the balancing circuit chambers to the dialyzer with the delivery strokes of the blood pumps.

In one set of embodiments, when running in such a balanced mode, if there is no delivery pressure from the blood flow pump, the balancing circuit pump diaphragm will push fluid across the dialyzer into the blood and the alternate pod of the balancing circuit will not completely fill. For this reason, the blood flow pump reports when it is actively delivering a stroke. When the blood flow pump is delivering a stroke the inside dialysate pump operates. When the blood flow pump is not delivering blood, the valves that control the flow from the dialyzer to the inside dialysate pumps (and other balancing valves ganged together with these valves, as previously discussed) may be closed to prevent any fluid transfer from occurring from the dialysate side to the blood side. During the time the blood flow pump is not delivering, the inside dialysate pumps are effectively frozen, and the inside dialysate pump delivery stroke resumes once the blood flow pump starts delivering again. The inside dialysate pump fill pressure can be set to a minimal positive value to ensure that the pump operates above atmosphere at minimal impedance. Also, the inside dialysate pump delivery pressure can be set to the blood flow pump pressure to generally match pressures on either side of the dialyzer, minimizing flow across the dialyzer during delivery strokes of the inside dialysate pump.

In another embodiment, the inside dialysate pump delivers dialysate to the dialyzer at a pressure slightly above the pressure at which blood is delivered to the dialyzer. This ensures that a full balance chamber of clean dialysate gets delivered to the dialyzer. On the return side, the inside dialysate pump can fill with spent dialysate from the dialyzer at a slightly lower pressure than the outlet pressure on the blood side of the dialyzer, ensuring that the receiving dialysate pump chamber can fill. This in turn ensures that there is enough dialysate available to complete a full stroke in the balancing chamber. Flows across the semi-permeable membrane caused by these differential pressures will tend to cancel each other; and the pumping algorithm otherwise attempts to match the average pressures on the dialysate and blood sides of the dialyzer.

It is generally beneficial to keep the blood flow as continuous as possible during therapy, as stagnant blood flow can result in blood clots. In addition, when the delivery flow rate on the blood flow pump is discontinuous, the balancing pump may pause its stroke more frequently, which can result in discontinuous and/or low dialysate flow rates. However, the flow through the blood flow pump can be discontinuous for various reasons. For instance, pressure may be limited within the blood flow pump, e.g., to +600 mmHg and/or −350 mmHg to provide safe pumping pressures for the patient. For instance, during dual needle flow, the two pod pumps of the blood flow pump can be programmed to run 180° out of phase with one another. If there were no limits on pressure, this phasing could always be achieved. However to provide safe blood flow for the patient these pressures are limited. If the impedance is high on the fill stroke (due to a small needle, very viscous blood, poor patient access, etc.), the negative pressure limit may be reached and the fill flow rate will be slower then the desired fill flow rate. Thus the delivery stroke must wait for the previous fill stroke to finish, resulting in a pause in the delivery flow rate of the blood flow pump. Similarly, during single needle flow, the blood flow pump may be run at 0° phase, where the two blood flow pump pod pumps are simultaneously emptied and filled. When both pod pumps are filled, the volumes of the two pod pumps are delivered. In an embodiment, the sequence of activation causes a first pod pump and then a second pod pump to fill, followed by the first pod pump emptying and then the second pod pump emptying. Thus the flow in single needle or single lumen arrangement may be discontinuous.

One method to control the pressure saturation limits would be to limit the desired flow rate to the slowest of the fill and deliver strokes. Although this would result in slower blood delivery flow rates, the flow rate would still be known and would be more continuous, which would allow for more accurate and continuous dialysate flow rates. Another method to make the blood flow rate more continuous in single needle operation would be to use maximum pressures to fill the pods so the fill time would be minimized. The desired deliver time could then be set to be the total desired stroke time minus the time that the fill stroke took. However, the less continuous the blood flow, the more the dialysate flow rate may have to be adjusted upward during blood delivery to the dialyzer to make up for the time that the dialysate pump is stopped when the blood flow pump is filling. If this is done with the correct timing, an average dialysate flow rate taken over several strokes can still match the desired dialysate flow rate.

Figure 5:
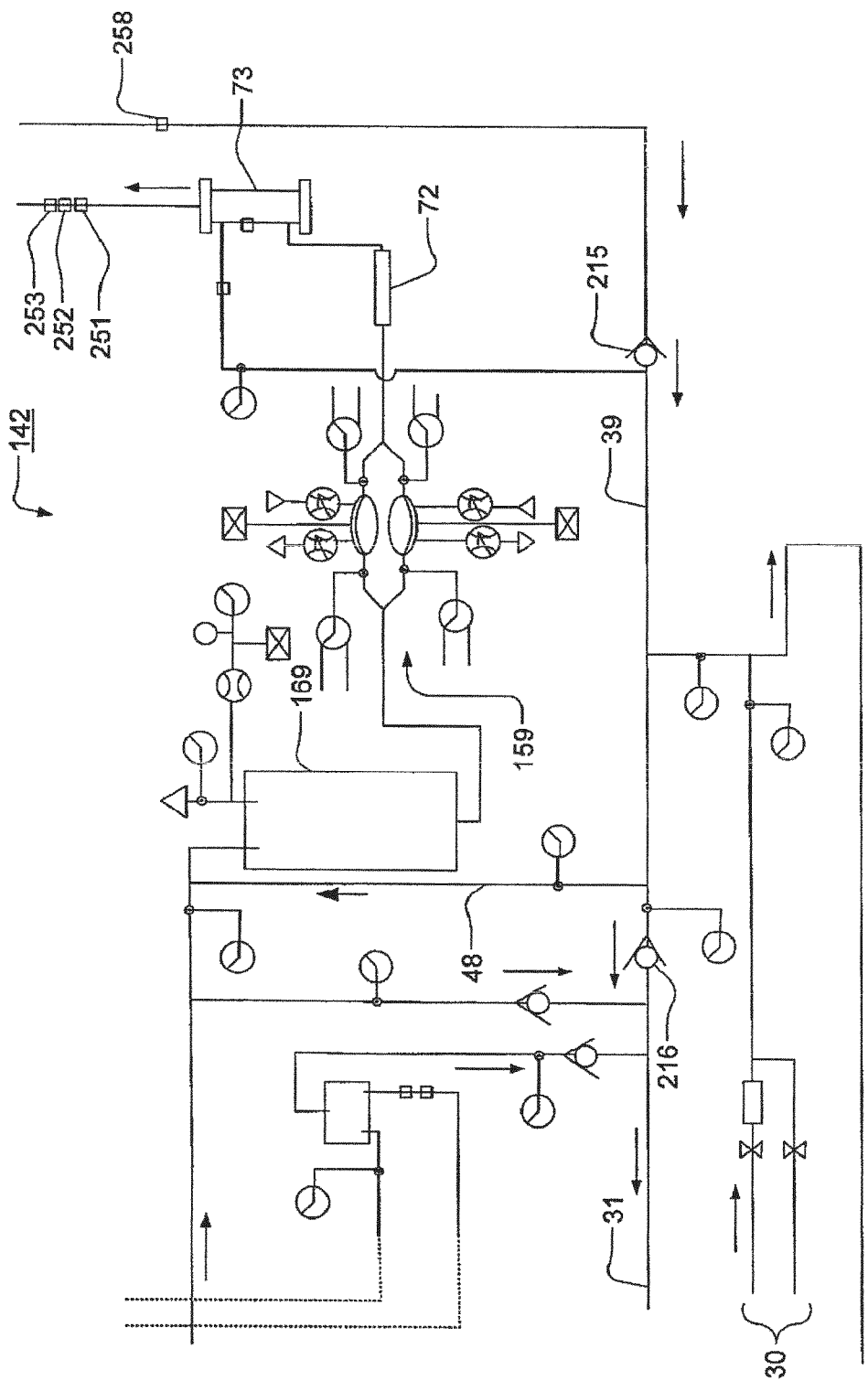
FIG. 5 is a schematic fluid flow diagram for the directing circuit of the FIG. 2 embodiment.

FIG. 5 shows a close up of the directing circuit 142 in the FIG. 2 embodiment. In this embodiment, the directing circuit 142 can provide dialysate from a dialysate tank 169 via a dialysate pump 159 to a heater 72 and the ultrafilter 73. The heater 72 may be used to warm the dialysate to body temperature, and/or a temperature such that the blood in the blood flow circuit is heated by the dialysate, and the blood returning to the patient is at body temperature or higher. In some cases, the heater 72 may be connected to a control system such that dialysate that is incorrectly heated (i.e., the dialysate is too hot or too cold) may be recycled (e.g., back to the dialysate tank 169) or sent to drain instead of being passed to the dialyzer. The heater 72 may also be used, in some embodiments, for disinfection or sterilization purposes. For instance, water may be passed through the hemodialysis system and heated using the heater such that the water is heated to a temperature able to cause disinfection or sterilization to occur, e.g., temperatures of at least about 70° C., at least about 80° C., at least about 90° C., at least about 100° C., at least about 110° C., etc.

The flow of dialysate through the directing circuit 142 may be controlled (at least in part) by operation of the dialysate pump 159. In addition, the dialysate pump 159 may control flow through the balancing circuit 143. For instance, as discussed above, fresh dialysate from the directing circuit 142 flows into balancing chambers 341 and 342 of balancing circuit 143. The dialysate pump 159 may be used as a driving force to cause the fresh dialysate to flow into these balancing chambers. In one set of embodiments, dialysate pump 159 includes a pod pump, e.g., similar to those described above.

The dialysate may also be filtered to remove contaminants, infectious organisms, pathogens, pyrogens, debris, and the like, for instance, using an ultrafilter 73. The ultrafilter 73 may be positioned in any suitable location in the dialysate flow path, for instance, between the directing circuit and the balancing circuit, e.g., as shown, and/or the ultrafilter 73 may be incorporated into the directing circuit or the balancing circuit. If an ultrafilter is used, its pore size may be chosen to prevent species such as these from passing through the filter.

In some cases, the ultrafilter 73 may be operated such that waste from the filter (e.g., the retentate stream) is passed to a waste stream, such as waste line 39 in FIG. 5. In some cases, the amount of dialysate flowing into the retentate stream may be controlled. For instance, if the retentate is too cold (i.e., heater 72 is not working, or heater 72 is not heating the dialysate to a sufficient temperature, the entire dialysate stream (or at least a portion of the dialysate) may be diverted to waste line 39, and optionally, recycled to dialysate tank 169 using line 48. Flow from the filter 73 may also be monitored for several reasons, e.g., using temperature sensors (e.g., sensors 251 and 252), conductivity sensors (for confirming dialysate concentration, e.g., sensor 253), or the like. An example of such sensors is discussed below; further non-limiting examples can be seen in a U.S. patent application Ser. No. 12/038,474, filed Feb. 27, 2008.

The ultrafilter and the dialyzer may provide redundant screening methods for the removal of contaminants, infectious organisms, pathogens, pyrogens, debris, and the like. Accordingly, any contaminant would have to pass through both the ultrafilter and the dialyzer before reaching a patient's blood. Even in the event that either the ultrafilter or dialyzer integrity fails, the other may still be able to maintain dialysate sterility and prevent contaminants from reaching the patient's blood.

The directing circuit 142 may also be able to route used dialysate coming from a balancing circuit to a drain, e.g., through waste line 39 to drain 31. The drain may be, for example, a municipal drain or a separate container for containing the waste (e.g., used dialysate) to be properly disposed of. In some cases, one or more check or "one-way" valves (e.g., check valves 215 and 216) may be used to control flow of waste from the directing circuit 142 and from the system 5. Also, in certain instances, a blood leak sensor (e.g., sensor 258) may be used to determine if blood is leaking through the dialyzer 14 into the dialysate flow path. In addition, a liquid sensor can be positioned in a collection pan at the bottom of the hemodialysis unit to indicate leakage of either blood or dialysate, or both, from any of the fluid circuits.

The directing circuit 142 may receive water from a water supply 30, e.g., from a container of water such as a bag, and/or from a device able to produce water, e.g., a reverse osmosis device. In some cases, the water entering the system is set at a certain purity, e.g., having ion concentrations below certain values. The water entering into the directing circuit 142 may be passed on to various locations, e.g., to a mixing circuit 25 for producing fresh dialysate and/or to waste line 39. In some cases, valves to the drain 31 and various recycle lines are opened, and conduits 67 may be connected between directing circuit 142 and blood flow circuit 141, such that water is able to flow continuously around the system. If heater 72 is also activated, the water passing through the system will be continuously heated, e.g., to a temperature sufficient to disinfect the system.

Figure 6:
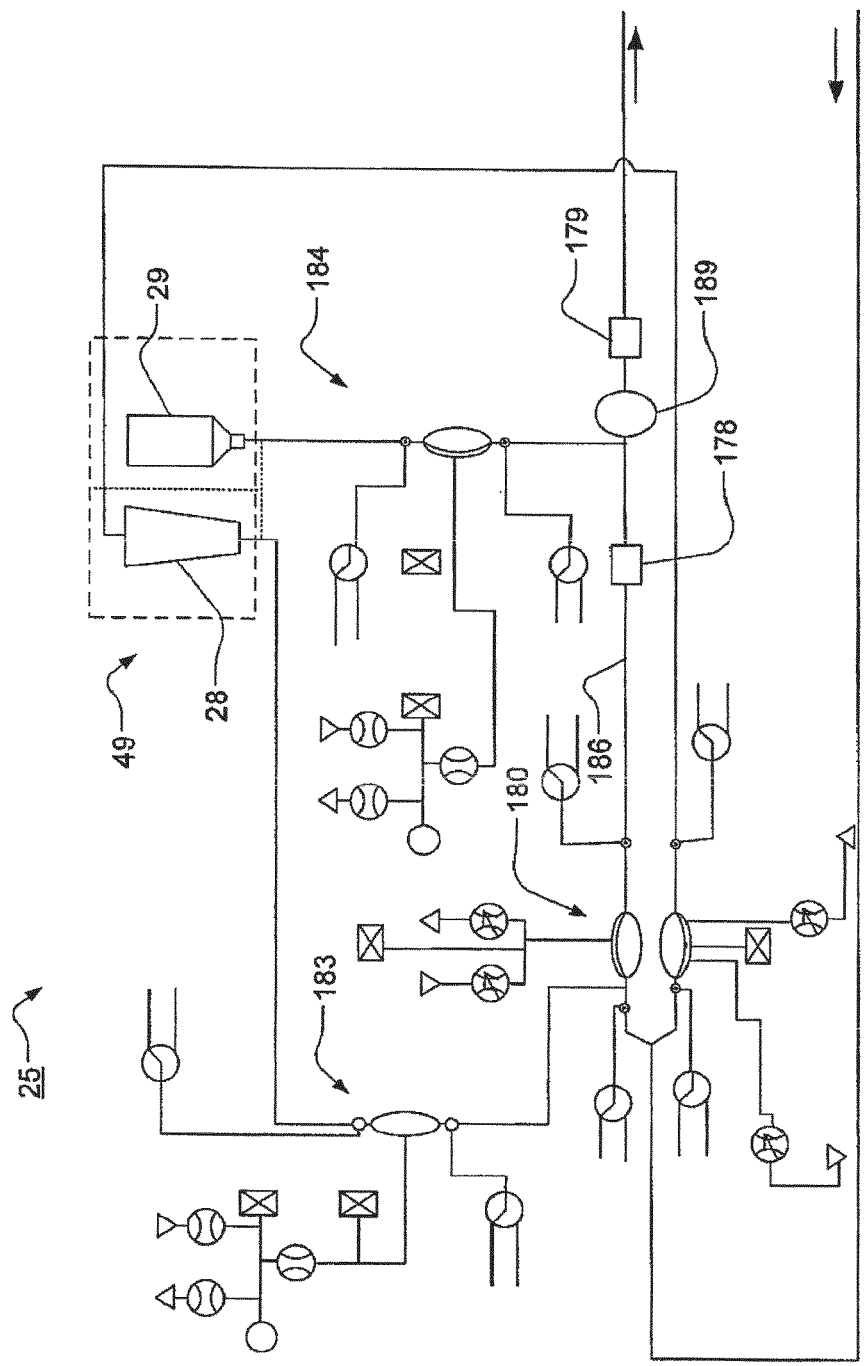
FIG. 6 is a schematic fluid flow diagram for the mixing circuit of the FIG. 2 embodiment.

FIG. 6 shows a close-up view of the mixing circuit 25 in the illustrative embodiment of FIG. 2. Water from the directing circuit 142 flows into the mixing circuit 25 due to action of a pump 180. In this embodiment, the pump 180 includes one or more pod pumps, similar to those described above. In some cases, a portion of the water is directed to reagent ingredients 49, e.g., for use in transporting the ingredients, such as the bicarbonate 28, through the mixing circuit 25. In some cases, sodium chloride and/or the sodium bicarbonate 28 may be provided in a powdered or granular form, which is mixed with water provided by the pump 180. Bicarbonate from bicarbonate source 28 is delivered via bicarbonate pump 183 to a mixing line 186, which also receives water from the directing circuit 142. Acid from an acid source 29 (which may be in a liquid form) is also pumped via an acid pump 184 to the mixing line 186. The ingredients 49 (water, bicarbonate, acid, NaCl, etc.) are mixed in mixing chamber 189 to produce dialysate, which then flows out of mixing circuit 25 to the directing circuit 142. Conductivity sensors 178 and 179 are positioned along mixing line 186 to ensure that as each ingredient is added to the mixing line, it is added at proper concentrations. The volumes delivered by the water pump 180 and/or the other pumps may be directly related to the conductivity measurements, so the volumetric measurements may be used as a cross-check on the composition of the dialysate that is produced. This may ensure that the dialysate composition remains safe even if a conductivity measurement becomes inaccurate during a therapy.

Figure 7:
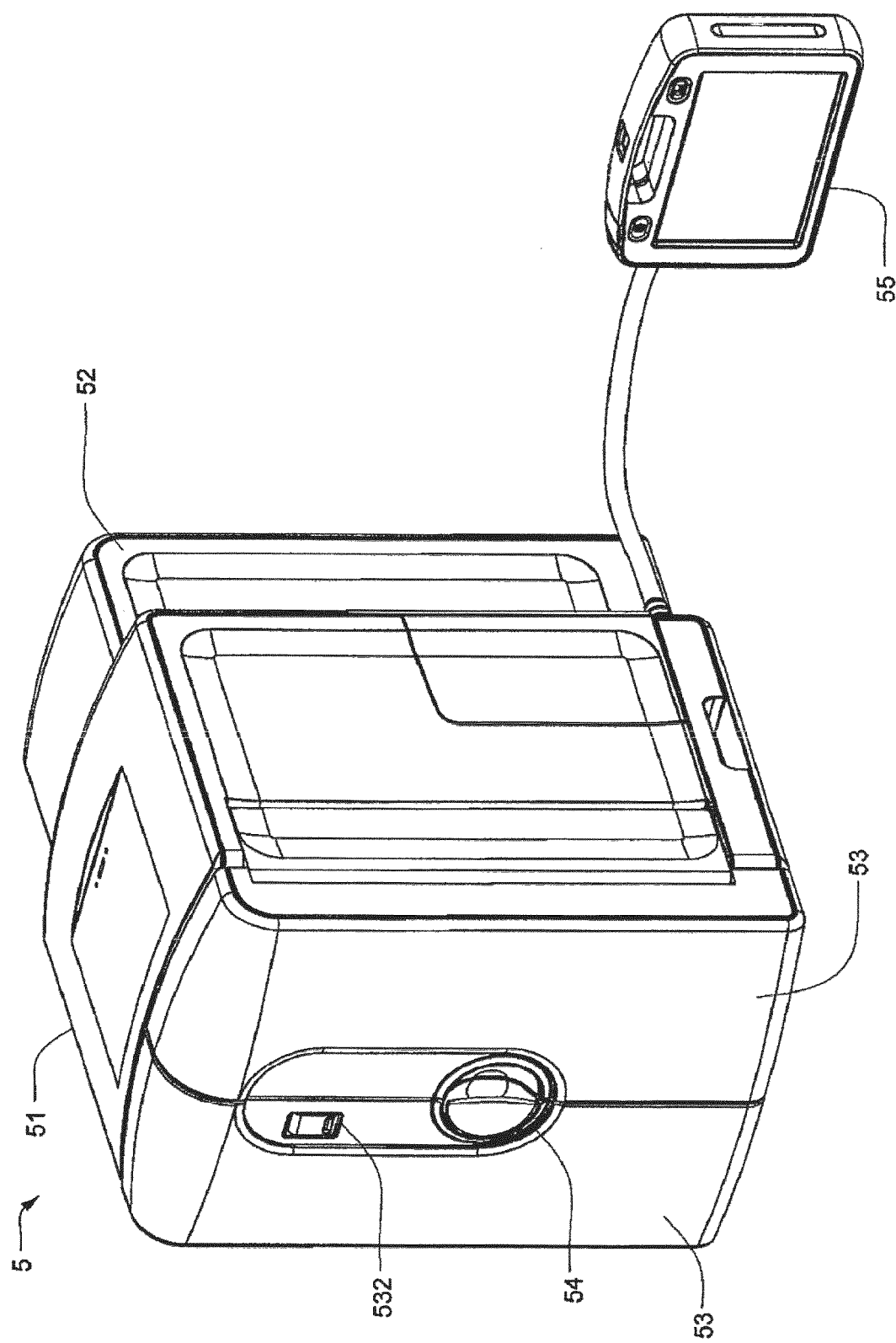
FIG. 7 is a right front perspective view of a hemodialysis system in an illustrative embodiment.

FIG. 7 shows a perspective view of a hemodialysis system 5 that incorporates various aspects of the invention. In accordance with one aspect of the invention, the system 5 includes a dialysis unit 51 and a power unit module 52 that are shown joined together. In this embodiment, the dialysis unit 51 has a housing that contains suitable components for performing hemodialysis, such as a dialyzer, one or more pumps to circulate blood through the dialyzer, a source of dialysate, and one or more pumps to circulate the dialysate through the dialyzer. For example, the dialysis unit 51 may include the mixing circuit 25, blood flow circuit 141, the balancing circuit 143 and the directing circuit 142 as described above. The dialysis unit 51 may also include all blood circuit connections and dialysate fluidic connections needed for operation of the system 5. Patient access and other connections may be revealed by opening side-by-side vertical doors 53 via a handle 54 at a front side of the dialysis unit 51 housing. In this embodiment, the dialysis unit 51 includes a control interface 55 (attached to the housing by a flexible cable in this embodiment) that a user may use to control operation of the dialysis unit 51. The control interface 55 may include a display screen with a touch sensitive overlay to allow touch control and interaction with a graphical user interface presented on the screen. The control interface 55 may also include other features, such as push buttons, a speaker, a microphone for receiving voice commands, a digital camera, and so on. The back side of the control interface 55 may include a retractable "kick-stand" (not shown) that allows the control interface 55 to be positioned on top of the dialysis unit 51 housing. Deploying the retractable "kick-stand" permits the control interface 55 to be placed in a near-vertical position to allow proper viewing of the display screen. In other embodiments, control interface 55 may comprise a tablet-style computer or handheld electronic communications device, either of which may communicate wirelessly with a controller housed within dialysis unit 51. Examples of wireless communications means may include Bluetooth® technology or wireless local area network technology such as Wi-Fi®.

The power unit 52 housing may contain suitable components for providing operating power to the dialysis unit 51, e.g., pneumatic pressure/vacuum to power the pumps, valves and other components of the dialysis unit 51. "Pneumatic," as used herein, means using air or other gas to move a flexible diaphragm or other member. (It should be noted that air is used by way of example only, and in other embodiments, other control fluids, such as nitrogen ($N_2$), $CO_2$, water, an oil, etc., may be used). As discussed above, the pumps and valves of the dialysis unit 51 may operate on pneumatic power, and thus the power unit 52 may provide one or more pneumatic sources for use by the dialysis unit 51. In this way, the dialysis unit 51 need not necessarily be arranged to generate and/or store the necessary pneumatic power needed, but instead may rely on the power unit module 52. The power unit 52 may include one or more pneumatic pumps to generate desired air pressure and/or vacuum, one or more accumulators or other devices to store pneumatic power, valves, conduits and/or other devices to control flow of pneumatic power in the power unit 52, as well as a controller having suitable components, such as a programmed general purpose data processor, memory, sensors (e.g., to detect pressure, temperature, etc.), relays, actuators, and so on.

In one embodiment, the pneumatic power (e.g., air under suitable pressure/vacuum) may be supplied by the power unit 52 to the dialysis unit 51 via one or more supply tanks or other pressure sources. For instance, if two tanks are used in the power unit 52, one supply tank may be a positive pressure reservoir, and in one embodiment, has a set point of 750 mmHg (gauge pressure) (1 mmHg is about 133.3 pascals). The other supply tank can be a vacuum or negative pressure reservoir, and in one embodiment, has a set point of −450 mmHg (gauge pressure). This pressure difference may be used, for instance, between the supply tanks and the required pod pump pressure to allow for accurate control of the variable valves to the pod pumps. The supply pressure limits can be set based on maximum pressures that can be set for the patient blood flow pump plus some margin to provide enough of a pressure difference for control of the variable valves. Thus, in some cases, the two tanks may be used to supply pressures and control fluids for all of the dialysis unit 51 functions.

In one embodiment, the power unit 52 may include two independent compressors to service the supply tanks. Pressure in the tanks can be controlled using any suitable technique, for instance, with a simple "bang-bang" controller (a controller that exists in two states, i.e., in an on or open state, and an off or closed state), or with more sophisticated control mechanisms, depending on the embodiment. As an example of a bang-bang controller, for the positive tank, if the actual pressure is less than a set point, the compressor servicing the positive tank is turned on. If the actual pressure is greater than a set point, the compressor servicing the positive tank is turned off. The same logic may be applied to the vacuum tank and control of the vacuum compressor with the exception that the sign of the set point term is reversed. If the pressure tanks are not being regulated, the compressor is turned off and the valves are closed.

Tighter control of the pressure tanks can be achieved by reducing the size of the hysteresis band, however this may result in higher cycling frequencies of the compressor. If very tight control of these reservoirs is required, the bang-bang controller could be replaced with a proportional-integral-derivative ("PID") controller and using pulse width modulation ("PWM") signals on the compressors. Other methods of control are also possible.

Other pressure sources may be used in other embodiments, and in some cases, more than one positive pressure source and/or more than one negative pressure source may be used. For instance, more than one positive pressure source may be used that provides different positive pressures (e.g., 1000 mmHg and 700 mmHg), which may be used to minimize leakage. For example, high positive pressure can be used to control valves, whereas lower positive pressures can be used to control pumps. This limits the amount of pressure that can potentially be sent to the dialyzer or to the patient, and helps to keep actuation of the pumps from overcoming the pressures applied to adjacent valves. A non-limiting example of a negative pressure is −400 mmHg. In some cases, the negative pressure source may be a vacuum pump, while the positive pressure pump may be an air compressor.

Figure 7A:
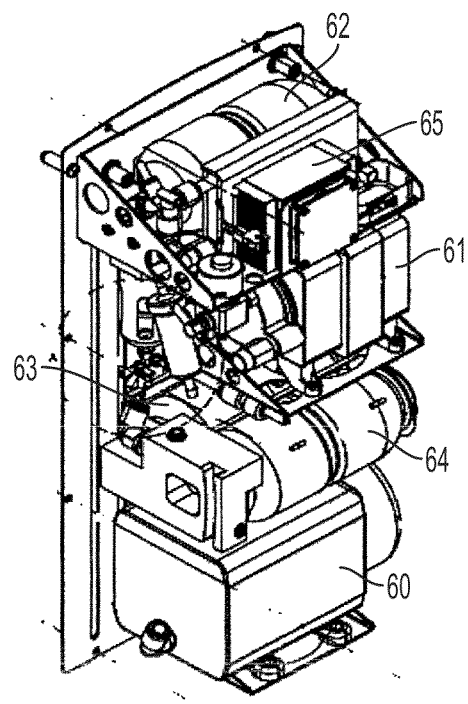
FIG. 7a is perspective view of selected components of a power unit in an illustrative embodiment.

In an embodiment, power unit 52 comprises a housing that may contain components as shown in FIG. 7a. In this example, a pump and pneumatic storage assembly is arranged to fit within power unit 52, and comprises a positive pressure pump 60, a negative pressure or vacuum pump 61, a high-positive pressure reservoir 62, a lower-positive pressure reservoir 63, a negative pressure reservoir 64, and a dehumidification or 'chiller' unit 65. The high-positive pressure reservoir 62, for example, may store air at pressures of about 1000-1100 or more mmHg, and the lower-positive pressure reservoir 63, for example, may store air at pressures of about 700-850 mmHg. The pressurized air generated by positive pressure pump 60 may be used to fill reservoir 63 by interposing a pressure regulator (not shown) between the outlet of pump 60 and the inlet of reservoir 63.

Figure 7B:
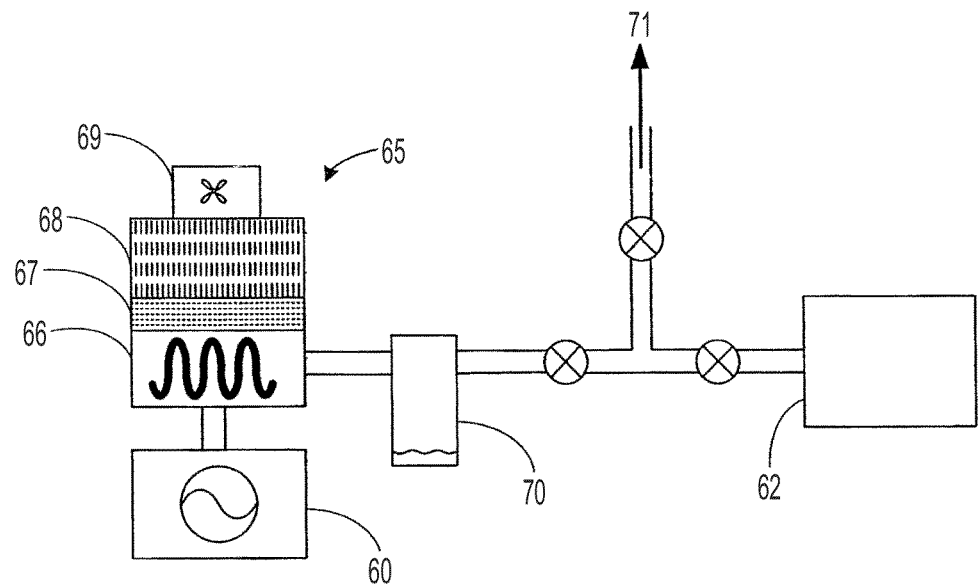
FIG. 7b is a schematic view of an air dehumidifier arrangement in an illustrative embodiment.
Figure 7C:
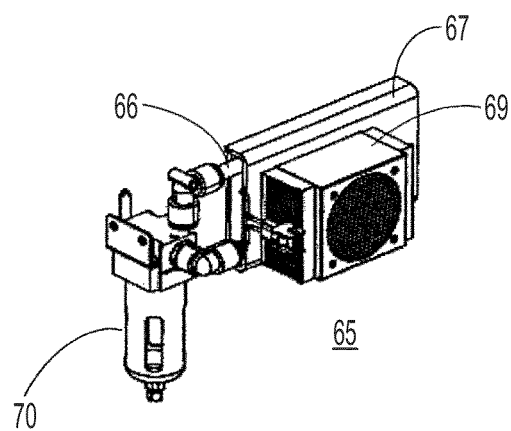
FIG. 7c is a perspective view of a dehumidifier arrangement in the FIG. 7a embodiment.

Chiller 65, or another suitable dehumidifier, may be interposed between the outlet of positive pressure pump 60 and the inlet of the one or more positive pressure reservoirs 62 and/or 63. De-humidification of the pressurized air may prevent water condensation inside pneumatic lines or manifold passages and valves driven by the positive pressure reservoirs 62 and/or 63. As shown schematically in FIG. 7b, the chiller 65 may include a metal coil conduit 66 through which air from compressor 60 is passed, and in which water may be condensed from the compressed air. A cooling element 67 may separate the compressed air coils from a heat exchanger 68, through which ambient air may be drawn, warmed and exhausted by fan 69. The heat exchanger rejects heat to the ambient environment, and a water trap 70 separates the condensed water from the compressed air. The dried compressed air is then available for storage in reservoir 62 (or via a pressure regulator for storage in low pressure reservoir 63), or for delivery to downstream devices 71 such as a valved pneumatic manifold. Cooling element 67 may be a commercially available electrically powered Peltier device such as device model C1-34-1604 from Tellurex, Inc. FIG. 7c shows an example of how chiller 65 may be arranged and configured to fit within the confines of power unit 52.

Figure 8:
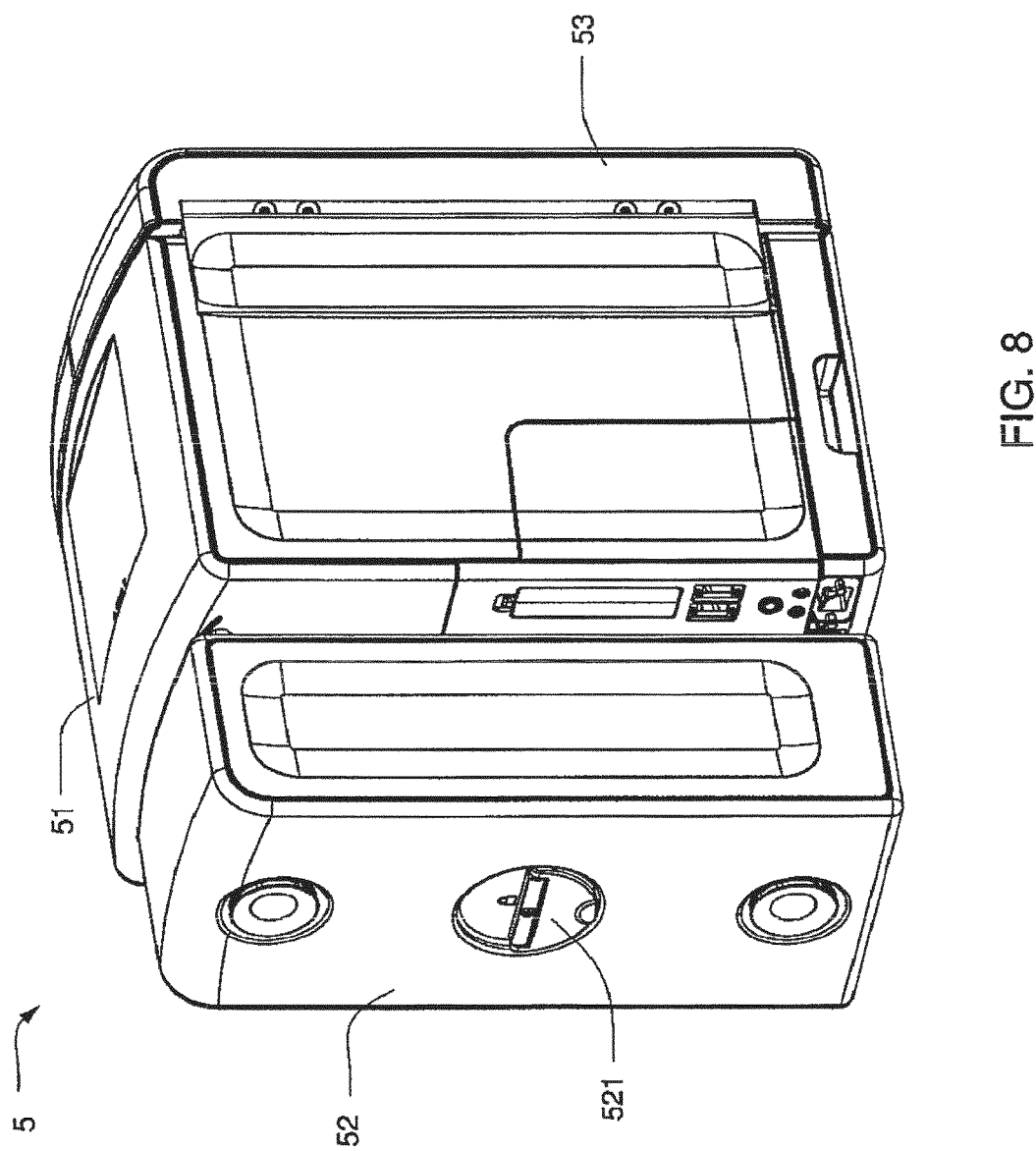
FIG. 8 is a left rear perspective view of the hemodialysis system of FIG. 7.

Moreover, the power unit 52 may be selectively connectable to the dialysis unit 51, e.g., to allow different power units 52 to be interchanged. For example, the dialysis unit 51 may be arranged to work with different types of power units 52, such as power units 52 that use electrical power to generate the pneumatic power supply, as well as power units 52 that use stored pneumatic power (e.g., pressurized air stored in one or more high pressure tanks). Thus, a power unit 52 may be interchanged for another unit 52, in case of failure or other requirements. For example, it may be desired to use the system 5 in an area where noise generation is unacceptable, such as when nearby people are sleeping. In this case, it may be desirable to use a power unit 52 that uses stored pneumatic power, rather than a unit 52 that generates pneumatic power by running pumps or other noise generating equipment. As shown in FIG. 8, the power unit 52 may be disconnected from the dialysis unit 51 by manipulating a handle 521. For example, turning the handle 521 may unlock the power unit 52 from the dialysis unit 51, disengaging not only mechanical connections between the housings, but also power and/or communications connections between the two. An interface (not shown) between the dialysis unit 51 and the power unit 52 may permit the units to exchange pneumatic power (from the power unit 52 to the dialysis unit 51) as well as electrical power, control communications, and other. The dialysis unit 51 may have connection points for electrical power (e.g., standard 115V, 15 amp power found in most home power outlets), external communication (such as Ethernet, or any other suitable connection suitable for communication), a water supply, and so on. The dialysis unit 51 may provide electrical power or other connections to the power unit 52, if desired.

The dialysis unit 51 may include a controller to control flow of control fluid for various components of the system 5, as well as perform other desired functions. In some cases, the control fluid may be held at different pressures within the various tubes or conduits. For instance, some of the control fluid may be held at positive pressure (i.e., greater than atmospheric pressure), while some of the control fluid may be held at negative pressures (less than atmospheric pressure). In addition, in certain embodiments, the controller may have components that are kept separate from the various liquid circuits. This configuration has a number of advantages. For example, in one embodiment, the liquid circuits in the dialysis unit 51 may be heated to disinfection temperatures and/or exposed to relatively high temperatures or other harsh conditions (e.g., radiation) to effect disinfection, while electronic components of the controller may not be exposed to such harsh conditions, and may even be kept separate by an insulating wall (e.g., a "firewall") or the like. That is, the dialysis unit housing may have two or more compartments, e.g., one compartment with electronic and other components that may be sensitive to heat or other conditions, and another compartment with liquid circuit components that are heated or otherwise treated for disinfection.

Thus, in some embodiments, the system 5 may include a "cold" section (which is not heated), and a "hot" section, portions of which may be heated, e.g., for disinfection purposes. The cold section may be insulated from the hot section through insulation. In one embodiment, the insulation may be molded foam insulation, but in other embodiments can be any type of insulation, including but not limited to a spray insulation, an air space, insulation cut from sheets, etc. In one embodiment, the cold section includes a circulation system, e.g., a fan and/or a grid to allow air to flow in and out of the cold box. In some cases, the insulation may be extended to cover access points to the "hot" section, e.g., doors, ports, gaskets, and the like. For instance, when the "hot" section is sealed, the insulation may completely surround the "hot" section in some cases.

Non-limiting examples of components that may be present within the "cold" section include power supplies, electronics, power cables, pneumatic controls, or the like. In some cases, at least some of the fluids going to and from the "hot" section may pass through the "cold" section; however, in other cases, the fluids may pass to the "hot" section without passing through the "cold" section.

Non-limiting examples of components that may be present within the "hot" section include cassettes (if present), fluid lines, temperature and conductivity sensors, blood leak sensors, heaters, other sensors, switches, emergency lights, or the like. In some cases, some electrical components may also be included in the "hot" section. These include, but are not limited to, a heater. In one embodiment, the heater can be used to heat the hot box itself, in addition to fluid. In some embodiments, the heater 72 heats the entire "hot" section to reach a desired temperature.

Figure 9:
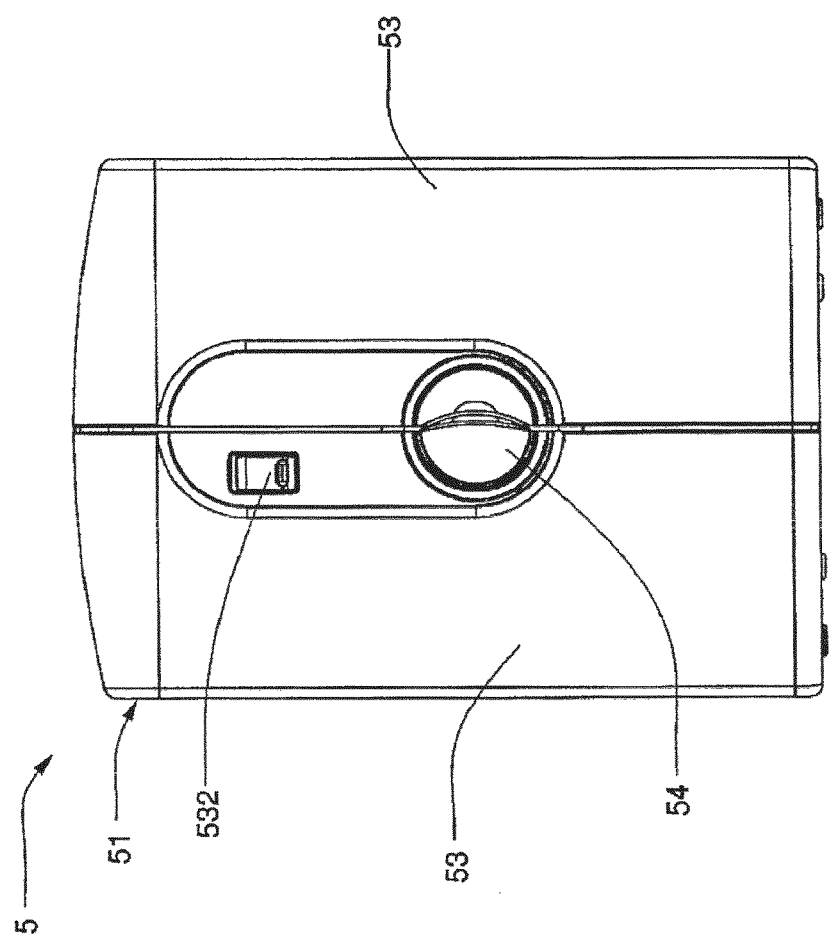
FIG. 9 is a front view of the hemodialysis system of FIG. 7.
Figure 10:
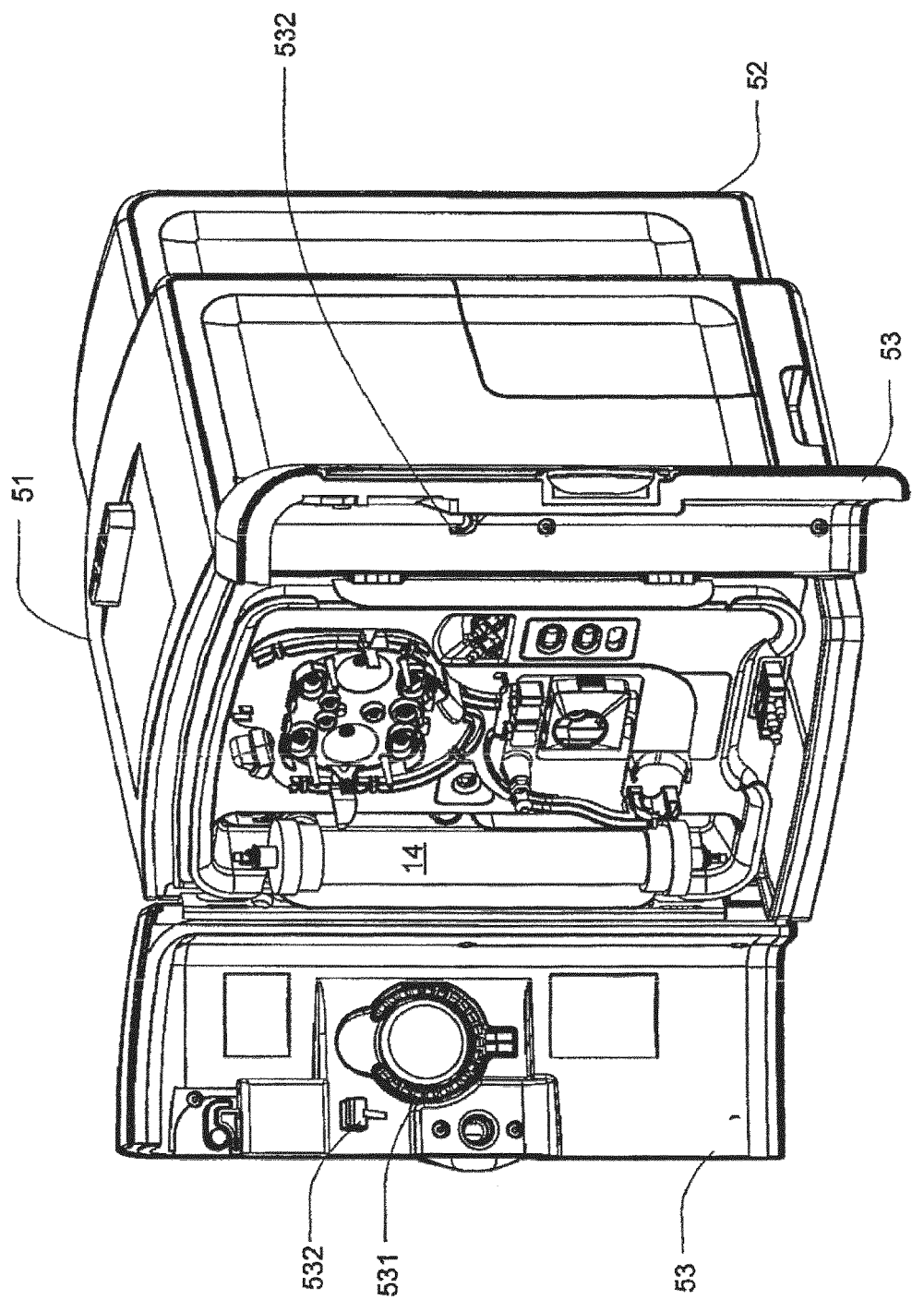
FIG. 10 is a right front perspective view of the view of the hemodialysis system of FIG. 7 with the doors in a first open position.
Figure 11:
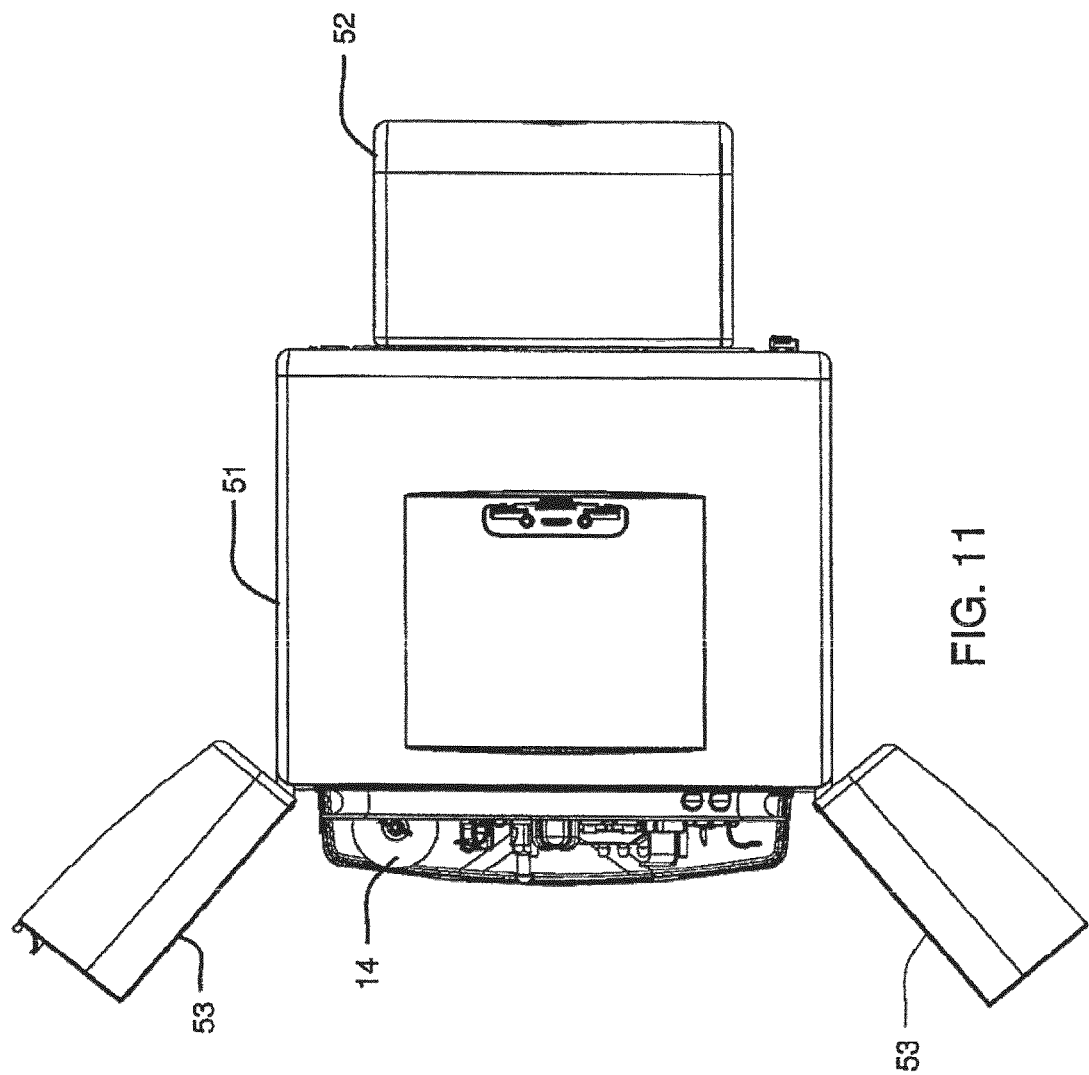
FIG. 11 is a top view of the hemodialysis system of FIG. 10.
Figure 12:
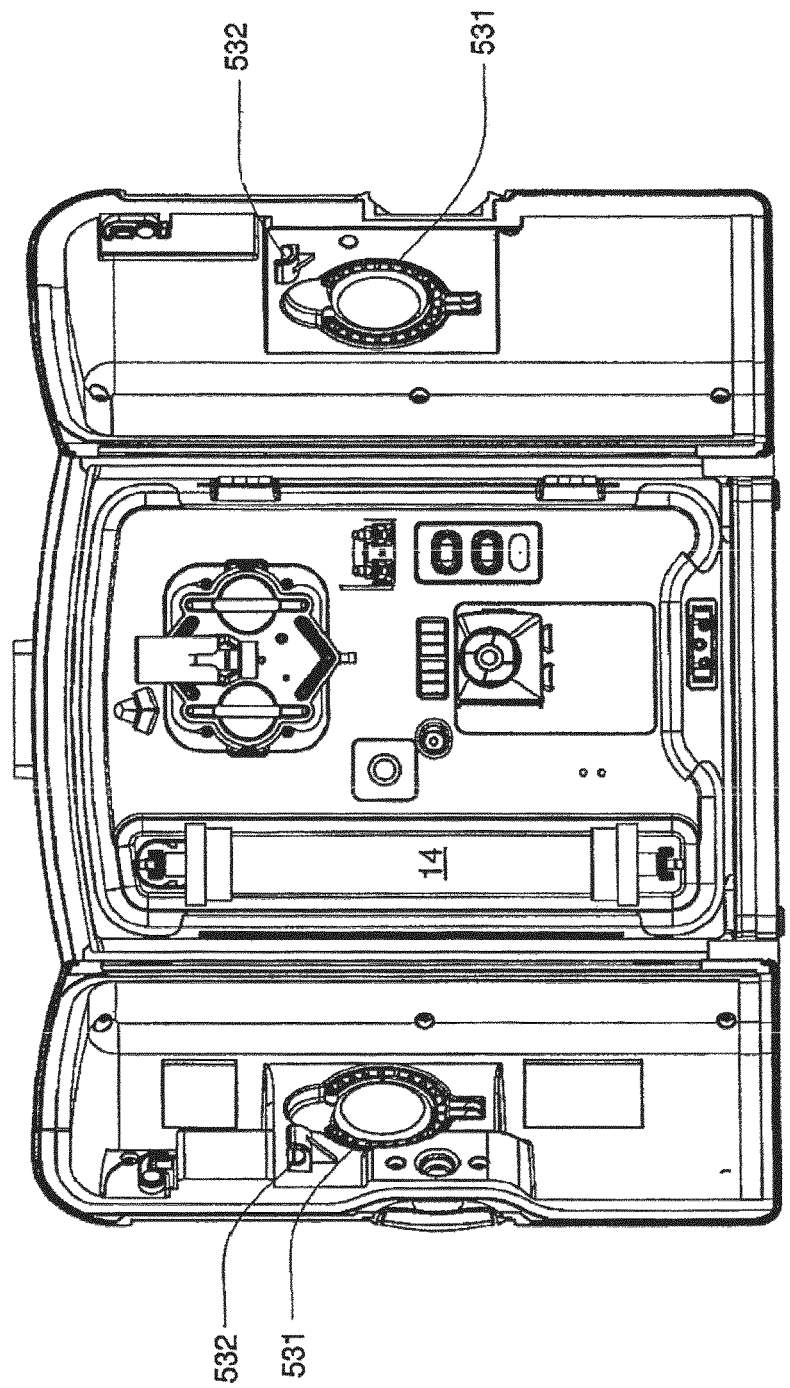
FIG. 12 is a front view of the hemodialysis system of FIG. 10.
Figure 13:
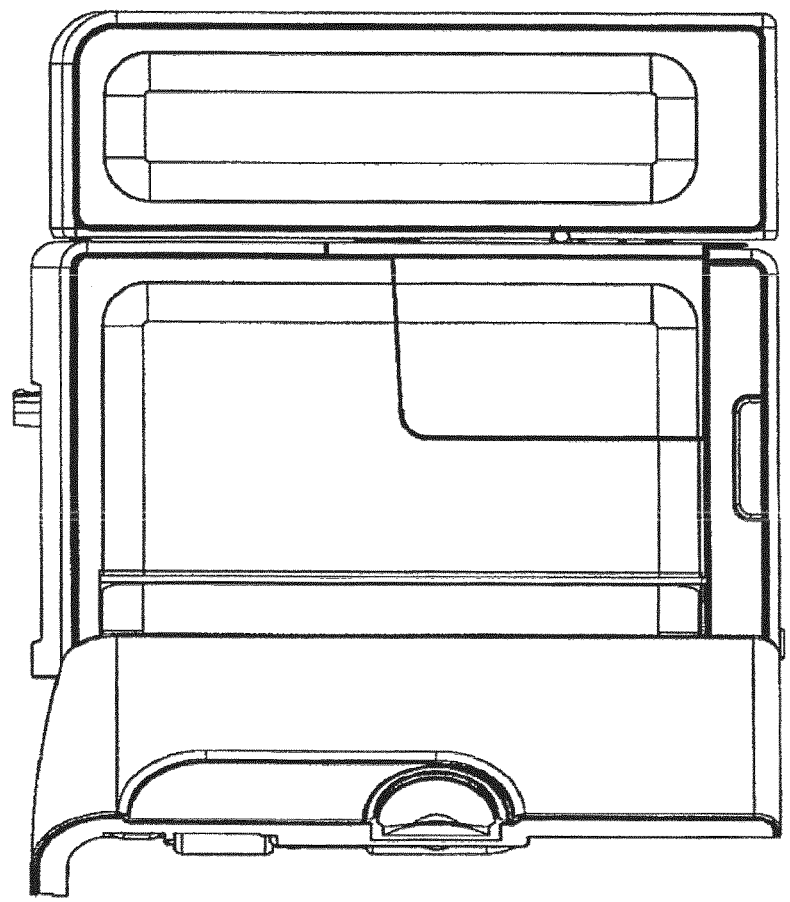
FIG. 13 is a right side view of the hemodialysis system of FIG. 10.

In accordance with an aspect of the invention, the dialysis unit 51 housing may include vertical side-by-side doors that can be opened to expose all mechanical interface points for blood flow circuitry and connections for dialysate circuitry, i.e., all connection points for patient blood connections and acid/bicarbonate connections, that must be made by a user to use the dialysis unit 51. FIG. 9 shows a front view of the dialysis unit 51 with the vertical side-by-side doors 53 in a closed state. In this arrangement, the doors 53 may block access to connection points for patient blood connections and acid/bicarbonate connections as well as seal the interior of the unit housing so as to allow heat retention suitable for disinfection. The seal provided by the doors 53 may be hermetic, preventing or substantially resisting any air exchange between the housing interior and an exterior environment, or may be of a somewhat lesser quality yet still allow for disinfection.

In this embodiment, the doors 53 are connected to the dialysis unit 51 housing by a dual hinge arrangement such that the doors 53 can be opened to two different states of opening. FIGS. 10-13 show the doors 53 in a first state of opening. In this state, the doors 53 expose all user-made connections for the blood circuit connections and for the dialyzer circuitry, including the dialyzer 14 itself and for reagent materials, such as consumable acid/bicarbonate materials. This position also exposes several other features, such as holders 531 for an acid/bicarbonate container (not shown) and hooks 532 that may be used to hold any suitable item, such as the control interface 55, which may be hung by its handle on one of the hooks 532. (See also FIG. 7 which shows a hook 532 on the front of the left door 53 which may be folded out to receive the control interface 55 or other item.) The holders 531 in this embodiment may be folded down from their position shown in the figures (i.e., folded up and into recesses in the doors 53) so as to extend horizontally from the doors 53. The holders 531 have a "C" shaped receiving section to receive and hold an acid/bicarbonate container, but of course could be shaped or otherwise arranged in any suitable way.

Figure 14:
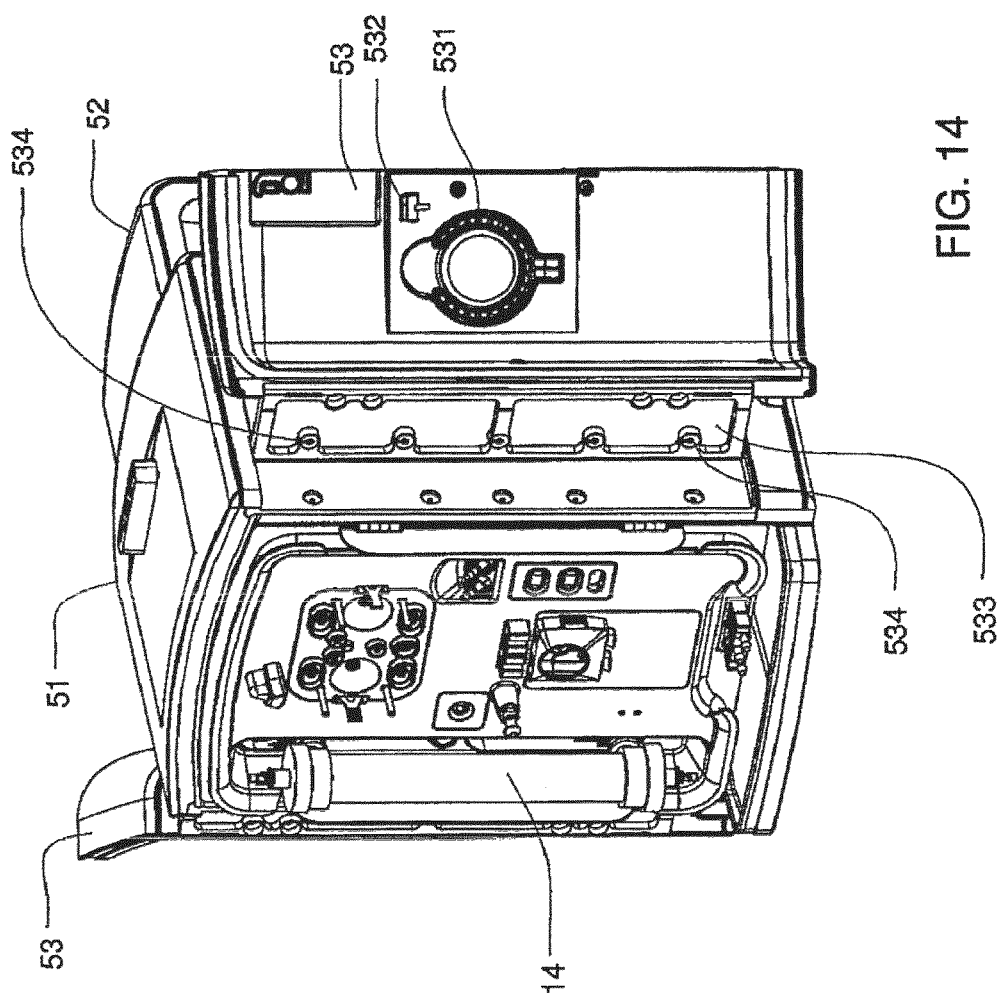
FIG. 14 is a right front perspective view of the view of the hemodialysis system of FIG. 7 with the doors in a second open position.
Figure 15:
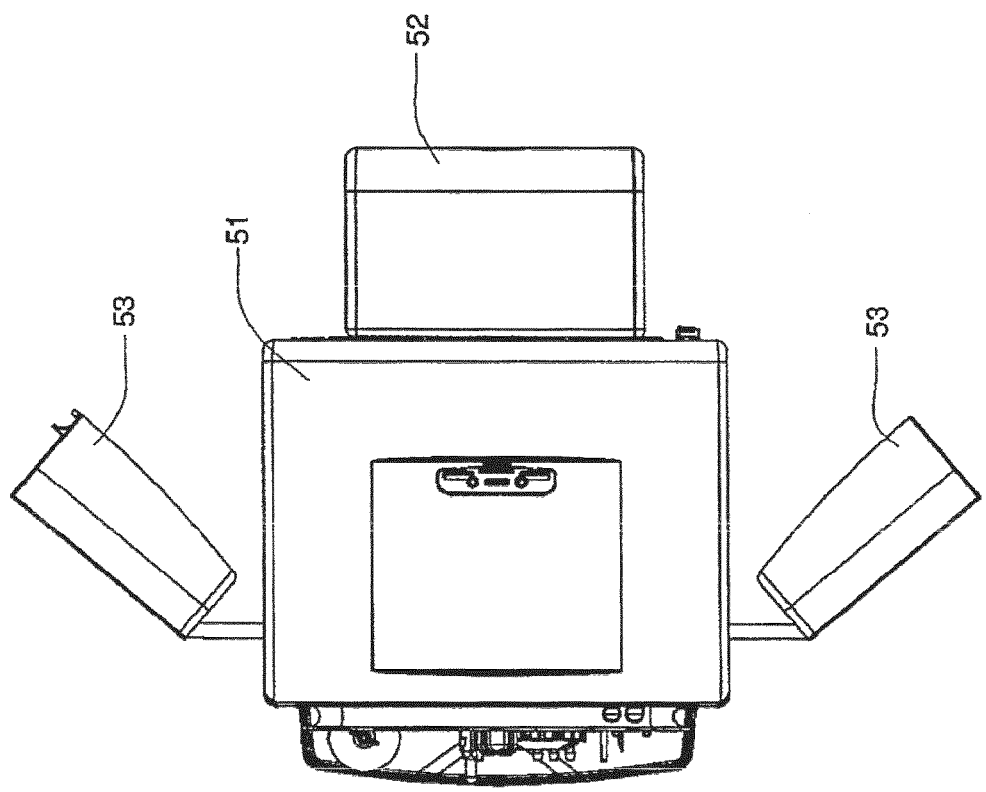
FIG. 15 is a top view of the hemodialysis system of FIG. 14.
Figure 16:
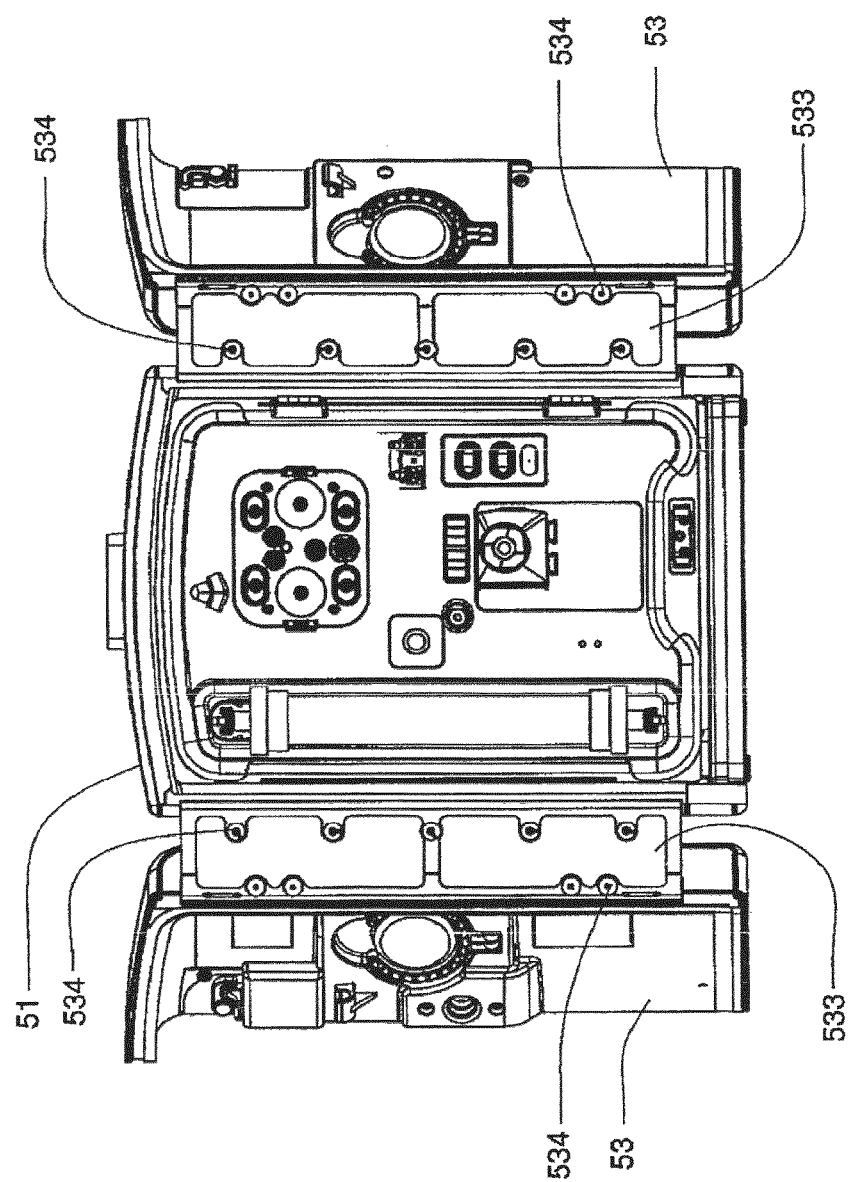
FIG. 16 is a front view of the hemodialysis system of FIG. 14.

FIGS. 14-16 show the doors 53 in a second state of opening in which a hinge plate 533 for each door 53 is pivoted outward and away from the dialysis unit housing 51.

The hinge plates 533, which in this embodiment extend vertically along almost the entire height of the dialysis unit housing 51, are pivotally attached to the doors 53 at a first, outer end, and are pivotally attached at a second inner end to the dialysis unit housing 51. (Of course, it should be understood that the hinge plates 533 could be arranged and/or positioned differently, e.g., at the top and bottom of the doors 53 as is found in many refrigerator door arrangements, each plates 533 may include two or more portions that are vertically separated from each other, etc.) Magnets 534 attached to the hinge plates 533 may interact with corresponding magnets (or other suitable components, such as a steel elements) attached to the dialysis unit housing 51 so as to attract the hinge plates 533 toward the dialysis unit housing 51, thus tending to keep the hinge plates 533 in the position shown in FIGS. 10-13. (Of course, the magnets 534 could be positioned on the unit housing, and the hinge plates 533 could have suitable elements (such as pieces of steel) that are attracted to the magnets 534.) The doors 53 in this embodiment also include magnets attached near the hinge plates 533 so that when the doors 53 are opened to the first state as shown in FIGS. 10-13, the magnets interact with corresponding magnets in the hinge plates 533 to help keep the doors 53 in an open position relative to the hinge plate 533. These magnets will also help maintain the relative position of the doors 53 and the hinge plates 533 when the hinge plates 533 are opened to the second state shown in FIGS. 13-16.

Although magnets are used in this illustrative embodiment as part of a retainer member to help the doors 53 and/or hinge plates 533 stay in a particular state of opening or closing, other arrangements for a retainer member are possible. For example, the hinge connection between the doors 53 and the hinge plates 533 and/or the connection between the hinge plates 533 and the housing 51 may include a detent arrangement that serves to resiliently hold the door 53 or hinge plate 533 in a particular position relative to the other part (the hinge plate or housing, respectively). In another embodiment, one or more springs may be used to help maintain the doors 53 in an open position relative to the hinge plates 533. In yet another embodiment, the hinge plates 533 may have a friction or interference fit with a portion of the housing 51 that tends to maintain the hinge plates 533 in the closed position (adjacent the housing). Accordingly, a retainer member that functions to help maintain a door 53 in a particular position relative to its hinge plate 533, and/or that functions to help maintain a hinge plate 533 in a particular position relative to the housing 51, may take any one of a number of possible arrangements.

Figure 17:
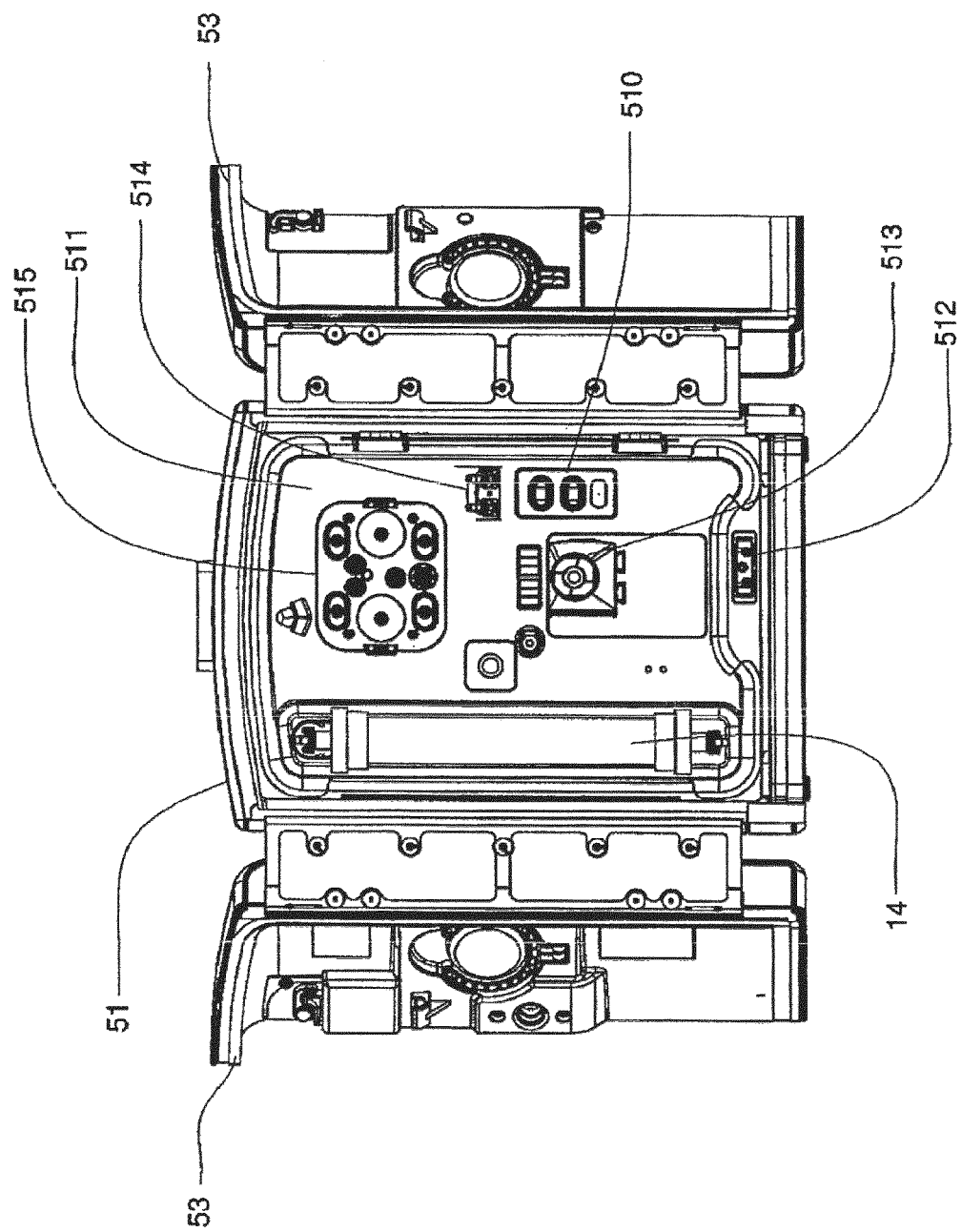
FIG. 17 is a front view of the hemodialysis system of FIG. 7 with the doors in an open position exposing a front panel of the system.

In accordance with another aspect of the invention, opening of the doors to the dialysis unit housing may reveal all of the user-made connections for blood circuit connections and dialysate fluidic connections needed for operation of the system 5. For example, as shown in FIG. 17, with the doors 53 in an open position (either the first or second state of opening) a front panel 511 of the dialysis unit 51 may be exposed. In this embodiment, the front panel 511 carries several items or connection points that must be accessed by a user. For example, the dialyzer 14, which must be periodically replaced, is mounted to the front panel 511. The dialyzer 14 must be connected not only to the blood flow circuit 141, but also the balancing circuit 143. Also, a connection point 512 for an acid/bicarbonate source 49 is located at a lower end of the front panel 511. It is at this connection point 512 that a user may connect a source of consumable reagent ingredients 49 used by the dialysis unit 51 in making dialysate. An occluder 513 is also mounted on the front panel 511. The occluder 513 receives tubes of the blood flow circuit and controls the open/closed state of the tubes based on system operation. The function of the occluder 513 is discussed in more detail in U.S. application Ser. No. 12/198,947, filed Aug. 27, 2008 and below. In short, the occluder 513 allows flow through the arterial and venous lines of the blood flow circuit unless there is a system problem, such as a leak, pump failure, overpressure situation, etc. In such case, the occluder 513 automatically closes the blood lines to prevent all flow to or from the patient. Also exposed on the front panel 511 are blood line connection points 514 for connecting the arterial and venous blood lines 203, 204 of the blood flow circuit 141 with the directing circuit 142 (as explained above with reference to FIGS. 2 and 3, the blood flow circuit 141 may be connected to the directing circuit 142). This connection is normally made at the end of treatment to allow the system to clean and disinfect the blood flow circuit 141. The front panel 511 also has a set of control ports 515 that mate with corresponding control ports on the blood pump portion of the blood flow circuit 141. The control ports 515 provide controlled levels of air pressure and/or vacuum to control the open/closed state of valves and to power the pumps of the blood flow circuit 141.

Figure 17A:
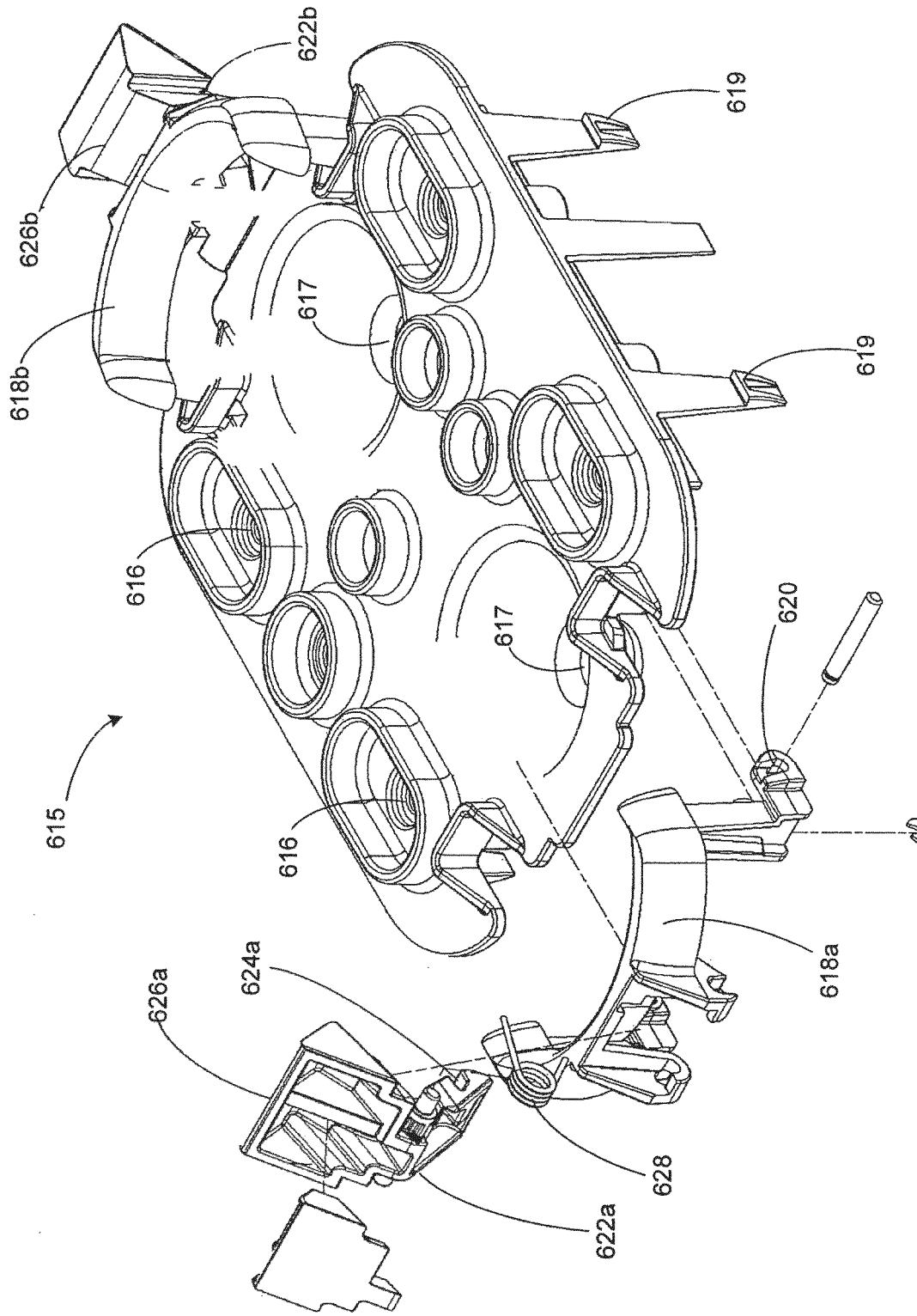
FIG. 17a is an exploded perspective view of a control port assembly arranged to interface with a blood pump assembly in an illustrative embodiment.
Figure 17B:
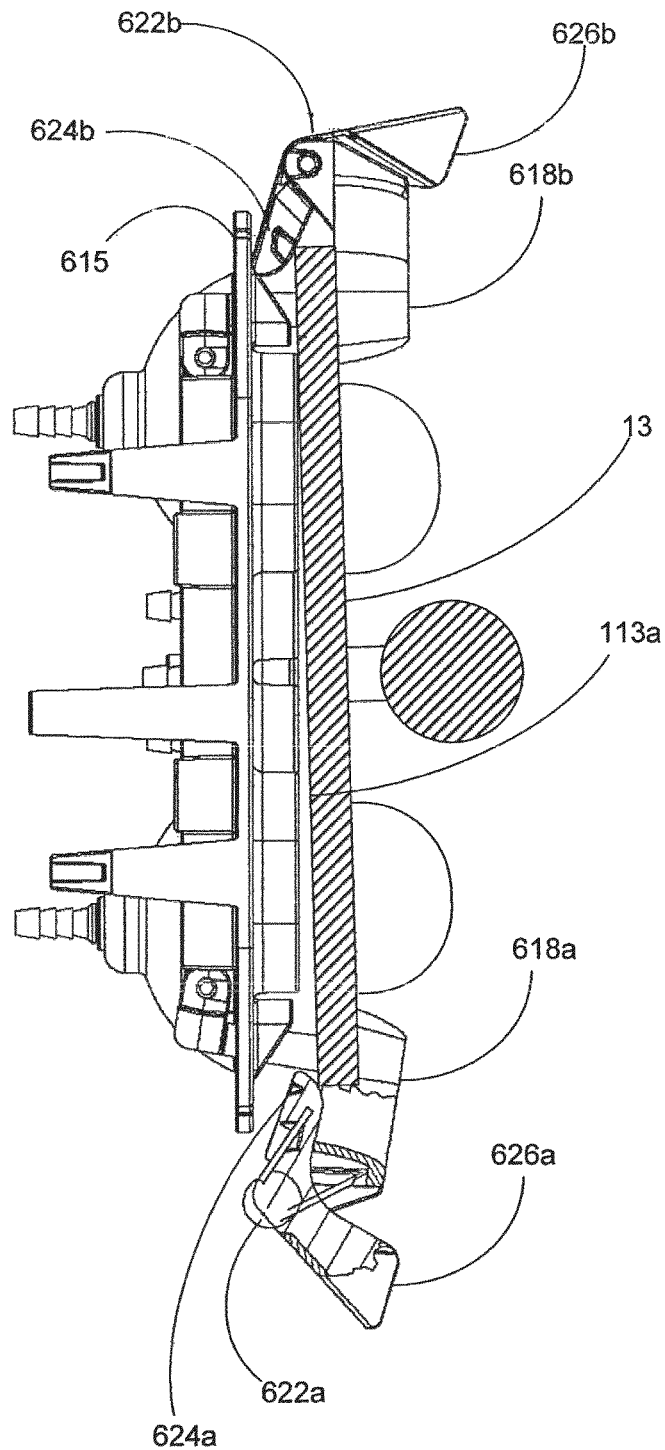
FIG. 17b is a cross sectional side view of the FIG. 17a embodiment with an engaged blood pump assembly.

In another aspect of the invention, FIG. 17a shows a perspective view of a control port assembly 615 onto which a blood pump assembly 13 may be mounted, and with which the fluidic control ports of the blood pump assembly 13 can connect. Shown, for example, are control ports 616 for controlling the actuation of valves on a blood pump assembly 13, and control ports 617 for controlling the actuation of pumps on a blood pump assembly 13. In order to secure a blood pump assembly 13 onto control port assembly 615, a latch member or other engagement device may be provided at one or more sides of, or within, control port assembly 615, or at a portion of front panel assembly 511 adjacent to, or within, the location of the control port assembly 615. (In the example shown, control port assembly 615 may be reversibly mounted onto front panel assembly 511 via retaining tabs 619). Alternately, or in addition, a disengagement or other ejection feature for a blood circuit assembly may be provided to help with removal of a blood pump assembly or other parts of a blood circuit assembly from the front panel 511. For example, a pair of cassette latching and ejection assemblies may be mounted on opposite sides of the control port assembly 615. In the FIG. 17a embodiment, a blood circuit assembly engagement device includes latch or retainer members 618a and 618b pivotably mounted to the sides of control port assembly 615. Preferably, the pivotal connections (e.g., pivotal connection 620) of latch members 618a and 618b are biased by a suitably disposed spring to urge latch members 618a and 618b to rotate toward each other and toward the surface of control port assembly 615, so that they can maintain contact with the edges or other parts of a blood pump assembly 13 (shown in cross-section in FIG. 17b) mounted on the control port assembly 615. This is more clearly shown in FIG. 17b, which is a top, sectional view of control port assembly 615, onto which is mounted a blood pump assembly 13. Latch member 618b is shown in FIG. 17b in its normally biased position, securing the outer edge of blood pump assembly 13 in connection with control port assembly 615. Latch member 618a, on the other hand, is shown in a partially retracted position, allowing blood pump assembly 13 to be partially separated from control port assembly 615. In a fully retracted position (not shown), latch member 618a or 618b clears the front edge of blood pump assembly 13, allowing it either to be removed from or installed or mounted onto control port assembly 615.

As shown in FIGS. 17a and 17b, in addition to a latch or retainer member 618a and 618b that may help to hold blood pump assembly 13 onto control port assembly 615, a separation assist member (or ejector element or member) 622a or 622b may also be included to assist a user in separating blood pump assembly 13 from control port assembly 615, and lifting it away from control port assembly 615. The separation assist member 622a or 622b may be pivotably mounted on the front panel assembly 511 in a location suitable for a contacting portion 624a or 624b of the separation assist member 622a and 622b to contact an edge of the undersurface 113a of blood pump assembly 13 to help lift it off the control port assembly 615 when the separation assist member 622a or 622b is rotated in an outward fashion. The engagement device may include an actuator to actuate the retainer members 618 and/or the ejector elements 622, such as a thumb- or finger-contacting element 626a or 626b that can be pressed laterally by a user to pivot separation assist member 622a or 622b outward to engage contacting portion 624a or 624b with the undersurface 113a of blood pump assembly 13. Preferably, a spring 628 may be included near the pivotal connection of separation assist member 622a or 622b, and suitably disposed to bias separation assist member 622a or 622b to urge contacting portion 624a or 624b away from contact with the undersurface 113a of blood pump assembly 13. That way, no intrinsic force from separation assist member 622a or 622b is acting to push blood pump assembly 13 away from control port assembly 615. In another preferred embodiment, separation assist member 622a or 622b may be pivotably mounted to latch member 618a or 618b, as shown in FIG. 17a. In this embodiment, a user may engage separation assist member 622a or 622b with the undersurface 113a of blood pump assembly 13, and simultaneously disengage latch member 618a and 618b from contact with the front edge or surface of blood pump assembly 13 by means of a single outward push of thumb- or finger-contacting element 626a or 626b. Thus, with the outward push of one or more actuators, such as a single element 626a or 626b, blood pump assembly 13 may be alternately seated and secured onto control port assembly 615, or separated from control port assembly 615, facilitating the installation and/or removal of blood pump assembly 13.

Figure 17C:
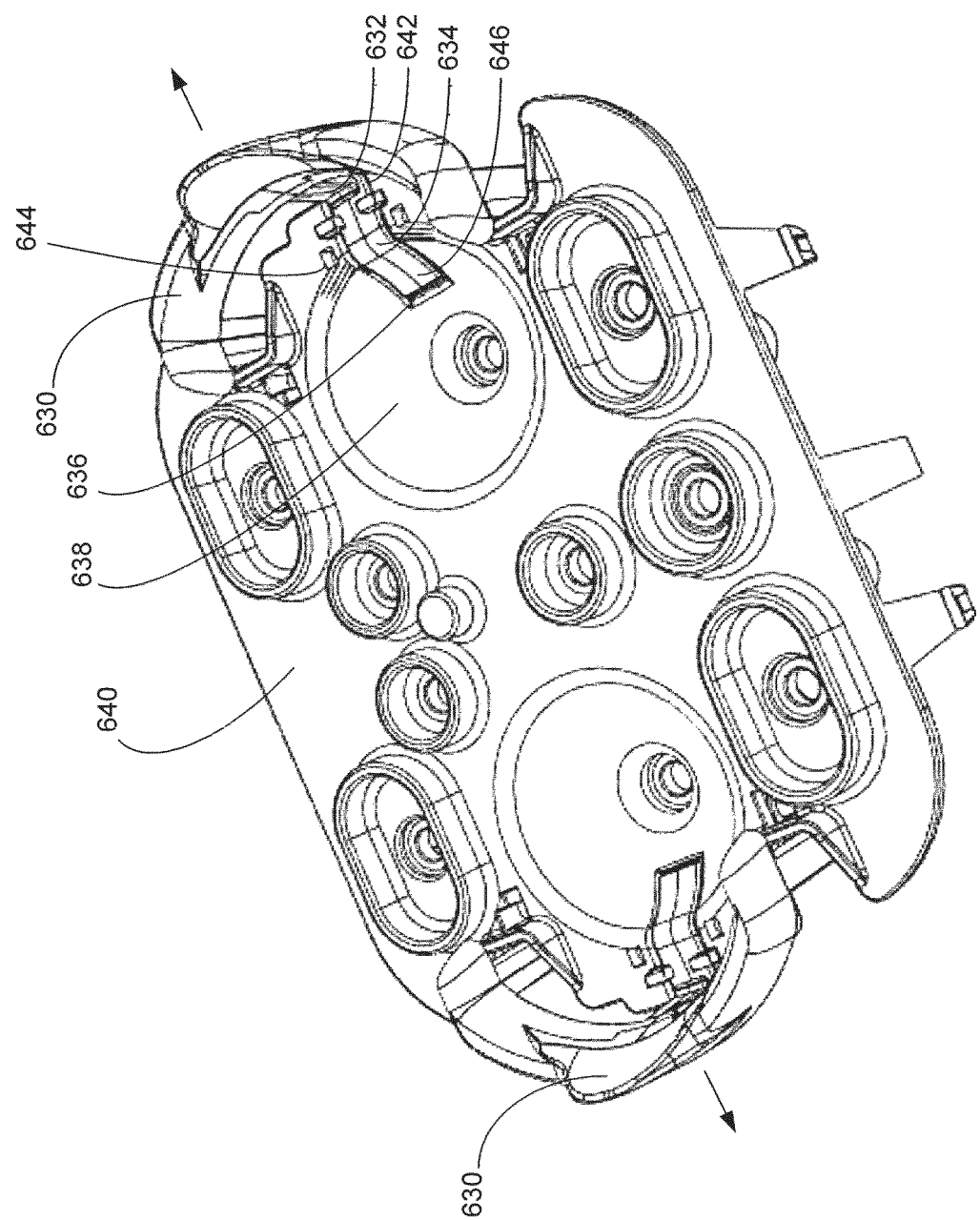
FIG. 17C shows a perspective view of a control port assembly with a pair of blood pump cassette latching and ejection assemblies in an illustrative embodiment.
Figures 17D, 17E:
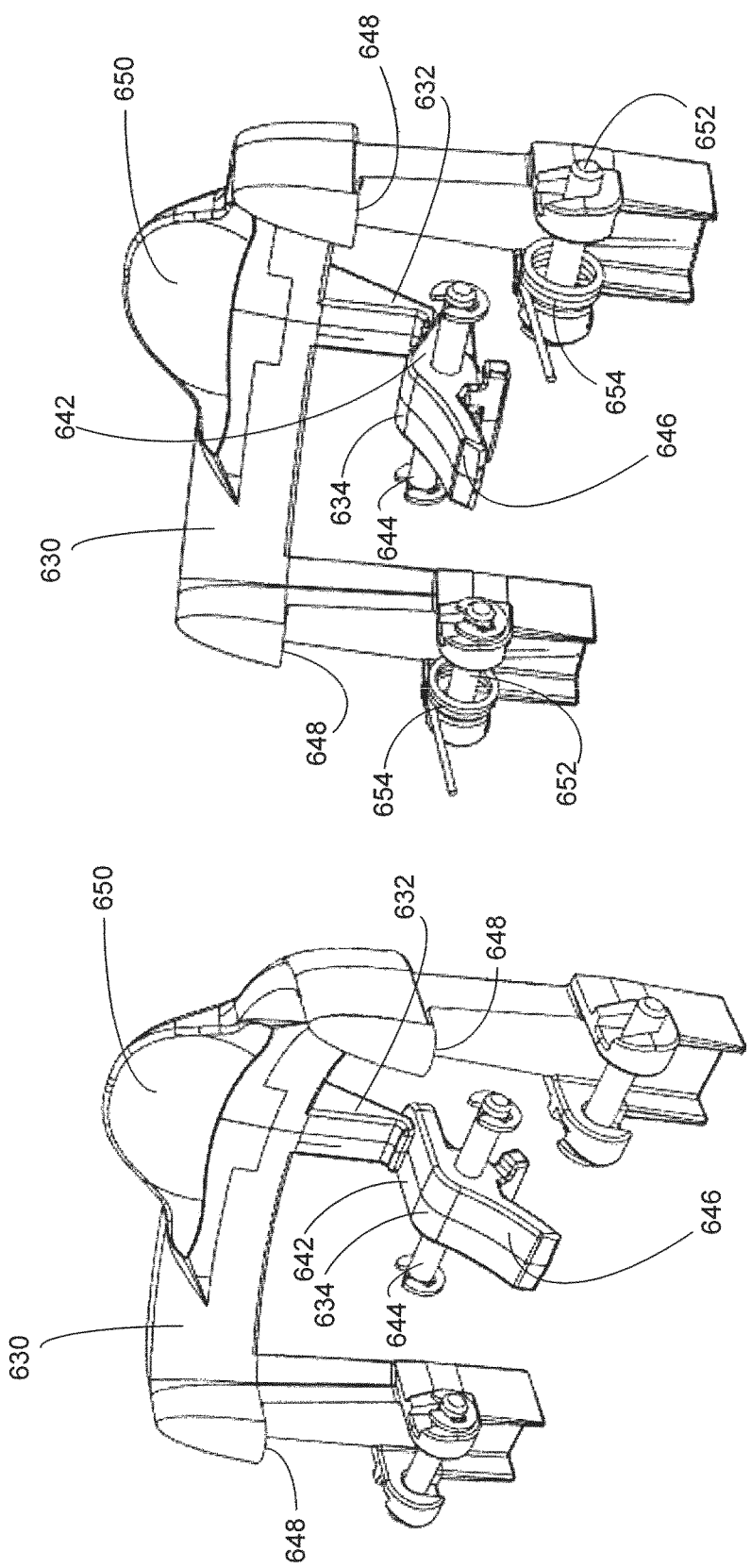
FIG. 17D shows an isolated view of a latching assembly with an ejection member in a retracted position in an illustrative embodiment.
FIG. 17E shows an isolated view of the latching assembly of FIG. 17D with an ejection member in an extended position in an illustrative embodiment.

FIG. 17C shows another embodiment of a blood circuit assembly engagement device, that in this embodiment includes a pair of blood pump cassette retainer and ejector elements. In this embodiment, cassette retainer element 630 includes a contacting member 632 that makes contact with an ejector (or separation assist) element 634. In a retracted state, ejector element 634 is positioned in a recessed area 636 of the blood pump pod recess 638 in the control port assembly 640. As retainer elements 630 are pivoted outward (direction of arrows in FIG. 17C), contacting member 632 presses against a proximal end 642 of the ejector element 634, whereupon ejector element 634 rotates about pivot axis 644, causing a distal end 646 of ejector element 634 to lift out of recess 636 to engage the rigid back wall of the actuation chamber of a mounted pump cassette, which is positioned within the blood pump pod recess 638. FIGS. 17D and 17E show isolated views of the engagement device, with a ejector element 634 in retracted (FIG. 17D) and extended (FIG. 17E) positions. In FIG. 17D, retainer element 630 is in a retaining position, with retention elements 648 rotated inward toward the center of control port assembly 640, and ejector element 634 in a recessed position with proximal portion 642 elevated and distal portion 646 depressed. In FIG. 17E, retainer element 630 is in a release position, with retention elements 648 rotated outward away from the center of control port assembly 640, and ejector element 634 in a raised position with proximal portion 642 lowered by contacting member 632 and distal portion 646 raised out of recess 636 to eject a cassette mounted in control port assembly 640. Thumb rest (actuator) 650 is shaped to conveniently allow a user to apply an outward force to release a cassette by applying one thumb on each of the opposing latching members 630 in a complete assembly as shown in FIG. 17C. In an embodiment, retainer element 630 rotates about an axis formed by pinions 652, equipped with springs 654 biased in a latching or retaining direction to help keep a cassette securely mounted on control port assembly 640. FIG. 17F shows a front view of a blood pump cassette 1000 (which is part of a blood circuit assembly) mounted to a panel of a dialysis unit, such as an exposed front panel 511. FIGS. 17G and 17H show cross-sectional views of blood pump cassette 1000 along the lines 17G-17G and 17H-17H, respectively, with the cassette 1000 properly seated on control port assembly 640. FIG. 17G shows the relationship between contacting members 632, ejector elements 634, and the rigid back walls 658 of the pump actuation chambers of cassette 1000. Ejector elements 634 are shown to be in fully retracted positions in their respective recessed areas 636 to allow pump cassette 1000 to be fully seated. FIG. 17H shows the relationship between retention elements 648 and the front plate 656 of cassette 1000. In this case, retention elements 648 are brought into apposition with the front plate 656, securing cassette 1000 onto control port assembly 640.

FIG. 17I shows a front view of the blood pump cassette from FIG. 17F in the process of being disengaged from the panel 511 of a dialysis unit. FIGS. 17J and 17K show cross-sectional views of blood pump cassette 1000 with the cassette 1000 partially lifted from its engagement with control port assembly 640. FIG. 17J shows the relationship between contacting members 632, ejector elements 634, and the rigid back walls 658 of the pump actuation chambers of cassette 1000. In this case, the distal ends 646 of ejector elements 634 are contacting and elevating cassette 1000 from its fully seated position in control port assembly 640. FIG. 17K shows the relationship between retention elements 648 and the front plate 656 of cassette 1000. In this case, the front plate 656 has been elevated above the retaining surface of retainer elements 648.

Also exposed on the front panel 511 in FIG. 17 is a user control panel 510. The user control panel 510 includes one or more buttons permitting the user to bypass the graphical user interface on control interface 55, providing an alternate method to control certain functions (e.g., critical functions) during hemodialysis. This may be important, for example, if the control interface 55 should ever fail during a dialysis treatment session. Non-limiting examples of critical functions can include a "stop dialysis" or "pause dialysis" command and an "infuse dialysate solution" command.

Figure 18:
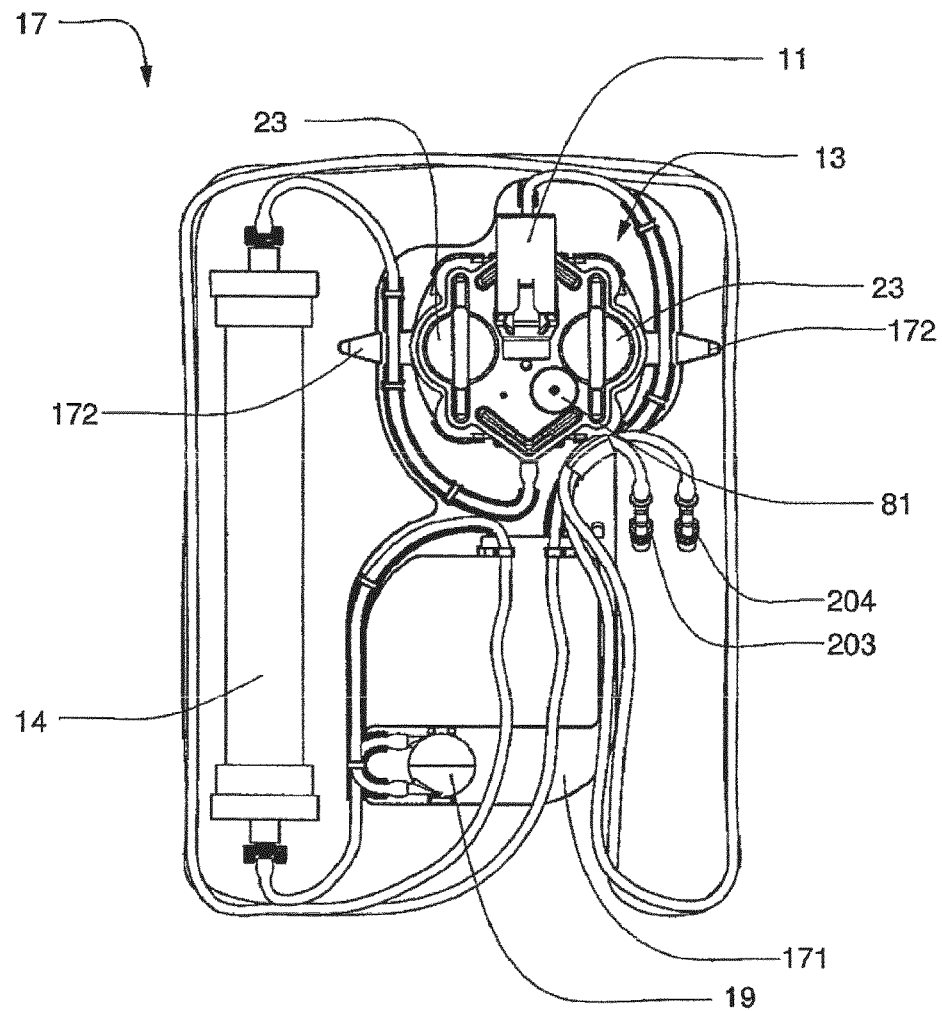
FIG. 18 is a front view of a blood circuit assembly for use with the system of FIG. 7.

FIG. 17 does not show the arterial and venous lines 203, 204 for the blood flow circuit 141 because in this embodiment and in accordance with another aspect of the invention, the blood flow circuit 141 is formed as a blood circuit assembly that is removable from the front panel 511 of the dialysis unit 51, and the blood circuit assembly is not mounted on the front panel 511 in FIG. 17. FIG. 18 shows a front view of the blood circuit assembly 17 in this embodiment along with the dialyzer 14. The blood circuit assembly 17 includes various components discussed above, for example with reference to FIG. 3, that are mounted to a blood circuit organizing tray 171. The arterial and venous lines 203 and 204 (e.g., including lengths of flexible silicone tubing) are terminated with blood line connectors that, in one aspect of the invention, are arranged to provide a plug-in or press-in connection with the blood line connection points 514 as well as provide a screw-type connection used with standard patient access points (e.g., luer type patient access connectors). The arterial line 203 leads to an inlet at the top of the blood pump 13, which includes two pod pumps 23, valves and other components for controlling blood flow. Associated with the blood pump 13 are an air filter 81, an anticoagulant pump 80 (not shown), and an anticoagulant supply 11 (such as a vial of heparin). (Details regarding the blood pump 13 in this illustrative embodiment may be found in U.S. patent application Ser. No. 11/871,680, filed Oct. 12, 2007, entitled "Pumping Cassette"; U.S. patent application Ser. No. 11/871,712, filed Oct. 12, 2007, entitled "Pumping Cassette"; U.S. patent application Ser. No. 11/871,787, filed Oct. 12, 2007, entitled "Pumping Cassette"; U.S. patent application Ser. No. 11/871,793, filed Oct. 12, 2007, entitled "Pumping Cassette"; and U.S. patent application Ser. No. 11/871,803, filed Oct. 12, 2007, entitled "Cassette System Integrated Apparatus.") Blood output from the blood pump 13 (the outlet is located at a bottom of the pump 13) flows to an inlet of the dialyzer 14 (at the top of the dialyzer 14), and out of the dialyzer (the dialyzer blood outlet is located at the bottom of the dialyzer 14) to the inlet of the air trap 19. The outlet of the air trap 19 is connected to the venous blood line 204. Connections to the inlet and outlet blood ports of the dialyzer 14 are made with typical screw-type connections.

Figure 18A:
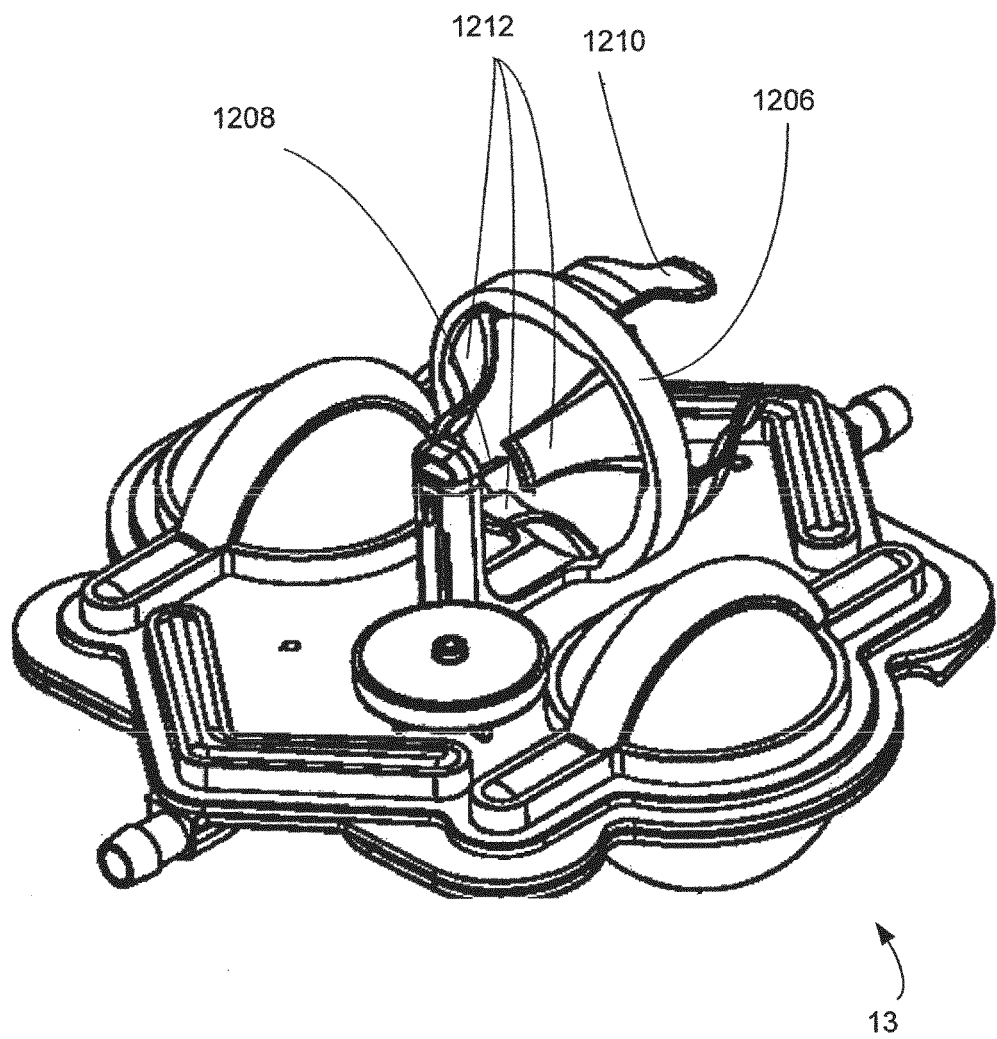
FIG. 18a is a perspective view of a blood pump having a medication holder in an illustrative embodiment.

FIG. 18a shows a perspective view of a blood pump 13 with an alternative embodiment of a vial receptacle or vial holder 1206 for holding or cradling a vial of medication 11 (such as, e.g., an anticoagulant) onto a hollow spike 1208 that is in fluid communication with pump 80 (schematically shown in FIG. 3) of the blood pump 13. In this embodiment, flexible upper arms 1210 serve to hold the body of vial 11 in place, and can flex to accommodate vials of various sizes. Lower arms 1212 help to align the inverted top of vial 11 with spike 1208 in order to prevent vial 11 from being spiked at an angle with respect to the inverted top of vial 11. Spiking the top of vial 11 in a substantially perpendicular manner may help to avoid any leaking of fluid from within vial 11 around the outside of spike 1208.

In accordance with another aspect of the invention, the air trap 19 is placed in the blood flow path after the blood exits the dialyzer and before it is returned to the patient. In an embodiment, air trap 19 can have a spherical or spheroid-shape container (i.e., a container having an approximately spherical inner wall), and have its inlet port located near the top and offset from the vertical axis of the container, and an outlet at a bottom of the container. (The vertical axis of the container is arranged in a vertical direction passing through the top and bottom "poles" of the approximately spherical container.) With the inlet port offset from the vertical axis (in this case set back toward the tray 171), blood is introduced into the container in a direction that is approximately perpendicular to the vertical axis of the container and that is approximately tangential to the spherical inner wall of the container. The curved shape of the inside wall of the trap can thus direct the blood to circulate along the inside wall as the blood gravitates to the bottom of the container (e.g., in a spiral like fashion), facilitating the removal of air bubbles from the blood. Air present in the blood exiting the outlet of the dialyzer 14 will enter at the top of the air trap 19 and remain at the top of the container as blood flows out the outlet at the bottom and to the venous blood line 204. By locating the inlet port near the top of trap 19, it is also possible to circulate blood through the trap with minimal or no air present within the container (as a "run-full" air trap. The ability to avoid an air-blood interface for routine circulation of blood in the trap can be advantageous. Placing the inlet port at or near the top of the container also allows most or all of the air present in the trap to be removed from the trap by reversing the flow of fluid through the blood tubing (i.e. from the bottom to the top of the trap 19, exiting through the inlet port of the trap 19).

In an embodiment, a self-sealing port, such as a self-sealing stopper with a split septum or membrane, or another arrangement, is located at the top of the trap, allowing the withdrawal of air from the container (e.g., by syringe). The blood-side surface of the self-sealing membrane can be situated nearly flush with the top of the interior of the trap, in order to facilitate cleaning of the self-sealing port during disinfection, e.g., by reversing flow through the air trap using a dialysate or other cleaning fluid. Also, the inlet, outlet and internal wall of the container and the self-sealing port may be arranged to substantially eliminate stagnation regions, i.e., allow for few or no regions where blood can stagnate or clot. The self-sealing port can also serve as a blood sampling site, and/or to allow the introduction of liquids, drugs or other compounds into the blood circuit. A sealed rubber-type stopper can be used if access with a needle is contemplated. Using a self-sealing stopper with split septum permits sampling and fluid delivery using a needleless system.

Figure 19:
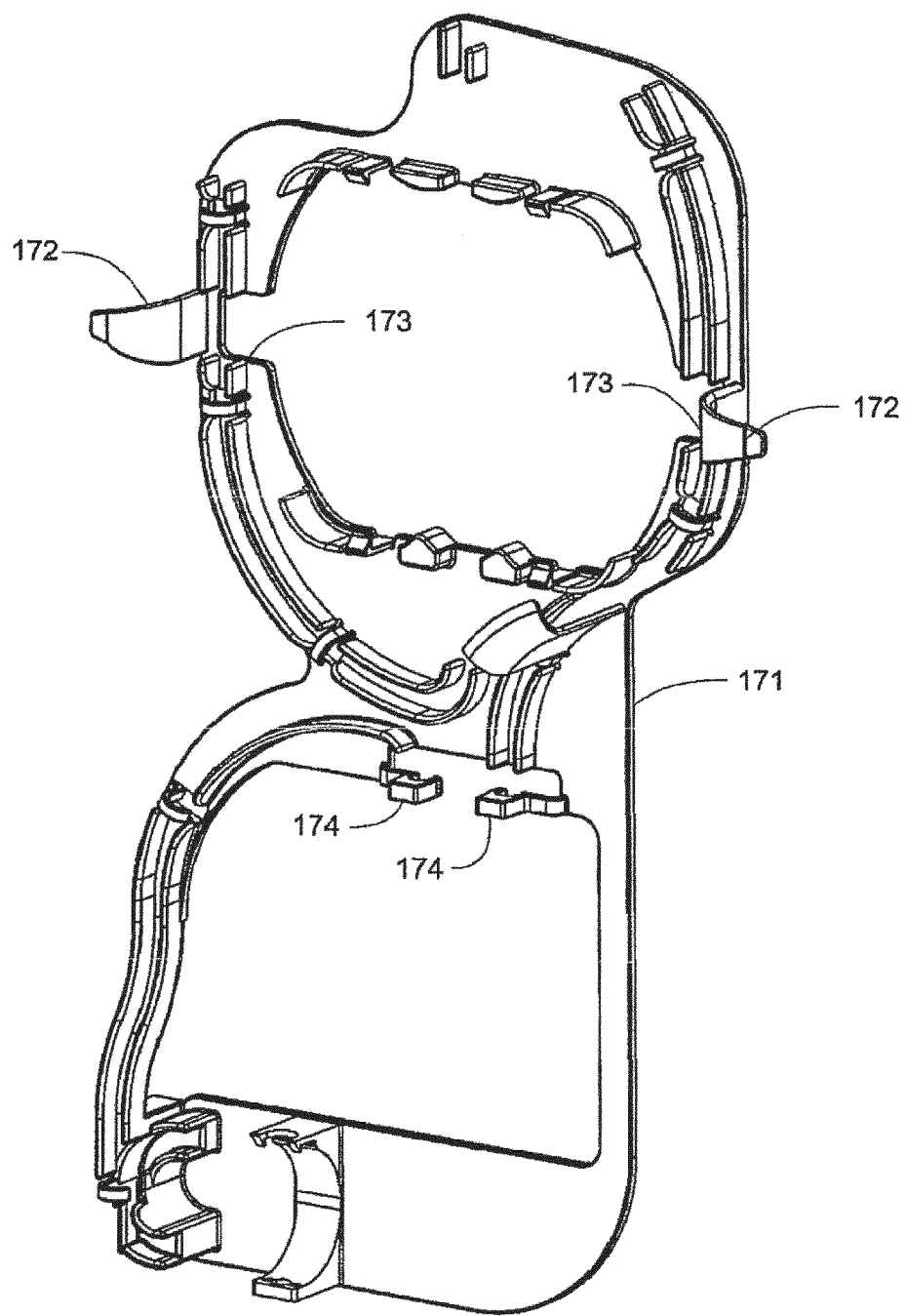
FIG. 19 right perspective view of a organizing tray for the blood circuit assembly of FIG. 18.

FIG. 19 shows the organizing tray 171 for the blood circuit assembly 17 without the various blood circuit assembly 17 components mounted. In accordance with one aspect of the invention, the organizing tray 171 includes handles 172 (in this embodiment, finger pulls) that a user can grip when mounting/dismounting the blood circuit assembly 17 to the front panel 511. Inward of the handles 172 are openings 173 that allow spring tabs on the front panel 511 to pass through and engage with the organizing tray 171 and/or the blood pump 13 cassette to hold the blood circuit assembly 17 in place on the front panel 511. In accordance with another aspect of the invention, the organizing tray 171 includes blood line engagement members 174 that each have a C-shaped recess or other hole through which a corresponding blood line 203, 204 passes. (In this context, a "hole" includes a recess like that shown in FIG. 19, a throughbore that has a continuous wall, e.g., as may be made by a drill, or other suitable opening.) As described in more detail below, the blood line engagement members 174 are used when mounting the blood lines 203, 204 in the occluder 513. In short, when mounting the blood lines 203, 204 in the occluder 513, the blood lines 203, 204 must be pulled and stretched downwardly (so as to reduce the outside diameter of the line) while being pushed horizontally into slots for the occluder 513. The blood line engagement members 174 function to both resist downward pulling on the blood lines 203, 204 (e.g., each line 203, 204 may include a stop ring above the respective engagement member 174 that cannot be pulled through the recess in the engagement member 174) as well as permit the user to press inwardly on the engagement member 174 to seat the lines 203, 204 in the occluder slots. The engagement members 174 are formed integrally with the organizing tray 171 so that a "living hinge" or relatively flexible portion of the organizing tray is positioned between the engagement member 174 and the main body of the organizing tray 171. This arrangement allows the engagement members 174 to be pushed inwardly relative to the organizing tray 171 as the connection portion between the engagement members 174 and the organizing tray main body flexes.

Figure 20:
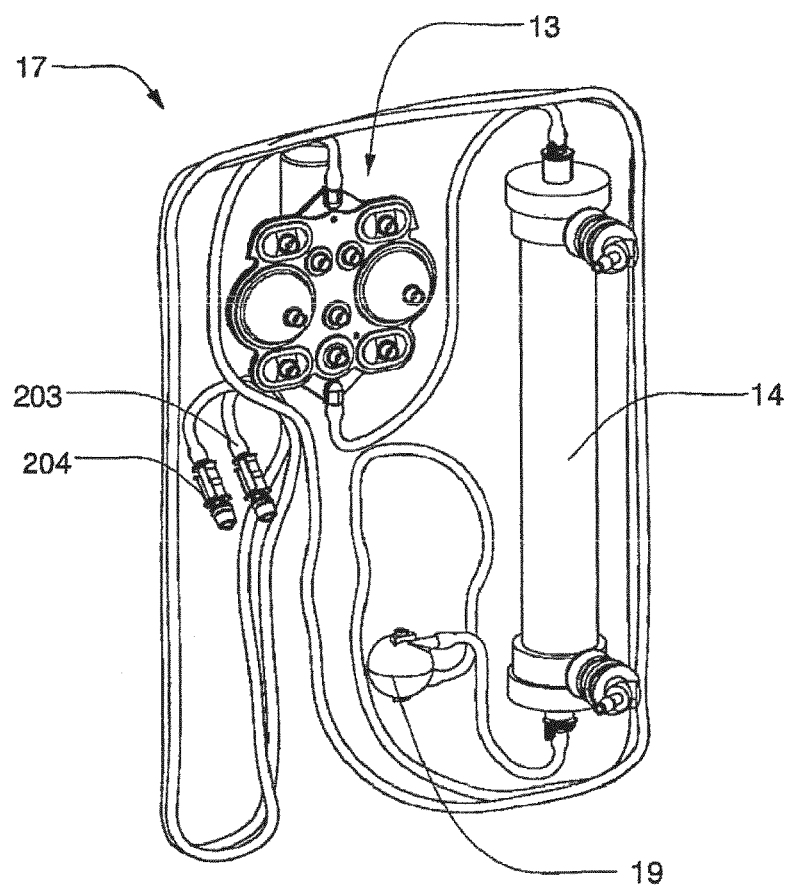
FIG. 20 is a left rear perspective view of the blood circuit assembly of FIG. 18.

FIG. 20 shows a rear view of the blood circuit assembly 17 with the organizing tray 171 removed. This view shows the rear side of the blood pump 13 section with control ports exposed. These control ports mate with corresponding ports 515 on the front panel 511 (see FIG. 17) so that pneumatic control (e.g., suitable air pressure or vacuum) can be applied to the pumps and valves to control their operation and flow through the blood circuit assembly 17. FIG. 20 also shows the offset of the inlet port of the air trap 19, i.e., the inlet port at the top of the air trap 19 is arranged to the rear of the vertical axis of the generally spherical container portion of the air trap 19.

Figure 20A:
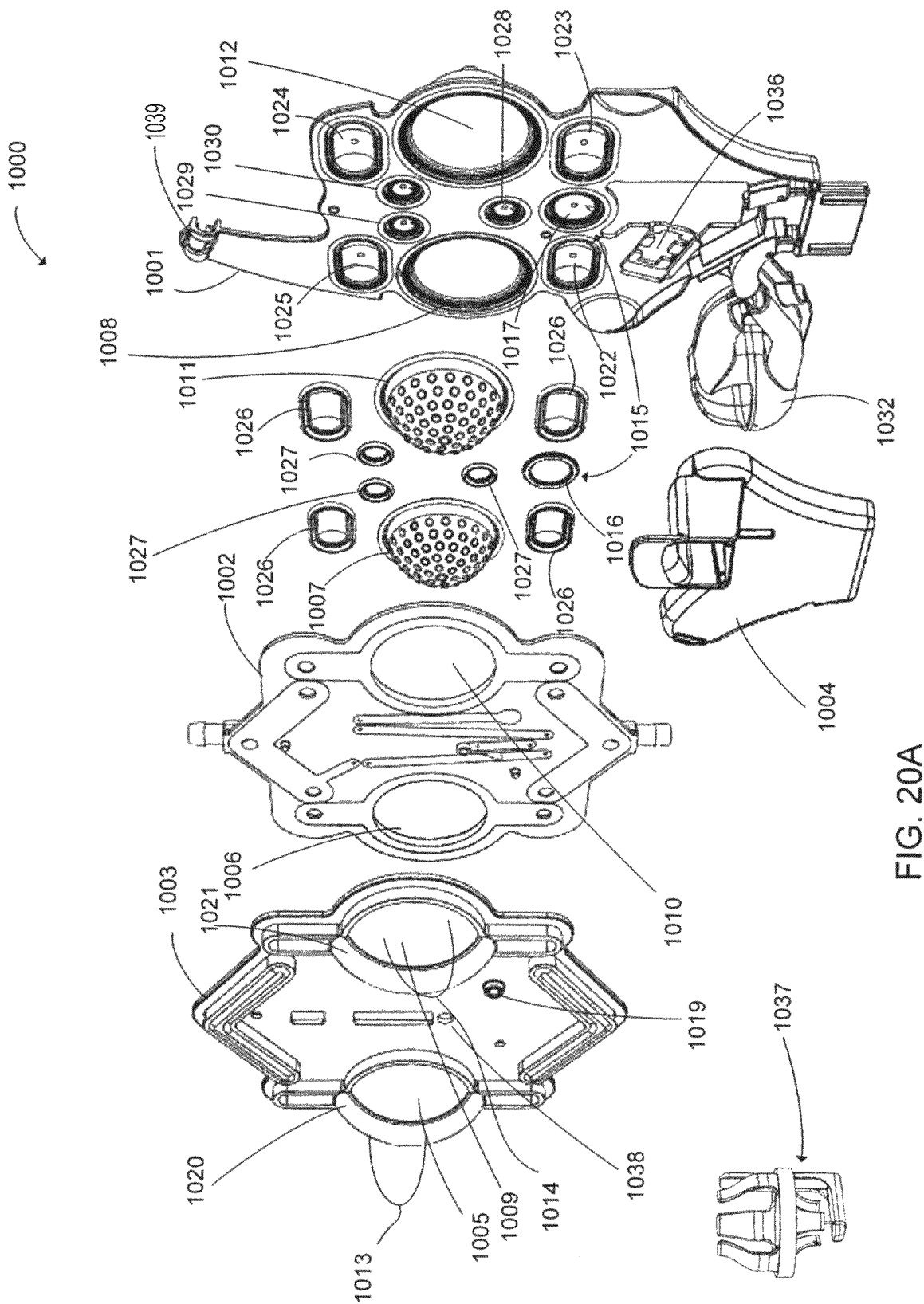
FIG. 20A is an front exploded view of an alternate embodiment of a blood pump cassette.
Figure 20B:
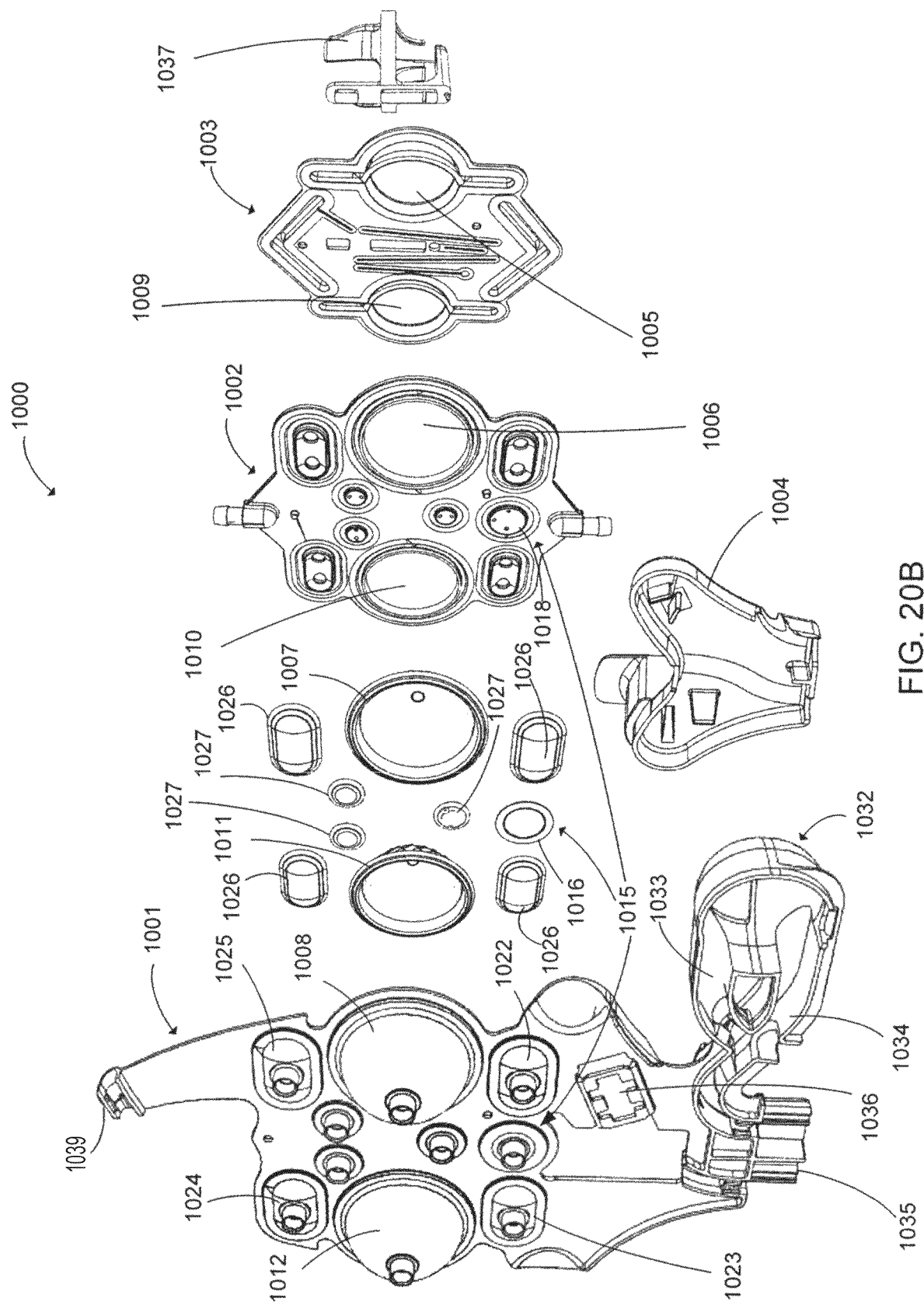
FIG. 20C is a front view of a bottom plate or back plate of the blood pump cassette of FIG. 20A.
FIG. 20D is a back view of a bottom plate or back plate of the blood pump cassette of FIG. 20A.

FIGS. 20A and 20B show exploded, perspective views of an alternative embodiment of a blood pump cassette 1000. FIG. 20A shows a front-perspective, exploded view of the cassette 1000 having a back (actuation side) plate 1001 that includes a tubing organizer formed with the back plate on a single molded piece of material. FIG. 20B shows a back-perspective, exploded view of the cassette 1000 of FIG. 20A. The cassette 1000 shown in FIGS. 20A-20D may be used in place of cassette 13 of FIG. 18A and organizing tray 171 of FIG. 19, combining many of the features of these components and substantially reducing the cost and complexity of manufacturing and assembling them.

The cassette 1000 includes a back plate 1001 that forms rigid outer walls of the actuation chambers of various valves and pumps, a mid plate 1002 that holds various valve and pump diaphragms and helps to define various flow paths in cassette 1000, and a front plate 1003 that forms rigid outer walls of some of the fluid chambers of the various valves and pumps of cassette 1000. The cassette 1000 optionally further includes a protective cover 1004 that is attachable to the front side of back plate 1001. The protective cover 1004 may include a holding arm for holding a vial that may be used for later mounting onto vial holder 1037. The protective cover 1004 can temporarily hold either an empty or full vial prior to inserting the vial into a vial holder 1037 for use during a procedure. That is, a vial may be coupled to a vial holder 1037 having a hollow spike that places the vial in vial holder 1037 in fluid communication with a fluid port 1038 in the front plate 1003. The vial may be filled, for example with anticoagulant medication for use during dialysis, or it may be empty and available for use during cleaning and disinfection procedures either before or after a dialysis treatment.

The cassette 1000 includes blood flow pumps 1013 and 1014 for moving liquid through the fluid flow side of the cassette 1000. That is, the cassette 1000 includes a left pump 1013 and a right pump 1014 for pumping fluid, which may be blood in the case of a hemodialysis apparatus. The pumps 1013 and 1014 (also referred to herein as pod pumps) may be actuated by a control fluid, such as air, a liquid, a gas, or other fluid that enters cassette 1000 through ports on back plate 1001. The left pod pump 1013 includes a rigid chamber wall 1005 formed on the front (or top) plate 1003, a rigid chamber wall 1008 formed on the back (or bottom) plate 1001, a hole 1006 formed on the middle plate 1002, and a flexible membrane 1007 that can flex between the rigid chamber walls 1013 and 1008. The space between the rigid chamber wall 1013 and the flexible member 1007 defines the fluid or blood side (i.e., fluid chamber) of the left pump 1013 and the space between the flexible membrane 1007 and the rigid chamber wall 1008 defines the pneumatic side (i.e., control chamber) of the left pump 1013. Likewise, the right pod pump 1014 includes a rigid chamber wall 1009 formed on the top plate 1003, a rigid chamber wall 1012 formed on the bottom plate 1001, a hole 1010 formed on the middle plate 1002, and a flexible membrane 1011 that can flex between the rigid chamber walls 1009 and 1012. The space between the rigid chamber wall 1009 and the flexible member 1011 defines the fluid or blood side (i.e., fluid chamber) of the right pump 1009 and the space between the flexible membrane 1011 and the rigid chamber wall 1012 defines the pneumatic side (i.e., control chamber) of the right pump 1014.

Each of the pod pumps 1013 and 1014 may include a pair of membrane-based entry/exit valves having fluid flow compartments formed from the top plate 1003 and control compartments formed from the bottom plate 1001. The valves may be actuated by the application of positive or negative fluid (e.g., pneumatic) pressure on individual flexible membranes via control ports on the bottom plate 1001. The fluid valves can be opened and closed to direct fluid flow when the pod pumps are pumping. Depending on how the valve actuations are sequenced in relation to the actuation of their associated pump, fluid may be pumped either in a forward direction, or in a backward direction. Non-limiting examples of pod pumps are described in U.S. patent application Ser. No. 11/787,212, filed Apr. 13, 2007, entitled "Fluid Pumping Systems, Devices and Methods," incorporated herein by reference. The pod pumps 1013 and 1014 may be operated in any suitable fashion, e.g., synchronously, asynchronously, in-phase, out-of-phase, etc., with fluid flow in either direction.

For hemodialysis applications, in some cases, an anticoagulant (e.g., heparin, or any other anticoagulant known to those of ordinary skill in the art) may be mixed with the blood within blood flow cassette 1000. For example, the anticoagulant may be contained within a vial (or other anticoagulant supply, such as a tube or a bag), and blood flow cassette 1000 may be able to receive the anticoagulant vial with a vial holder 1037 (which, in one embodiment, includes a needle or hollow spike) that can pierce the seal of the vial. The spike may be formed from plastic, stainless steel, or another suitable material, and may be a sterilizable material in some cases, e.g., the material may be able to withstand sufficiently high temperatures and/or chemical exposure so as to sterilize the material. As an example, the spike may be used to pierce the seal of the vial, such that anticoagulant can flow into blood flow cassette 1000 to be mixed with the blood in the blood flow path. In other cases, the vial may be filled or partially filled with water or dialysate during cleaning, disinfecting or priming operations.

A third pump 1015, which can act as a metering pump in some cases, in cassette 1000 can be used to control the flow of medication from an attached vial (such as anticoagulant) into a fluid path within the cassette 1000. Metering pump 1015 may be of the same or of a different design from the pumps 1013 and 1014. For example, metering pump 1015 may be a pod pump and may be actuated by a control fluid, such as air. For example, as is shown in FIGS. 20A-20D, the metering pump 1015 may include a rigid chamber wall 1015 formed within the back plate 1001, a rigid chamber wall 1018 formed on the mid plate 1002 (see FIG. 20B), and a flexible diaphragm 1015 dividing the pod into a fluid compartment or chamber and a control compartment or chamber. Valves 1028, 1029, 1030 may be connected to fluid flow paths joining in various combinations fluid port 1038, vent port 1019, a fluid flow path leading to or from a first or second pump (such as pump 1013), and a fluid flow path leading to or from metering pump 1015. The flow of medication (e.g., anticoagulant) or other fluid from an attached vial into a main fluid flow path in the cassette 1000 may thus be controlled by metering pump 1015; and periodically, air may be introduced from vent port 1019 by metering pump 1015 into an attached vial through port 1038 to equalize pressure within an attached vial with ambient pressure as medication or other fluid is withdrawn from the vial.

The cassette 1000 may also include an air vent coupled to a port 1019. Air may be introduced into the flow path of metering pump 1015 to equalize pressure in an attached vial with ambient pressure. In this case, valve 1029 closes flow between metering pump 1015 and the main flow path of the first 1013 (or second 1014) pump. In some cases, metering pump 1015 may also introduce air into the main flow path of the first 1013 or second 1014 pumps in order to allow a system controller to control the emptying of the blood or liquid carrying components of the system.

The pod pumps 1013 and 1014 include raised flow path 1020 and 1021 on the chambers 1005 and 1009, respectively. The raised flow paths 1020 and 1021 allow fluid to continue to flow through the pod pumps 1013 and 1014 after the diaphragms (i.e., flexible membranes) 1007 and 1011 reach the end of a stroke.

The cassette 1000 includes several valves 1022, 1023, 1024 and 1025 formed within the back plate 1001. The actuation (or pneumatic) side of the valves 1022-1025 and 1028-1030 are formed from bottom plate 1001, and have corresponding actuation ports for the entry or egress of control (e.g. pneumatic) fluid. Several diaphragms 1026 and 1027 installed on midplate 1002 complete the valves, while diaphragms 1007, 1011 and 1016 complete the pod pumps 1013, 1014 and metering pump 1015. The metering pump 1015 is completed by diaphragm 1016. In a preferred embodiment, the valves are actuated pneumatically, and as the valve diaphragm is pulled away from the adjacent holes in midplate 1002, liquid is drawn in, and as the diaphragm is pushed toward the holes, liquid is pushed through. The fluid flow is directed by the appropriate sequencing of the opening and closing of the valves 1022-1025, and 1028-1030.

The metering pump 1015 includes three passageways connected to the fluid chamber 1018 defined in the mid plate 1002. One passageway allows air from vent 1019 to be pulled into the metering pump 1015, a second passageway allows the air to be pushed to the spike/source container connected to vial holder 1037, and also alternately draws liquid from the source container or vial, and the third passageway allows the liquid from the source container to be pushed by the metering pump 1015 to a main fluid line connected to first pump 1013 (or pump 1014 in an alternate embodiment). Valves 1028, 1029, and 1030 determine whether the metering pump 1015 moves fluid or air, and in which direction.

Figure 20C:
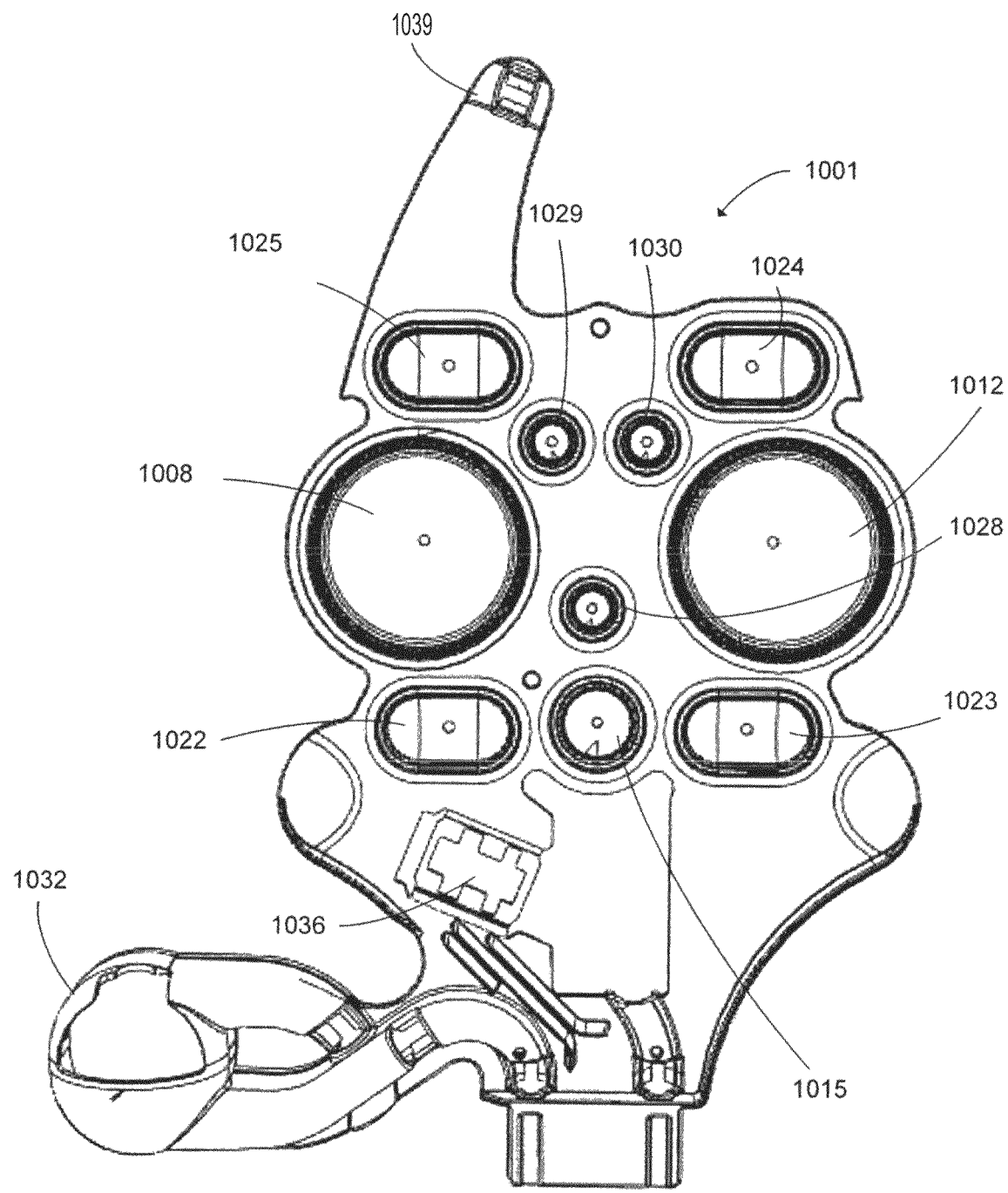
Figure 20D:
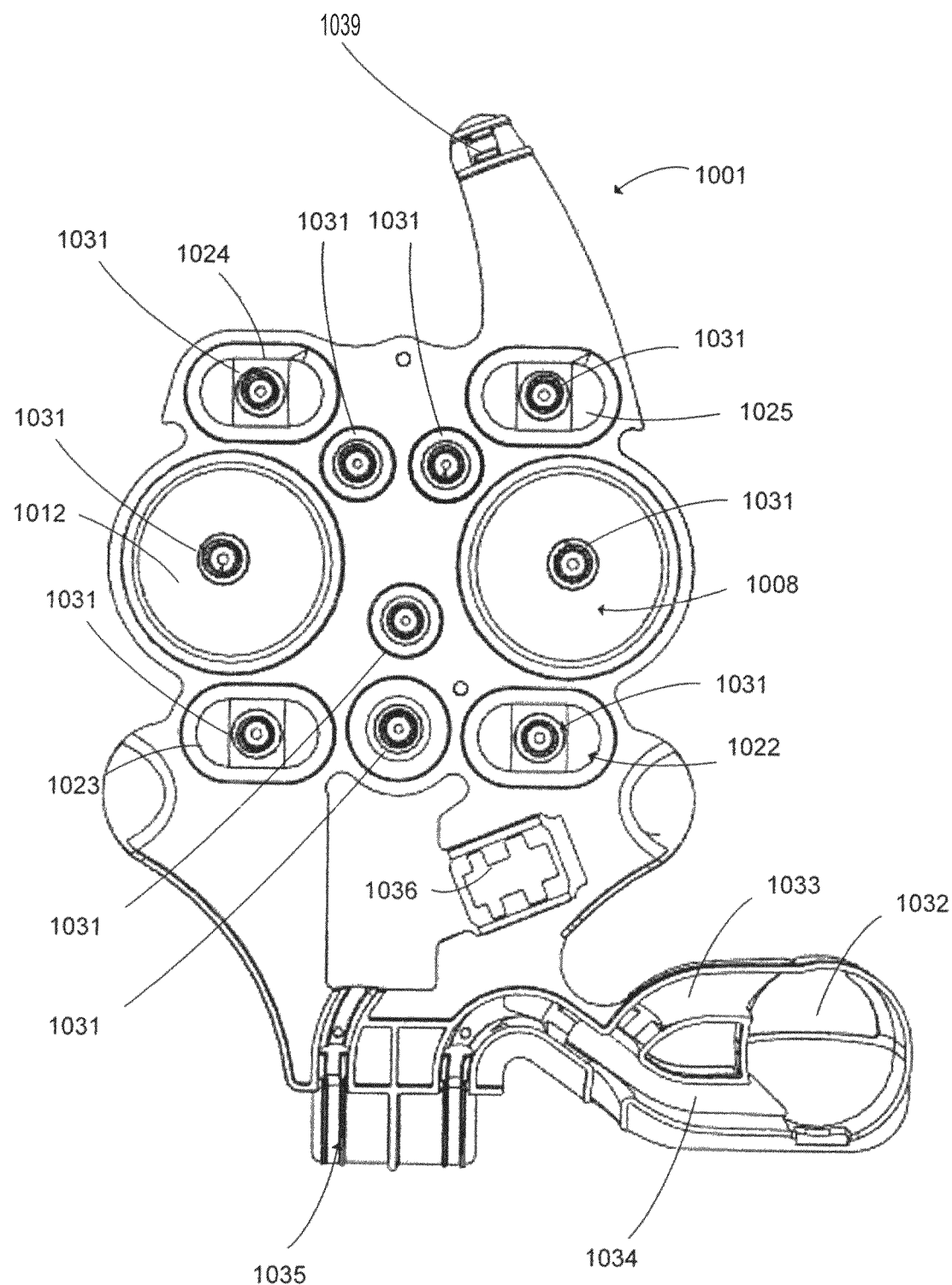

Referring next to FIG. 20C, the inner view of the bottom plate 1100 is shown. The inside view of the pod pumps 1008 and 1012, the metering pump 1015, and the valves 1022, 1023, 1028, 1025, 1029, 1030, and 1024 actuation/air chambers are shown. The pod pumps 1008 and 1012, the metering pump 1015 and the valves 1022, 1023, 1028, 1025, 1029, 1030, and 1024 are actuated by a pneumatic air source. Referring now to FIG. 20D, the outer side of the bottom plate 1100 is shown. The source of control fluid (e.g. air under positive or negative pressure) is connected to this side of the cassette. In one embodiment, tubes connect to various ports 1031. In other embodiments, the ports 1031 are arranged to plug into a control port assembly (e.g., control port assembly 615 in FIG. 17A) on the front panel of dialysis unit 51 (e.g., front panel 511 in FIG. 17).

Figure 21:
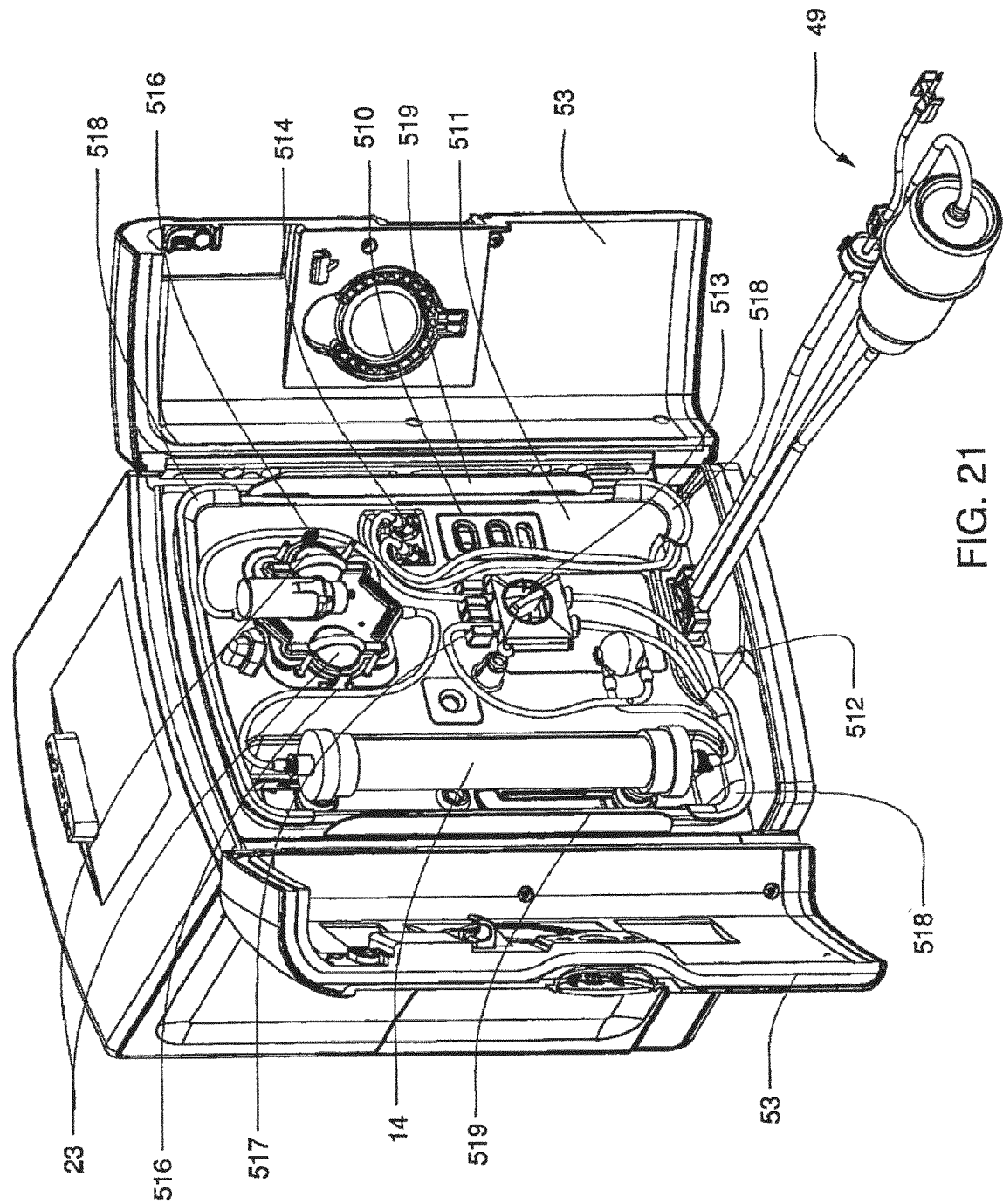
FIG. 21 shows a left front perspective view of the front panel of the system of FIG. 7.
Figure 22:
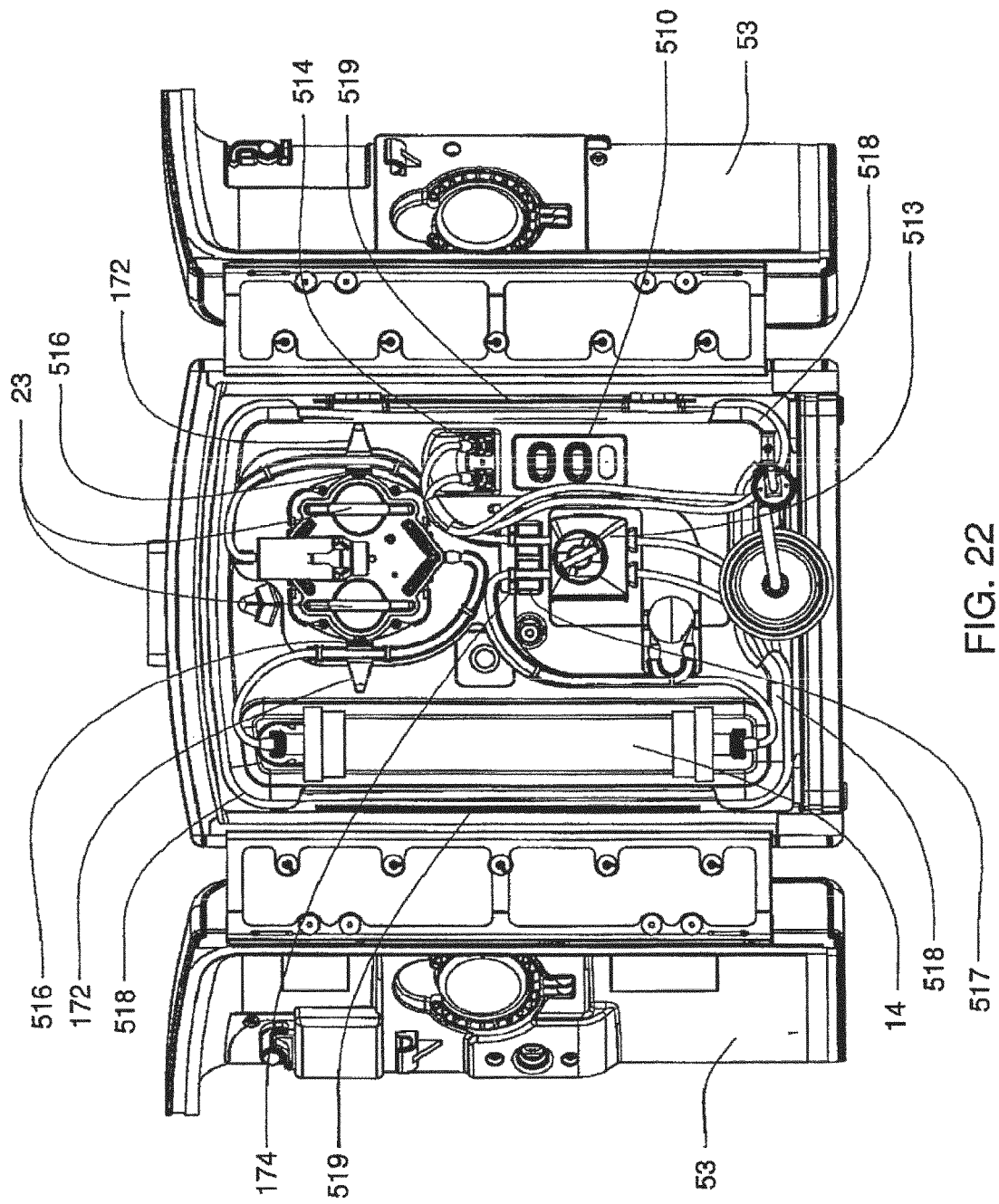
FIG. 22 shows a front view of the front panel of the system of FIG. 7.

Referring now to FIGS. 20A-20D, the bottom plate 1001 includes various organizer features integrated thereon. The bottom plate 1001 includes an air trap retaining member 1032 having tube guides 1033 and 1034 defined on the bottom plate 1001. The tube guides 1033 and 1034 guide a tube to and from an air trap disposed within the air trap retaining member 1032. The bottom plate 1001 also includes additional tube guides 1035 and 1039. The bottom plate 1001 also defines a receiving portion 1036 to receive an electrical connector that may be used in an arrangement to monitor for disconnection of the arterial or venous lines from a patient during therapy. FIG. 21 shows a perspective view of the front panel 511 of the dialysis unit 51 with the blood circuit assembly 17 mounted to the front panel 511 without the organizing tray 171. (Normally, the blood circuit assembly 17 would include the organizing tray 171, but the tray 171 is not shown in the example so as to more clearly show components at the front panel 511.) On opposite sides of the blood pump 13 cassette, the front panel 511 has spring tabs 516 that extend forwardly and resiliently engage with the blood pump cassette and/or the organizing tray 171 to retain the blood circuit assembly 17 in place. The tabs 516 may include a barb or other feature to help retain the blood circuit assembly 17 in place. The spring tabs 516 may be flexed outwardly to release their hold on the blood circuit assembly 17, allowing its removal. However, in the absence of an outwardly directed force on the spring tabs 516, the tabs 516 will remain engaged with the blood circuit assembly 17. FIG. 22 shows a front view of the front panel 511 with the organizing tray 171 of the blood circuit assembly 17 included. To remove the blood circuit assembly 17 from the front panel 511, a user may place index fingers behind the handles 172 while simultaneously placing thumbs on the inner side of the spring tabs 516 (the sides nearest the blood pumps 23) and flexing the spring tabs 516 outwardly and away from the pumps 23. This causes the spring tabs 516 to release the blood circuit assembly 17, e.g., disengagement of barbs on the tabs 516 from the blood pump 13 and/or the organizing tray 171. Of course, to remove the blood circuit assembly 17, other connections must be removed, including connections to the dialyzer 14 and the blood line connection points 514, as well as removal of the lines 203, 204 from the occluder 513. When mounting the blood circuit assembly 17 to the front panel 511, the organizing tray 171 may be grasped at the handles 172 and properly aligned, e.g., so that the spring tabs 516 are aligned to pass through the openings 173 and the control ports of the blood pump 13 cassette are aligned with the corresponding ports 515 on the front panel 511. The blood circuit assembly 17 may then be simply pushed into place, so that the spring tabs 516 engage with the organizing tray 171 and/or the blood pump cassette. Other connections can then be made, such as connections to the dialyzer 14, mounting of the blood lines 203,204 with the occluder 513, etc.

FIG. 21 also shows the slots 517 that hold the blood lines 203, 204 for leading into the occluder 513. The slots 517 define a channel that is slightly smaller than the outside diameter of the blood lines 203, 204 so that the lines 203, 204 tend to remain in the slots 517 after placement in the slots. This helps to ensure proper association of the lines with the occluder 513. Once the blood circuit assembly 17 is mounted on the spring tabs 516, the user may then engage the blood lines 203, 204 with the slots 517 by stretching the lines 203, 204 downward (with the engagement members 174 on the organizing tray 171 engaging the stop ring or other feature on the respective line 203, 204 and resisting the downward pull) and pushing the lines 203, 204 into a corresponding slot. The lines 203, 204 can be pushed into place by pressing inwardly on the engagement members 174, which as described above, are flexible and bend inwardly relative to the organizing tray 171. The lines 203, 204 can then be routed through the occluder 513.

In accordance with another aspect of the invention, the front panel 511 includes a blood line wrap feature around the periphery of the front panel 511. In this illustrative embodiment, the front panel 511 includes flanged portions 518 along the top edge and at lower corners of the front panel 511. This allows a user to wrap the blood lines 203, 204 around the periphery of the front panel 511 by placing the lines 203, 204 in a channel defined by the flanged portions 518. The lines 203, 204 may be wrapped in a clockwise direction, starting from a point near the bottom of the dialyzer 14, and ending at a point near the lower right corner of the front panel 511. The blood lines 203, 204 may then be connected at the blood line connection points 514, e.g., to allow disinfecting fluid to be circulated through the blood lines 203, 204. As a result, the blood lines 203, 204 can be neatly retained on the front panel 511, allowing easy access to other components on the front panel 511 and allowing the user to close the doors 53 with minimal concern for pinching the blood lines 203, 204 between the doors 53 and the dialyzer unit housing 51. Alternatively, the blood lines 203, 204 may be first connected at the blood line connection points 514, and then wrapped in a clockwise direction, starting from a point near the bottom of the dialyzer 14, and ending at a point near the lower right corner of the front panel 511. This ensures that the blood lines are properly distributed along the flanged portions 518 to reach the connection points 514. Vertical fences 519 may also be provided along the left and right sides of the front panel 511 to help keep the blood lines 203, 204 in a desired position and away from the hinge plates 533 and other possible pinch points.

Figure 5A:
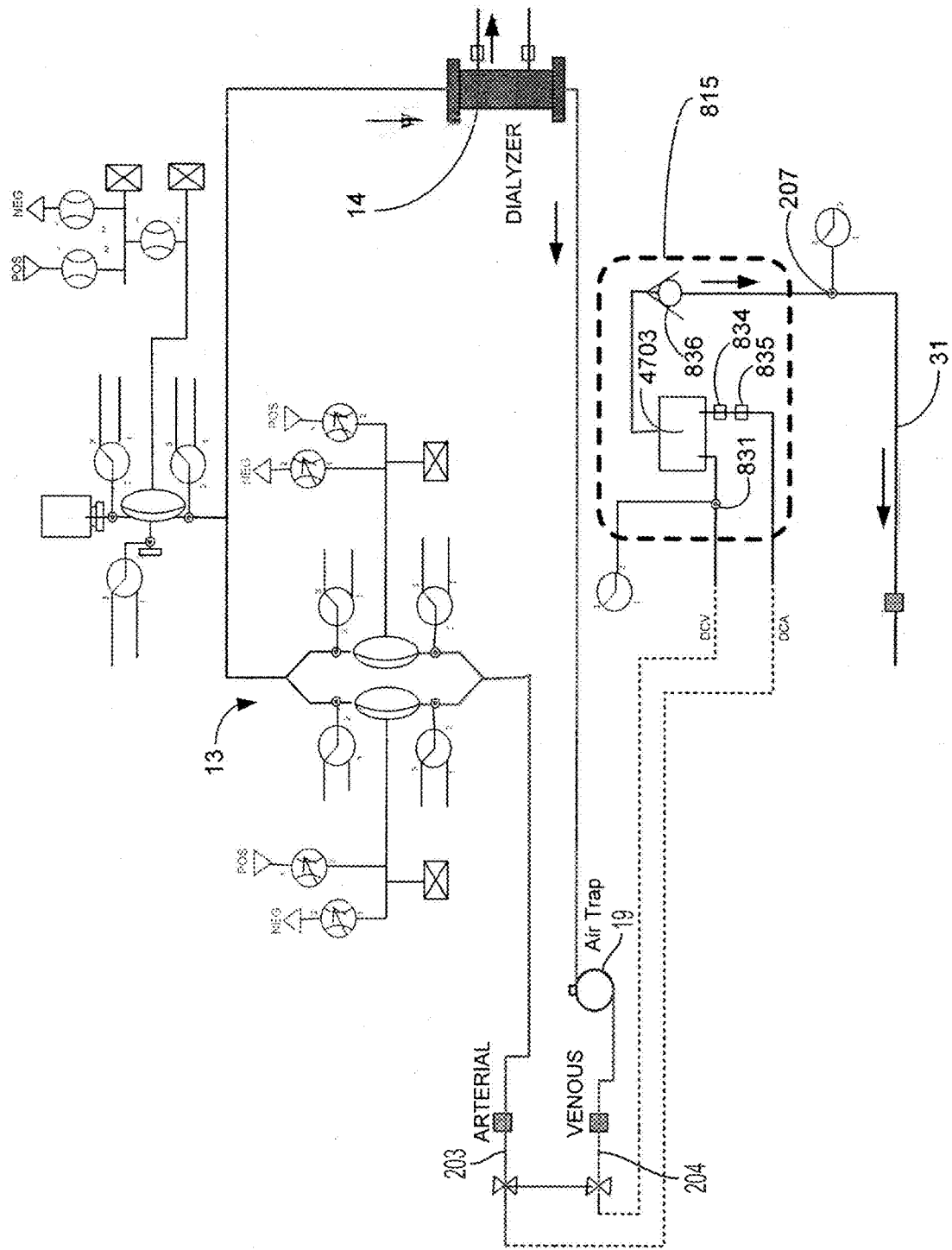
FIG. 5A is a schematic fluid flow diagram illustrating a flow path for a drain assembly in an illustrative embodiment.
Figure 21A:
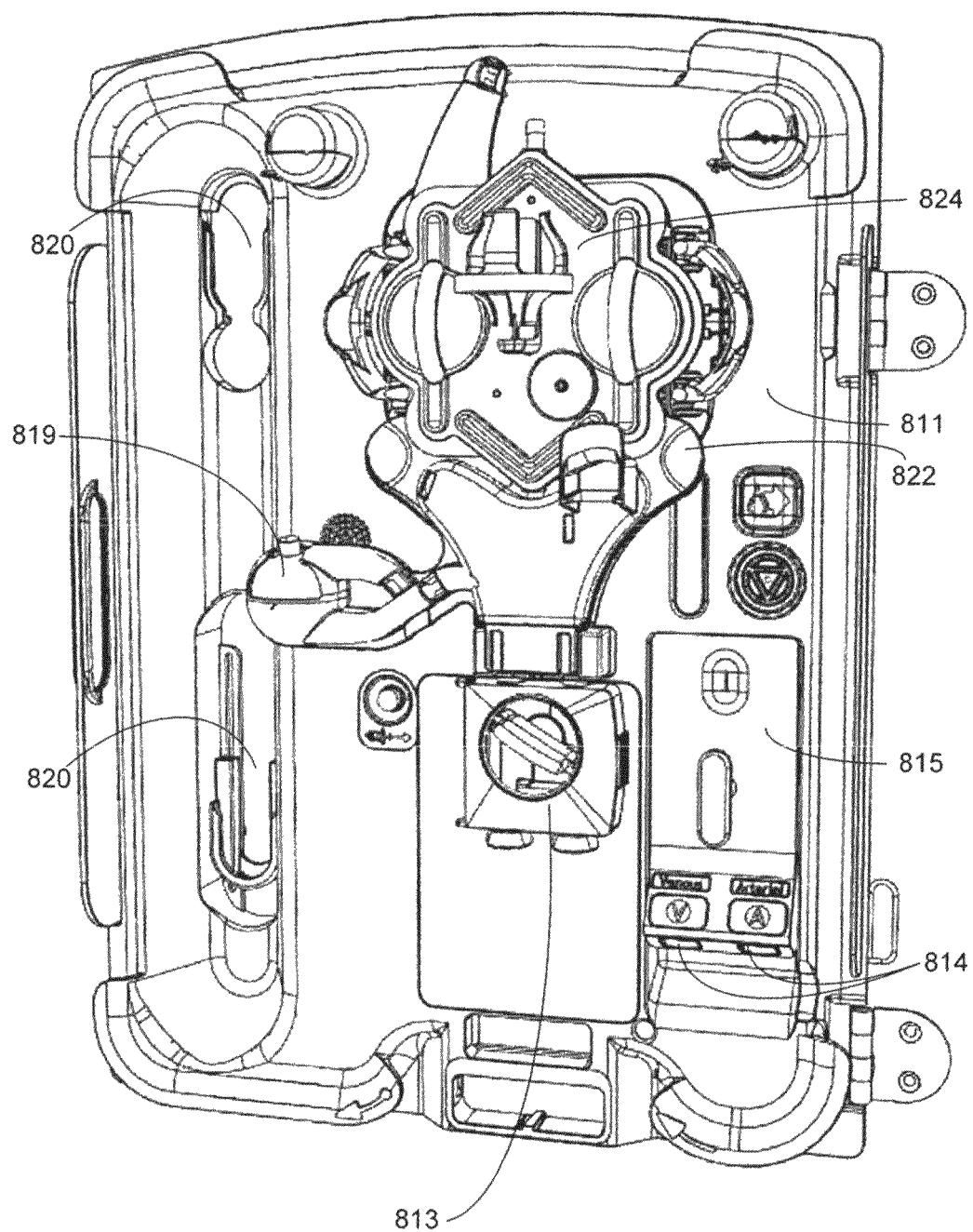
FIG. 21A shows a front view of an alternate embodiment of a front panel assembly in an illustrative embodiment.

In another aspect, as shown in FIG. 21A, an alternate embodiment of a front panel assembly 811 may include a modular drain assembly (or drain cassette) 815 having connection points 814 into which the arterial and venous blood lines may be connected. As shown in FIG. 5A, the drain cassette 815 includes a common pathway to a drain line 31 for both the arterial and venous blood lines during priming, cleaning and disinfecting operations. Water, dialysate solution or another fluid may be introduced into the blood pathways of dialysis system 5 through the semipermeable membrane of dialyzer 14 in order to expel air from the blood pathways and to prime the blood pathways, or in order to clean and disinfect the blood pathways. The drain cassette 815 may optionally include a valve in one or both arterial or venous blood pathways. In an embodiment, an electronically controlled valve 831 in or near the modular drain cassette 815 in the venous line may permit the blood pumps on the blood pump cassette 13 to sequentially fill or clear the arterial line while the valve 831 in the venous line is closed, and then fill or clear the venous line upon opening of the valve. In this method, any air or contaminants in the arterial line are forced to the drain outlet of the drain cassette 815, rather than into the venous tubing. Alternately, the valve 831 may be arranged to control flow between the arterial line and the drain, e.g., so contents in the venous line can be forced to the drain outlet rather than into the arterial line. The drain cassette 815 may also optionally include conductivity and/or temperature sensors 834, 835. A temperature sensor may be used, for example to monitor the temperature of the fluid circulating through the blood lines during heat disinfection. Conductivity sensors may be used to monitor the conductivity of water or dialysate solution being circulated through the blood lines during tests of the urea or sodium clearance of a dialyzer, for example. An electronically controlled drain control valve 207 may be placed either at the drain outlet of drain cassette 815, or it may be positioned external to the drain cassette 815 (as shown in FIG. 5A). Drain control valve 207 may be useful, for example, when heated water or chemical disinfectant is being circulated within the blood circuit components of dialysis unit 51. The drain cassette 815 may be constructed for ease of connection to and disconnection from the front panel 511 or 811 of dialysis unit 51. A single handle-operated latch (such as a bayonet connection, for example,) may be included which secures the drain cassette 815 onto the front panel by a turn of the handle.

Figure 21B:
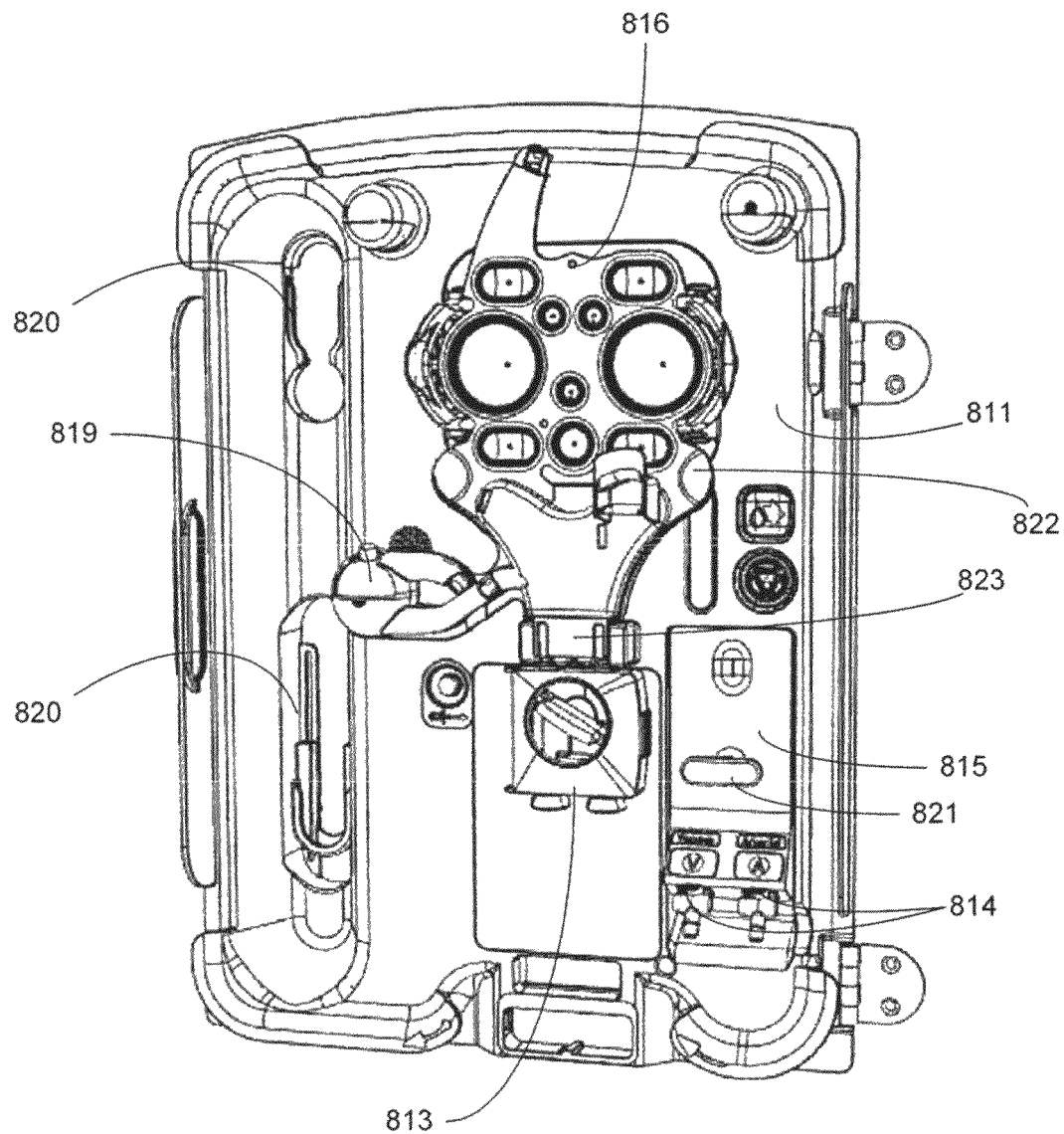
FIG. 21B shows the front panel assembly of FIG. 21A with the top and middle plate components of the blood pump cassette removed for clarity in an illustrative embodiment.

FIG. 21A also shows an alternate embodiment of a blood pump cassette and organizing tray assembly. In some embodiments, the organizing tray 822 may be incorporated in the pneumatic actuation plate (or back plate) of the blood pump cassette 824. FIG. 21B shows the front panel assembly 811 with the top and middle plate components of blood pump cassette 824 removed for clarity. In this example, the organizing tray 822 and the back plate 816 of blood pump cassette 824 have been combined into a single molded piece. In this example, the air trap 819 is supported by an extension of the organizing tray 822 and is located in a vertically more elevated position than in the embodiment shown in FIG. 19 and FIG. 29. Moving the air trap to a higher position relative to the occluder 813 or the air-in-line detectors 823 may increase the ability of the blood pump in a reverse-flow procedure to draw any air bubbles present in the venous tubing into the air trap 819. For example, the an inlet of the air trap 819 may be supported by the organizing tray 822 at a position above an outlet of the air trap when the blood circuit assembly is mounted to a dialysis unit. In addition or alternately, the inlet and/or outlet of the air trap may be supported by the organizing tray at a position above a highest point of flexible tubing that extends from the outlet of the air trap to the occluder position. Such an arrangement may help expel any air in the venous tubing into the air trap 819.

In another aspect of the invention, a modular drain cassette may be included, having the function of monitoring and draining fluid (such as water or dialysate solution) flowing through the blood circuit of the dialysis unit 51—the blood circuit including the blood pumps, the blood flow compartments of the dialyzer, the air trap and the arterial and venous blood tubing. As shown in FIG. 5A, when the arterial and venous blood tubing is not connected to a patient, it may be connected to a drain chamber/air trap 4703, which ultimately leads to a drain line 31. This connection allows for the circulation of heated water, for example, for cleaning and disinfection of the blood circuit components, for determination of dialyzer clearance characteristics, or for priming of the blood circuit with dialysate solution. In one aspect of the invention, a drain cassette 815 may comprise a drain chamber/air trap 4703, a valve 831 on one or both of the arterial and venous blood lines, a check valve 836 in the drain line, and temperature and conductivity sensors 834, 835 into one modular component that can be readily connected to or disconnected from the front panel of dialysis unit 51. As shown in FIG. 21A, in an embodiment, the arterial and venous blood lines may be connected to the drain cassette 815 via connection points 814 on front panel 811. The drain cassette 815 may include a channel or chamber which merges fluid flow from the venous and arterial blood lines, exiting via a common outlet to a drain line 31.

As noted previously, the drain cassette 815 may optionally include a valve 831 in the venous path (or, alternatively in the arterial path, or both paths). In a preferred embodiment, the valve 831 is a pneumatically operated membrane valve, which is actuated by an electromechanical valve plumbed to a pneumatic pressure source and under the control of an electronic controller. The drain cassette 815 may also optionally include conductivity and thermal probes 834, 835 in the fluid flow channel or chamber within the housing of the cassette 815. In a preferred embodiment, the drain outlet, the pneumatic control port and the electrical connections for the conductivity and thermal sensors comprise paired connectors, one member of each pair rigidly attached to the housing of the drain cassette 815, and the other member of each pair rigidly attached to the front panel 811 of dialysis unit 51 in order to allow a user to mount or dismount drain cassette 815 quickly and easily from front panel 811. As with the other blood circuit components of the front panel 511 or 811 (including dialyzer 14, blood pump cassette 13 or 824, air trap 19 or 819, and arterial and venous blood lines), drain cassette 815 may be configured to be readily dismountable from dialysis unit 51.

Figure 31:
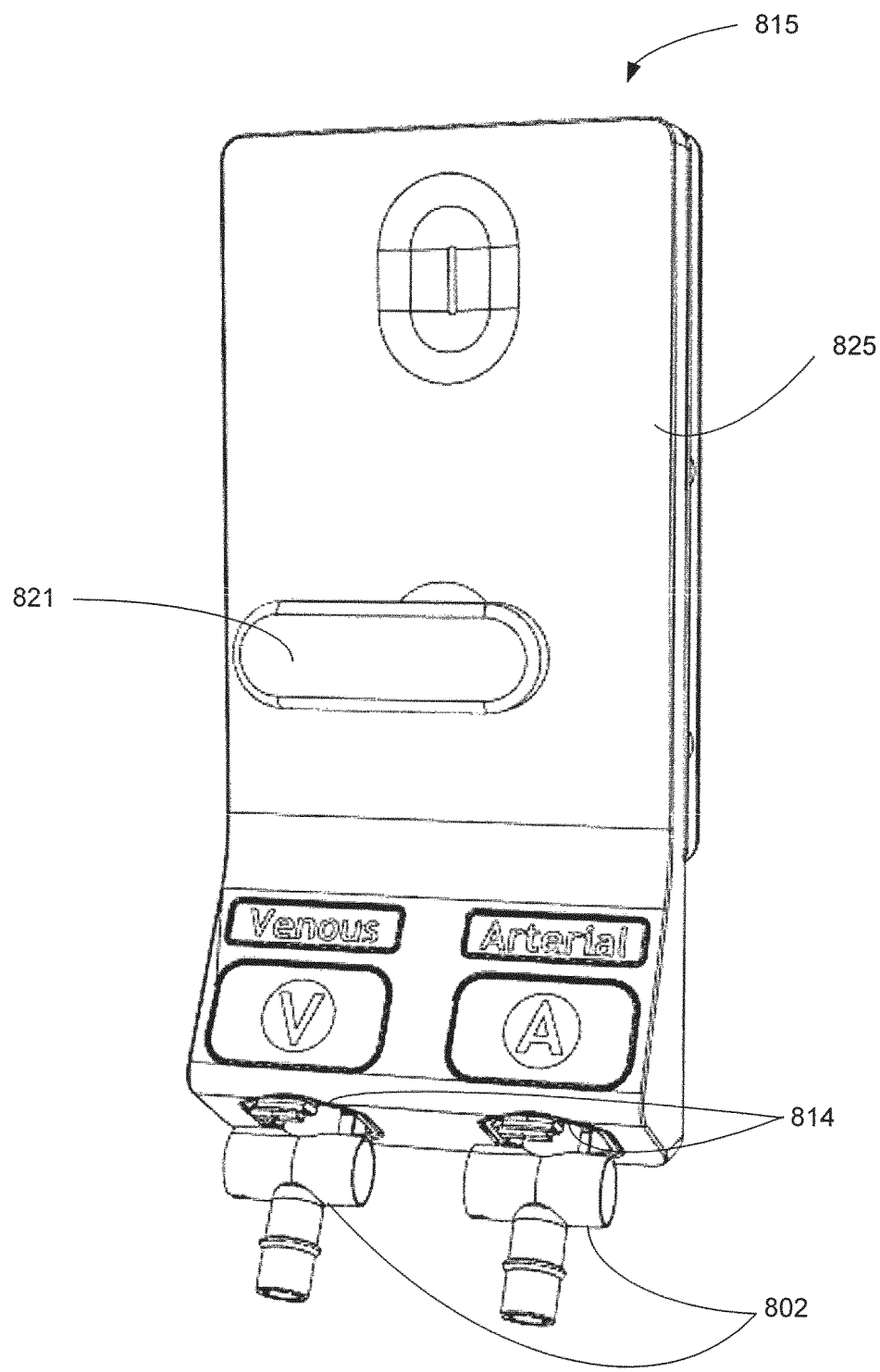
FIG. 31 shows an exemplary modular drain cassette in an illustrative embodiment.

FIG. 31 shows an exemplary modular drain cassette 815. In this view, the escutcheon 825 of the drain cassette 815 includes markings identifying the arterial and venous line connection points 814. A handle 821 anterior to the escutcheon 825 may be grasped with a single hand and turned to engage or disengage the drain cassette 815 from the front panel 811. Blood line connectors 802 for each of the arterial and venous blood lines are shown engaged within their respective connection ports or points 814 on the drain cassette 815.

Figure 32:
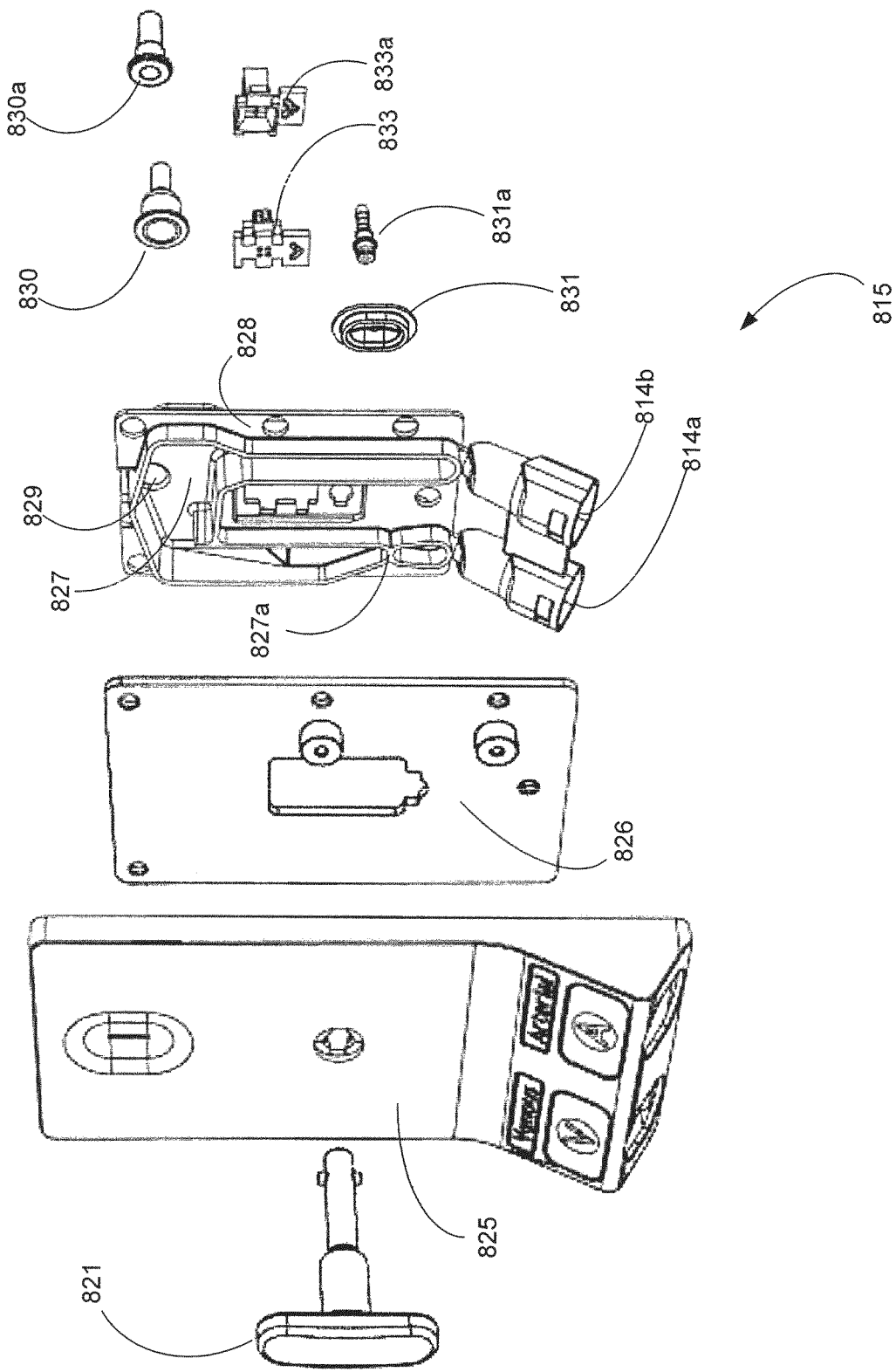
FIG. 32 shows the drain cassette of FIG. 31 in an exploded view with an escutcheon positioned anterior to a front wall of the drain cassette in an illustrative embodiment.

FIG. 32 shows drain cassette 815 in an exploded view, with escutcheon 825 anterior to the front wall 826 of the drain cassette 815. In this example, front wall 826 sealingly forms a front wall for the common channel or chamber 827 of the housing 828 of drain cassette 815. A common outlet 829 to a drain line from the channel 827 is equipped with a fluid connector 830 mounted on the back wall of housing 828, which optionally may include a one-way check valve (e.g., such as a duckbill valve) to prevent fluid within the drain line from re-entering the channel 827. A mating connector 830a is mounted on front panel 811, and is connected to a fluid line ultimately leading to drain. Outlet 829 is preferably positioned higher than either fluid connection points 814a and 814b, in order to trap and ultimately expel to drain any air that may be present in the arterial or venous blood lines when connected to drain cassette 815. In this regard, the fluid channel 827 may have a U shape, with the venous and arterial blood line connectors 802 fluidly coupling with a respective connection port 814a, 814b at ends of the U shape, and the drain outlet port 829 located at the bend of the U shape. A valve 831 may be present on one or both fluid channel portions of channel 827 leading from connection points 814a and 814b. Thus, the valve may controllably open and close fluid communication in the channel 827 between the connection ports 814 and the drain outlet port 829. In embodiments where only one valve 831 is provided in the channel 827, flow between one connection port 814 and the outlet drain port 829 may be controlled by the valve while fluid communication between the other connection port 814 and the drain outlet port 829 may be permanently open. In the illustrated example, a pneumatically actuated membrane valve 831 mounted on the back of housing 828 is positioned over the portion of the channel 827a leading from venous blood line connection point 814a. A mating pneumatic connector 831a mounted on the front panel 811 supplies valve 831 with positive or negative pneumatic pressure to actuate the valve, a pneumatic pressure line extending to front panel 811 from a pneumatic pressure distribution module or manifold located in a rear portion of dialysis unit 51. Both connectors 830 and 831 may be constructed to form radial sealing engagements (e.g., using elastomeric O-rings) with mating connectors 830a and 831a on the front panel 811 in order to allow for drain cassette 815 to be plugged into or unplugged from front panel 811 with relative ease. Similarly, an electrical connector 833 may be mounted on the back wall of housing 828 to make electrical connections outside of channel 827 with temperature and/or conductivity probes positioned within channel 827. Electrical connector 833 may be constructed to form a keyed connection with a mating electrical connector 833a on front panel 811 in order to facilitate engagement and disengagement of the connector when drain cassette 815 is installed or removed from front panel 811. In some embodiments, the connections of the outlet drain port connector 830, the valve control port connector 831 and the electrical connector 833 to respective connectors on the panel 511 may be made essentially simultaneously and/or in a single operation, e.g., by pushing the drain cassette 815 into place on the panel 511.

Figure 33:
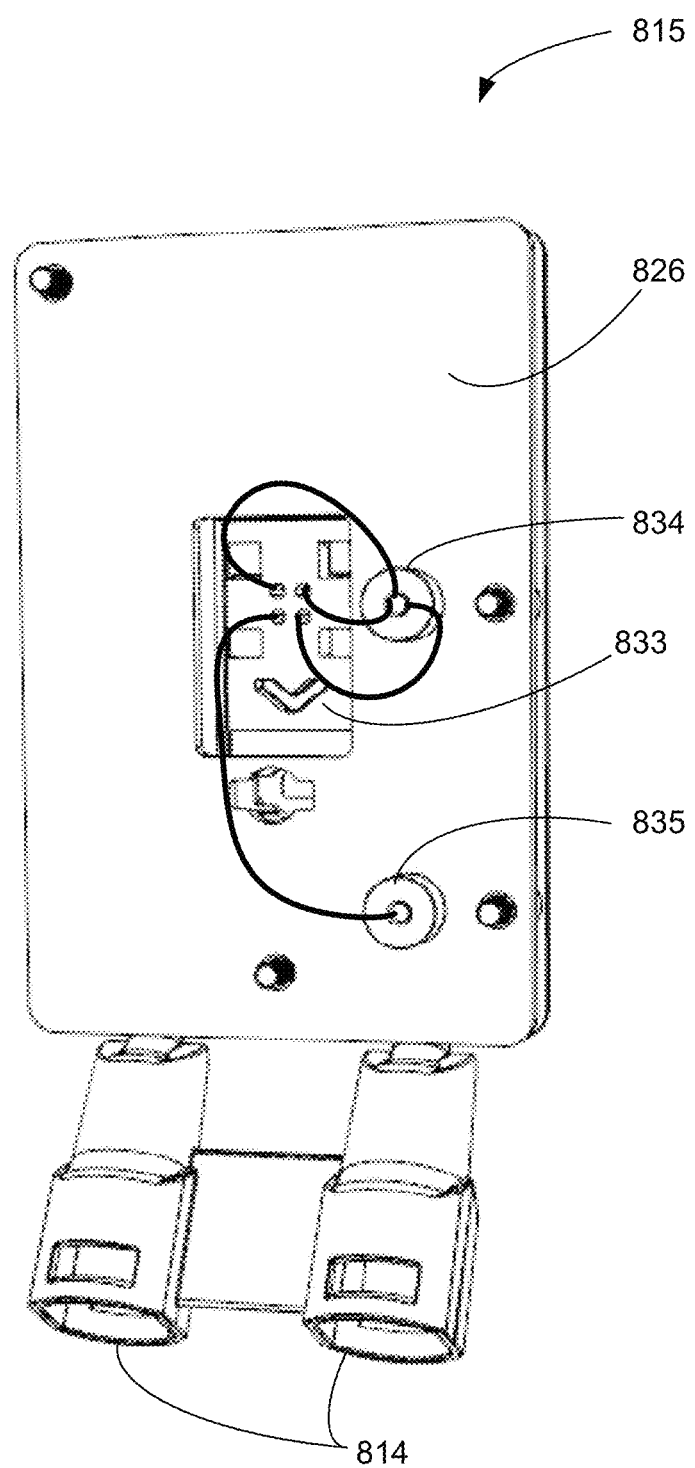
FIG. 33 shows a perspective view of the front wall of the drain cassette of FIG. 31 in an illustrative embodiment.

FIG. 33 shows a perspective view of drain cassette front wall 826. In which electrical connections are illustrated between probes 834 and 835 and connector 833. In this example, probe 834 comprises a thermistor and one of a pair of conductivity sensors, extending into channel 827 to detect both fluid temperature and conductivity. Probe 835 similarly extends into channel 827 as the second probe in a pair of conductivity sensors extending into channel 827.

Figure 34:
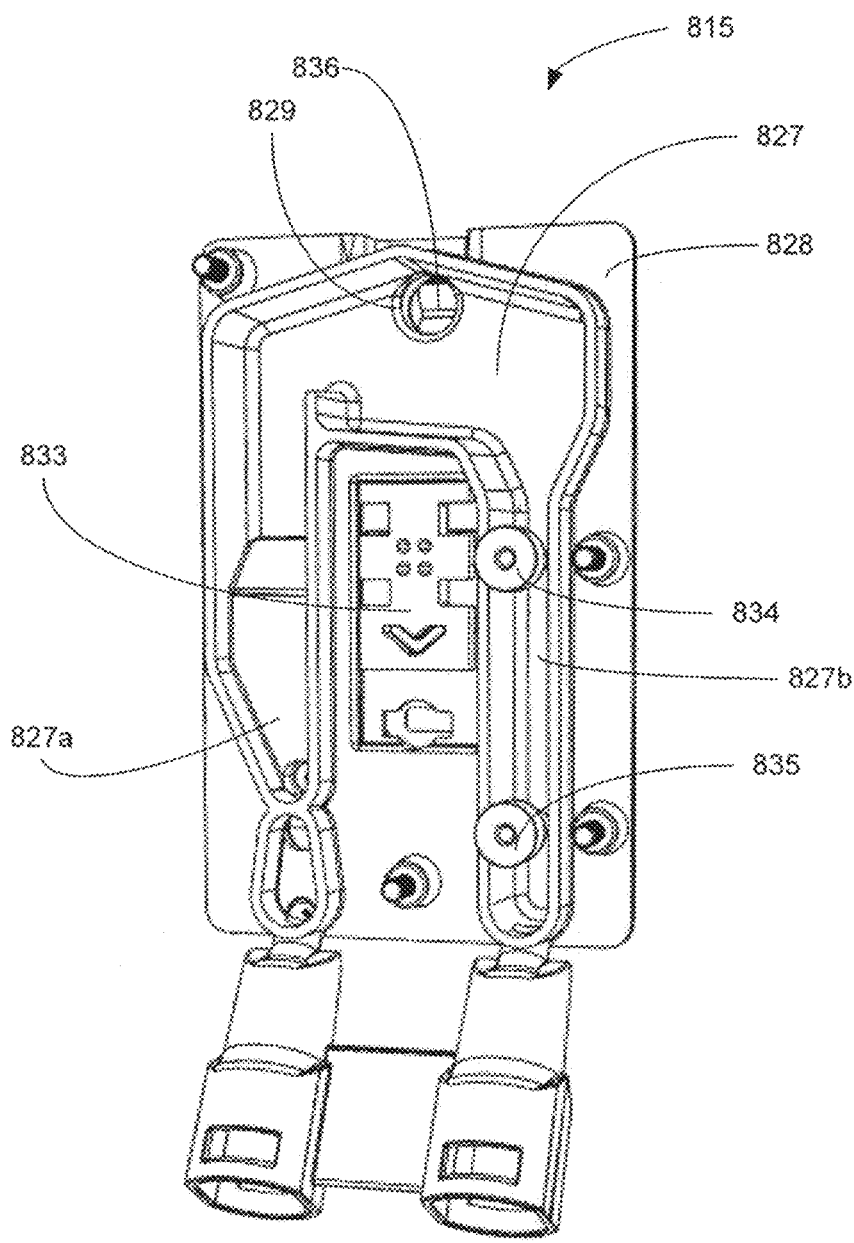
FIG. 34 shows a main housing of the drain cassette of FIG. 31 with the front wall removed for clarity purposes in an illustrative embodiment.

FIG. 34 shows the main housing 828 of drain cassette 815, the front wall 826 having been removed for clarity. Thermal and/or conductivity probes 834 and 835 are shown to illustrate their positioning in a portion 827b of fluid flow channel 827. (Each probe, although sealingly installed on front wall 826, has an elongated element that penetrates through front wall 826 to reside in some portion of fluid channel 827). Electrical connector 833 is shown to be positioned in an area of housing 828 that is outside channel 827. In an embodiment, a check valve, such as a duckbill valve 836, may be mounted within drain connector 830 (shown in FIG. 32).

Figure 35:
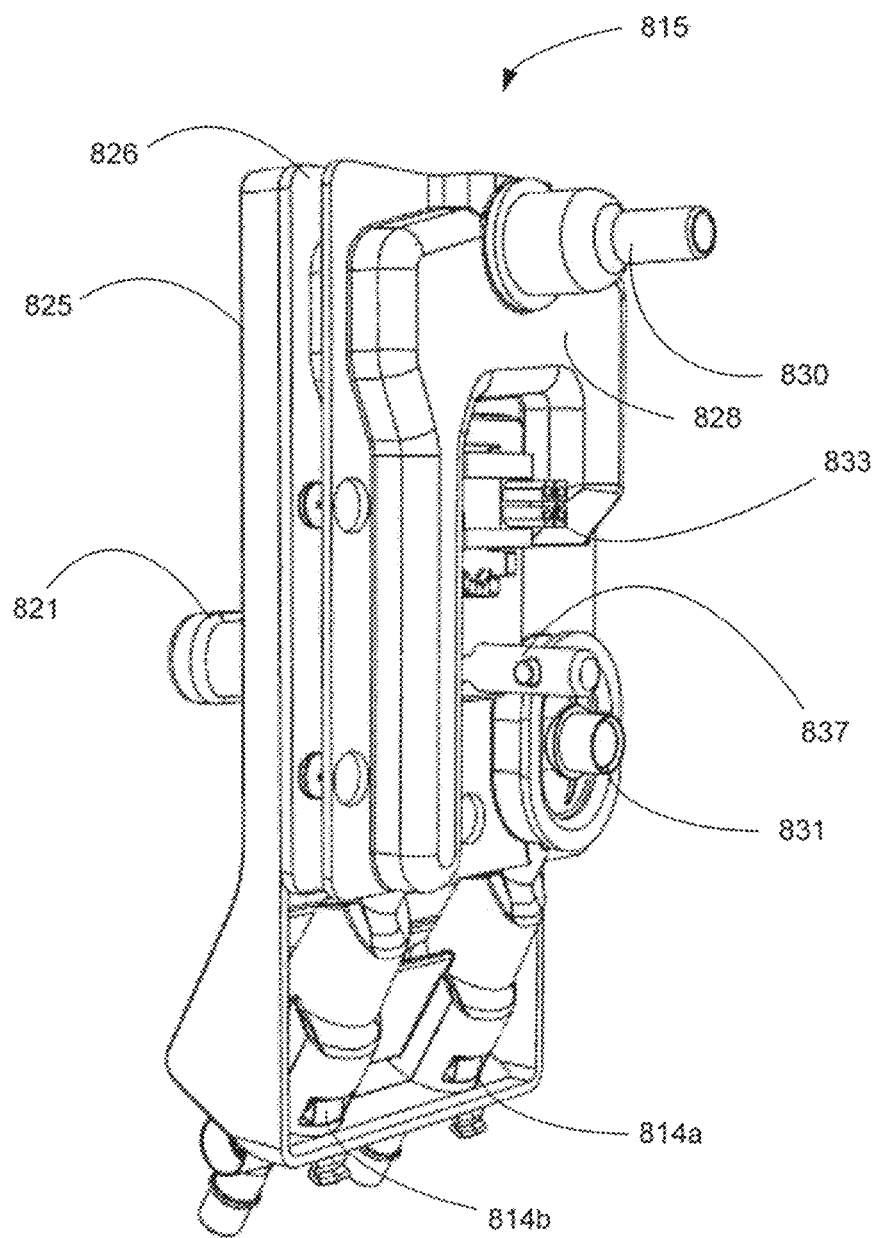
FIG. 35 shows a rear, perspective view of the drain cassette of FIG. 31 in an illustrative embodiment.

FIG. 35 shows a rear perspective view of drain cassette 815. Male fluidic connector 830 is arranged to connect to a mating connector 830a on front panel 811, which is connected to a drain line. Male pneumatic connector 831 is arranged to connect to a mating connector 831a on front panel 811, which is connected to a pneumatic pressure line. Male electrical connector 833 is arranged to connect to a mating connector 833a on front panel 811, which carries electrical connections from thermal and/or conductivity sensors in housing 828 to a system controller in a rear portion of dialysis unit 51. Latch member 837, connected to handle 821, is arranged to insert into a keyhole of front panel 811 in order to engage and lock drain cassette 815 onto front panel 811.

Figure 36:
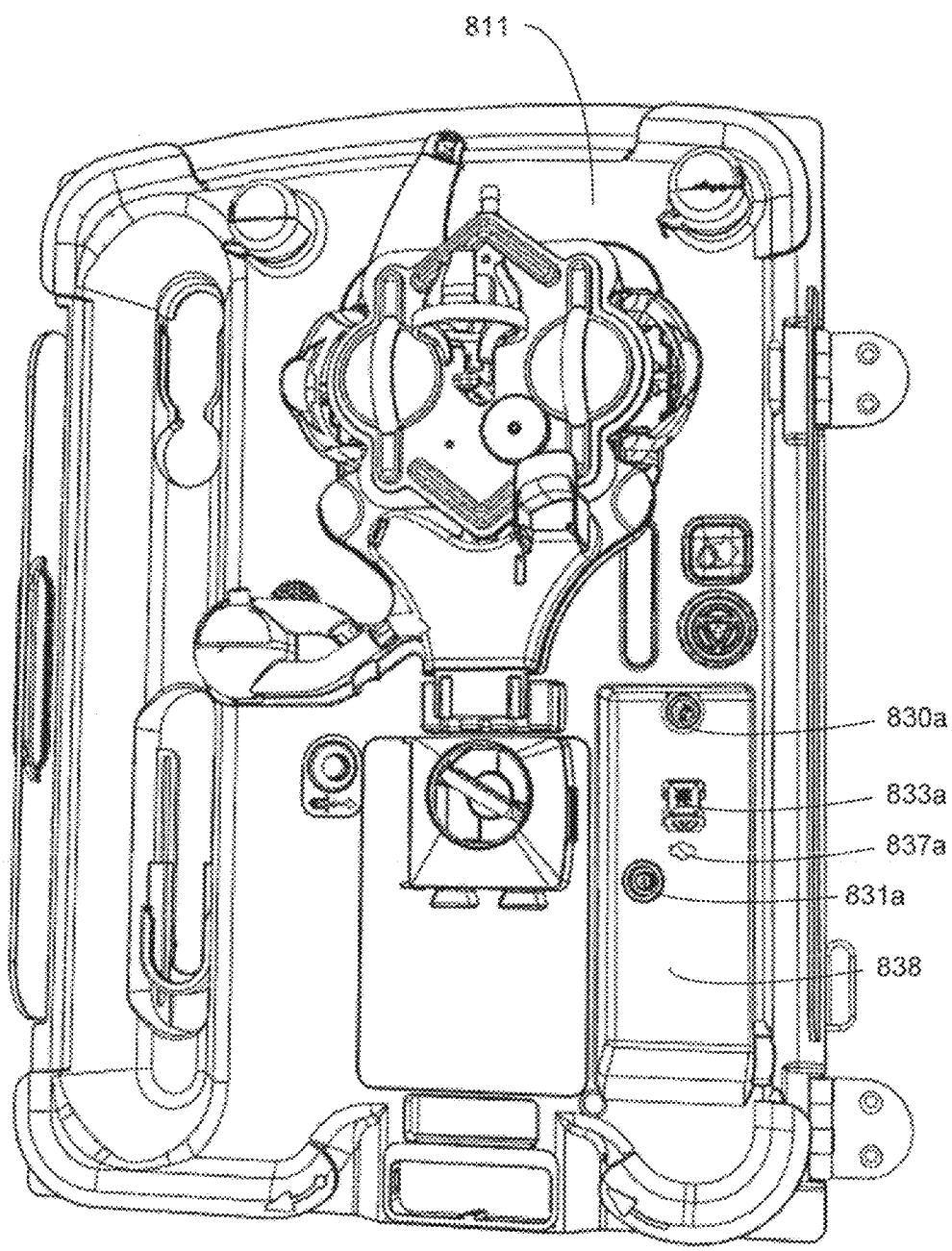
FIG. 36 shows a front panel in which a drain cassette has been dismounted in an illustrative embodiment.

FIG. 36 shows front panel 811 in which drain cassette 815 has been dismounted. Drain cassette recess 838 is arranged to accept drain cassette 815. The user need only align drain connector 830, pneumatic valve connector 831 and electrical connector 833 on drain cassette 815 with their counterpart connectors 830a, 831a and 833a on front panel 811 and push the cassette 815 into place to make the needed pneumatic and electrical connections. Latch member 837 of handle 821 on drain cassette 815 is inserted into keyhole 837*a*, and handle 821 may be turned ¼ or ½ turn to lock drain cassette 815 into recess 838, resulting in an arrangement of the front panel as shown in FIG. 21B.

The modular features of drain cassette 815 advantageously allow a user to easily mount and dismount substantially all of the blood-bearing components of the dialysis system (except possibly for distal portions of drain line 31). Thus, the dialysis unit 51 may be made available for use by more than one individual by simply swapping out the blood bearing components (e.g., a blood circuit assembly and drain cassette), each set of which is assigned to each individual user. The microbiological barriers afforded by the dialyzer semi-permeable membrane, by an ultrafilter for incoming water or dialysate within the dialysate-side circuit, and by the dialysate-side disinfection procedures between each use of the dialysis unit 51 allow for the dialysate-side components to be reusable among different users. Having a modular drain cassette 815 along with the other modular blood circuit components allows the dialysis unit 51 to be used as conveniently in a multi-user clinic setting as in a single-user home setting.

Figure 23:
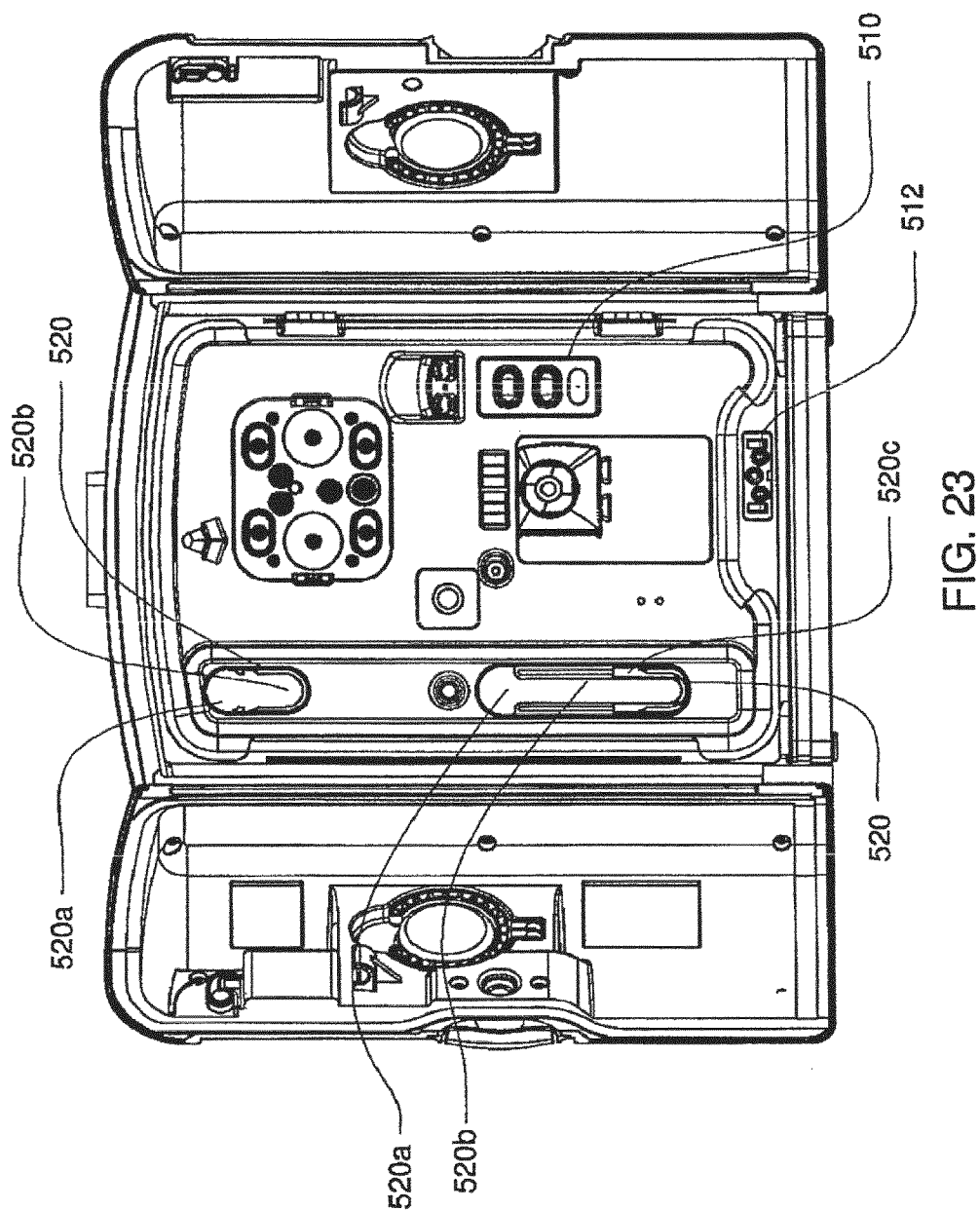
FIG. 23 shows a front view of the front panel of the system of FIG. 7 with a pair of mounting features for the dialyzer.
Figure 24:
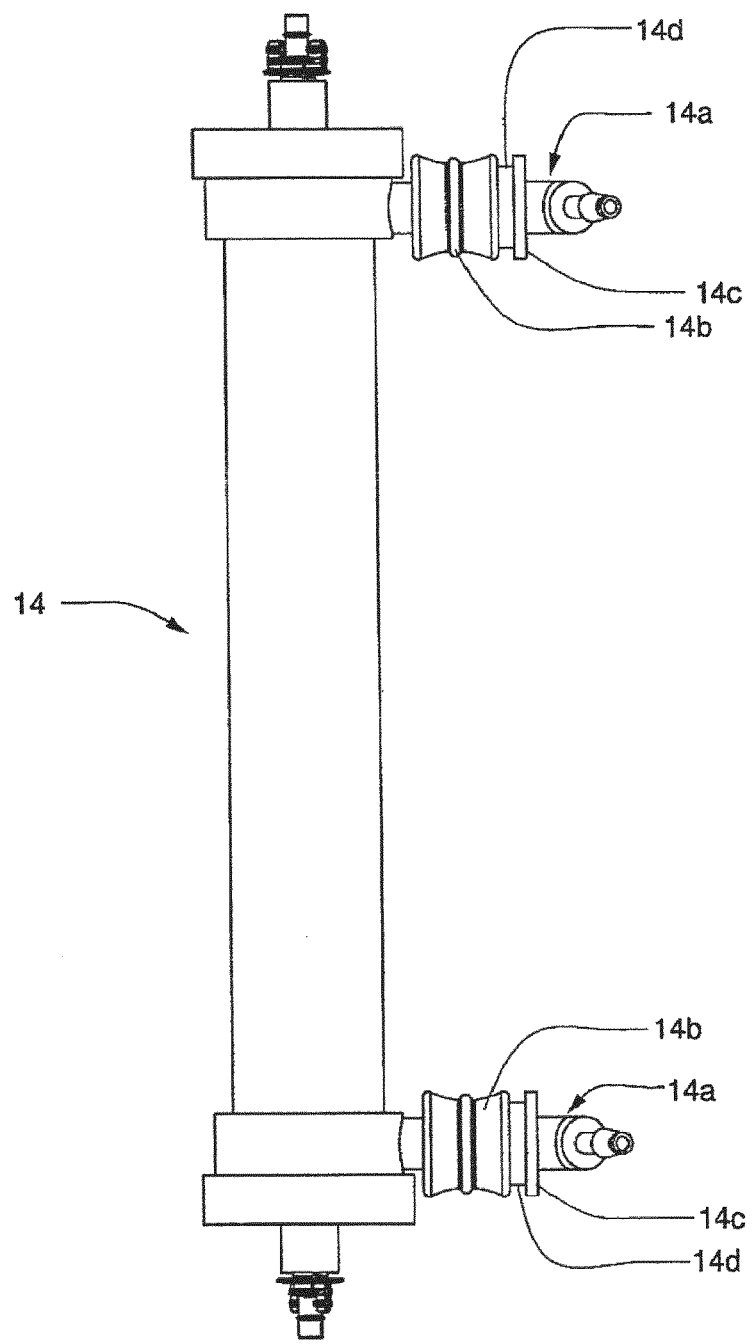
FIG. 24 shows a side view of a dialyzer with quick-connect fittings attached to the dialysate inlet/outlet ports of the dialyzer.

In accordance with another aspect of the invention, the front panel 511 of the dialysis unit 51 (or other suitable component) may be arranged to accommodate a variety of differently sized and/or shaped dialyzer units 14. Different patients, and in some cases even the same patient over time, may be prescribed different dialyzers so as to provide different treatment conditions. Thus, the dialysis unit 51 is preferably arranged to operate with multiple different types of dialyzers 14. In many cases, different dialyzers 14 have different dimensions, such as the overall diameter and/or length of the dialyzer unit. In this illustrative embodiment as shown in FIG. 23, the front panel 511 includes a dialyzer mount with a pair of "keyhole" features 520 that are arranged to engage with a respective dialysate quick-connect fitting on the dialyzer 14. Each keyhole feature 520 includes an upper insertion area 520*a* sized to receive a portion of the quick-connect fitting and a lower flanged portion 520*b* that has a width that is smaller than an overall diameter of the quick-connect fitting and that engages with a grooved area of the quick-connect fitting. So as to aid in understanding of these features, FIG. 24 shows a dialyzer 14 with quick connect fittings 14*a* attached at dialysate inlet and outlet ports of the dialyzer 14. (Blood inlet and outlet ports are located at the extreme top and bottom of the dialyzer 14 shown in FIG. 24.) The quick connect fittings 14*a* shown are of a standard type, and most, if not all, dialyzers 14 have dialysate inlet/outlet ports that are arranged to engage with the standard quick connect fittings 14*a*. The quick connect fittings 14*a* each include a slide element 14*b* that is moved to the right (as shown in FIG. 24) relative to a base 14*c* to allow the fitting 14*a* to be engaged with a dialysate port on the dialyzer 14. When the slide element 14*b* is moved to allow the fitting 14*a* to be attached to the dialyzer 14, a groove 14*d* is closed. However, once the fitting 14*a* is properly seated on the inlet/outlet port of the dialyzer 14, the slide element 14*b* may be released, allowing a spring (not shown) to move the slide to the left as shown in FIG. 24, reestablishing the groove 14*d* to the condition shown in FIG. 24. Thus, when the quick connect fitting 14*a* is properly engaged with the dialyzer 14, the groove 14*d* will be present as shown in FIG. 24.

To mount the dialyzer 14 to the keyhole features 520, the quick connect fittings 14*a* may be partially inserted into the upper insertion area 520*a* of the top and bottom keyhole features, respectively, so that the groove 14*d* of each fitting 14*a* is aligned with a flange of the lower flanged portion 520*b* of the keyhole features 520. (Note that the upper insertion area 520 of the bottom keyhole feature 520 may be made longer than that shown in FIG. 23 to allow the accommodation of a wider range of dialyzer lengths.) With the grooves 14*d* aligned with the flanges, the dialyzer 14 may be lowered so that the quick connect fittings 14*a* are fully received into the lower flanged portions 520*b* of the keyhole features 520.

In accordance with another aspect of the invention, one or both of the keyhole features 520 may be adjustable so that the weight of the dialyzer 14 is shared by both lower flanged portions 520*b* of the keyhole features 520. For example, in this illustrative embodiment, the bottom keyhole feature 520 has part of the lower flanged portion 520*b* adjustable in vertical position relative to the top keyhole feature 520. In this way, the portion of the lower flanged portion 520*b* may be adjusted in vertical position so that, with the top quick connect fitting 14*a* supported by the flanged portion 520*b* of the top keyhole feature 520, the movable portion of the flanged portion 520*b* of the bottom keyhole feature can be moved, e.g., upwardly, so that the bottom quick connect fitting 14*a* is also supported by the flanged portion 520*b*. Thus, the weight of the dialyzer 14 can be shared by both keyhole features 520. The flanged portion 520*b* may be made adjustable in any suitable way. In this embodiment, the flanged portion 520*b* has a "U" shaped member 520*c* that is vertically slidable along the vertical flanges and can be fixed in place by tightening a set of thumb screws. The "U" shaped member 520*c* may engage the quick connect fitting 14*a* so that the "U" shaped member 520*c* supports the weight (at least in part) of the dialyzer 14.

Although in the embodiment above, the dialyzer 14 is supported by keyhole features in the front panel 511, a support arrangement for the dialyzer may be configured in other ways. For example, the upper insertion area 520*a* is not necessarily required. Instead, only flange portions (e.g., in the shape of a "U" shaped flange having opposed flange portions) may be provided to engage the dialyzer quick connect fittings. The flange portions may be offset from the front surface of the front panel 511 to provide clearance for the fitting and allow the flange portions to engage with the grooves of the quick connect fittings. Also, the flange portions need not be provided in a vertical orientation as shown, but instead may be oriented at an angle to the vertical, e.g., in a horizontal arrangement. The flange portions may have a detent, catch, or other feature to help maintain the dialyzer in place as well.

Figure 25:
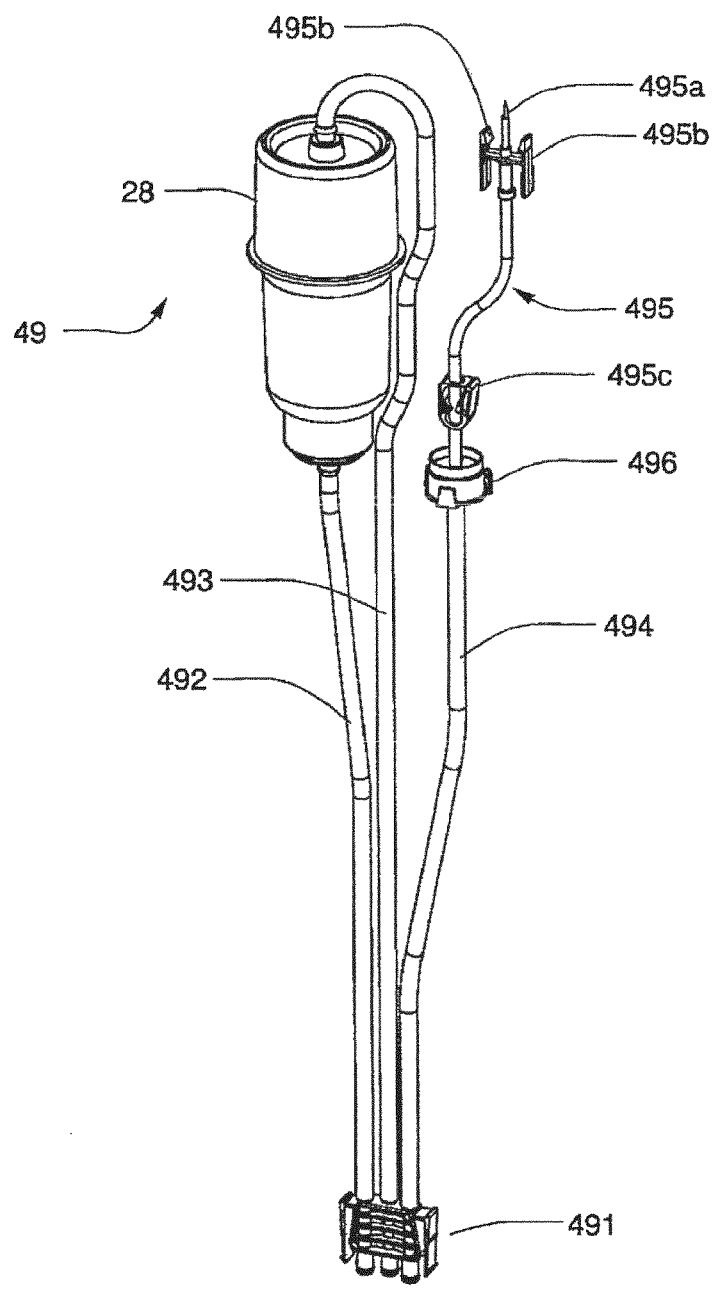
FIG. 25 shows a right perspective view of a reagent supply for use with the system of FIG. 7.

In accordance with another aspect of the invention, a bicarbonate, acid and/or other reagent supply device may be selectively associated with the dialysis unit. As described above, the dialysis unit 51 requires a supply of certain chemicals to generate dialysate and/or other materials needed for system operation. FIG. 25 shows a reagent supply 49 used to provide acid, bicarbonate and/or other materials to the dialysis unit 52. (FIG. 21 shows the reagent supply 49 attached to the acid/bicarbonate connection point 512 on the front panel 511.) The reagent supply 49 in this illustrative embodiment includes an E-prong connector 491 that is arranged to mate with the acid/bicarbonate connection point 512. As with other connections made by the user at the front panel 511, e.g., including the blood line connections at the connection point 514, the mating connectors may be color coded or otherwise marked to help ensure proper connections are made. For example, the E-prong connector 491 and the acid/bicarbonate connection point 512 may be colored orange, while the arterial line 203 and its mating connection at the connection point 514 may be colored red, and the venous line 204 and its mating connection at the connection point 514 are colored blue. Leading from the E-prong connector 491 are a bicarbonate supply line 492, a water supply line 493 and an acid supply line 494. (See FIG. 6 and the accompanying description regarding the function of these lines.) The water supply line 493 provides water to a bicarbonate supply 28 (which in this embodiment is a 750 g Altracart Bicarbonate cartridge (#500750A) sold by Baxter International Inc. that includes a powdered bicarbonate material, but may be any suitable supply), which provides bicarbonate to the dialysis unit 51 via the bicarbonate supply line 492. In this embodiment, the acid supply line 494 leads to an acid bag spike 495, which may be used to pierce and draw a suitable acid from a IV-type bag or other container. In this embodiment, the acid bag spike 495 includes a spike member 495a and a pair of spring clips 495b. The spring clips 495b are joined together at center portions by a connecting bar such that the spring clips 495b and the connecting bar form an "H" shape and allow the spring clips 495b to be pivoted relative to each other when proximal ends of the spring clips 495b are squeezed toward each other. The spring clips 495b may be arranged to engage with a connector element on an acid bag (or other acid supply, not shown) so that the spike member 495a remains engaged with the bag until a user disengages the clips 495b. For example, distal ends of the clips 495b may include barbs that engage with the acid supply, and the clips may be disengaged from the acid supply by squeezing proximal ends of the clips 495b together to disengage the barb elements at the distal ends of the clips 495b from the acid supply. The acid bag spike 495 may also include a valve 495c (in this case, a pinch clamp) to open/close the line of the acid bag spike 495. In accordance with one aspect of the invention, the acid bag spike 495 may be replaced (disconnected from the acid supply line 494 at a cap connector 496) with another component, such as an acid jug straw (not shown) or other arrangement. When used with a jug straw, the cap connector 496 may be engaged with an acid jug opening such that the cap connector 496 covers the opening, like a cap. Alternatively, the jug straw can terminate in a spike, which then has the ability to penetrate a self-sealing (e.g. rubber) membrane covering the opening of the acid jug. Thus, different types of components may be attached to the acid supply line 494 depending on the acid supply arrangement (such as a jug, bottle, bag, or other).

Figure 26:
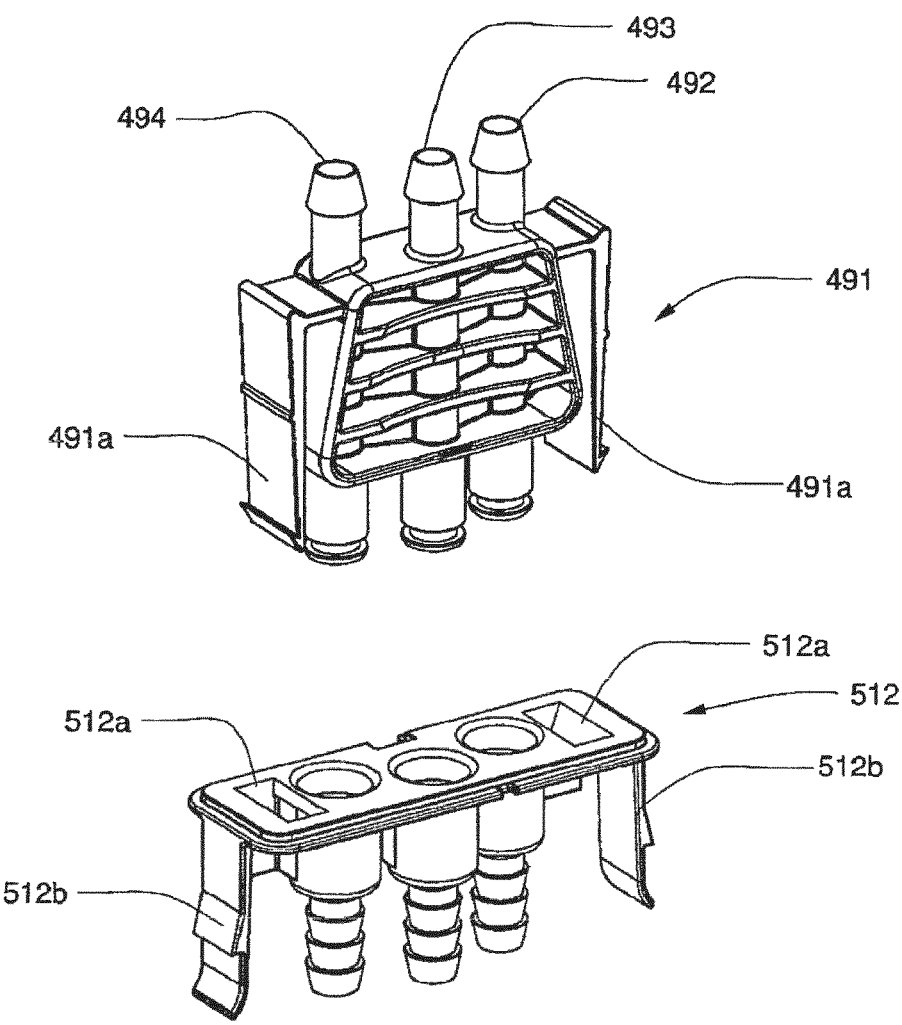
FIG. 26 shows a perspective view of an E-prong connector for the reagent supply of FIG. 25 and a corresponding connection point at the front panel of the hemodialysis system.

FIG. 26 shows a close up view of the E-prong connector 491 and the corresponding connection point 512 at the front panel 511. The E-prong connector 491 has three parallel prongs (corresponding to the bicarbonate and acid supply lines 492 and 494 and the water supply line 493) that that engage with corresponding receiving holes in the connection point 512. The E-prong connector 491 and receiving holes in the connection point 512 are arranged so that a center lumen (the water supply line 493) is arranged above, or otherwise out of, a common plane of the two outer lumens (the bicarbonate and acid supply lines 492 and 494). In this way, it is ensured that the bicarbonate and acid supply lines 492 and 494 are properly connected since the E-prong connector 491 cannot be engaged with the connection point 512 unless appropriately oriented. The E-prong connector 491 includes a pair of spring tabs 491a that can be engaged with corresponding slots 512a in the connection point 512, e.g., when the prongs are properly seated in receiving holes of the connection point 512. With the tabs 491a engaged in the slots 512a, the E-prong connector 491 cannot be easily removed from the connection point 512, helping reduce the likelihood of an accidental disconnection. The E-prong connector 491 may be disconnected by pressing the tabs 491a toward each other so that barbs at the distal ends of the tabs 491a disengage from the slots 512a. The connection point 512 has similar spring tabs 512b which allow the connection point 512 to be connected to and disconnected from the front panel 511.

In accordance with another aspect of the invention, a disinfect connector (not shown) engages with connection point 512 for use during a disinfection procedure. The disinfect connector has three parallel prongs having a similar orientation as the E-prong connector 491, so that the prongs may engage with the receiving holes in connection point 512. The channels in the prongs of the disinfect connector terminate within a common chamber within the disinfect connector. Thus, during a disinfect procedure, the bicarbonate flow line, acid flow line and water flow line are all interconnected, permitting disinfection of each of these flow lines during the disinfect procedure. (This is shown as a dashed inverted "T" line at 49 in FIG. 6).

Figure 27:
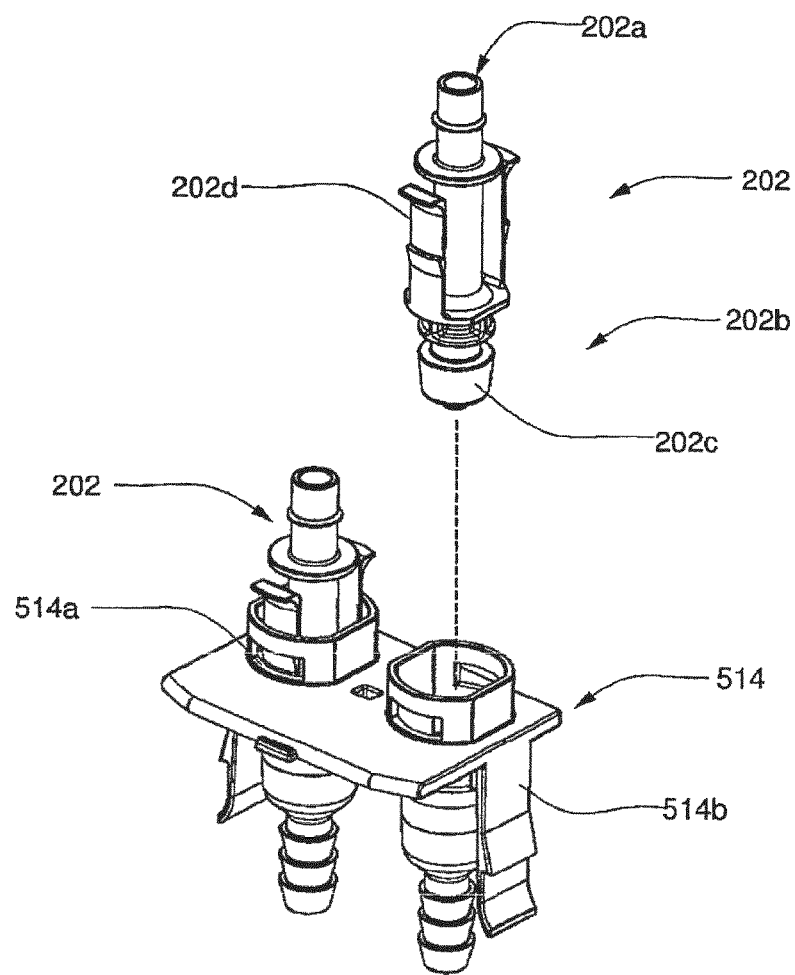
FIG. 27 shows a perspective view of a pair of blood line connectors for the blood circuit assembly and a corresponding connection point at the front panel of the hemodialysis system.
Figure 28:
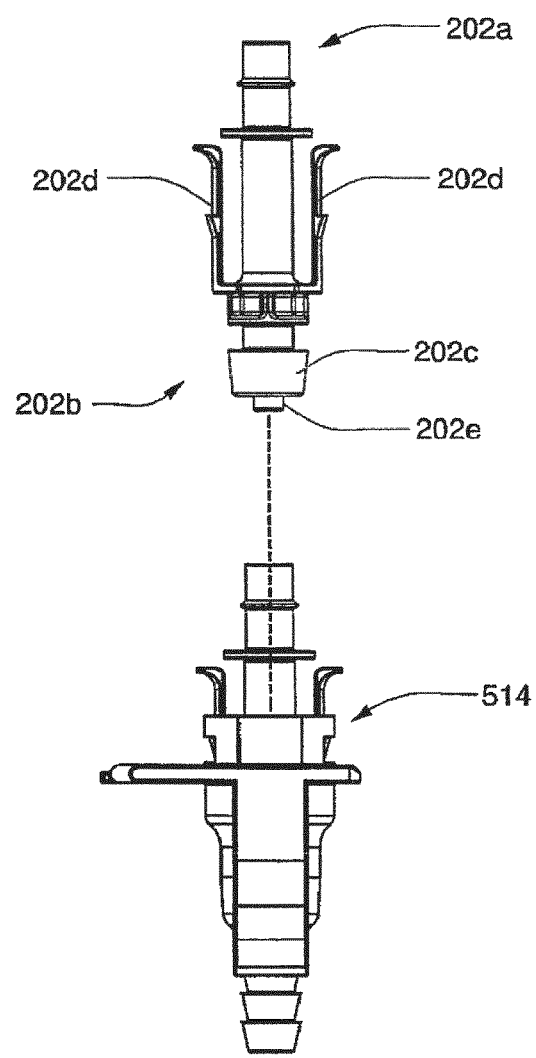
FIG. 28 shows a side view of a blood line connector and connection point of FIG. 27

In accordance with another aspect of the invention, the blood lines 203, 204 are equipped with a connector that enables two types of connections to be made. One type of connection is a plug-in or press-in connection by which the connector can be pushed into a receiving lumen and a leakfree connection made without requiring rotation of the connector or the receiving lumen. A second type of connection is a screw-type connection by which a leakfree connection can be made by a threaded engagement of the connector with a complementary element. For example, FIGS. 27 and 28 show a perspective view and a side view of a blood line connector 202 that is used with the blood lines 203, 204 and that can engage with the blood line connection point 514 on the front panel 511. The connector 202 includes a tube connection end 202a that connects to the corresponding blood line 203, 204, and a patient access connection end 202b that is arranged to connect to both a patient access as well as the connection point 514 to establish a leakfree connection. At the patient access connection end 202b, the connector 202 includes a frustoconical member 202c that has an internally threaded portion arranged to engage with an externally threaded patient access. For example, the frustoconical member 202c may be part of a male-type luer connector that includes the central tube 202e extending from the center of the frustoconical member 202c. When making the luer connection, the tube 202e may extend into a female luer connector at the patient access and the threaded portion on the interior of the frustoconical member 202c may engage with a thread on the female luer connector of the patient access (whether arterial or venous). Such luer connections are standard when connecting blood lines to a patient access. However, the connector 202 may also be engaged with the connection point 514 by simply pushing the patient access connection end 202b into a receiving hole of the connection point 514. When making this connection, the exterior of the frustoconical member 202c may engage with a suitable seat, or other surface or element in the connection point 514 (such as a valve seat, O-ring, or other) so that a seal is formed between the frustoconical member 202c and the connection point 514. The central tube 202e may also, or instead, be used to engage with the connection point 514 to establish a suitable seal. Locking arms 202d that extend rearwardly from the frustoconical member 202c may engage with holes 514a in the connection point 514 (e.g., barbed portions on the arms 202d may engage with the holes

514a) to help maintain the connector 202 in the receiving hole of the connection point 514. The connector 202 may be released by pressing the arms 202d toward each other (e.g., by pressing on finger depression portions at the distal ends of the arms 202d), thereby disengaging the barbs from the holes 514a, and withdrawing the connector 202. Note that the connection point 514 may include spring tabs 514b to allow the connection point 514 to be selectively engaged/disengaged at the front panel 511. The connectors 202 may be made in any suitable way, such as by molding of plastic as a single unitary part.

Figure 29:
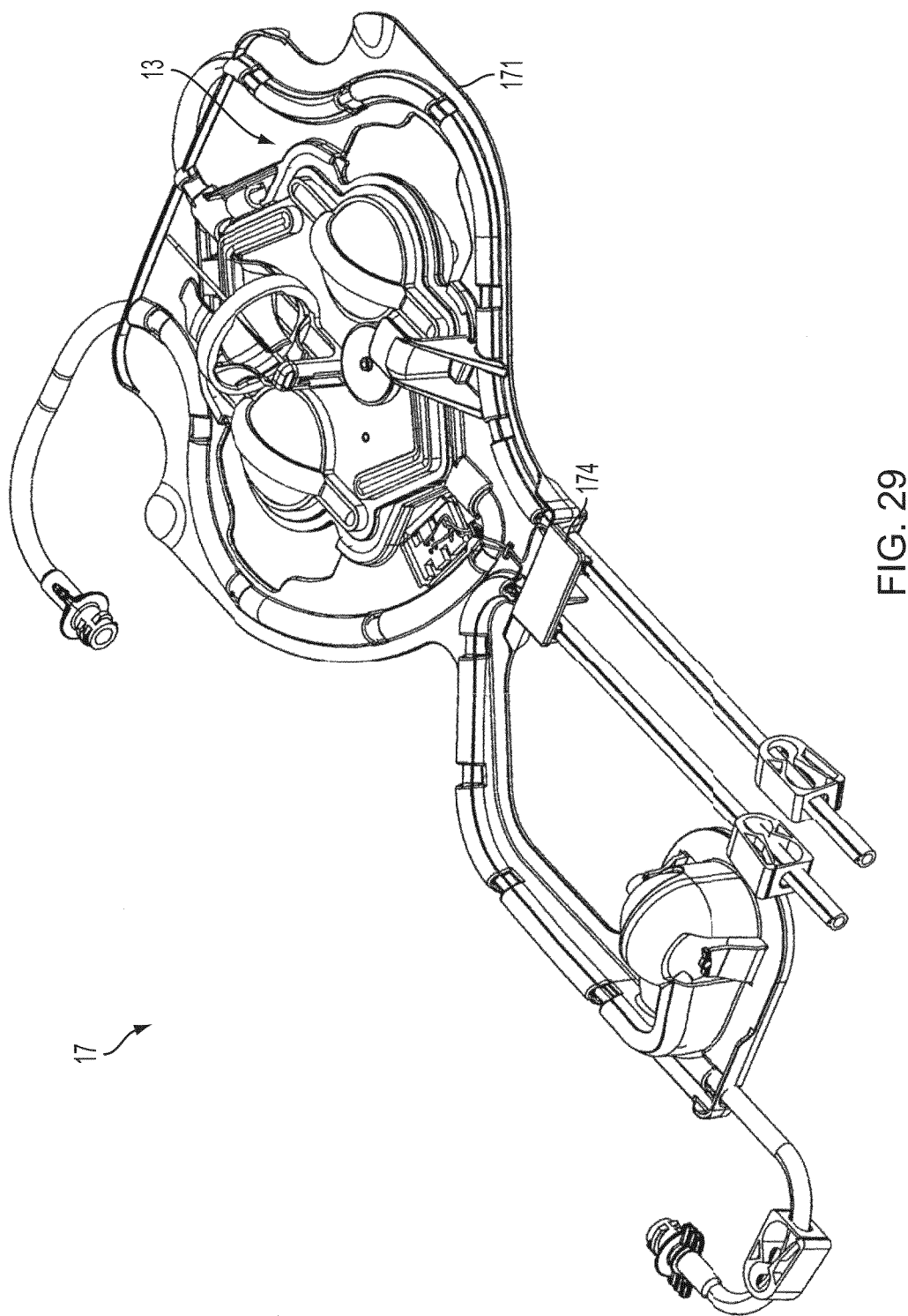
FIG. 29 is a perspective view of a blood circuit assembly in an alternate embodiment.
Figure 30:
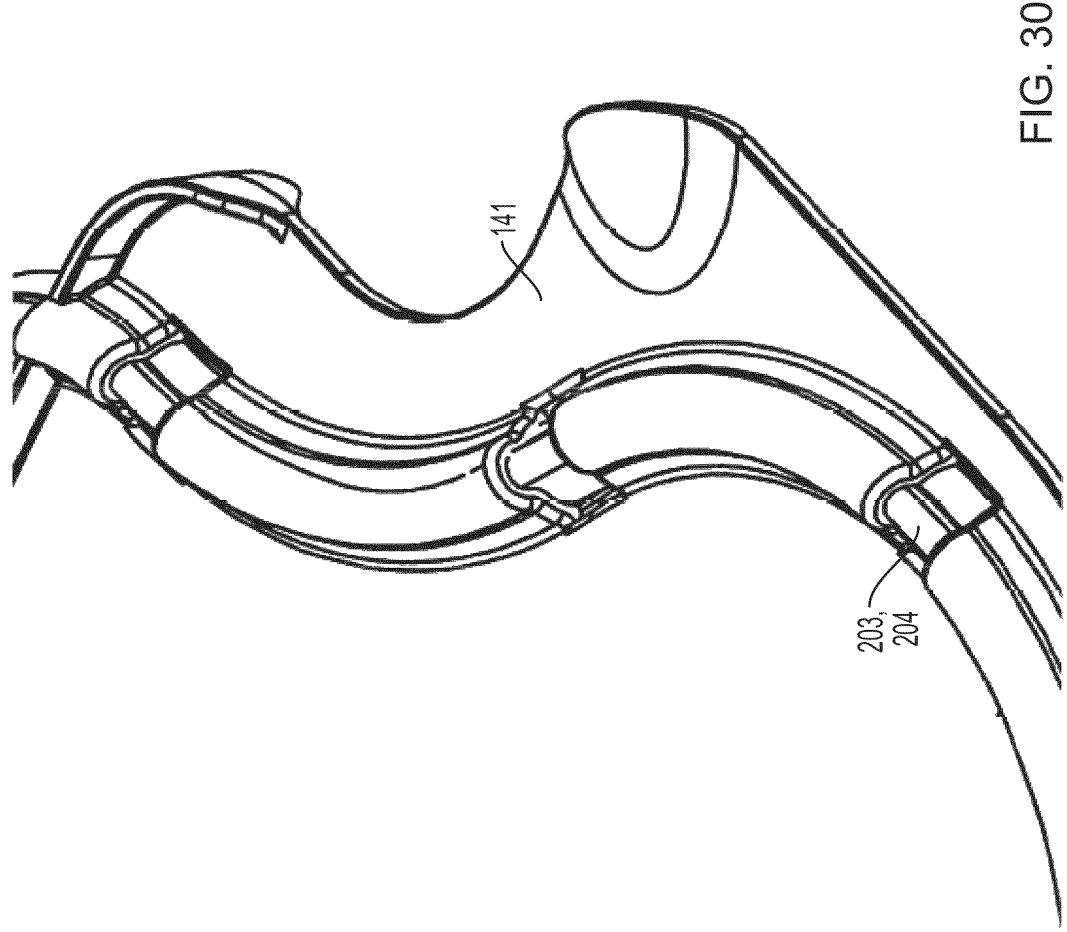
FIG. 30 is a close up view of a portion of the blood circuit assembly of FIG. 29.

FIG. 29 shows a perspective view of a blood circuit assembly 17 in an alternate embodiment. This embodiment is different from that shown in FIGS. 18 and 19 in a few ways. For example, in this embodiment, the blood lines 203 and 204 have a cross section having a shape similar to a "figure 8" in which one portion of the "figure 8" includes a lumen to carry blood or other fluid, and another portion of the "figure 8" carries a conductor. That is, the blood lines 203 and 204 include a lumen through which blood and other fluids may flow, and another lumen through which an electrical conductor may pass. Further detail regarding this and other arrangement is provided below with reference to FIGS. 37-49. As also discussed in more detail below, the electrical conductor may be used to detect disconnection of a blood line 203, 204 from a patient or other connection point. Additionally, the organizing tray 171 in FIG. 29 is different from that shown in FIG. 19 in that the engagement members 174 may include a slot or hole that the blood lines 203, 204 are engaged with, but in this embodiment, the engagement members 174 need not engage the blood lines 203, 204 so as to resist pulling of the lines 203, 204 downwardly, e.g., for mounting the lines in an occluder. Instead, in this embodiment, the blood lines 203, 204 may be allowed to move freely with respect to the engagement members 174. Another modification in the embodiment is that the engagement members 174 include a push plate that spans across both lines 203, 204. This is in contrast to the arrangement in FIG. 19 where each line 203, 204 is engaged by engagement members 174 that are independent of each other. The arrangement in FIG. 29 may provide an advantage in some embodiments that allows a user to engage the lines 203, 204 with respect to slots 517 that lead to an occluder in an single operation. (See FIG. 22) In one embodiment, the slots 517 may each be associated with an air detector that operates to detect whether there are air bubbles in the lines 203, 204 (e.g., by optical detection or other so that air in a line 203 or 204 can be detected by a respective air detector in one of the slots 517). Thus, the engagement members 174 may function to associate the lines with an air detector or other feature in addition to, or instead of, an occluder or other arrangement that positions the lines 203, 204 in a desired way. In this embodiment, the engagement features 174 include slots arranged on an underside of the push plate that engage with a narrower portion of the lines 203, 204 (e.g., the portion that carries the electrical conductor) so as to position the conductor near the push plate. This may help position the lines 203, 204 in the slots 517 in such a way that the conductor does not interfere with an air detector operating to detect air in the lines 203, 204. As mentioned above, the slots on the push plate that engage with the lines 203, 204 may engage the lines so that the lines do not rotate relative to the push plate, but are allowed to move along their length relative to the push plate. FIG. 30 shows a closeup view of a portion of the blood circuit assembly of FIG. 29 and illustrates how a portion of the organizing tray 171 may be arranged to at least partially conform to the shape of a blood line 203, 204 held by the tray 171. Similar to the engagement members 174, the tray 171 portions that engage with the lines 203, 204 may be arranged to orient the lines 203, 204 so that the conductor portion of the line faces outwardly. This may help properly position the lines 203, 204 for the engagement members 174 or other portions of the assembly 17.

It should be understood that any and all of the aspects of invention described herein may be combined with or otherwise incorporated with any of the other aspects of invention and/or embodiments described. For example, a dialysis system incorporating one or more aspects of invention described herein may include a line disconnection function like that described in connection with FIGS. 37-49. Such a disconnection function may include features such as 1) an electrical circuit or other suitable circuitry to detect a change in voltage, resistance or other characteristic indicative of a disconnection of a blood line 203, 204 with respect to an associated connector, 2) positioning of detection electrodes suitably near a patient or other reference, 3) one or more connector arrangements, 4) blood line tubing arrangements or other suitable arrangements in which a blood line carries both a fluid flow lumen and an electrically conductive feature, and so on. For example, in one aspect of the invention, a blood circuit assembly may include blood lines, one or more blood pumps, an air trap and electrical circuitry components suitable for use in detecting disconnection/connection of one or more blood lines on an organizing tray. Such an arrangement may allow a user to make several different connections, whether fluidic, pneumatic and/or electrical, in a relatively uncomplicated and straightforward way.

Accordingly, aspects of the invention relate generally to systems and methods to detect disconnection of an indwelling vascular line being used in a dialysis treatment, such as a catheter or needle, or its attached tubing. If not quickly detected, a disconnection can lead to rapid exsanguination, particularly when the blood in the catheter or tubing is under positive pressure. Examples of circumstances involving positive intravascular pressure include the positive pressure associated with an artery or arterio-venous fistula, or the positive pressure associated with an extracorporeal blood pump circuit. In hemodialysis, for example, a blood pump can generate blood flow rates of 400-500 ml/min, making rapid, reliable disconnect detection particularly desirable. Indeed any medical treatment involving relatively high flow or high pressure extracorporeal circulation (such as, for example, hemoperfusion or cardiopulmonary bypass) can be made safer by having an effective system to monitor the integrity of the arterial (withdrawal) and venous (return) blood lines.

In hemodialysis, for example, extracorporeal blood circulation can be accomplished with vascular access using either a single indwelling catheter, or two separate indwelling catheters. In a single catheter system, blood is alternately withdrawn from and returned to the body via the same cannula. A disconnection in this system can be quickly detected by placing an air monitor in the line at or near the pump inlet, because air will be drawn into the line from the disconnection site during the blood withdrawal phase of the pumping. On the other hand, in a two-catheter system, blood is typically continuously withdrawn from the body via one catheter inserted in a blood vessel or fistula, and returned to the body via the second catheter inserted in the same vessel some distance from the first catheter, or in a separate blood vessel altogether. In the two-catheter system, it is also possible to monitor for catheter or tubing dislodgement in the blood withdrawal or 'arterial' segment by using a sensor to detect the presence of air being entrained into the arterial tubing as blood is withdrawn from the blood vessel under negative pump pressure and/or positive fistula pressure. However, air-in-line detection cannot reliably detect a disconnection of the venous (return) segment of the extracorporeal circuit. In this case, if the blood-withdrawal path remains intact, air will not be introduced into the line. Thus it is particularly important to be able to detect a disruption in the continuity of the return line from the extracorporeal pump to the vascular access site.

In one aspect, the invention comprises a system for detecting whether a vascular access device, such as a needle, cannula, catheter, etc. becomes disconnected or dislodged from a blood vessel or vascular graft. The system includes a fluid delivery device that provides for the flow of a liquid through a tube or conduit into the blood vessel via an indwelling needle or catheter at a first site on the blood vessel or graft. The fluid may be an electrolyte solution or other solution suitable for intravenous infusion, or it may be blood or blood components. An electrode is disposed to be in contact or fluid communication with the lumen of the conduit, and a second electrode is disposed to be in fluid communication with blood within the blood vessel or graft via a second on the blood vessel or graft. An electronic circuit is connected to the first and second electrodes, and configured to deliver a control signal to the first and second electrodes in order to measure the electrical resistance of the fluid between the first and second electrodes, such that at least one of the electrodes is located closer to the blood vessel or graft than to the fluid delivery device. In some embodiments the electrode is located at about 50-70% of the distance from the fluid delivery device to the blood vessel or graft. In other embodiments, the electrode is located at about 70-90% or more of the distance from the fluid delivery device to the blood vessel or graft. The fluid delivery device can include a pump, either for blood or for other therapeutic or diagnostic fluid. The fluid delivery device can be part of a hemodialysis blood flow circuit, which may or may not include a blood pump, a dialyzer cartridge, or an air trap and associated tubing. The second electrode may be placed in contact with the lumen of a second conduit or tube that is in fluid communication with the blood vessel or graft at the second site. The second conduit may form part of a fluid flow path from the blood vessel or graft to the fluid delivery device. The fluid in the second conduit may be blood being delivered to an extracorporeal blood flow circuit.

The system may comprise a first and second connector connecting a pair of vascular access catheters accessing a blood vessel segment or vascular graft segment at two different sites. The first and second connectors may each connect to a flexible tube leading to the fluid delivery device. Each connector may include an electrode that is exposed to the lumen of the connector. A wire may be attached to each connector, the wire being connectable on its other end to the electronic circuit. The flexible tubes may be double lumen tubes having a first lumen for carrying fluid and a second lumen for carrying a wire. The wires of each tube may be connected on the other end of the tube to a connector for connection to the electronic circuit.

The electronic circuit or an associated microprocessor may be configured to convert the voltages measured across terminals connected to the electrodes by the electronic circuit into resistance values. The system may comprise a controller configured to receive a signal from the electronic circuit or microprocessor, the signal representing the electrical resistance between the electrodes, the controller being programmed to trigger an alert signal when the electrical resistance value exceeds a pre-determined threshold. The alert signal may be an audible or visual signal to the person whose blood vessel is being accessed, and optionally an alert signal may include an electrical command to a tubing occluder apparatus. The tubing occluder apparatus may be actuated to mechanically occlude one or more of the tubes leading from the vascular access sites. The tubing occluder may operate in a number of ways, such as, for example electromechanically, hydraulically, or pneumatically.

In another aspect, the invention comprises an apparatus for monitoring the continuity between a vascular access device and a blood vessel or vascular graft segment, comprising, a first and second vascular connector, the first connector being attached on a proximal end to a distal end of a fluid-carrying lumen of a first double-lumen tube, and the second connector being attached on a proximal end to a distal end of a fluid-carrying lumen of a second double-lumen tube. The first connector comprises a first electrode in contact with a lumen of the first connector and electrically connected to a wire within a wire-carrying lumen of the first double-lumen tube, and the second connector comprises a second electrode in contact with a lumen of the second connector and electrically connected to a wire within a wire-carrying lumen of the second double-lumen tube. The wire within the first double-lumen tube and the wire within the second double-lumen tube are each connected to an electrical connector at a proximal end of the double-lumen tubes. The distal end of each connector may be configured with a locking feature to provide a reversible, air-tight connection between the connector and a mating connector of a vascular catheter. The proximal end of the double-lumen tubes can be connected to a blood pump on an arterial side, and an air trap on a venous side; and in a hemodialysis system, the blood pump and air trap may each be reversibly connectable to a dialyzer cartridge.

In another aspect, the invention comprises a vascular connector comprising a proximal fluid connection end, a distal fluid connection end, and an electrode configured to electrically connect a fluid-carrying lumen of the connector with a wire external to the vascular connector. The proximal end of the connector may be configured to connect with a flexible tube, and the distal end of the connector may be configured to connect with a mating connector of a vascular catheter. The electrode may be installed in a conduit on the connector that connects the lumen of the connector to the exterior of the connector. The electrode may be lodged into the conduit in a manner to provide an air-tight seal between the lumen and the exterior of the connector. An elastomeric member such as an O-ring may be installed between the electrode and the conduit to contribute to the air-tight seal.

In another aspect, the invention comprises an electrical circuit for measuring the resistance of a liquid between a first and second electrode, the first electrode connected to a first terminal of the electrical circuit, and the second electrode connected to a second terminal of the electrical circuit, comprising a capacitor C1 connected on a first end to the first terminal and a capacitor C2 connected on a first end to the second terminal; a known reference resistance Rref connected on a first end to a second end of capacitor C1; switching means for connecting either (a) a first reference voltage V+ to a second end of Rref, and a lower second reference voltage V− to a second end of C2 to form a first switch configuration or; (b) the first reference voltage V+ to the second end of C2 and the lower second reference voltage V− to the second end of Rref to form a second switch configuration; and measuring means for measuring a voltage Vsense at the connection between C1 and Rref; such that the electrical circuit is configured to determine the value of the resistance of the liquid based on the known reference resistance Rref and the observed voltage Vsense for each of the first and second switch configurations. The resistance Rref may be chosen to be a value that permits conductivity measurement of an electrolyte solution or other solution suitable for intravenous infusion. The electrolyte solution may include dialysate solution. The resistance Rref may also be chosen to permit measurement of the resistance of a volume of blood between the first and second electrodes.

Conductivity Circuit

Figure 37:
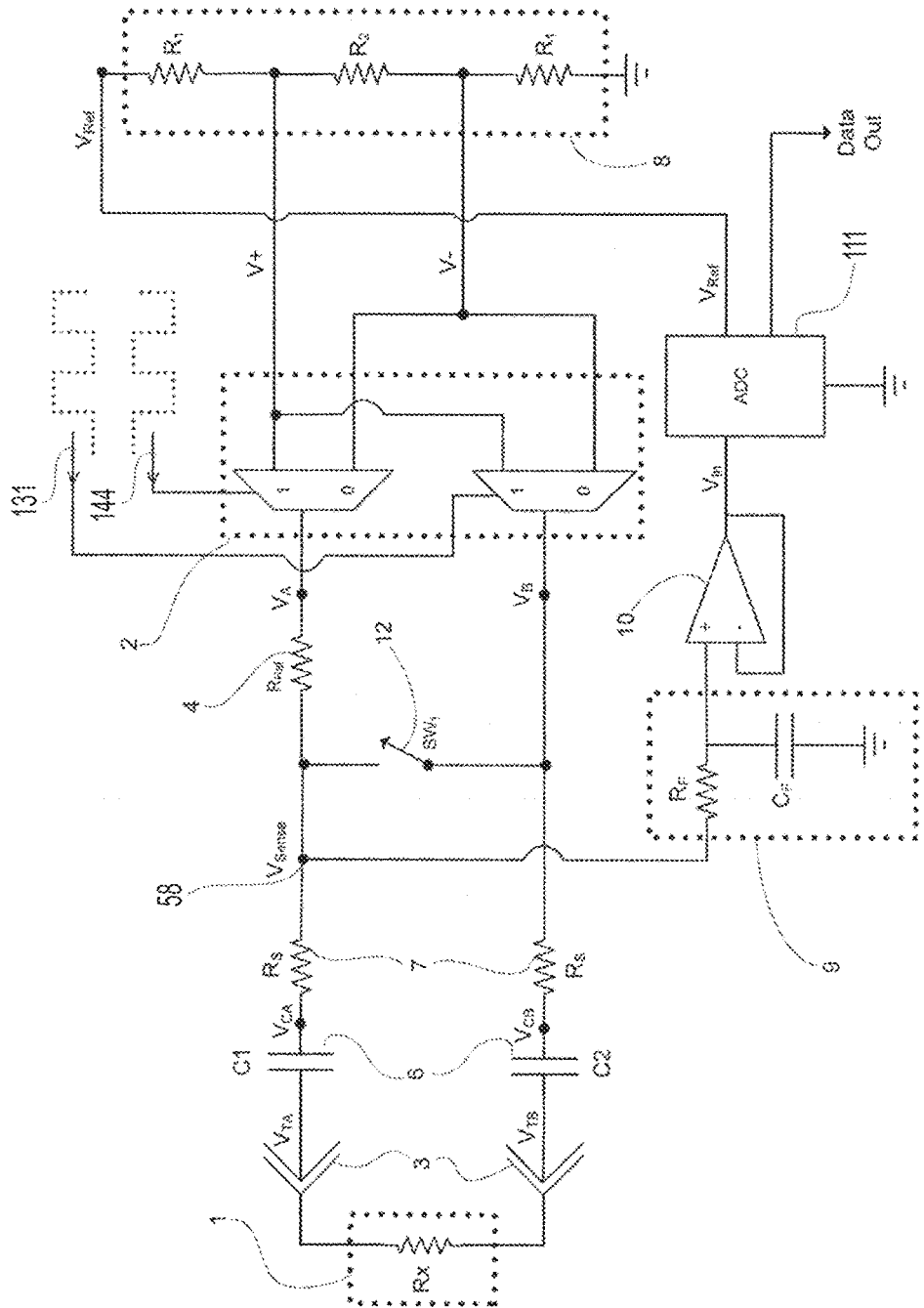
FIG. 37 is a schematic representation of a conductivity circuit in an illustrative embodiment.

An exemplary electrical circuit shown in FIG. 37 can be used to measure the electrical conductivity or resistance of a subject fluid. In one embodiment, the fluid may be an electrolyte solution or dialysate fluid, and the circuit may ultimately provide a measurement of the conductivity of the fluid to ensure its compatibility for intravascular administration. In addition to monitoring the concentration of dissolved solutes in the fluid, the electrical circuit can also monitor for any interruption in the continuity of the fluid between the electrodes connected to the circuit. For example, it can be used to monitor an intravenous fluid line for the presence of air bubbles, or for the presence of a contaminating substance. In another embodiment, the fluid may be blood, and a change in the measured electrical resistance of a blood flow path (for example, in a conduit) may be used to indicate if a discontinuity occurs between the blood flow path and measuring electrodes. For example, the blood flow path may comprise a column of blood between two electrodes that includes indwelling needles or catheters in a segment of a blood vessel, arterio-venous fistula or graft. Vascular access disconnection can result in the introduction of air into the blood flow path, causing a change in the resistivity of the blood column between the electrodes. The electrical circuit can be readily modified (depending on its application) to adjust for the difference between the impedance of a blood flow path and that of dialysate fluid.

The circuit shown in FIG. 37 may be used to measure an unknown resistance Rx of a subject media 1 using inexpensive electronic components, particularly where the unknown resistance involves a conductive path through an electrolytic fluid. A switching network 2 comprising a pair of multiplexers allows the connection of nodes VA and to reference voltages V+ and V−. The subject media 1 having unknown resistance Rx is connected to terminals VTA and VTB 3, and forms a voltage divider with reference resistor Rref 4. To make a conductivity measurement, alternating voltages can be presented to the subject media 1 via switching network 2 to the voltage divider created by the known reference resistor Rref 4 (680 ohms, for example, in the case of dialysate fluid) and the unknown resistance Rx of the subject media 1. The midpoint of the voltage divider is measured. The signal Vsense at point 8 is buffered by amplifier 10 to make the input signal Vin of the analog-to-digital converter (ADC) 111. Vsense switches between two values as the voltage divider is driven first one way and then the other way. This signal is valid only for a short period of time after switching because the fluid in the conductivity cell 1 is AC coupled into the circuit through capacitors C1 and C2 6. Thus DC-blocking capacitors C1 and C2 6 may be used to prevent DC currents from passing through the unknown resistance (which may include a conductive path through electrolytic fluid or blood). In an embodiment, series capacitors C can each comprise two capacitors in parallel, one having a value, e.g., of 0.1 uF, and the other having a value, e.g., of 10 uF. Series resistors 7 may be used to reduce exposure by the switch network and other sense circuitry to noise and surge voltages. ADC 111 can take multiple samples of the signal as the circuit is switched between the two configurations.

Figure 38:
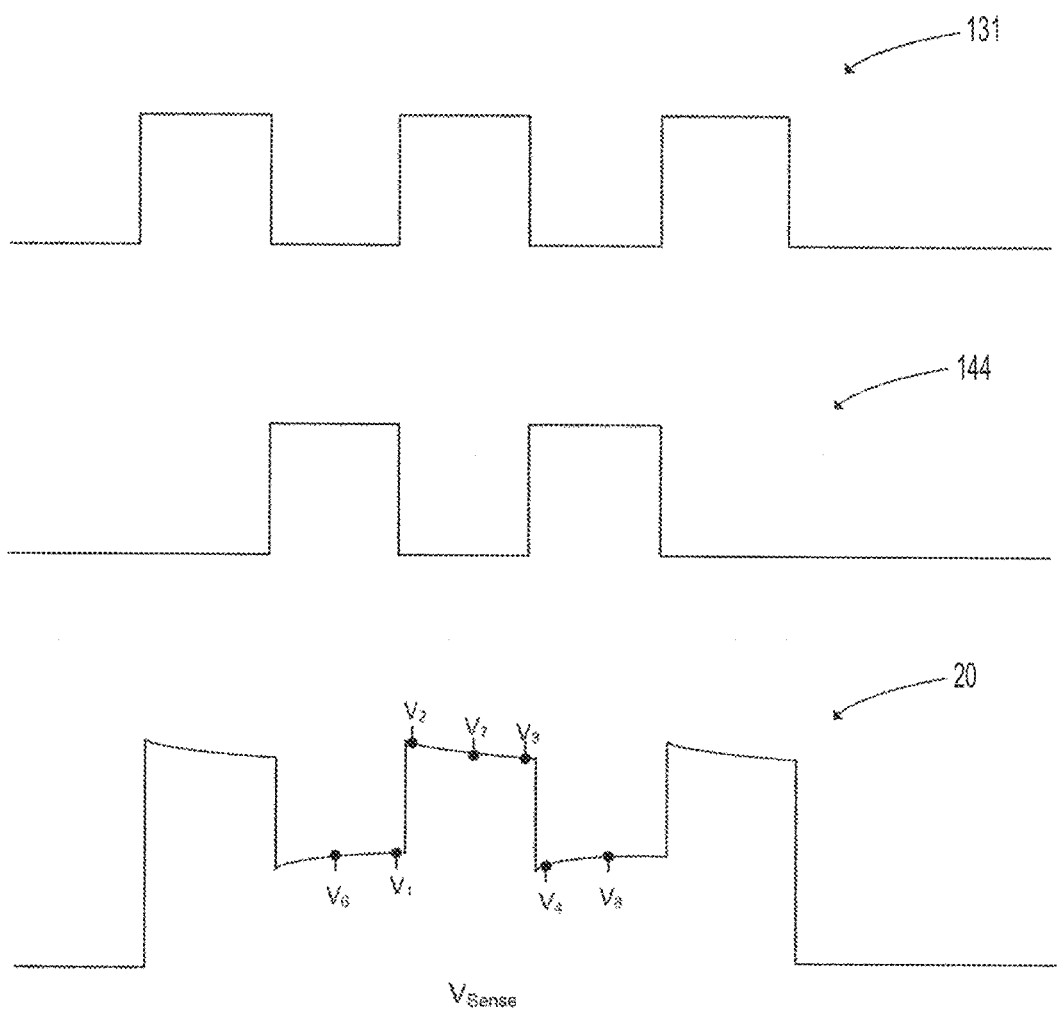
FIG. 38 is a diagram of the electrical waveforms processed by the circuit of FIG. 37.

The switching network 2 can be driven by a pair of alternating binary control signals 131, 144 that connect VA to V+ and VB to V− during one half-cycle, and VB to V+ and VA to V− during the other half-cycle. This results in a waveform at the Vsense node 58 that is similar to the waveform 20 shown in FIG. 38. In this embodiment, Vref is 4 volts, resulting in a Vsense amplitude of less than 4 volts, as shown in FIG. 38. A voltage divider 8 creates the voltages V+ and V− that are near the positive reference voltage Vref and near ground, respectively. In one embodiment, R1 can have a value of 10 ohms, and R2 can have a value of 2K ohms When both multiplexers of switching network 2 are commanded to zero, the circuit is at rest and the lower voltage is presented to terminals VTA and VTB 3. When VA is high and VB is low, the higher voltage is presented to the reference resistor Rref 4 and the lower voltage is presented to the subject media 1 having unknown resistance Rx. When VB is high and VA is low, the higher voltage is presented to the subject media 1 having unknown resistance Rx and the lower voltage is presented to the reference resistor Rref 4.

A change in voltage ΔVsense before and after each square wave edge, can be shown to depend only on the reference resistance Rref 4, the unknown resistance Rx of subject media 1, and any series resistance (including, e.g., Rs 7), and is generally independent of series capacitance C1 or C2 6, since during this short time period the capacitor acts as an incremental short circuit. In particular, $$\Delta\alpha = \Delta V\text{sense}/(V+ - V-) = (R_y - R_{\text{ref}} - R_{\text{th}})/(R_y + R_{\text{ref}} + R_{\text{th}}) = (\rho - 1)/(\rho + 1)$$

where Ry=Rx+2Rs+Rth, where Rth=source series resistance from multiplexer 2 and voltage divider 8, and ρ=Ry/(Rref+Rth). (Source series resistance Rth, can be derived as the sum of the resistance of multiplexer 2 and the Thevenin equivalent resistance of the voltage divider 8. For example, for R1=10 ohms, R2=2K ohms, then Rth=R1.parallel.(R1+R2)=9.95 ohms). Thus, if Ry is a short circuit, then ρ=0 and Δα=−1. The sense node's change in voltage ΔVsense is then equal to the voltage change at VB which has an amplitude opposite to the drive node at VA. If Ry is an open circuit, then ρ=∞ and Δα=1. The sense node's change in voltage ΔVsense is then equal to the voltage change at the drive node VA. Accordingly, if this change in voltage is measured, the preceding equations can be solved for the unknown resistance Rx:

$$Rx = \rho(R_{\text{ref}} + R_{\text{th}}) - 2R_s - R_{\text{th}}, \text{ where } \rho = (1 + \Delta\alpha)/(1 - \Delta\alpha)$$

As shown in FIG. 37, a low-pass filter 9 can be formed by resistor Rf and capacitor Cf, to filter out high-frequency noise. In one exemplary arrangement, Rf can have a value of 1K ohms, and Cf can have a value of 0.001 uF. Buffer amplifier 10 and analog-to-digital converter (ADC) 111 can then measure the sensed voltage for a computer or digital signal processor (not shown).

The reference voltages V+ and V− may be advantageously derived from a voltage divider 8 so that V+ is close to the reference voltage Vref of the ADC 111, and V− is close to the ground reference voltage of the ADC 111. For example, for R1=10 ohms, R2=2 kohms, and Vref=4.0V, then V+=3.980V, and V−=0.020V. This places both voltages within but near the edges of the active sensing region of the ADC 111, where they can be used for calibration (discussed below). Switch SW1 12 may be used to help calibrate the load resistance sensing.

Several improvements may decrease errors related to variations of component values. First, a calibration step can be introduced where VA is switched to V+ for a relatively long period of time, until settles and is approximately equal to V+, at which point ADC 111 can take a measurement of Vsense. A second calibration step can involve switching VA to V− for a relatively long period of time, until Vsense settles and is approximately equal to V−, at which point ADC 111 can take another measurement of Vsense. This allows the ADC 111 to measure both V+ and V−.

Secondly, as shown in FIG. 38, while the square wave is switching, ADC 111 readings before and after both edges of the switching waveform may be used to compute the dimensionless quantity Aα:

$$\Delta\alpha = \Delta V\text{sense}/(V+-V-) = [(V2-V1)+(V3-V4)]/2(V+-V-)$$

As a result, both edges of the waveform can be used to measure ΔVsense=[(V2−V1)+(V3−V4)]/2, so that asymmetric responses to the circuit are likely to be canceled out. Alternatively, an average voltage at about the midpoint of the waveform may be used; so that, for example, Δα=ΔVsense/(V+−V−)=[(V7−V6)+(V7−V8)]/2(V+−V−), and ΔVsense=[(V7−V6)+(V7−V8)]/2. In addition, only differential measurements of the input signal Vin of the ADC 111 can be used. Thus, any offset errors of the buffer amplifier 10 and ADC 111 can be canceled out. Also, Aα is a ratiometric quantity based on measurements using the same signal path. Thus, any gain errors of the ADC 111 can also be canceled out.

The reference resistor Rref 4 may be optimally chosen to be equal to the geometric mean of the endpoints of the desired range of unknown resistances, taking series resistances Rs 7 into account. For example, if Rs=100 ohms and Rx varies from 100 ohms to 3000 ohms, then Ry=Rx+2R, varies from 300 ohms to 3200 ohms, and Rref should be approximately the square root of (300 ohms3200 ohms) =980 ohms. To measure an unknown resistance in the range of 100 k-300 k ohms (as in, for example, a column of blood extending from one electrode to another via an arteriovenous fistula), the reference resistor Rref 4 can be changed to approximately 200 k ohms and the filter capacitor Rf of low pass filter 9 at the input to the buffering amplifier 10 can be removed completely.

Because a voltage divider's output is a nonlinear function of its resistance ratio, errors or noise in readings from the ADC 111 produce their lowest fractional error (sensitivity) in the resultant calculation of Ry when it is equal to Rref, and the sensitivity increases the more Ry diverges from the reference resistance Rref. Specifically, it can be shown that the sensitivity in resistance ratio is as follows:

$$S\rho = (1/\rho) \cdot \partial\rho/\partial\Delta\alpha = 2/[(1+\Delta\alpha)(1-\Delta\alpha)] = 2/[1-(\Delta\alpha)^2]$$

When Ry=Rref, ρ=1, Δα=0 and Sρ=2. Thus, for a change in Δα of 0.001 (0.1% of the ADC full-scale) around this point, the calculated resistance Ry changes by 0.002 or 0.2%. The sensitivity increases as ρ diverges from 1, as shown in Table 1.

TABLE 1

| P | Δα | Sρ |
|---|---|---|
| 1 0 2 | | |
| 2, 0.5 | .+−.0.333 | 2.25 |
| 4, 0.25 | .+−.0.6 | 3.13 |
| 5.83, 0.172 | .+−.0.707 | 4 |

TABLE 1-continued

| P | Δα | Sρ |
|---|---|---|
| 10, 0.1 | .+−.0.818 | 6.05 |
| 20, 0.05 | .+−.0.905 | 11.03 |

Figure 39:
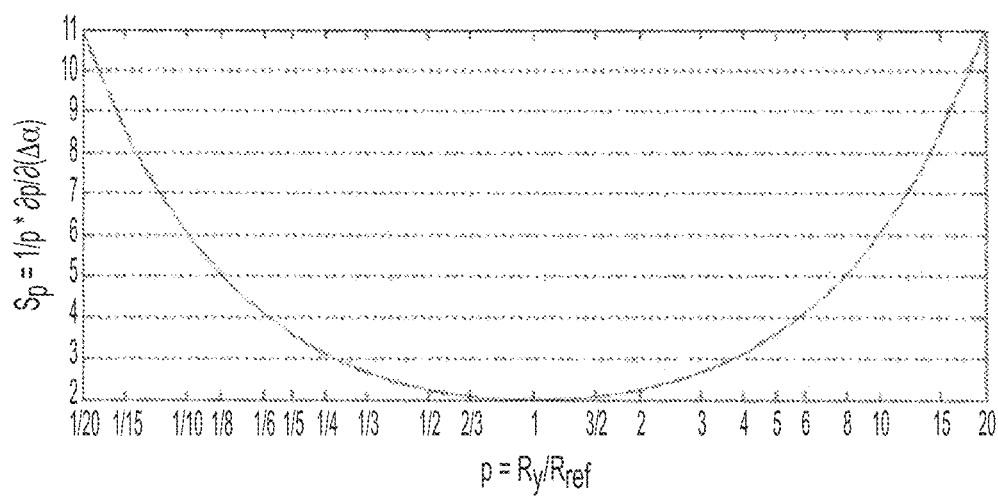
FIG. 39 is a representative graph of the noise/error sensitivity of the circuit of FIG. 37 plotted against the ratio of unknown/reference resistance in the circuit.

FIG. 39 shows that the noise/error sensitivity doubles at about a 6:1 ratio of unknown/reference resistance, and triples at a 10:1 ratio. Resistance measurements outside this range may suffer in their increased sensitivity to noise and error.

For calibration purposes, a switch SW1 12 can be used to make resistance measurements to calibrate out a point at Rx=0. Preferably this switch 12 should be placed across the terminals VTA and VTB 3, or as close to the terminals as feasible, which would give a true zero-point calibration. In practice, however, locating the switch 12 close to the terminals VTA and VTB 3 may make the switch 12 prone to external noise and surge voltages, and may introduce DC leakage current into the subject media 1.

The series capacitances C1 and C2 6, and the use of square waves are important for unknown resistances that include an electrolytic conductive path. There are at least two reasons for this. First, it may be important in many applications to prevent DC current from flowing through an electrolyte solution or a bodily fluid having similar properties; otherwise electroplating and/or electrolysis of electrodes at the terminals VTA and VTB 3 can occur. In this circuit, the capacitors C1 and C2 6 block DC currents. Furthermore, because the capacitors may allow very small currents to flow (microamps or less), using an alternating square wave voltage may help to limit the average current further.

Secondly, in the event that a small electrochemical DC voltage is induced in the subject media 1 (for example, the electrodes in a fluid path may oxidize over time at different rates), this DC voltage can be blocked by the capacitors C1 and C2 6. Because the method for calculating resistance takes differential measurements, any residual DC voltage may be canceled out through the process of calculating the unknown resistance Rx of subject media 1.

Vascular Disconnect Detector

With the appropriate modifications of a conductivity measurement circuit such as the one described above, it is possible to detect the conductivity and changes in the conductivity of blood. More specifically, it is possible to detect the change that occurs in the conductivity of a volume of blood when air enters the volume. This situation can occur, for example, when an intravascular access site becomes dislodged in an extracorporeal blood circuit.

The circuit shown in FIG. 37 can be used to measure the resistance of a volume of fluid in a conductivity cell or conduit 1. For measurements of Rx of a conductivity cell 1 representing the resistance or conductivity of a volume of dialysate solution, a convenient value for the reference resistor Rref 4 can be chosen to be approximately 680 ohms. For measurements of Rx of a conduit 1 representing the resistance or conductivity of a column of blood extending from a first cannula or needle, through an arterio-venous fistula, to a second cannula or needle, a convenient value for the reference resistor Rref 4 can be chosen to be approximately 200 k ohms.

The advantages of using this circuit to monitor the continuity of a column of a bodily fluid such as blood or plasma include the following: Capacitive coupling to the conductivity cell or conduit 1 blocks DC current which could cause plating and corrosion of electrodes at terminals VTA and VTB; Voltages and current levels are very low and decoupled for patient safety; Current only flows briefly while the measurement is being taken. No current flows between measurements.

With the lower reference resistor Rref 4 value (e.g. 680 ohms), this circuit is appropriately configured for dialysate conductivity measurements. With a much higher reference resistor Rref 4 value (e.g. 200 k ohms) this circuit is appropriately configured for measuring the resistance between an arterial needle and a venous needle to detect vascular needle dislodgement from an arterio-venous fistula.

Electrode Placement

The continuity of a fluid column leading from a fluid delivery apparatus to a patient's blood vessel or vascular graft can be monitored using the electronic circuit described above. The fluid being delivered may include blood or any electrolyte solution, including dialysate fluid. Although the following discussion will involve a hemodialysis system, the same principles of operation of the invention can apply to any device that is configured to deliver a fluid to a patient via a vascular access. In an embodiment illustrated by FIG. 40, the conductivity of a volume of blood or other fluid within a fluid flow circuit 100 of a hemodialysis machine 200 can be monitored electronically, using electrodes on each end of the volume that make direct contact with the blood or other fluid. Using an electrical circuit such as the one shown in FIG. 37, one electrode can be connected to the VTA terminal, and the other electrode can be connected to the VTB terminal of the circuit. The voltages applied to the electrodes by the circuit can be sufficiently small (e.g., about 4 volts or less), sufficiently brief, and with DC voltages sufficiently decoupled so as to prevent any harm to the patient. In this example, a fluid flow circuit 100 is shown, including an arterial access needle 102, an arterial catheter tubing 104, an arterial catheter tubing connector 106, arterial blood circuit tubing 108, a transition 110 between the blood circuit tubing 108 and hemodialysis machine 200, a blood pump inlet line 112, a blood pump 13, a blood pump outlet line 116, a dialyzer 14, a dialyzer outlet line 120, air trap 122, a transition 124 between hemodialysis machine 200 and venous blood circuit tubing 126, a venous catheter tubing connector 128, a venous catheter tubing 130, a venous access needle 132, and the intraluminal volume of that portion of the patient's blood vessel or fistula 134 that lies between the arterial access needle 102, and the venous access needle 132. It should be noted that the invention described herein also encompasses circumstances in which the arterial access needle may reside in one blood vessel of a patient, while the venous access needle may reside in a separate blood vessel some distance away from the arterial access site. Furthermore, the circuit described above may be used to monitor the integrity of a vascular access in a fluid delivery system that does not have the venous return line shown in FIG. 40. In that case, for example, an electrode at location B could be paired with an electrode in contact with fluid in a dead-end line communicating with a second needle or cannula accessing the blood vessel or vascular graft. In another example, an indwelling hollow cannula or solid trocar in the vascular segment can be equipped with a conductive wire which could then serve as the second electrode in the monitoring system. The vascular segment being accessed may be a surgically constructed arterio-venous fistula, and may also include an artificial conduit such as a GoreTex® vascular graft. The term 'arterial' is used herein to denote the portion of the blood flow circuit that conducts blood away from the patient and toward the hemodialysis machine 200. The term 'venous' is used to denote the portion of the blood flow circuit that conducts blood away from the hemodialysis machine 200 and back toward the patient. The term 'access needle' is used to denote a needle or catheter device that penetrates the patient's vascular segment or fistula. In different embodiments it may be permanently fused or reversibly connected to a corresponding catheter tubing 104, 130.

The continuity of any segment of the fluid flow circuit 100 can be monitored by positioning two electrodes in contact with the fluid on either side of the fluid and blood-containing segment of interest. In order to monitor for a disconnection of the arterial access needle 102, or the arterial catheter tubing 104, or the venous access needle 132 or venous catheter tubing 130, one electrode can be placed in continuity with the lumen of the venous side of the blood flow circuit, while a second electrode is placed in continuity with the lumen of the arterial side of the blood flow circuit. In one embodiment, the two electrodes can be positioned on or near the dialysis machine 200, with an electrode in contact with blood upstream of blood pump 110, and a second electrode in contact with blood downstream of the dialyzer 14 and/or air trap 122. For example, the electrodes can be incorporated into transition locations 110 and 124.

In another embodiment, one of the electrodes can be positioned to be in contact with the fluid in the fluid flow circuit 100 at a point that is closer to the vascular access site 134 than it is to the equipment (e.g. a dialysis machine) used to deliver fluid flow to the accessed blood vessel or vascular graft. In a preferred embodiment, both electrodes can be positioned to be nearer to the patient's blood vessel or vascular graft than the equipment associated with the dialysis machine 200. This may further reduce electrical interference associated with the dialysis machine 200. An electrode A can be conveniently placed at or near the arterial catheter tubing connector 106 and a second electrode B can be conveniently placed at or near the venous catheter tubing connector 128. In this arrangement, the electrical continuity pathway from the first electrode through the patient's vascular access to the second electrode is much shorter—and the electrical resistance lower—than the pathway extending back toward the dialysis machine 200. In some cases, the access catheters 104 and 130 can be as short as about a foot, whereas the arterial and venous tubings 108 and 126 can be about six feet long. Because of the electrical conductive properties of the fluid in the circuit, the electrical resistance associated with the pathway incorporating tubing 108 and 126, and components of the dialysis machine 200, can be many times greater than the electrical resistance associated with the pathway through the patient's blood vessel or fistula 134.

Electrical interference associated with the dialysis machine 200 is thus reduced, and a change in electrical resistance due to an access-related disconnection can more easily be detected. Preferably, the electrodes A and B are positioned to be more than 50% of the distance from the dialysis machine to the patient. More preferably (and more conveniently), the electrodes A and B are located near the last disengageable fluid connection before reaching the patient. In one embodiment of a hemodialysis system, the blood tubing 108 and 126 is approximately 6 feet in length, and the arterial and venous catheter tubes 104, 130 are about two feet or less in length. A convenient location for electrodes A and B would then be at the arterial line and venous line connectors 106, 128 (which can be, e.g. Luer type connectors or modifications thereof) that connect the arterial and venous blood circuit tubes 108, 126 with the arterial and venous catheter tubes 104, 130.

Connector Electrodes

Figure 41A:
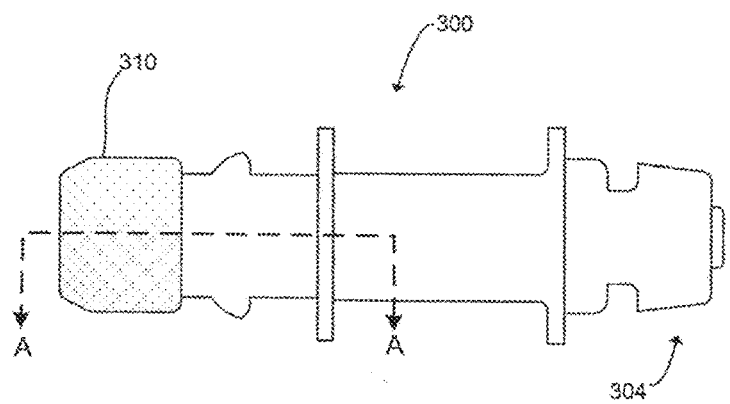
FIG. 41A is a side view of a connector that may be used in the blood flow circuit of FIG. 4.
Figure 41B:
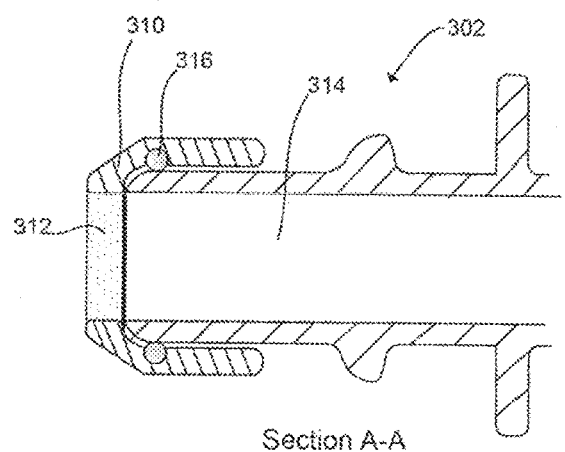
FIG. 41B is a cross-sectional view of the connector of FIG. 41A.

As shown in FIGS. 41A and 41B, in one embodiment, a blood line connector for the blood circuit of a hemodialysis system may incorporate electrodes that can make contact with any liquid within the lumen of the connector. In one aspect, the electrode can comprise an annular conductive cap 310 placed at the tube-connection or proximal end 302 of any suitable connector, such as, for example connector 300. The electrode is preferably constructed from a durable and non-corrosive material, such as, for example, stainless steel. The distal coupling end 304 of connector 300 can be constructed to make a sealing engagement with a corresponding Luer-type connector of an arterial or venous catheter, for example. The inner annular surface 312 of the cap 310—in part or in whole—can make contact with any liquid present within the lumen 314 of the connector. As shown in FIG. 41B, an O-ring 316 or a suitable sealant can be placed between the cap electrode 310 and the proximal end 302 of the connector to maintain a fluid-tight connection between the connector and any flexible tubing attached to the connector.

An elastomeric O-ring may be particularly useful in hemodialysis or other extracorporeal systems in which the blood-carrying components are subjected to disinfection or sterilization using heated liquids. The thermal coefficients of expansion of the plastic components of a connector may be sufficiently different from that of an incorporated metal electrode that a permanent seal may not be preserved after one or more sterilization or disinfection procedures. Adding an elastomeric component such as an O-ring at the junction between an electrode and the connector seat on which it is positioned may preserve the seal by accommodating the different rates of expansion and contraction between the electrode and the connector.

Figure 42:
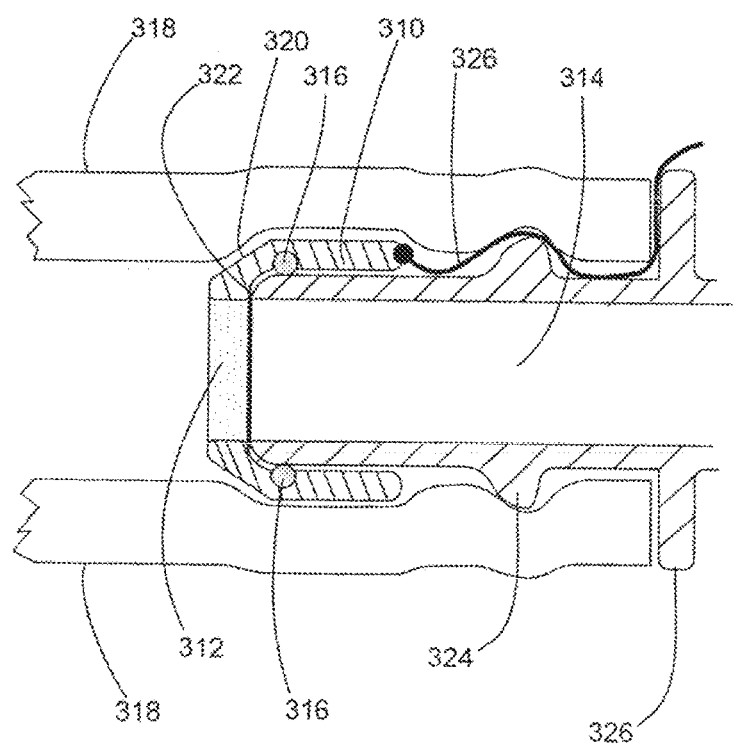
FIG. 42 is a cross-sectional view of the connector of FIGS. 41A and 41B, with an attached wire and flexible tubing.

As shown in FIG. 42, in one embodiment, a conductive electrode 310 (constructed of, e.g., stainless steel) can be incorporated into a portion of a connector 300 (either at its proximal end 302, or alternatively at its distal connecting end 304), over which the end of a flexible tubing 318 can be placed. In this embodiment, the electrode 310 is generally cylindrical, and has a taper 320 on a proximal end to permit an easier slip-fit attachment of the end of a segment of flexible tubing 318 over the outside surface of the electrode 310. As shown in FIG. 42, the internal surface of the electrode 310 has an internal ledge 322 that allows the electrode cap 310 to slip over and abut a proximal end 302 of connector 300. Connector 300 can be constructed of any suitable hard material, including metal or more typically a plastic material. The ledge 322 helps to ensure that a smaller diameter inner surface 312 of electrode 310 is properly positioned to make contact with any liquid (e.g. blood) that passes through the lumen 314 of connector 300. The connections between connector 300 and electrode 310, and electrode 310 and the termination of an overlying flexible tubing 318 can be made air tight or permanent with any suitable adhesive compatible with the compositions of the components.

To ensure a more secure seal to prevent blood leakage between the connector and electrode, and to limit the area under the electrode where blood elements may migrate and become lodged, an O-ring 316 can be incorporated into the inner surface of electrode 310 near the electrode internal ledge 320. This is seen in enlarged detail in FIG. 42. In this example, the O-ring 316 seals between the stainless steel electrode 310 and the distal end 302 of connector 300. A barb element 324 on the proximal end 302 of connector 300 can be incorporated in the connector design in order to hold the stretched end of the flexible tubing 318 onto the proximal end 302 of connector 300. In an embodiment, the electrode 310 is held in place by the portion of the flexible tube that is stretched over both the electrode 310 and the barb 324 of connector 300.

A wire 326 can be soldered, welded or otherwise secured onto the outer surface of electrode 310, and can travel under the overlying stretched tubing 318 until exiting more distally along the connector 300. The wire can thus conduct electrical signals to and from the electrode 310 as the internal surface 312 makes contact with the intraluminal fluid (e.g. blood). In the example shown, wire 326 is soldered to a distal portion of electrode 310 and travels under tubing 318, to emerge at the abutment of tubing 318 with a corresponding stop 326 of connector 300.

Figure 43A:
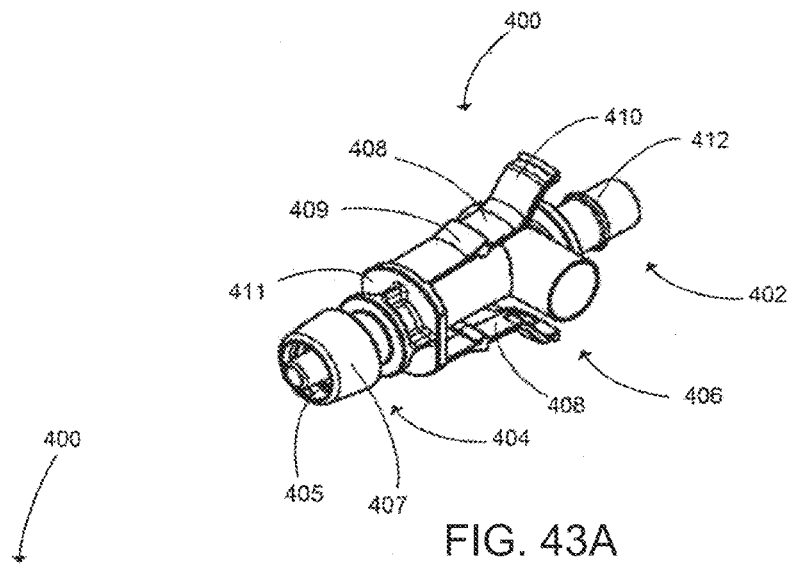
FIG. 43A is a perspective view of an alternate embodiment of a connector that may be used in the blood flow circuit of FIG. 40.
Figure 43B:
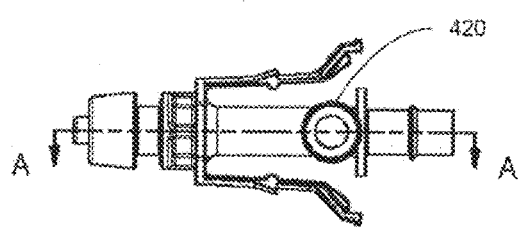
FIG. 43B is a top view of the connector of FIG. 43A.
Figure 43C:
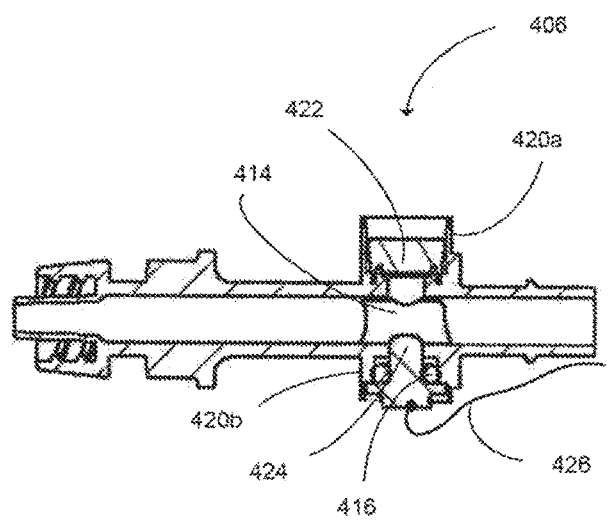
FIG. 43C is a cross-sectional view of the connector of FIG. 43B.

In another embodiment as shown in FIGS. 43A-43C, a connector 400 as described in U.S. Patent Application Publication No. 2010/0056975 (the contents of which are hereby incorporated by reference) has been modified so that a mid-portion 406 of the connector 400 can incorporate an electrode. Placement of the electrode along the mid-portion 406 of the connector 400 avoids having to alter the distal coupling end 404 of the connector, and avoids any alteration of the interaction between the termination of the flexible tubing and the proximal end 402 of the connector. In this example, the blood line connector 400 is constructed to make two different types of sealing connections on its distal coupling end 404, including an internal screw-type connection 405 for a Luer-type connector of a patient access line, and an external press-in type connection 407 with a dialysis machine port for recirculation of priming and disinfecting fluid through the blood carrying components of a dialysis system. The press-in feature 407 is formed having a frustoconical shape on the outside surface of the distal end 404 of the connector 400, while the Luer-compatible screw-type feature 405 is formed on the corresponding internal surface of the distal end 404 of the connector 400. The outside surface of the frustoconical member is constructed to make sealing engagement with the seat of a mating connector of a dialysis machine 200 or other device. A pair of locking arms 408 extending proximally from the distal coupling end 404 of the connector 400 can each have a barbed portion 409 to engage a corresponding locking feature on a mating connector on the dialysis machine, and a finger depression portion 410 to aid in disengaging the barbed portions 409 from the dialysis machine. The barbed portion 409 helps to lock the frustoconical member in sealing engagement with its mating connector on the dialysis machine when making a press-in type of connection. The distal ends of the locking arms can be constructed to attach to the connector via a flange 411 located proximal to the frustoconical portion 407 of the connector 400. The connector 400 has a proximal tubing attachment end 402 to sealingly engage a flexible tube. The tubing attachment end 402 may have one or more barb features 412 to help prevent disengagement of the end of a flexible tube from the connector 400.

FIG. 43B shows a side view of connector 400, bringing into view an access feature or port 420 that can permit placement of an electrode in direct communication with the lumen of connector 400. In other embodiments, the access feature may house an elastomeric stopper—with or without a septum—to permit sampling of fluid from within the lumen 414 of connector 400 using a syringe with a sharp or blunt needle. Alternatively, the feature may serve as a port to allow connection of another fluid line to the lumen 414 of connector 400.

In yet another embodiment, the mid-portion 406 of connector 400 may have two access ports, as shown in the cross-sectional view of FIG. 43C. A fluid access port 420*a* can serve as a sampling port, and an electrode port 420*b* can serve as an electrode cradle. An elastomeric stopper 422 within sampling port 420*a* can be shaped to extend to the lumen 414 of connector 400, simultaneously permitting sampling of fluid in the lumen 414 with a needle, while maintaining an air-tight seal. Alternatively, a Luer-type connector having a septated cap or seal can be incorporated into the port, which is capable of connecting with a syringe or catheter having a mating Luer-type connector. An electrode port 420*b* can serve as a seat or cradle for an electrode 424. In can be press-fit or cemented into position, and sealed with an adhesive, or with an O-ring 416 as shown. A wire 426 can be soldered, welded or otherwise secured onto the outer surface of electrode 424, and can travel proximally toward dialysis machine 200 with the arterial tubing 108 or venous tubing 126 to which connector 400 is attached.

In any of the above electrode embodiments, the electrodes may be replaced by a suitably sized thermistor, or combination of a thermistor and electrical conductor, for the additional purpose of monitoring the temperature of the fluid passing through connector 300, 400 or variants thereof.

Wire Assembly

In one embodiment, the wires carrying electrical signals to or from a pair of electrodes on connectors 106, 128 (one on the arterial side and one on the venous side of the blood flow circuit) can travel separate and apart from the blood tubing 108, 126 back toward dialysis machine 200, where they ultimately terminate and connect to, a conductivity detecting circuit, such as the conductivity circuit shown in FIG. 37. The conductivity circuit, in turn, provides an appropriately configured signal to a processor on the dialysis machine to determine whether a change in fluid conductivity consistent with an access disconnection has occurred. If so, the processor can trigger an alarm condition, or can initiate a shut-down of blood pump 13, and trigger a mechanical occlusion of blood tubing 108 and/or 126, for example.

Figure 44A:
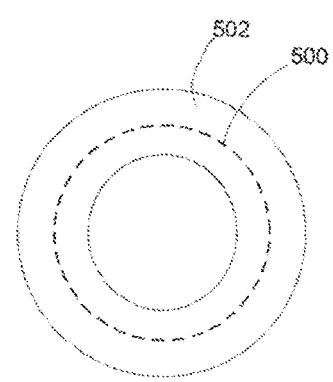
FIGS. 44A-D are various cross-sectional views of a flexible tube incorporating a conductive wire.
Figure 44B:
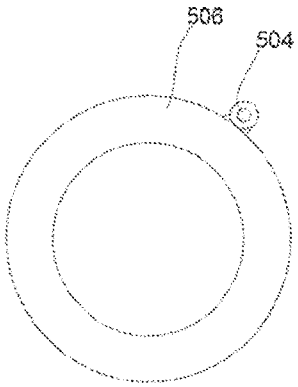
Figure 44C:
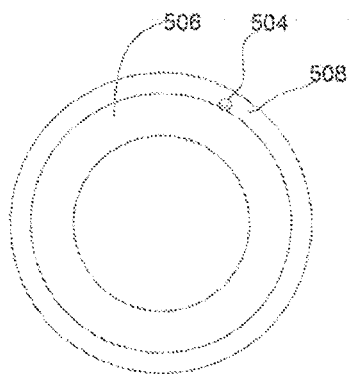
Figure 44D:
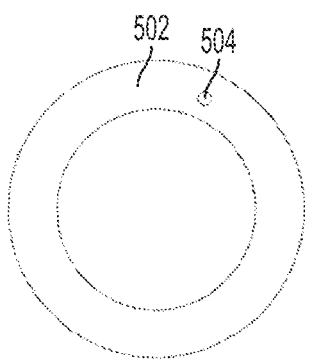

Wires that extend together or separately between the dialysis machine and the patient are at risk of getting tangled, broken or becoming disconnected. Therefore, preferably, each wire 326 or 426 can be attached, fused, or otherwise incorporated into its associated tubing 108, 128. Incorporating a wire into its associated tubing provides a convenient way of protecting the wires and connections, and simplifying the interface between the patient and the dialysis apparatus. Exemplary methods of achieving this are shown in FIGS. 44A-44D. In a preferred embodiment, the tubing is comprised of a flexible material (e.g., silicone) that can be formed in an extrusion process. As shown in FIG. 44A, a loose wire mesh may be embedded in the flexible silicone tubing as it is formed and extruded, similar to fiber reinforcement of flexible tubing. As shown in FIG. 41A, a wire mesh 500 can be embedded within the wall of the flexible tubing 502 during extrusion, in a manner similar to the construction of a fiber-reinforced tube. As shown in FIG. 44B, an insulated wire 504 can be joined to the external surface of its adjacent tubing 506, either during a secondary extrusion process, or a process in which the two structures are joined by an adhesive, for example. As shown in FIG. 44C, a second extrusion producing a secondary concentric layer of tubing material 508 can be made to capture a wire running along the external surface of the tubing after the primary extrusion. As shown in FIG. 44D, the tubing 502 during formation can also be co-extruded with a wire 504 embedded in the wall of the tubing.

Figure 45:
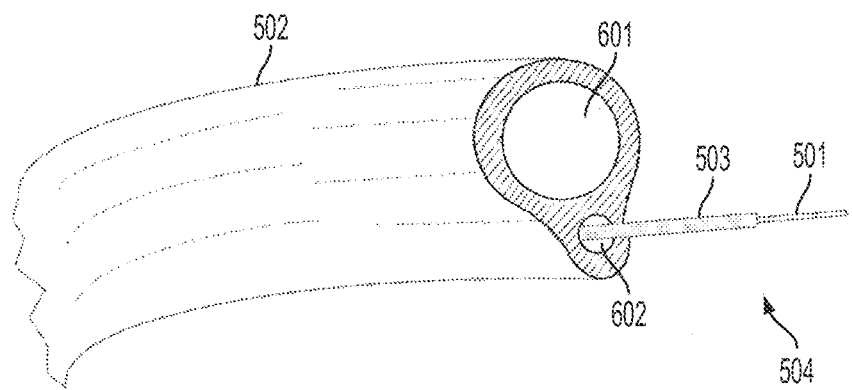
FIG. 45 is a perspective view of a flexible double-lumen tube having a fluid-carrying lumen and a wire-carrying lumen.

In some of the above methods, the resulting tube-wire combination may have a tendency to curl because of the difference in thermal coefficients of expansion between the wire and the silicone material of the tubing. As the material cools after extrusion, the silicone may capture the embedded wire tightly, causing the cooled tube-wire bundle to curl. In a preferred embodiment, the wire lumen of the extrusion die is constructed to be large enough to accommodate a cross-sectional area significantly larger than the cross-sectional area of the wire to be embedded. Then as the silicone cools, the passageway surrounding the wire does not shrink to the point of tightly encasing the wire. A co-extrusion process incorporating an insulated wire can generate a tube-wire bundle as shown in FIG. 45. In this example, flexible tubing 502 is a co-extrusion of a fluid-carrying lumen 601 and a wire-carrying lumen 602. Preferably, the wire 501 is multi-stranded for flexibility and durability, and is coated or sheathed in a durable, flexible synthetic insulating material 503, such as, for example, PTFE. A PTFE-based sheath 503 of the stranded wire 501 can sustain the high temperatures associated with the silicone tubing extrusion process, so that its integrity is maintained along the section 504 of the wire that ultimately exits the tubing for connection either to the dialysis machine 200 or the patient line connectors 106, 128. A coating or sheathing may also help prevent the wire from adhering to the side walls of the wire-carrying lumen after extrusion and during cooling.

Figure 46:
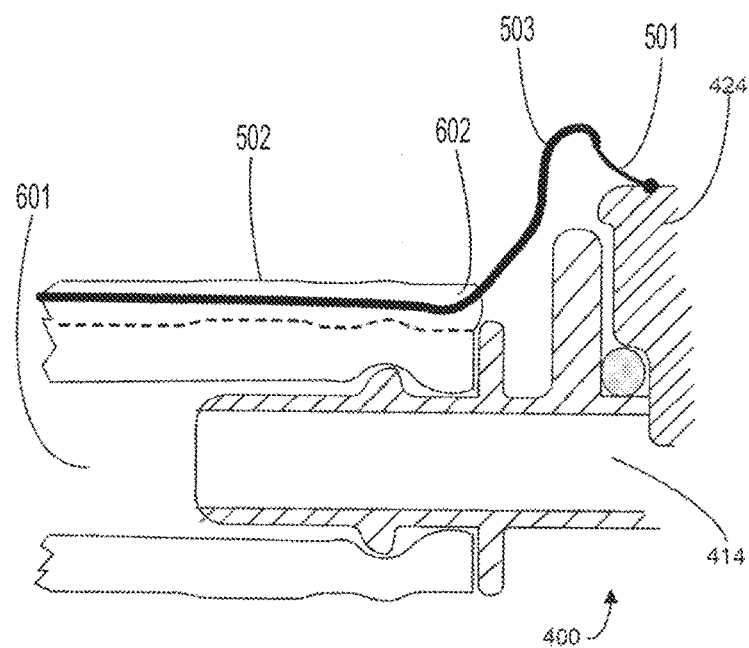
FIG. 46 is a cross-sectional view of a connector similar to the connector of FIGS. 43A-C, with an attached wire and tubing.

FIG. 46 shows a cross-sectional view of an exemplary connector-wire-tubing assembly. The proximal tubing connection end of a connector 400 is shown with the end of a double-lumen tubing 502 attached. The fluid-carrying lumen 601 is press-fit and/or cemented to the proximal end of connector 400, allowing for fluid flow through the central lumen 414 of connector 400. Stranded wire 501 is soldered or otherwise attached to electrode 424, which is in conductive contact with any fluid present within the lumen 414 of connector 400. The non-connecting portion of the wire 501 that travels outside tubing 502 is preferably sheathed in an insulating synthetic coating, such as, for example, PTFE. Optionally, this portion of both the exposed and sheathed wire may also be sealed with a sealant, such as RTV. The sheathed wire 503 enters the wire-carrying lumen 602 of tubing 502 near its termination onto connector 400. The wire/tubing bundle then makes its way toward the dialysis machine 200, where the wire emerges from the tubing to make a connection to a conductivity circuit such as the one shown in FIG. 37.

Figure 47:
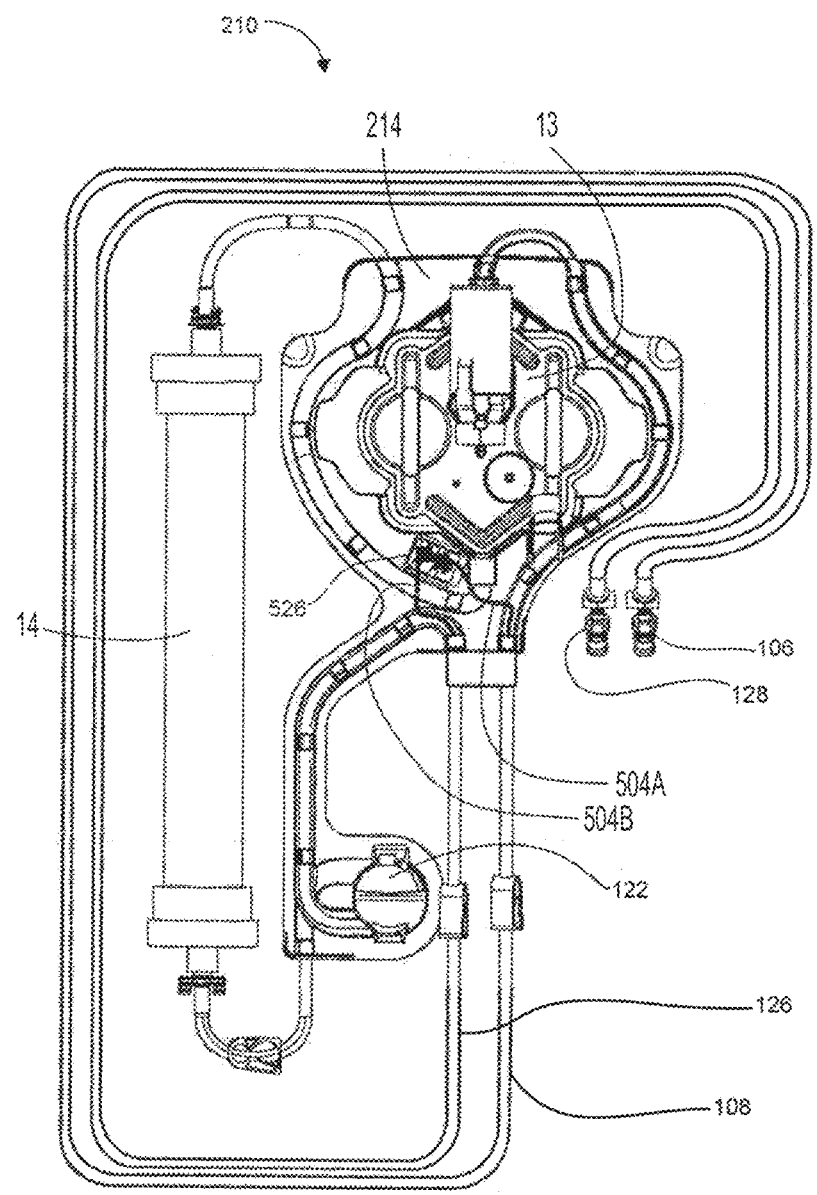
FIG. 47 is a plan view of an extracorporeal blood flow circuit used in a representative hemodialysis system.
Figure 48:
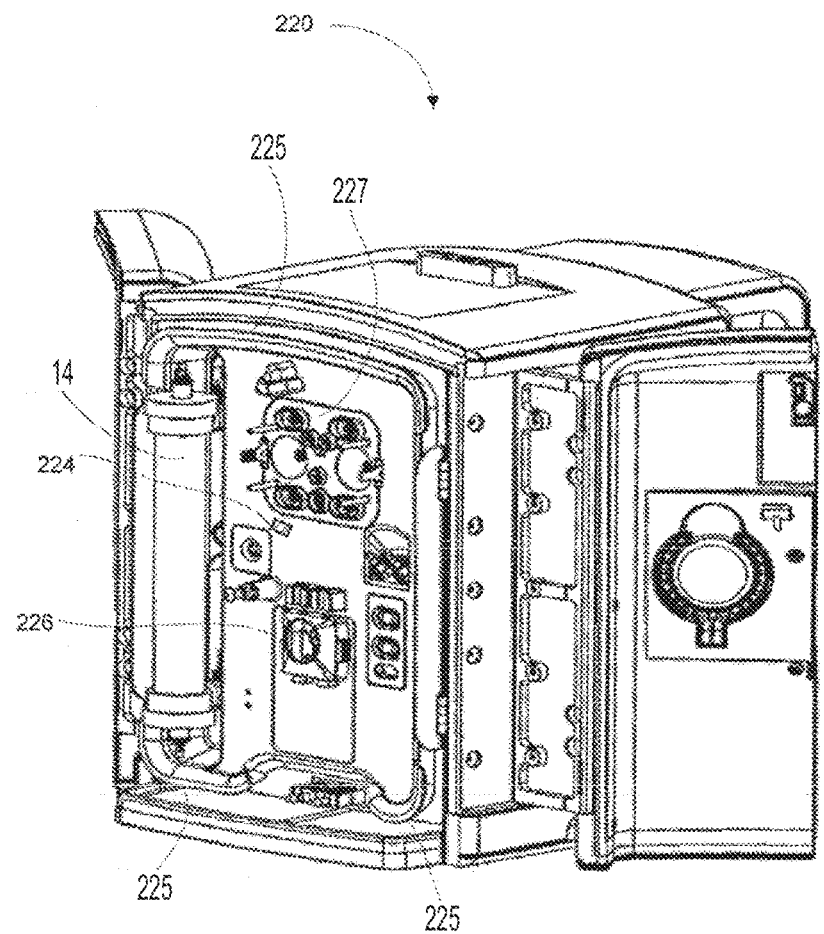
FIG. 48 is a perspective view of a hemodialysis apparatus configured to receive and operate the extracorporeal blood flow circuit of FIG. 47.

FIG. 47 shows an exemplary extracorporeal circuit 210 that may be used as a removable, replaceable unit in a hemodialysis apparatus 220 as shown in FIG. 48. In this embodiment, the extracorporeal circuit comprises a blood pump cassette 13, dialyzer 14, venous return air trap 122, arterial blood tubing 108, venous blood tubing 126, arterial catheter connector 106, and venous catheter connector 128. The arterial 106 and venous 128 connectors may be of a type similar to the connector 300 shown in FIGS. 41A and 41B, or similar to the connector 400 shown in FIGS. 43A-43C, or variants thereof. The arterial 108 and venous 126 blood tubes may be of a type shown in FIGS. 44A-44D, or FIG. 45. Wires forming terminal connections to electrodes on connectors 106 and 128 may exit arterial 106 and venous 126 tubes as segments 504A and 504B to make a connection with a connector that ultimately passes the connection through on the dialysis apparatus to terminals associated with a conductivity circuit such as that shown in FIG. 37. In the embodiment shown, the connector 526 is mounted to a support structure 214 for the blood pump 13 and air trap 122.

FIG. 48 shows an exemplary hemodialysis apparatus 220 that is configured to receive the extracorporeal circuit 210 shown in FIG. 47. In this illustration, the dialyzer 14 is already mounted onto the apparatus 220. A base unit 227 receives the control ports of a mating blood pump cassette 13. Sets of raceways or tracks 225 help to organize the pair of arterial 106 and venous 126 blood tubes when not extended out and connected with a patient. A connector 224 receives and passes through the connections made between wire segments 504A and 504B and connector 526 to the terminal connections of a conductivity circuit such as that shown in FIG. 1. A tubing occluder 226 is positioned to receive venous blood tube 126 after it exits air trap 122, and arterial blood tube 108 before it reaches blood pump cassette 13. The occluder 226 may be actuated pneumatically or electromechanically, for example, whenever an alarm condition occurs that requires cessation of extracorporeal blood flow. A set of arms of occluder 226 can be configured to rotate against the walls of the flexible tubes, constricting or stopping fluid flow within them. Thus, a controller installed within apparatus 220 can receive a signal from a conductivity circuit similar to FIG. 37, the signal representing the electrical resistance of the column of fluid or blood between the electrodes mounted on connectors 106 and 128. Because the connectors are positioned much closer fluidically to the patient's blood vessel or fistula 134 than to the blood pump 13, dialyzer 14 and air trap 122, the signal associated with the fluid path through the blood vessel or fistula 134 can discriminate between an intact and an interrupted column of blood or fluid between the connectors 106/128 and the patient's blood vessel or fistula 134. The controller can be programmed to respond to an electrical resistance detected by the conductivity circuit found to exceed a pre-determined value. Depending on the circumstances, the controller may then trigger an alarm to alert the patient to a possible disconnection of blood flow, and may also optionally command the occluder 226 to cease extracorporeal flow to and from the patient.

Operation of the Disconnect Detection Circuit

Figure 40:
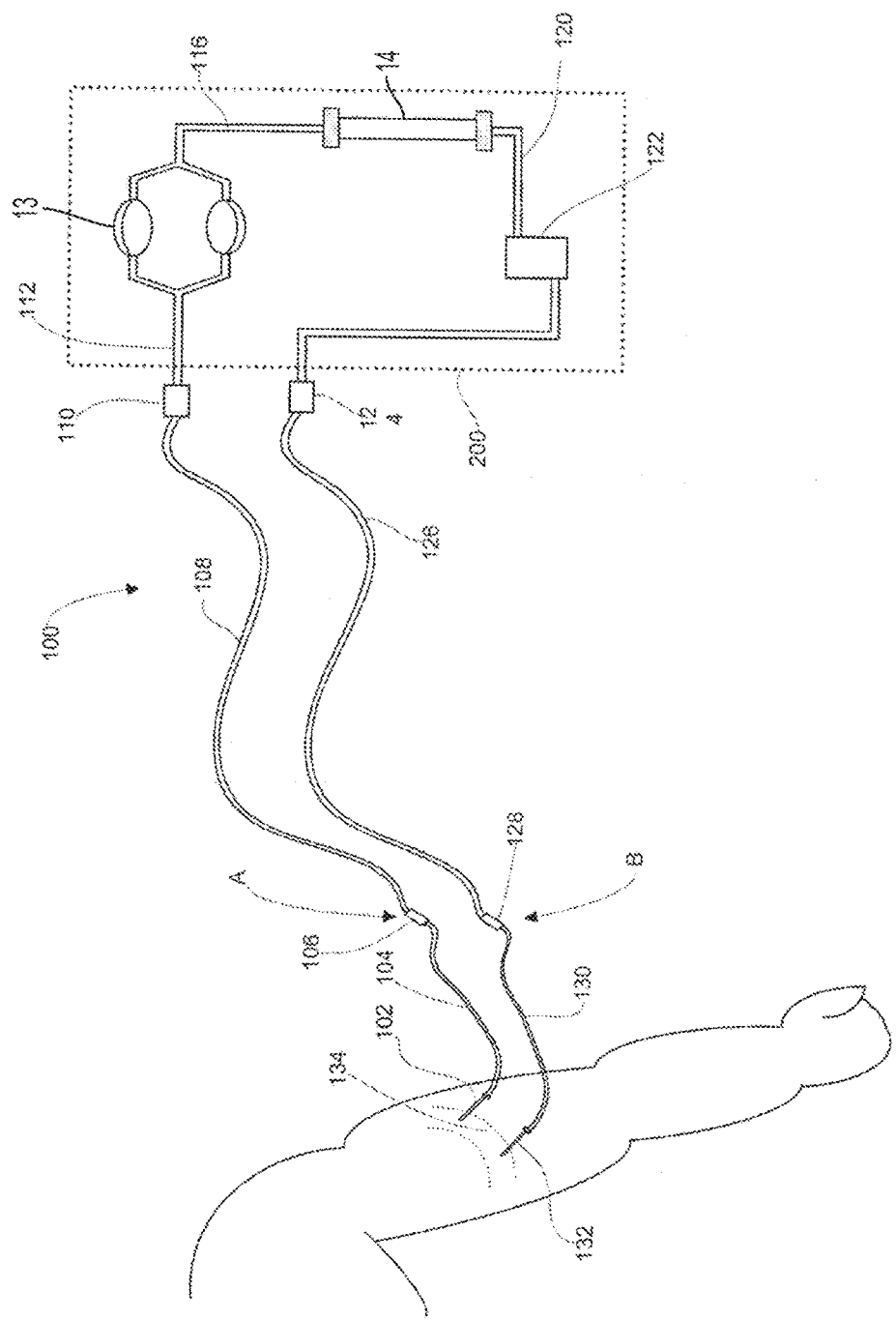
FIG. 40 is a schematic representation of an exemplary blood flow circuit of a hemodialysis system.
Figure 49:
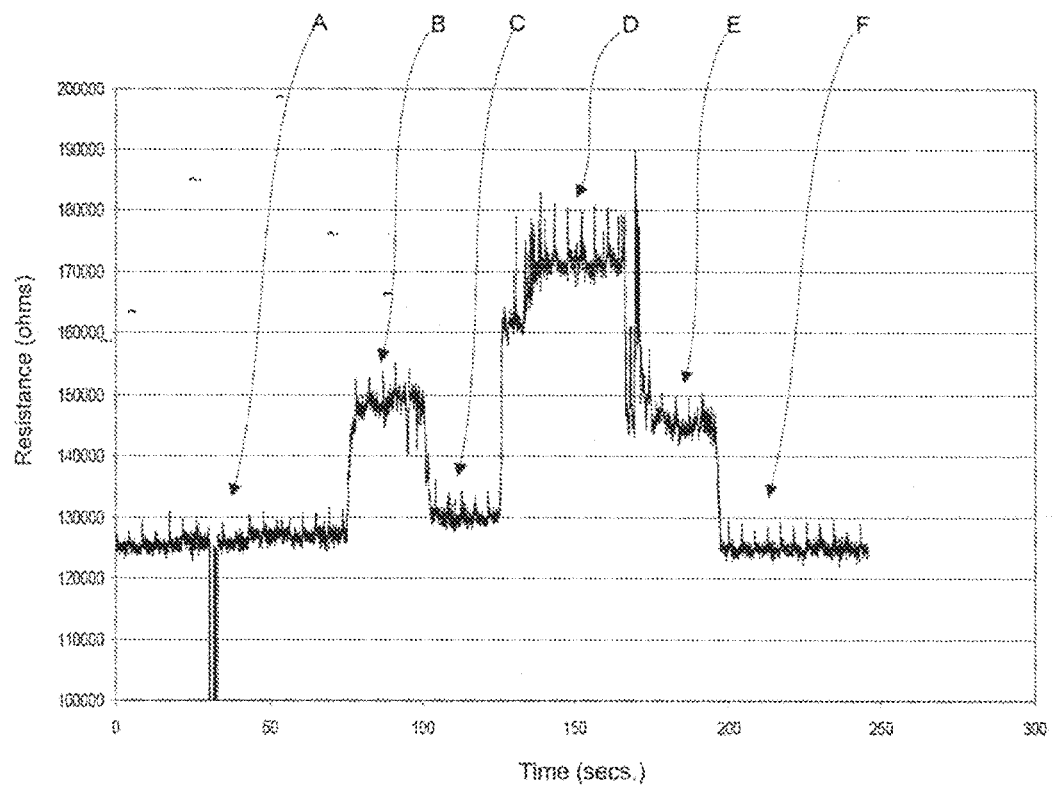
FIG. 49 is a representative plot of the resistance measured by the conductivity circuit of FIG. 37 under various conditions.

FIG. 49 shows test results utilizing the disconnect detection circuit described above and shown in FIG. 37. In this case, a hemodialysis blood circuit and apparatus was employed that is similar to that disclosed in U.S. Patent Application Publication Nos. 2009/01 14582 and 2010/0056975, (the contents of which are hereby incorporated by reference). The extracorporeal circuit 210 shown in FIG. 47, comprises a blood pump 13, dialyzer 14, air trap 122, venous blood circuit tubing 126, and arterial blood circuit tubing 108. Extracorporeal circuit 210 mates to a hemodialysis apparatus 220 similar to the one shown in FIG. 48. The blood flow circuit tested included a pair of membrane-based blood pumps arranged on a blood pump cassette 13 shown in FIG. 47, a dialyzer 14, a venous return air trap 122, an arterial blood tubing set 108, a venous blood tubing set 126, arterial and venous connectors 106 and 128, and catheter tubing sets 104, 130 connected to vascular access needles 102, 132 as shown in FIG. 40. The needles 102, 132 were placed in a container holding anticoagulated bovine blood. The blood tubing set 108 and 126 was approximately six feet long, and the catheter tubing sets 104 and 130 were approximately two feet long or less. The needles were alternately manually placed in or withdrawn from the container during blood flow to simulate disconnection of a needle from a fistula or blood vessel. Periods A, C and F in FIG. 49 represent the times during which the needles were submerged in the blood in the container. The electrical resistance measured by the disconnect detection circuit shown in FIG. 37 during these periods averaged between 120,000 and 130,000 ohms. Periods B and E in FIG. 49 represent the times during which the venous return needle 132 (under positive pressure from the blood pumps) was withdrawn several centimeters above the surface of the blood within the container, forming a stream of blood mixed with air as the blood exited the venous return needle and entered the container of blood below. The electrical resistance measured during these periods averaged between 140,000 and 150,000 ohms. Period D represents the time during which one of the needles was completely removed from the container, creating a fully open electrical circuit. The electrical resistance measured during this period averaged between about 160,000 and 180,000 ohms. Thus a controller can be readily programmed to distinguish the difference in the monitored resistance of the electrical circuit between an uninterrupted and an interrupted flow of blood. These results showed that an interruption of the continuity of the blood between the arterial 102 and venous 132 needles can reliably produce a detectible change in the measured electrical resistance between two electrodes when placed relatively closer to the arterial and venous access sites than to the blood processing components 13, 14 and 122 of the extracorporeal blood circuit. Furthermore, even a partial interruption of the continuity of blood flow (as in the streaming of blood through air) can be reliably detected, albeit with a smaller change in the measured electrical resistance.

Occluder

As mentioned above, an occluder, such as the occluder 513 in FIG. 17, can be used to control flow through lines of a blood circuit assembly, e.g., at a point between a patient connection of the blood lines 203, 204 and other portions of the assembly. Below, various aspects of the invention relating to an occluder, which may be employed alone or in any suitable combination with other features described herein, are described, along with one or more specific embodiments.

In accordance with one aspect of the disclosed invention, an occlusion assembly for compressing at least one flexible tube, for example a pair of flexible tubes is described. The occlusion assembly includes a tube occluder comprising a mechanism configured to occlude fluid flow within one or more flexible tubes, and in certain embodiments one or more pairs of flexible tubes. In certain embodiments, the tube occluder of the occlusion assembly comprises at least one occluding member, and in a specific embodiment comprises an occluding member for each section of tubing placed within the assembly. In certain such embodiments, each occluding member is pressed or otherwise forced or urged into an occluding position by an element that slides along a side of the occluding member, causing the occluding member to pivot at its proximal end and to translate toward the tubing at its distal end. In an embodiment, the element is positioned between two occluding members and acts to spread the distal ends of the occluding members away from each other as they press against their respective tubes. In a preferred option, a main spring urges the spreading element toward the distal ends of the occluding elements into an occluding position. The spreading element may be moved against the biasing force of the main spring into a non-occluding position near the proximal ends of the occluding elements either manually through a button and linkage assembly coupled to the spreading element, or by control of a controller activating an actuator that is also coupled to the spreading element. A hinged door may be configured to cover the occluding elements and their respective sections of tubing. Activation of the actuator may be prevented if the door is not properly closed over the occluding elements. Optionally, a retention element to hold the spreading element in a non-occluding position may be enabled when the door is in an open position. Enabling the retention element allows the spreader to be held in a non-occluding position without continued application of force by a user on the button or by continued activation of the actuator. The retention element may be disabled when the door is closed, so that the spreading element may be free to be moved into and out of an occluding position, either manually or via the actuator.

Figure 50:
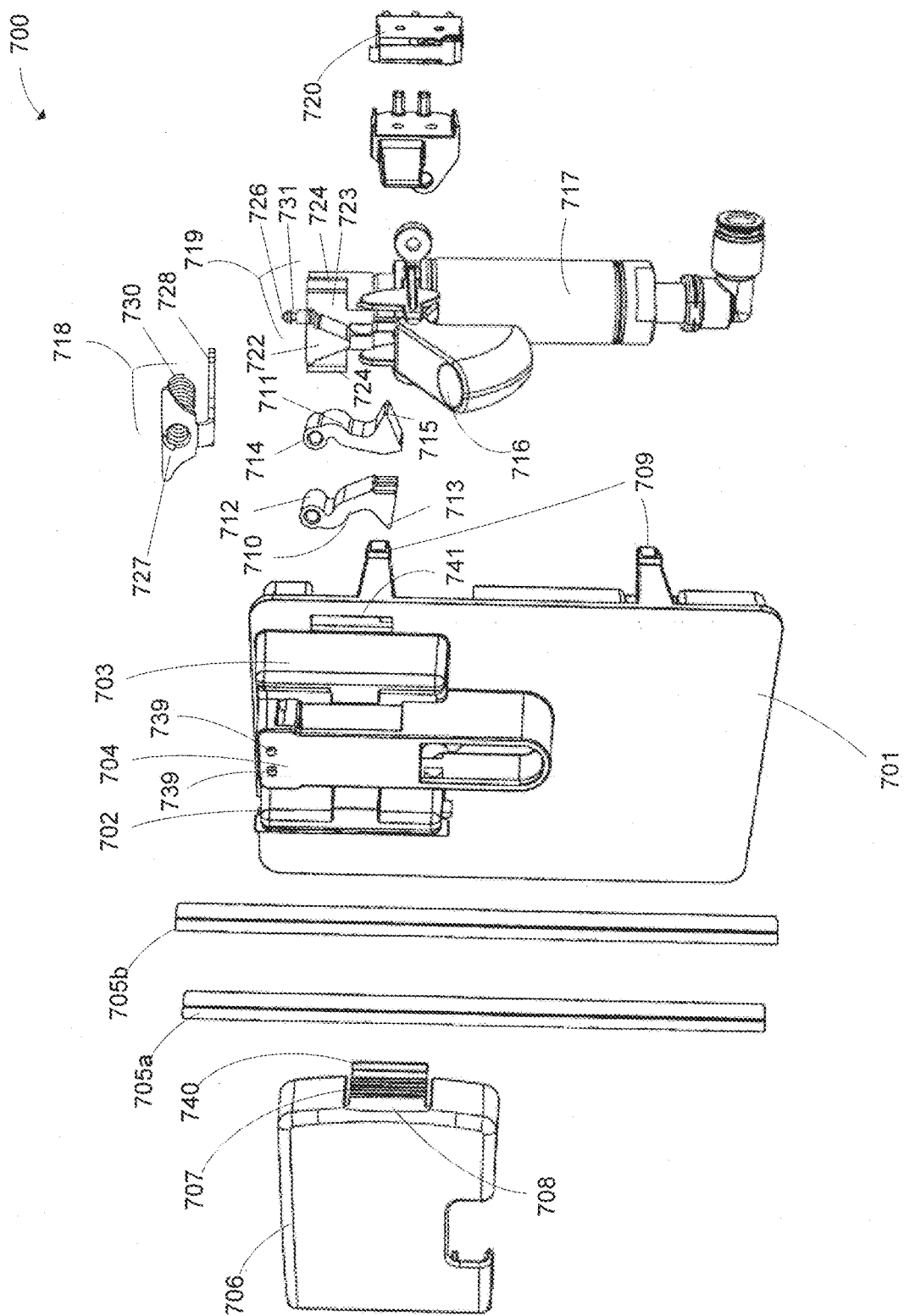
FIG. 50 shows an exploded, perspective view of an occlusion assembly from a front angle in accordance with an embodiment of the present disclosure.
Figure 51:
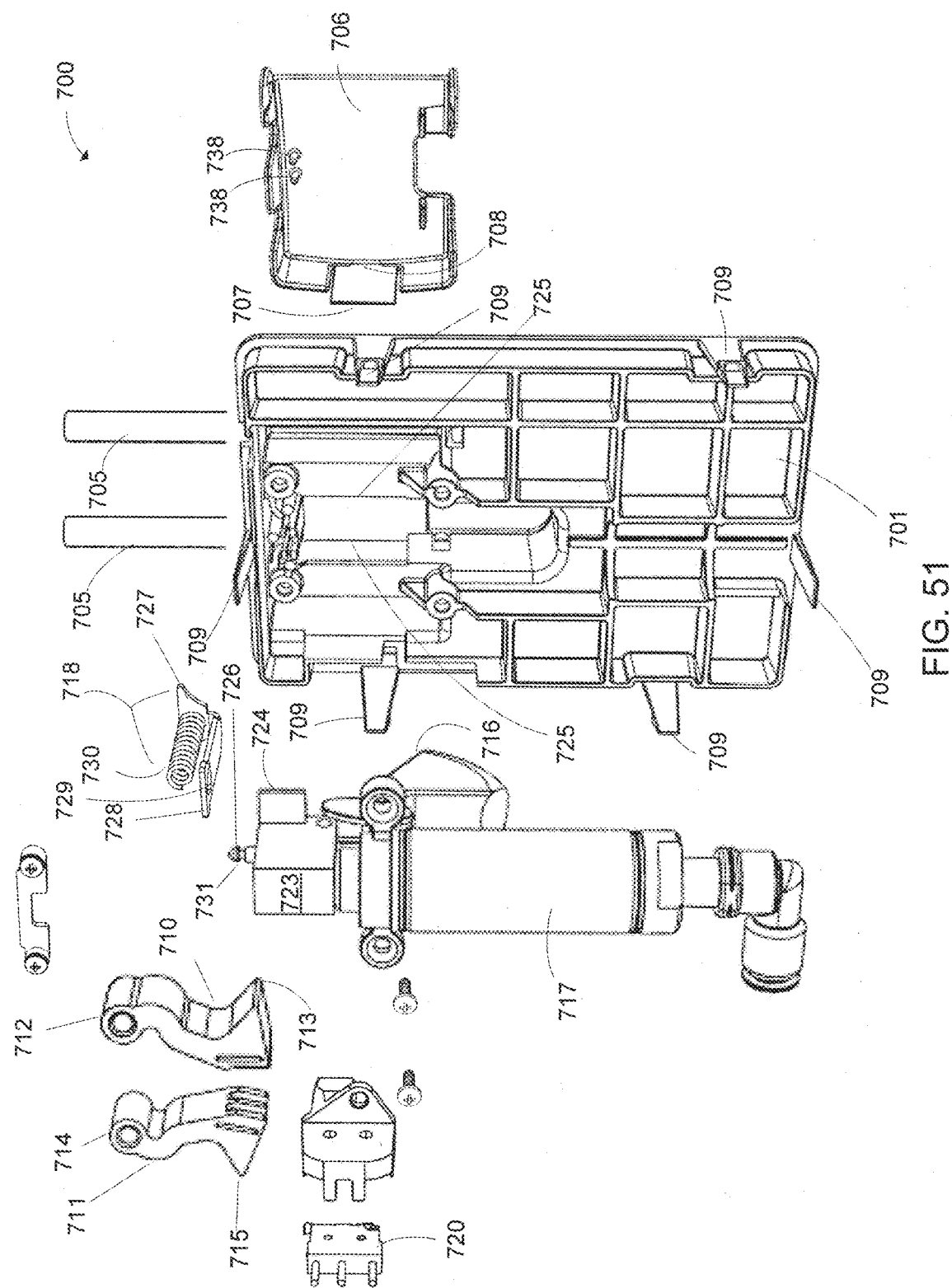
FIG. 51 shows an exploded, perspective view of the occlusion assembly of FIG. 1 from a back angle.

FIGS. 50 and 51 show exploded, perspective views of an occlusion assembly 700 in accordance with an embodiment of the present disclosure. FIG. 50 shows an exploded, perspective view of the occlusion assembly 700 from a front angle and FIG. 51 shows an exploded, perspective view of the occlusion assembly 700 from a back angle.

The occlusion assembly 700 receives a pair of tubes 705 and is configured to occlude the tubes 705 using a pinching action at approximately the same level along the length of assembly 700. The pinching action reduces the size of an inner fluid pathway of each tube 705 to restrict the flow of fluid therethrough. The occlusion assembly 700 may be used with an infusion pump, in a dialysis machine, in hemodialysis, in peritoneal dialysis, in hemofiltration, in hemodiafiltration, in intestinal dialysis, and the like.

The occlusion assembly 700 includes a frame 701. In some embodiments, the frame 701 includes tabs or snaps 709 for securing the frame to corresponding slots on a front panel of a blood filtration device, such as a hemodialysis apparatus.

Figure 52:
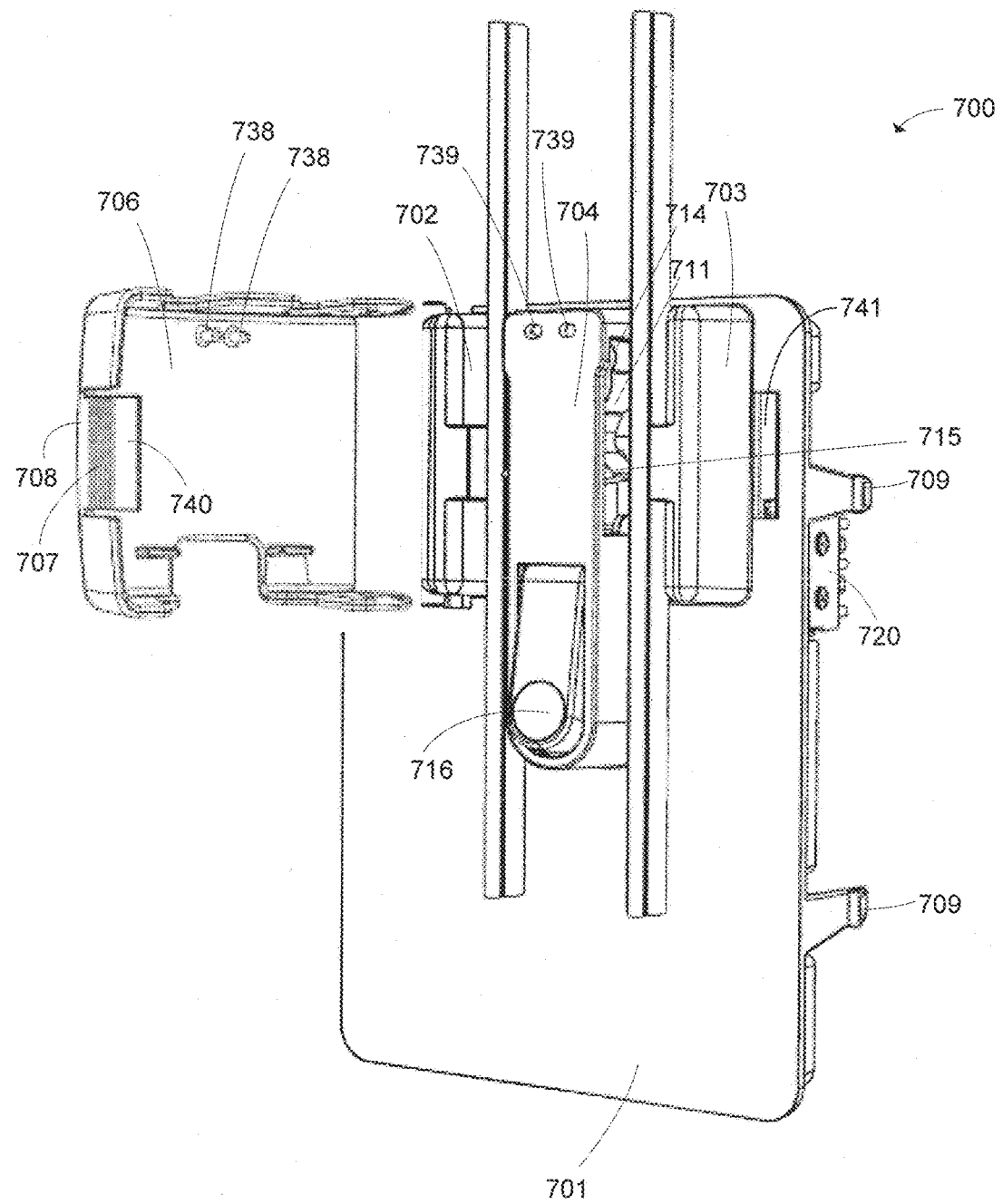
FIG. 52 shows a front, perspective view of the occlusion assembly of FIG. 1 with the door open and the button pressed to illustrate loading of a tube.
Figure 53:
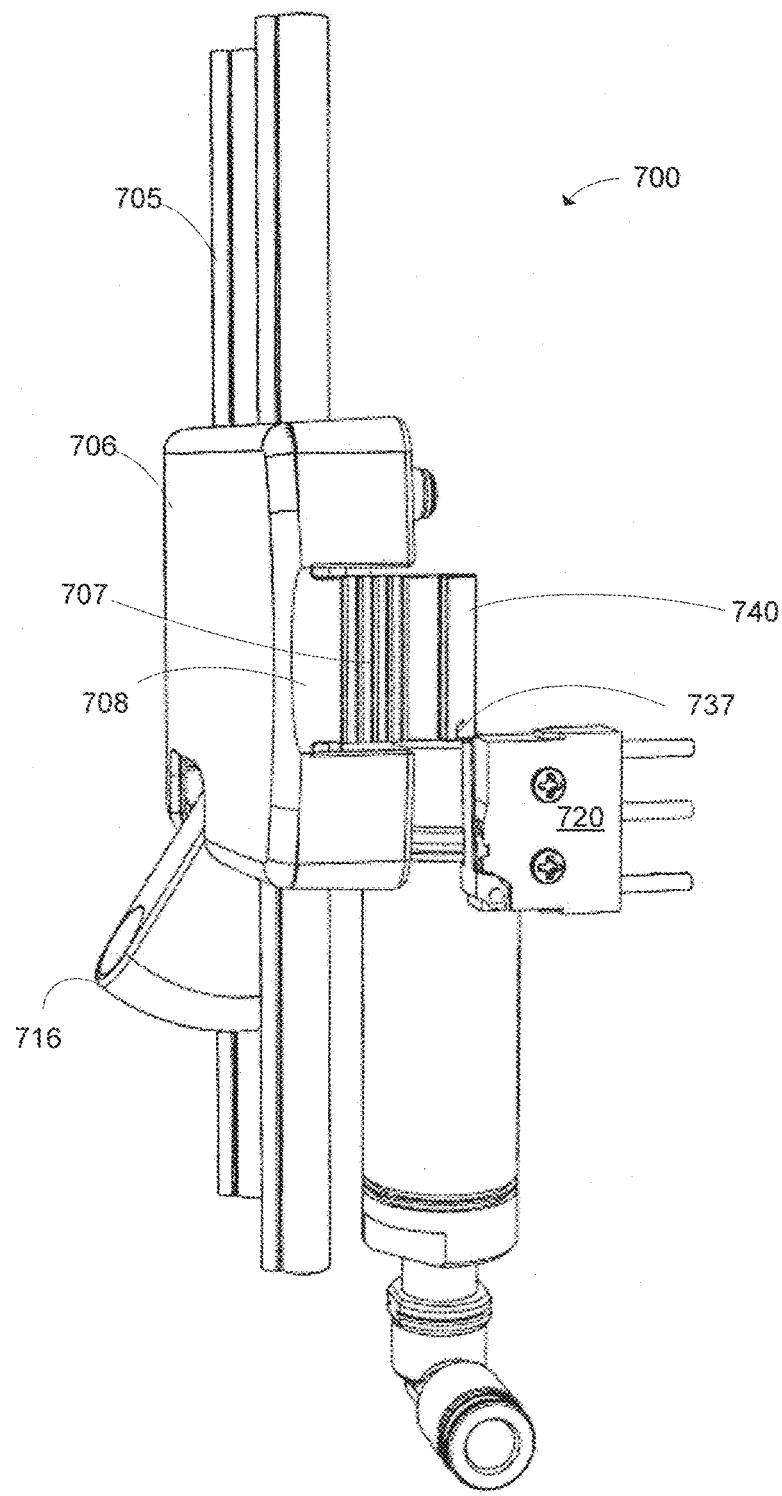
FIG. 53 shows a close-up perspective view of the occlusion assembly of FIG. 1, showing the door engaging a switch when the door is closed.

The frame 701 includes anvils or blocks 702 and 703 against which a tube 705 is compressed by the occluding ends 713 of a pair of occluding arms 710 and 711, and a tube guide 704 to position each tube 705 against blocks 702 and 703. The tube guide 704 and blocks 702 and 703 are configured to each position a tube 705 in a predetermined position adjacent to each of the blocks 702 and 703. The occlusion assembly 700 also includes a door 706 which is pivotally mounted to the frame 701. The door 706 can shut against the frame 701 to secure the tubes 705 between each of the blocks 702 and 703 and the tube guide 704. The door 706 includes a latch 707 co-molded with the door 706 via a resilient, flexible base portion (e.g., via a living hinge) 708 to secure the door 706 to the frame 701 in a closed position. However, the latch 707 could be arranged in other suitable ways, such as including a latch element that is adhered, welded, bolted or otherwise attached to the door 706. As shown in FIGS. 50, 52 and 53, the latch 707 may be pressed laterally to release a catch 740 from engagement with a corresponding slot 741 on frame 701 to open the door 706.

The occlusion assembly 700 includes two arms 710 and 711. The first arm 710 includes a pivoting end 712 and an occluding end 713; likewise, the second arm 711 includes a pivoting end 714 and an occluding end 715. The two arms 710 and 711 operate together to occlude the tubes 705 when a button 716 is released and door 706 is closed, or when an actuator 717 is deactivated.

Figure 54:
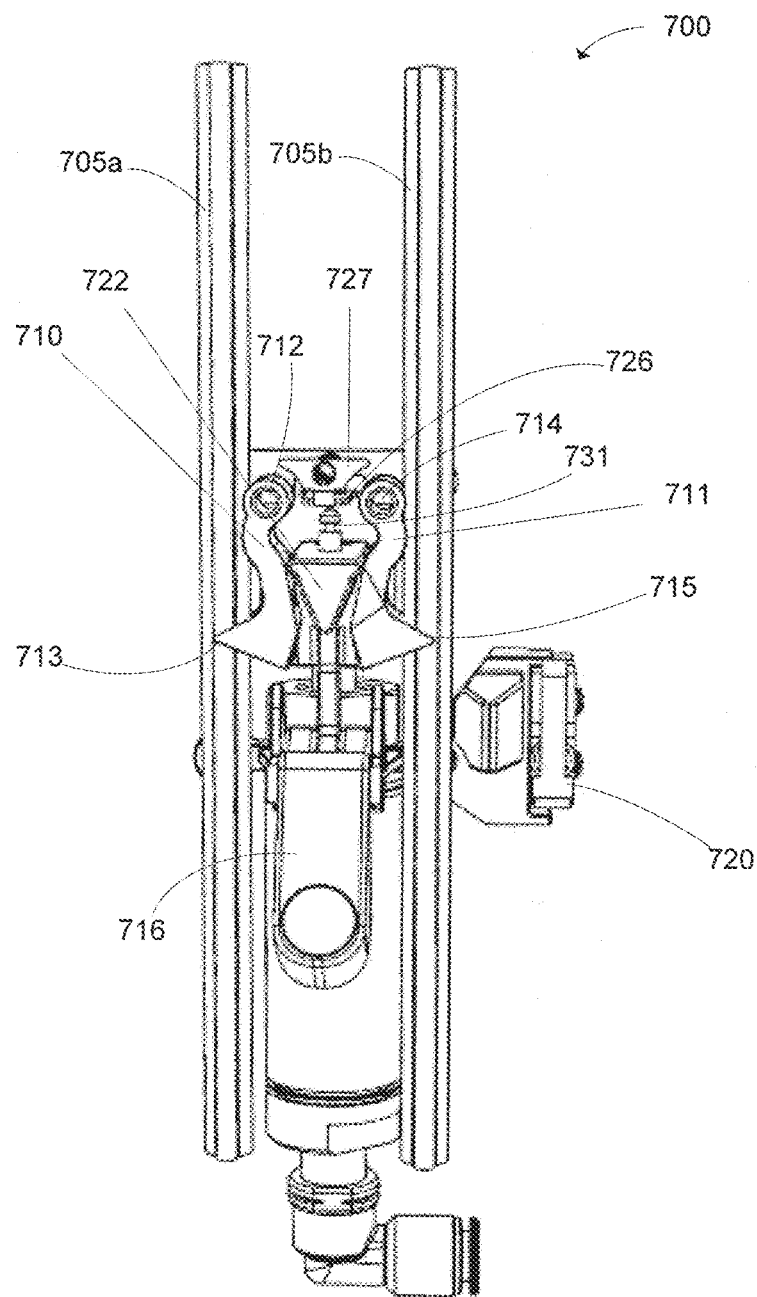
FIG. 54 shows the front of the occlusion assembly of FIG. 1 without the door and frame to illustrate the arms fully occluding flexible tubes.

FIG. 52 shows a front, perspective view of the occlusion assembly 700 with the door 706 open and the button 716 pressed to illustrate release of occluding arms 710 and 711 to permit loading and unloading of the tubes 705 in accordance with an embodiment of the present disclosure. FIG. 54 shows the front of the occlusion assembly 700 of FIG. 50 without the door 706 and frame 701 to illustrate the arms 710 and 711 fully occluding the tubes 705a, b in accordance with an embodiment of the present disclosure. As shown in FIG. 54, a wedge element or spreader 722 contacts the facing sides of occluding arms 710 and 711, which under spring force can apply pressure to occluding arms 710 and 711 to press the occluding ends 713 and 715 of occluding arms 710 and 711 against a portion of tubes 705a, b. A user may release the occluding arms 710 and 711 by pressing button 716, which causes spreader 722 to withdraw away from occluding arms 710 and 711, releasing the pressure of spreader 722 being applied to the distal ends of occluding arms 710 and 711. In some aspects, the manual actuator (e.g. button 716) acts as an override mechanism to an automated actuator (such as, for example, a pneumatically operated piston/cylinder apparatus) connected to a tubing occluder element (e.g., the spreader 722). The manual actuator is operatively coupled to the tubing occluder to cause essentially linear motion of at least a portion of the tubing occluder, moving the occluding member from an occluding position to a non-occluding position upon manual operation of the override mechanism by a user.

Similarly, activation of an actuator may release occluding arms 710 and 711 by causing spreader 722 to withdraw away from the occluding ends 713, 715 of occluding arms 710 and 711. In one embodiment, as shown in FIG. 50, spreader 722 may be formed of, co-molded with, attached to or otherwise connected to a carriage assembly 723, which in turn is connected to an actuating arm of the actuator (see, e.g., FIGS. 56 and 57). The actuator may comprise, for example, a motor and gear assembly (e.g., rack and pinion assembly or worm-type gear assembly), a solenoid, a hydraulic cylinder or a pneumatic cylinder, among others. In a preferred embodiment, the actuator comprises a pneumatic cylinder 717 that causes an actuating arm comprising a piston arm 742 to extend linearly against a spring force (which in an embodiment may be a coil spring 745 within cylinder 717 as shown in FIG. 60). As shown in FIG. 60, in a perspective side view of a pneumatically operated linear actuator 717, piston arm 742 is connected to carriage 723. When activated by pneumatic pressure, actuator 717 extends piston arm 742 and moves carriage 723 and attached spreader 722 in a direction that withdraws spreader 722 from engagement with the distal ends 713, 715 of the occluding arms 710 and 711. (For clarity, occluding arm 711, frame 701, door 706, block 703 and tube guide 704, among other elements, have been removed from FIGS. 58-60). Preferably, a main spring that is either external or internal to cylinder/actuator 717 may apply a biasing force to piston arm 742 or carriage 723 to cause spreader 722 to move occluding arms 710 and 711 to an occluding position. In the event of a loss of power or pneumatic pressure, the occluding arms 710 and 711 will default to an occluding mode, preventing the flow of fluid through tubes 705. As illustrated in a cross-sectional view of occlusion assembly 700 in FIG. 60, in an embodiment, a coil spring 745 may be placed within the cylinder 743 to provide a biasing force against which piston 744 may move piston arm 742 under pneumatic pressure. Pneumatic pressure may be supplied to linear actuator 717 from a pressure source (e.g., a tank pressurized by a pump) regulated by an intervening electromechanical valve under control of an electronic controller.

Figure 59:
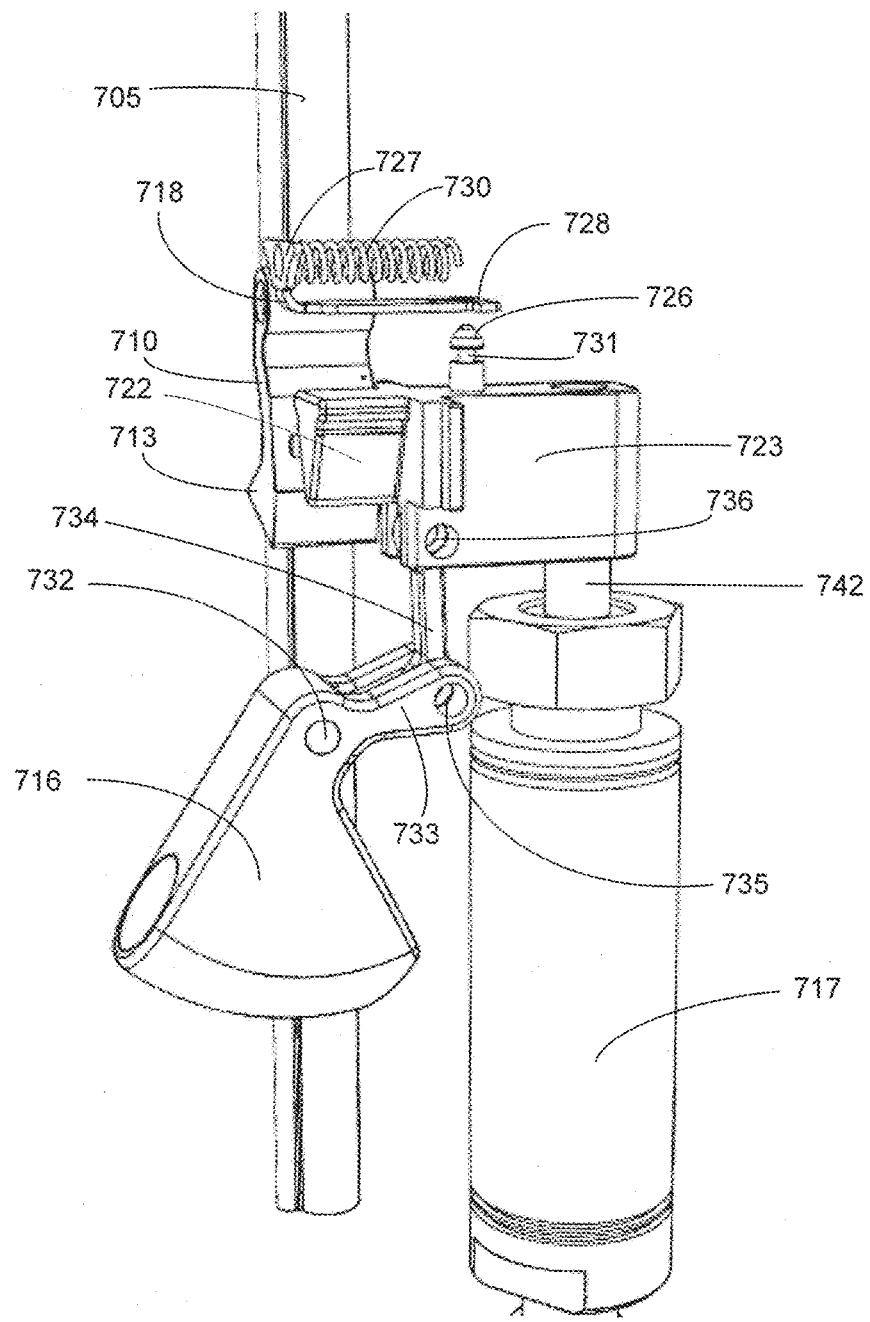
FIG. 59 shows a side perspective view of several working parts of the occlusion assembly of FIG. 1 in an occluding state.
Figure 60:
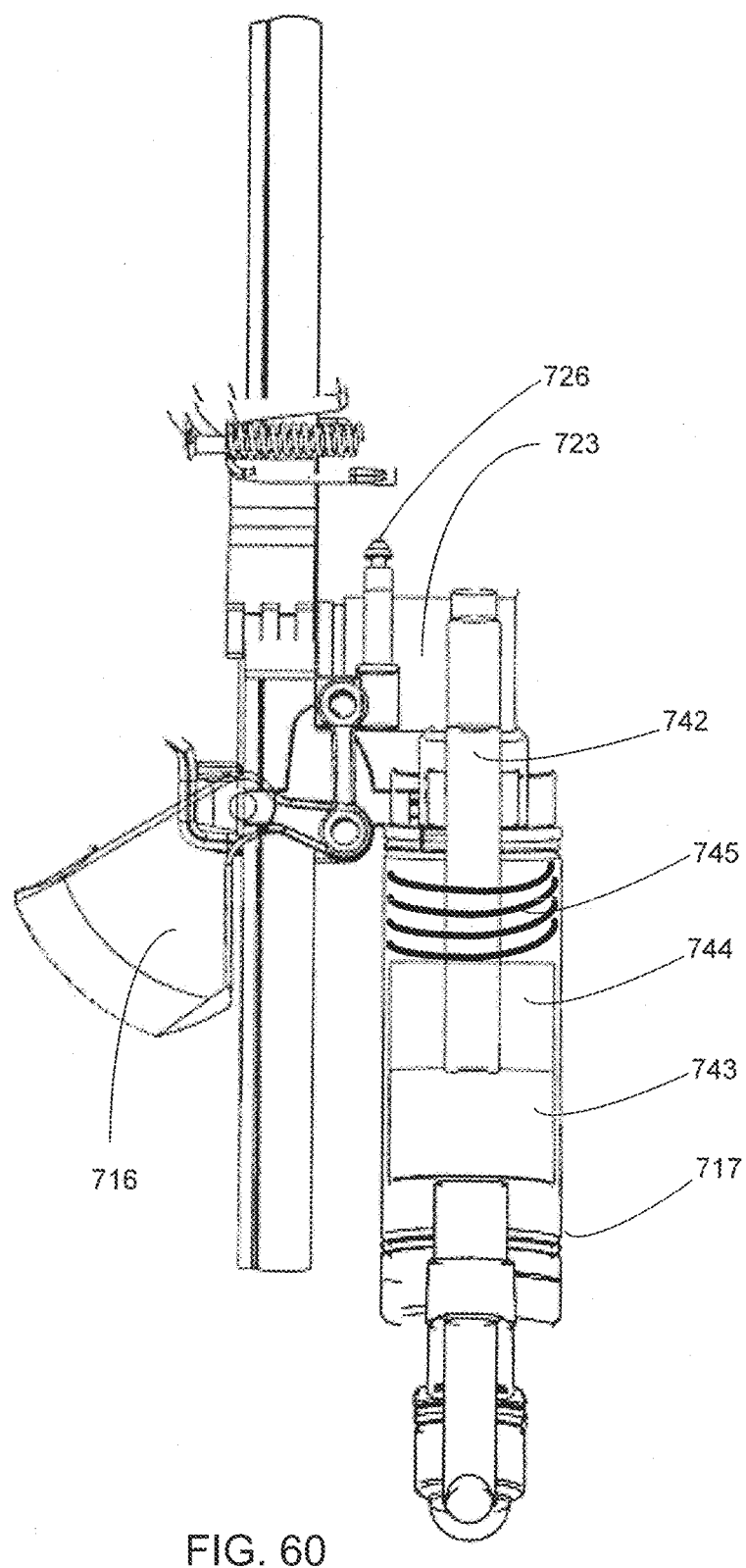
FIG. 60 shows a side, cross-sectional view of an actuator of the occlusion assembly of FIG. 1, illustrating a location for a main spring for the assembly.

As shown in FIGS. 54 and 59, when the linear actuator 717 is fully retracted, the carriage 723 carries spreader 722 along the facing sides of the occluder arms 710 and 711 to rotate them into an occluding position. The first arm 710 pivots about its pivoting end 712 to cause the occluding end 713 to press against first tube 705a that is restrained by block 702 (see FIG. 54). The second arm 711 pivots about its pivoting end 714 such that the occluding end 715 can press against second tube 705b which is restrained by block 703.

Figure 55:
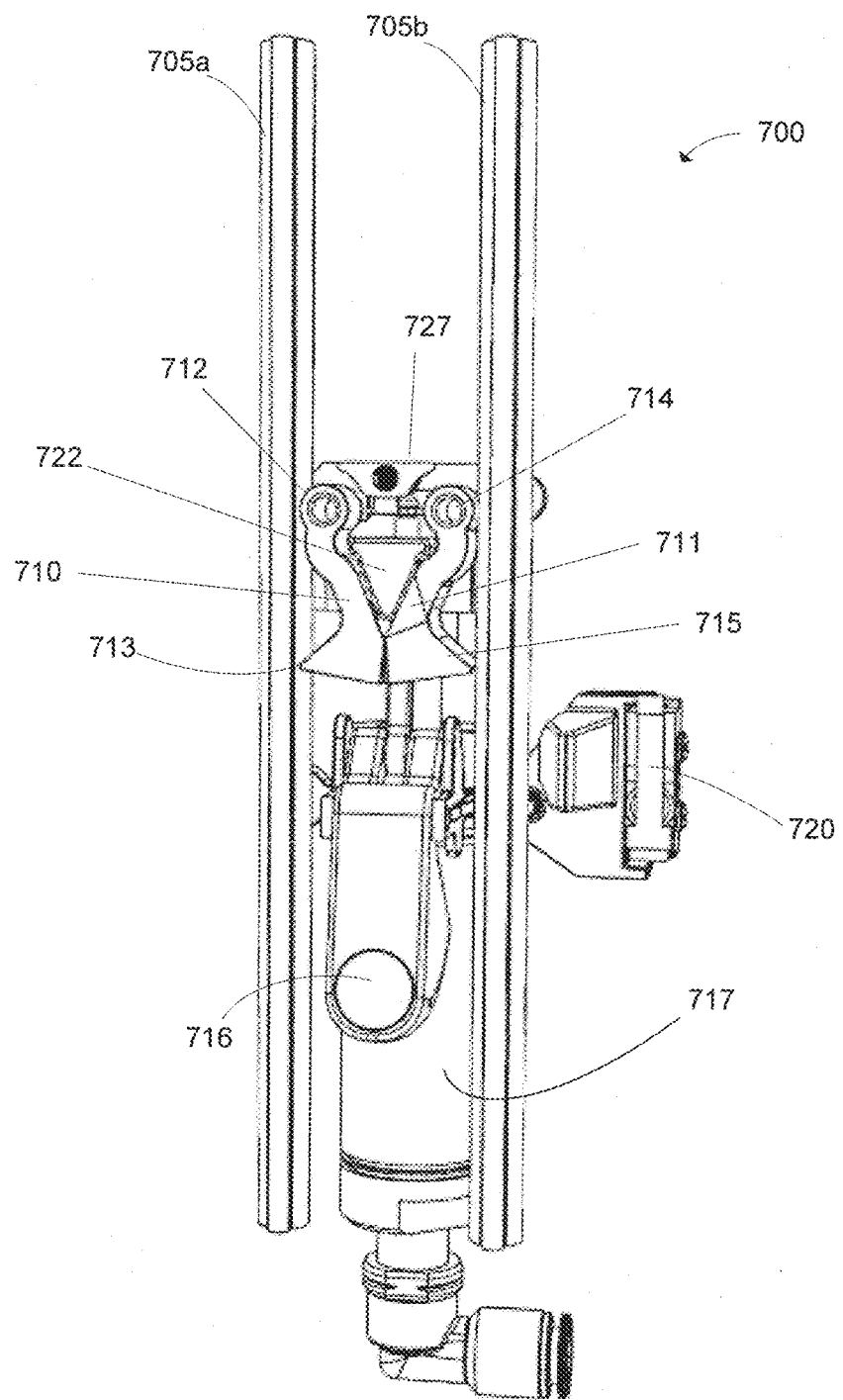
FIG. 55 shows the front of the occlusion assembly of FIG. 1 without the door and frame to illustrate the arms in a non-occluding position.
Figure 58:
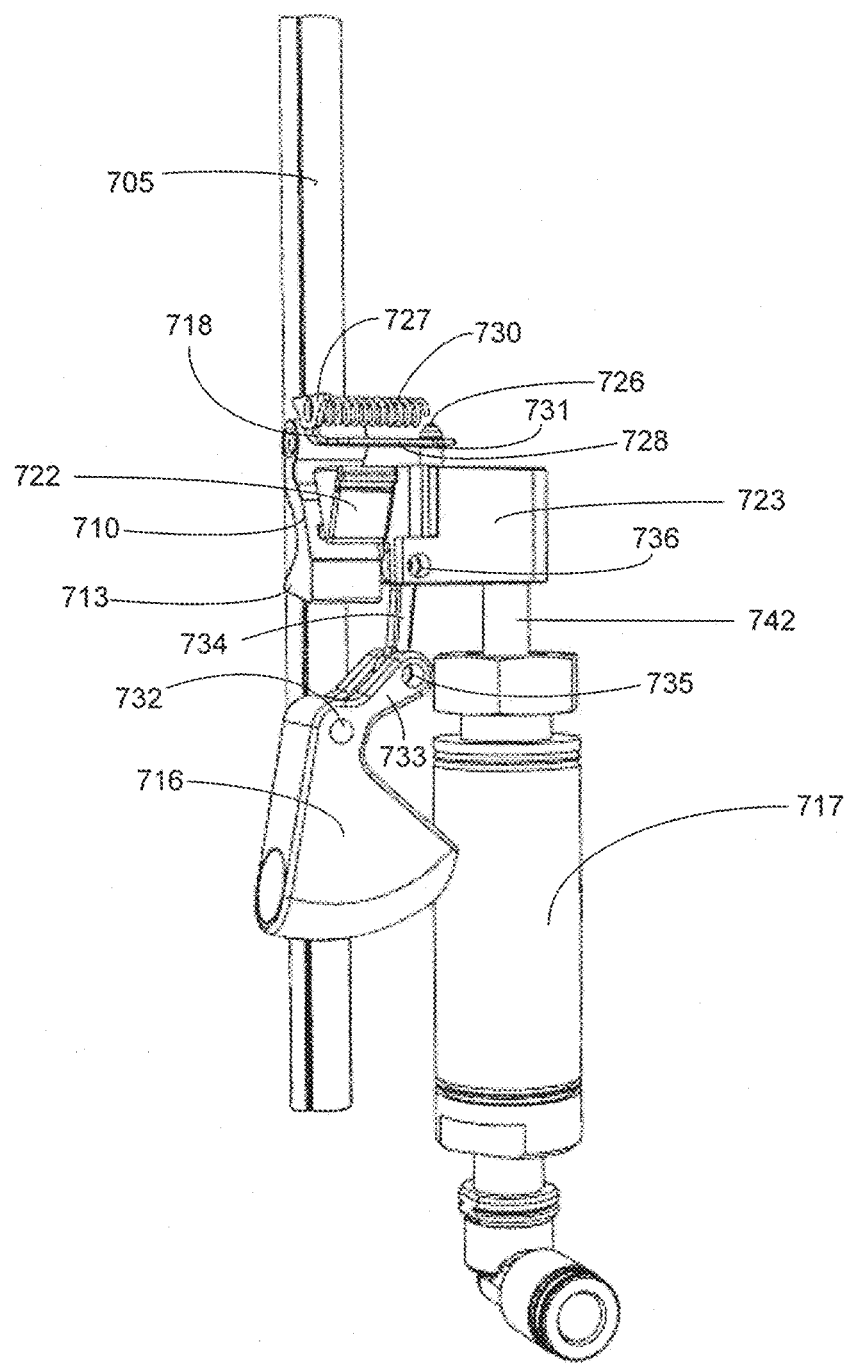
FIG. 58 shows a side perspective view of several working parts of the occlusion assembly of FIG. 1 in a non-occluding state.

FIGS. 55 and 58 show occlusion assembly 700 in a non-occluding state (frame 701, door 706. Blocks 702, 703, and other elements removed for clarity). When the button 716 is pressed or the linear actuator 717 is activated, the carriage 723 and attached spreader 722 move distally away from the actuator 717, allowing occluder arms 710 and 711 to rotate about pivot points 712 and 714 into a non-occluding position. The elastic resilience of the tubes 705a, b may cause the arms 710 and 711 to pivot towards each other. In some embodiments of the present disclosure, small magnets (not explicitly shown) embedded in the arms 710 and 711 pull the arms 710 and 711 towards each other to facilitate the retraction of the occluding ends 713 and 715 away from the tubes 705. In other embodiments, small springs (not shown) may bias occluding arms 710 and 711 to pivot toward each other, the spring constants being weak enough to be overcome by the main spring (e.g., spring 745) biasing carriage 723 or spreader 722 into retracted (occluding) positions.

FIG. 53 shows a perspective side view of the occlusion assembly 700 of FIG. 50 (frame 701 removed for clarity) showing the door 706 engaging a switch 720 when the door 706 is closed in accordance with an embodiment of the present disclosure. As shown in FIG. 53, the hinge portion 708 of latch 707 is coupled to an engagement member or catch 740 that can snap into a cooperating slot 741 of the frame 701 (see, e.g., FIGS. 50 and 53). As the door 706 is closed, a portion of the catch 740 of latch 707 of the door 706 engages a spring-loaded switch 720, which in an embodiment includes a spring arm 737 of the switch 720.

Engagement of switch 720 by closure of door 706 signals an electronic controller (not shown) that the door 706 is properly closed, and that linear actuator 717 may be activated to release occluders 710 and 711 to allow fluid to flow through tubes 705. The door 706 closure signal may also cause the controller to perform other functions, such as, for example, instructing a pump coupled to the tubes 705 to begin pumping fluid within tubes 705.

Figure 56:
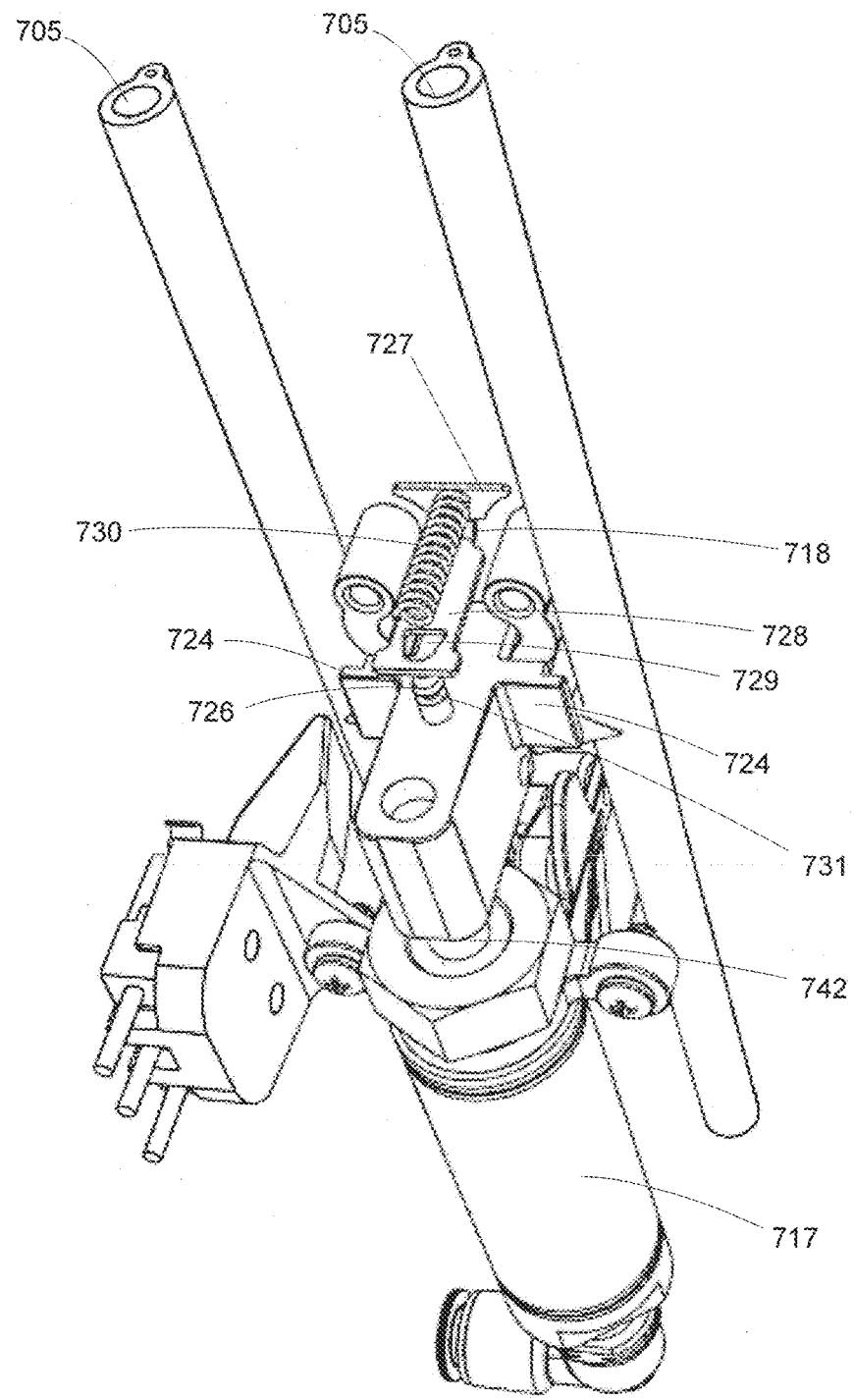
FIG. 56 is a rear/top perspective view of the occlusion assembly of FIG. 1 with an actuator arm in a fully retracted position.

FIG. 56 shows the back of the occlusion assembly 700 of FIG. 50 with the linear actuator 717 in a fully retracted position (i.e., in the occluding position) in accordance with an embodiment of the present disclosure. FIG. 56 shows the back side of the occlusion assembly 700 in the same configuration as shown for the front view of occlusion assembly 700 in FIG. 54. FIG. 56 shows several working parts of the occlusion assembly 700 of FIG. 50 to illustrate the operation of the actuator 717 and carriage 723 in accordance with an embodiment of the present disclosure. The carriage 723 moves with the extension or retraction of the piston arm 742 or with the actuation of the button 716. The carriage 723 includes guides 724 co-molded with or otherwise attached to the carriage 723. The guides 724 guide the carriage 723 as it moves via actuation of the piston arm 742 or with the actuation of the button 716. The guides 724 interface with tracks 725 of the frame 701 (see, e.g., FIG. 51).

In an optional embodiment, when door 706 is open, actuation of button 716 by a user or activation of actuator 717 by a controller causes carriage 723 and spreader 722 to move into a non-occluding position, and a retaining element or assembly allows the non-occluding position to be held without further force being applied either by the user or by the actuator 717. In an exemplary embodiment shown in FIG. 56, the carriage 723 may incorporate a latching pin 726 to cooperate with a slot or hole in a retention member 718.

The retention member 718 includes a surface 727 positioned to be contacted by pins 738 located on the inside of door 706 when it is closed (see, e.g., FIGS. 51 and 52). Through holes 739 allow pins 738 to contact a portion of retention member 718 to displace it in a rearward direction. In the illustrated embodiment, pins 738 contact front plate 727 of retention member 718. Retention member 718 also includes a surface having a slot or hole 729 positioned to receive the head of a latching pin 726, which in the illustrated embodiment comprises a horizontal plate 728 defining a receiving portion 729. Retention member 718 is arranged to slide within grooves or guides of the frame 701 (not shown) in response to contact by the pins 738 when the door 706 is closed or opened (see, e.g. FIG. 51). A spring 730 mounted on the frame 701 may be biased to urge the retention member 718 forward to a stop feature (not shown) on the frame 701 so that opening the door 706 allows the retention member 718 to slide forward, re-aligning the receiving portion 729 in relation to the latching pin 726. When the door 706 is closed (see FIG. 50 or 51), the pins 738 on the door 706 press against the front plate 727 which compresses the spring 730 such that the receiving portion 729 of the horizontal plate 728 is positioned directly over the latching pin 726. Upon alignment of the receiving portion 729 with the latching pin 726, the area of the receiving portion 729 is large enough to allow the latching pin 726 to be released by the retention member 718, thereby allowing the carriage 723 to be subject to the spring force of the main spring 745 in the actuator 717. If pneumatic pressure is not then being applied to the actuator 717, the carriage 723 is then free to move into an occluding position. The retention member 718 in the disabled state (i.e., inoperative state) allows the latching pin 726 to move freely through the receiving portion 729 as the carriage 723 moves between the fully extended position and the fully retracted position.

Figure 57:
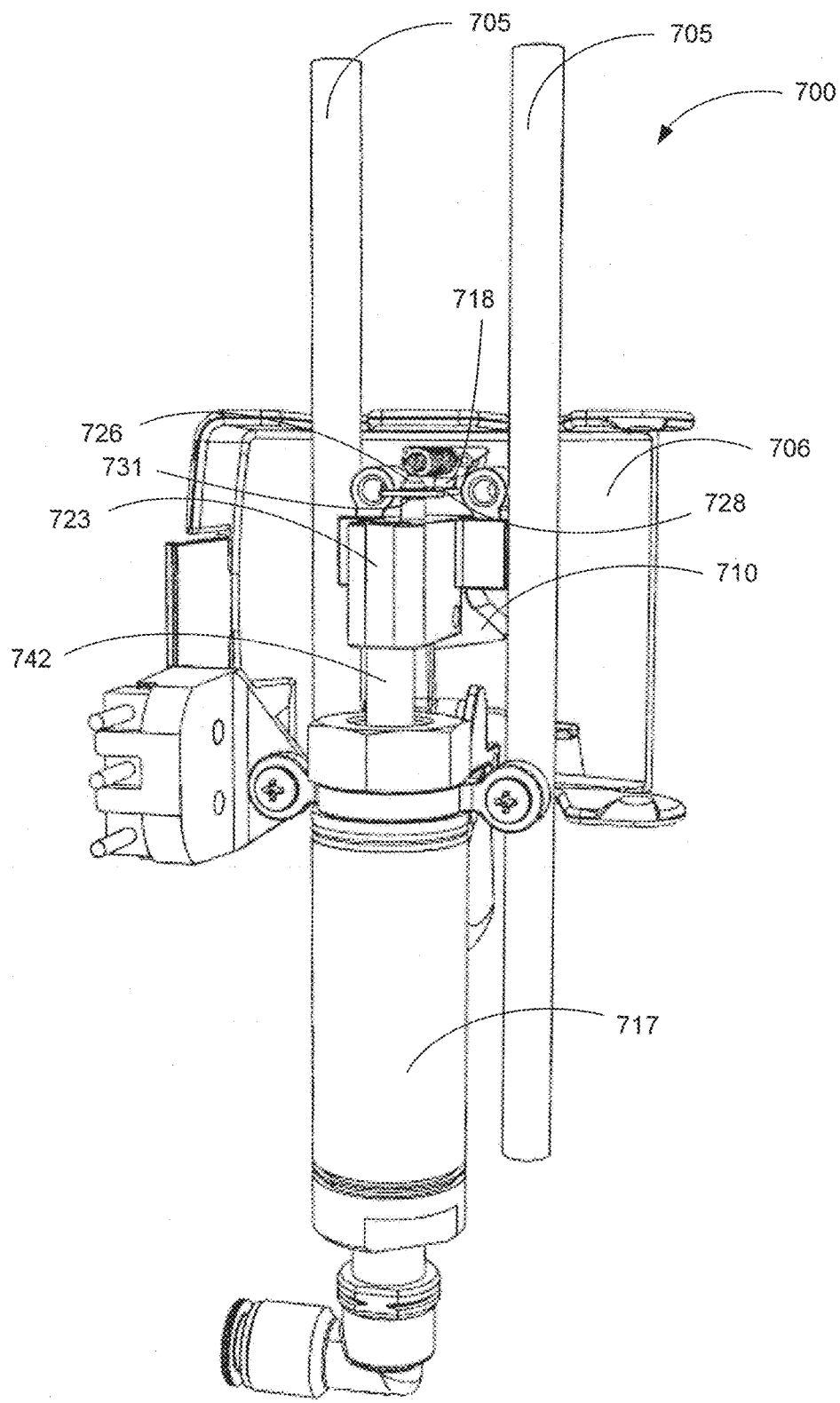
FIG. 57 is a rear perspective view of the occlusion assembly of FIG. 1 with an actuator arm in a fully extended position.

FIG. 57 is a rear view of the occlusion assembly 700 with the actuator 717 activated, and the piston arm 742 in an extended position to place the occluding arms 710, 711 in a non-occluding state. In this view, the head of the latching pin 726 is noted to be above the plane of the horizontal plate 728 of the retention member 718, and the recessed region 731 of the latching pin 726 is noted to be aligned with the receiving portion 729 of the retention member 718. In this illustration, door 706 is in a closed position, implying that the receiving portion 729 is in a sufficiently rearward position to prevent the latching pin 726 from being latched into the retention member 718.

When the door 706 is sufficiently opened, the pins 738 of the door 706 do not press against the front plate 727 and the spring 730 applies a force on the front plate 727 such that the receiving portion 729 of the retention member 718 is positioned to allow the latching pin 726 to engage an edge of the receiving portion 729 and latch to the retention member 718. The latching pin 726 moves into the receiving portion 729 pulling the front plate 727 rearward against the force of the spring 730 when the receiving portion 729 is positioned to latch to the latching pin 726. When the head of latching pin 726 moves sufficiently through the receiving portion 729, a recessed region 731 below the head of latching pin 726 becomes co-aligned with the horizontal plate 728 which moves as the edge of the receiving portion 729 moves into the recessed region 731 under the force of the spring 730 as applied to the front plate 727. When the pins 738 of the door 706 sufficiently engage the front plate 727, the receiving portion 729 is positioned to release the latching pin 726 from the latch 718. Thus, when the door 706 is open, the carriage 723 and spreader 722 can be held in a non-occluding position without the continuous application of force by the actuator 717 or by a user pressing against the button 716. This permits a user to load and unload tubing from occlusion assembly 700 without simultaneously having to apply force on the button 716. However, upon the closing of the door 706, the retention member 718 is no longer operative, and in the absence of continued application of force by either the actuator 717 or through the button 716, the carriage 723 and spreader 722 will move into a position to cause the occluding arms 710 and 711 to rotate to an occluding position.

FIGS. 58 and 59 show a side perspective view of several working parts of the occlusion assembly 700 of FIG. 50, with frame 701, blocks 702, 703, tube guide 704, door 706, occluding arm 711 and other parts removed for clarity. In FIG. 58, the piston arm 742 is fully extended in accordance with an embodiment of the present disclosure. FIG. 58 shows the latching pin 726 latched onto the retention member 718. That is, assuming that door 706 is in an open position, the horizontal plate 728 is positioned by the force of spring 730 to engage the recessed region 731 of the latching pin 726.

FIG. 59 shows a side, perspective view of the occlusion assembly 700 of FIG. 50 with the piston arm 742 in a fully retracted position, with certain elements removed as in FIG. 58 for clarity. In this example, the latching pin 726 is shown to be completely disengaged from the retention member 718; and in the absence of an activating force on the actuator 717 or a pressing force on the button 716, the piston arm 742, carriage 723 and spreader 722 are free to retract under the force of a main spring 745 (see FIG. 60) biased against the extension of piston arm 742. The spreader 722 then moves toward the occluding ends 713, 715 of the occluding arms 710, 711. In an embodiment, as shown in FIGS. 58 and 59, the button 716 pivots about a pivot 732 to raise a lever arm 733 when the button 716 is pressed. The lever arm 733 is pivotally connected to a connecting member 734 via a proximal pivot 735. The connecting member 734 in turn is pivotally connected to the carriage 723 via a distal pivot 736. When the button 716 is pressed or the piston arm 742 moves the carriage 723 toward the retention member 718, the connecting member 734 moves with the carriage 723, rotating the button 716 about the pivot 732 as shown in FIG. 58.

Figure 61:
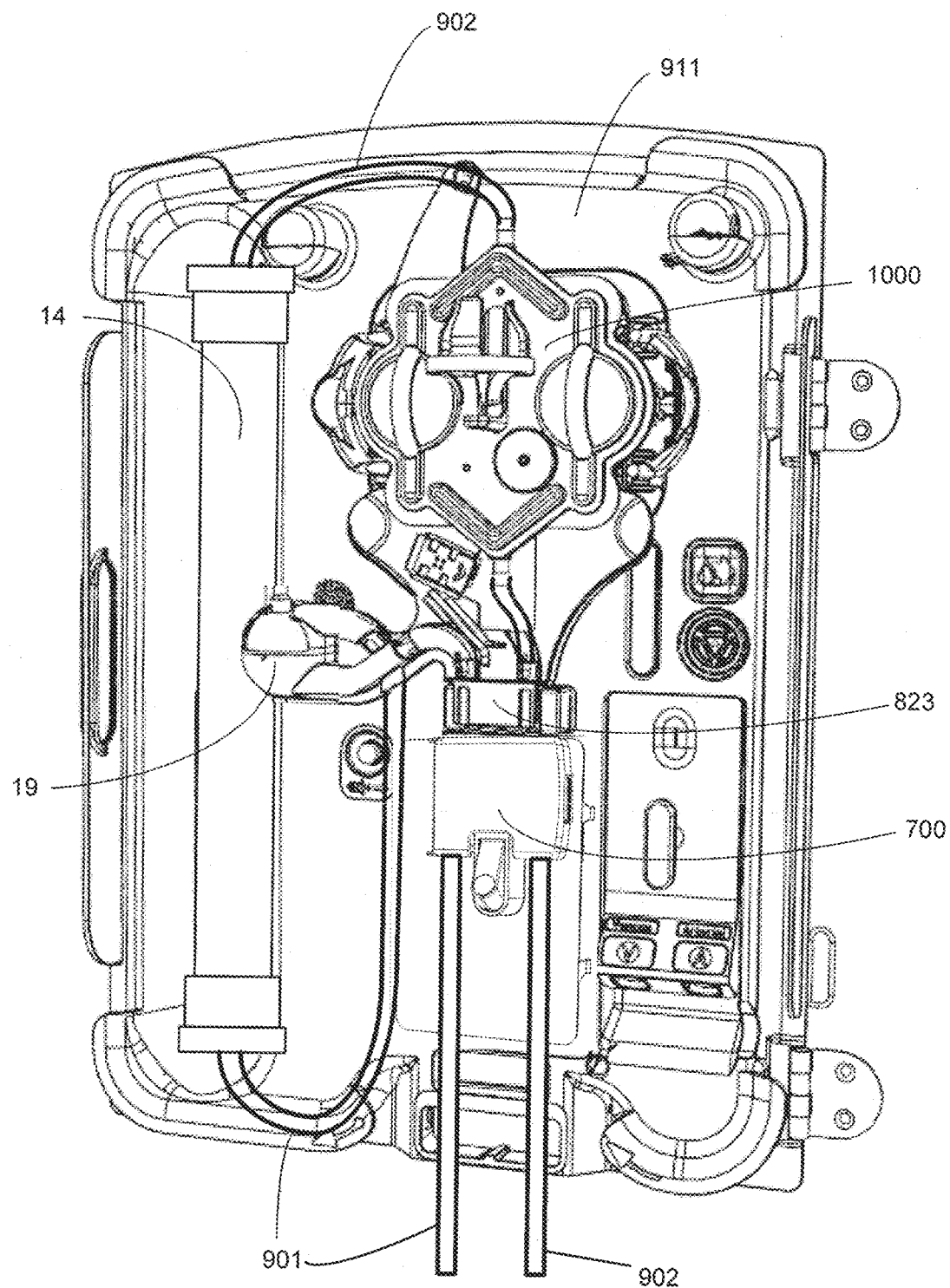
FIG. 61 shows the occlusion assembly of FIG. 50 mounted in a front panel assembly of a hemodialysis apparatus in accordance with an embodiment of the present disclosure.

FIG. 61 shows the occlusion assembly 700 of FIG. 50 used in a front-panel assembly 911 of a dialysis system in accordance with an embodiment of the present disclosure. The occlusion assembly 700 occludes flexible tubes 901, 902 through which blood flows to and from a patient. The right side tube 902 carries blood from a patient into a blood pump assembly 1000 (an arterial blood line) and the left side tube 901 carries blood from a dialyzer 14 back to the patient after passing through an air trap 19 (a venous blood line). The occlusion assembly 700 can occlude the flow of blood through both of these patient tubes 901, 902 simultaneously.

As discussed in detail above, the tubes 901, 902 are connected to a blood pump cassette or assembly 1000, which is a modular unit that may be mounted onto and dismounted from the front-panel 911. Both of the patient tubes 901, 902 may be provided as an assembly with the blood pump cassette 1000 and air trap 19, and may be loaded into the occlusion assembly 700 when the blood-pump cassette 1000 is mounted onto the front-panel 911. In this embodiment, the occlusion assembly 700 forms a permanent part of the front panel 911.

When the occlusion assembly 700 is in the non-occluding state, pumps located on blood pump cassette 1000 may be activated to pump blood from a patient through the right tube 902, up through the blood pumps and through a dialyzer 14. Blood processed by the dialyzer 14 then returns to the patient via tube 901 after first passing through an air trap 19 and an air-in-line detector 823.

The following are each incorporated herein by reference in their entireties: U.S. Provisional Patent Application Ser. No. 60/903,582, filed Feb. 27, 2007, entitled "Hemodialysis System and Methods"; U.S. Provisional Patent Application Ser. No. 60/904,024, filed Feb. 27, 2007, entitled "Hemodialysis System and Methods"; U.S. patent application Ser. No. 11/787,213, filed Apr. 13, 2007, entitled "Heat Exchange Systems, Devices and Methods"; U.S. patent application Ser. No. 11/787,212, filed Apr. 13, 2007, entitled "Fluid Pumping Systems, Devices and Methods"; U.S. patent application Ser. No. 11/787,112, filed Apr. 13, 2007, entitled "Thermal and Conductivity Sensing Systems, Devices and Methods"; U.S. patent application Ser. No. 11/871,680, filed Oct. 12, 2007, entitled "Pumping Cassette"; U.S. patent application Ser. No. 11/871,712, filed Oct. 12, 2007, entitled "Pumping Cassette"; U.S. patent application Ser. No. 11/871,787, filed Oct. 12, 2007, entitled "Pumping Cassette"; U.S. patent application Ser. No. 11/871,793, filed Oct. 12, 2007, entitled "Pumping Cassette"; and U.S. patent application Ser. No. 11/871,803, filed Oct. 12, 2007, entitled "Cassette System Integrated Apparatus." In addition, the following are incorporated by reference in their entireties: U.S. Pat. No. 4,808,161, issued Feb. 28, 1989, entitled "Pressure-Measurement Flow Control System"; U.S. Pat. No. 4,826,482, issued May 2, 1989, entitled "Enhanced Pressure Measurement Flow Control System"; U.S. Pat. No. 4,976,162, issued Dec. 11, 1990, entitled "Enhanced Pressure Measurement Flow Control System"; U.S. Pat. No. 5,088,515, issued Feb. 18, 1992, entitled "Valve System with Removable Fluid Interface"; and U.S. Pat. No. 5,350,357, issued Sep. 27, 1994, entitled "Peritoneal Dialysis Systems Employing a Liquid Distribution and Pumping Cassette that Emulates Gravity Flow." Also incorporated herein by reference are a U.S. Patent Application entitled "Sensor Apparatus Systems, Devices and Methods," filed on even date herewith (Ser. No. 12/038,474), and a U.S. Patent Application entitled "Cassette System Integrated Apparatus," filed on even date herewith (Ser. No. 12/038,648).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

The indefinite articles "a" and "an," as used herein in the specification and in the claims, unless clearly indicated to the contrary, should be understood to mean "at least one."

What is claimed is:

1. A blood circuit assembly for a dialysis unit, comprising:
a pair of pneumatic pumps for circulating blood received from a patient through a circuit including a dialyzer unit and returning the blood to the patient, the pneumatic pumps having pneumatic control ports arranged for alignment and mating with corresponding ports located on an exposed panel of the dialysis unit by pushing the control ports into engagement with the corresponding ports with mounting of the blood circuit assembly to the exposed panel;
an air trap having an inlet and an outlet arranged to remove air from blood circulating in the circuit;
a single unitary member that defines, at least in part, the pumps, a retaining member for the air trap and a plurality of routing channels for flexible tubing, the plurality of routing channels including a routing channel for a tube extending from the outlet of the air trap to an occluder position, the retaining member for the air trap being configured to support the air trap at a location above a lowermost part of the routing channel for the tube and above an air-in-line detector configured to detect air in the tube;
a pair of dialyzer connections arranged to connect to the inlet and outlet of a dialyzer unit;
a pair of blood line connectors, including an arterial blood line connector for receiving blood from the patient and providing blood to the pneumatic pumps and a venous blood line connector for returning blood to the patient; and
flexible tubing fluidly connecting the pumps, the air trap, the dialyzer connections and the blood line connectors.

2. The blood circuit assembly of claim 1, further comprising an anticoagulant connection for engaging with an anticoagulant source and providing anticoagulant into the circuit.

3. The blood circuit assembly of claim 2, further comprising a pump for pumping anticoagulant from the anticoagulant source to the circuit.

4. The blood circuit assembly of claim 3, wherein the pair of pneumatic pumps, the anticoagulant connection, and the anticoagulant pump are part of a pump cassette.

5. The blood circuit assembly of claim 4, wherein the arterial blood line connector is connected to an inlet for the pump cassette, an outlet for the pump cassette is connected to a dialyzer inlet connector, a dialyzer outlet connector is connected to the inlet of the air trap, and an outlet of the air trap is connected to the venous blood line connector.

6. The blood circuit assembly of claim 2, wherein the anticoagulant connection includes a vial holder and a spike, and the anticoagulant source is a vial of heparin.

7. The blood circuit assembly of claim 1, wherein the inlet of the air trap is supported by the single unitary member at a position above the outlet of the air trap when the blood circuit assembly is mounted to a dialysis unit.

8. The blood circuit assembly of claim 1, wherein the pneumatic pumps are diaphragm pumps.

9. The blood circuit assembly of claim 1, wherein the blood line connectors are arranged for a threaded luer-type connection to a patient access, and are arranged for a press-in type connection to the dialysis unit.

10. The blood circuit assembly of claim 9, wherein the blood line connectors include a frustoconical member with an internal thread for the luer-type connection, and a central tube extending from a center of the frustoconical member.

11. The blood circuit assembly of claim 1, wherein the single unitary member includes tube engagement members having a hole through which a respective tube passes, the engagement members engaging with the respective tube to allow the tube to be pulled and stretched for engagement with an occluder of the dialysis unit.

12. The blood circuit assembly of claim 1, wherein the single unitary member defines the pneumatic control ports for the pumps.

13. The blood circuit assembly of claim 1, wherein the single unitary member defines a concave chamber portion for the pumps.

14. The blood circuit assembly of claim 1, wherein the single unitary member defines a chamber portion of a plurality of valves used to control flow through the pumps.

15. The blood circuit assembly of claim 1, wherein the single unitary member defines routing channels for flexible tubing to position the tubing for engagement with an occluder when the assembly is mounted to the dialysis unit.

16. A blood circuit assembly and drain cassette for a dialysis unit, the blood circuit assembly comprising:
a blood pump cassette comprising a pair of pneumatic pumps for circulating blood received from a patient through a circuit including a dialyzer unit and returning the blood to the patient;
an organizing tray formed as a single unitary member with a back plate of the blood pump cassette;
an air trap attached to the organizing tray arranged to remove air from blood circulating in the circuit;
a pair of dialyzer connections fluidly connected to the air trap and the pumps and arranged to connect to the inlet and outlet of a dialyzer unit;
a pair of blood line connectors fluidly connected to the pumps and the air trap, including an arterial blood line connector for receiving blood from the patient and providing blood to the pneumatic pumps and a venous blood line connector for returning blood to the patient; and
flexible tubing fluidly connecting the pumps, the air trap, the dialyzer connections and the blood line connectors;
wherein the organizing tray engages with at least a portion of the flexible tubing to position the flexible tubing for mounting at an occluder position for interaction with an occluder of the dialysis unit, and wherein the organizing tray supports the air trap at a location that is above the occluder position and above an air-in-line detector configured to detect air in a tube extending from an outlet of the air trap to the occluder position.

17. The blood circuit assembly of claim 16, wherein single unitary member additionally defines a plurality of routing channels for at least a portion of the flexible tubing.

18. The blood circuit assembly of claim 16, wherein the single unitary member additionally defines an air trap cavity that receives the air trap.

19. The blood circuit assembly of claim 16, wherein the pneumatic pumps comprise pneumatic control ports arranged for alignment and mating with corresponding ports located on an exposed panel of the dialysis unit by pushing the control ports into engagement with the corresponding ports with mounting of the blood circuit assembly to the exposed panel, and the single unitary member defines the pneumatic control ports for the pumps.

20. The blood circuit assembly of claim 16, wherein the single unitary member defines a concave chamber portion for the pumps.

21. The blood circuit assembly of claim 16, wherein the single unitary member defines a chamber portion of a plurality of valves used to control flow through the pumps.

22. The blood circuit assembly of claim 16, wherein the single unitary member defines routing channels for flexible tubing to position the tubing at the occluder position for engagement with an occluder when the assembly is mounted to the dialysis unit.

23. The blood circuit assembly of claim 16, wherein the arterial blood line connector is connected to an inlet for the pneumatic pumps, an outlet for the pneumatic pumps is connected to a dialyzer inlet connector, a dialyzer outlet connector is connected to the inlet of the air trap, and an outlet of the air trap is connected to the venous blood line connector.

24. The blood circuit assembly of claim 16, wherein an inlet of the air trap is supported by the organizing tray at a position above the outlet of the air trap when the blood circuit assembly is mounted to a dialysis unit.

25. The blood circuit assembly of claim 24, wherein the inlet of the air trap is supported by the organizing tray at a position above a highest point of flexible tubing that extends from the outlet of the air trap to the occluder position.

* * * * *